(12) United States Patent
Oba et al.

(10) Patent No.: US 10,639,143 B2
(45) Date of Patent: May 5, 2020

(54) MULTI-PORTION REPLACEMENT HEART VALVE PROSTHESIS

(71) Applicant: Edwards Lifesciences Corporation, Irvine, CA (US)

(72) Inventors: Travis Zenyo Oba, Yorba Linda, CA (US); Matthew A. Peterson, Costa Mesa, CA (US); Glen T. Rabito, Lake Forest, CA (US); Alexander H. Cooper, Costa Mesa, CA (US); David Robert Landon, Costa Mesa, CA (US); J. Brent Ratz, Winchester, MA (US); Seung-Beom Yi, Mission Viejo, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 15/687,184

(22) Filed: Aug. 25, 2017

(65) Prior Publication Data

US 2018/0055629 A1    Mar. 1, 2018

Related U.S. Application Data

(60) Provisional application No. 62/380,061, filed on Aug. 26, 2016.

(51) Int. Cl.
*A61F 2/24* (2006.01)
*A61L 27/04* (2006.01)
*A61L 27/36* (2006.01)

(52) U.S. Cl.
CPC .......... *A61F 2/2409* (2013.01); *A61F 2/2418* (2013.01); *A61L 27/04* (2013.01);
(Continued)

(58) Field of Classification Search
CPC ....................................................... A61F 2/24
See application file for complete search history.

(56) References Cited

U.S. PATENT DOCUMENTS

| 3,657,744 A | 4/1972 | Ersek |
| 3,671,979 A | 6/1972 | Moulopoulos |

(Continued)

FOREIGN PATENT DOCUMENTS

| CA | 2304325 A1 | 10/2000 |
| CA | 2827556 A1 | 7/2012 |

(Continued)

OTHER PUBLICATIONS

Int'l. Search Report for PCT/US2017/048729, dated Dec. 5, 2017.
(Continued)

*Primary Examiner* — Matthew W Schall
(74) *Attorney, Agent, or Firm* — Knobbe Martens Olson & Bear LLP

(57) ABSTRACT

A replacement mitral valve prosthesis includes a support structure and a valve body having three flexible leaflets. The support structure preferably includes an internal valve frame and an external sealing frame. The valve frame supports the flexible leaflets. The sealing frame is adapted to conform to the shape of the native mitral valve annulus. The sealing frame may be coupled to an inlet end of the valve frame, an outlet end of the valve frame, or both. A plurality of anchors are coupled to the outlet end of the valve frame. The anchors extend radially outwardly for placement behind native leaflets. The prosthesis preferably includes a skirt disposed along an exterior of the external sealing frame. The prosthesis is collapsible for delivery into the heart via a delivery catheter. The prosthesis is configured to self-expand for deployment in the heart when released from the delivery catheter.

18 Claims, 85 Drawing Sheets

(52) U.S. Cl.
CPC ......... *A61L 27/3625* (2013.01); *A61F 2/2412* (2013.01); *A61F 2/2436* (2013.01); *A61F 2220/0008* (2013.01); *A61F 2220/0075* (2013.01); *A61F 2230/0093* (2013.01); *A61F 2250/0018* (2013.01); *A61F 2250/0039* (2013.01); *A61F 2250/0063* (2013.01); *A61L 2430/20* (2013.01)

(56) References Cited

U.S. PATENT DOCUMENTS

| | | |
|---|---|---|
| 3,739,402 A | 6/1973 | Cooley et al. |
| 4,056,854 A | 11/1977 | Boretos et al. |
| 4,079,468 A | 3/1978 | Liotta et al. |
| 4,204,283 A | 5/1980 | Bellhouse et al. |
| 4,222,126 A | 9/1980 | Boretos et al. |
| 4,265,694 A | 5/1981 | Boretos et al. |
| 4,339,831 A | 7/1982 | Johnson |
| 4,340,977 A | 7/1982 | Brownlee et al. |
| 4,470,157 A | 9/1984 | Love |
| 4,477,930 A | 10/1984 | Totten et al. |
| 4,490,859 A | 1/1985 | Black et al. |
| 4,553,545 A | 11/1985 | Maass et al. |
| 4,777,951 A | 10/1988 | Cribier et al. |
| 4,865,600 A | 9/1989 | Carpentier et al. |
| 4,994,077 A | 2/1991 | Dobben |
| 5,326,371 A | 7/1994 | Love et al. |
| 5,332,402 A | 7/1994 | Teitelbaum |
| 5,370,685 A | 12/1994 | Stevens |
| 5,411,552 A | 5/1995 | Andersen et al. |
| 5,415,667 A | 5/1995 | Frater |
| 5,545,214 A | 8/1996 | Stevens |
| 5,554,185 A | 9/1996 | Block et al. |
| 5,697,382 A | 12/1997 | Love et al. |
| 5,840,081 A | 11/1998 | Andersen et al. |
| 5,855,601 A | 1/1999 | Bessler et al. |
| 5,957,949 A | 9/1999 | Leonhardt et al. |
| 6,086,612 A | 7/2000 | Jansen |
| 6,113,631 A | 9/2000 | Jansen |
| 6,168,614 B1 | 1/2001 | Andersen et al. |
| 6,251,093 B1 | 6/2001 | Valley et al. |
| 6,312,465 B1 | 11/2001 | Griffin et al. |
| 6,358,277 B1 | 3/2002 | Duran |
| 6,440,164 B1 | 8/2002 | DiMatteo et al. |
| 6,458,153 B1 | 10/2002 | Bailey et al. |
| 6,482,228 B1 | 11/2002 | Norred |
| 6,527,800 B1 | 3/2003 | McGuckin, Jr. et al. |
| 6,582,462 B1 | 6/2003 | Andersen et al. |
| 6,610,088 B1 | 8/2003 | Gabbay |
| 6,629,534 B1 | 10/2003 | St. Goar et al. |
| 6,652,578 B2 | 11/2003 | Bailey et al. |
| 6,676,698 B2 | 1/2004 | McGuckin, Jr. et al. |
| 6,695,878 B2 | 2/2004 | McGuckin, Jr. et al. |
| 6,712,836 B1 | 3/2004 | Berg et al. |
| 6,730,118 B2 | 5/2004 | Spenser et al. |
| 6,767,362 B2 | 7/2004 | Schreck |
| 6,780,200 B2 | 8/2004 | Jansen |
| 6,790,229 B1 | 9/2004 | Berreklouw |
| 6,790,230 B2 | 9/2004 | Beyersdorf et al. |
| 6,875,231 B2 | 4/2005 | Anduiza et al. |
| 6,893,460 B2 | 5/2005 | Spenser et al. |
| 6,908,481 B2 | 6/2005 | Cribier |
| 7,018,406 B2 | 3/2006 | Seguin et al. |
| 7,186,265 B2 | 3/2007 | Sharkawy et al. |
| 7,198,646 B2 | 4/2007 | Figulla et al. |
| 7,201,772 B2 | 4/2007 | Schwammenthal et al. |
| 7,276,078 B2 | 10/2007 | Spenser et al. |
| 7,329,278 B2 | 2/2008 | Seguin et al. |
| 7,381,219 B2 | 6/2008 | Salahieh et al. |
| 7,393,360 B2 | 7/2008 | Spenser et al. |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,510,575 B2 | 3/2009 | Spenser et al. |
| 7,524,330 B2 | 4/2009 | Berreklouw |
| 7,585,321 B2 | 9/2009 | Cribier |
| 7,618,446 B2 | 11/2009 | Andersen et al. |
| 7,621,948 B2 | 11/2009 | Herrmann et al. |
| 7,628,805 B2 | 12/2009 | Spenser et al. |
| 7,748,389 B2 | 7/2010 | Salahieh et al. |
| 7,753,949 B2 | 7/2010 | Lamphere et al. |
| 7,803,185 B2 | 9/2010 | Gabbay |
| 7,806,919 B2 | 10/2010 | Bloom et al. |
| 7,815,673 B2 | 10/2010 | Bloom et al. |
| 7,824,443 B2 | 11/2010 | Salahieh et al. |
| 7,892,281 B2 | 2/2011 | Seguin et al. |
| 7,914,569 B2 | 3/2011 | Nguyen et al. |
| 7,947,075 B2 | 5/2011 | Goetz et al. |
| 7,959,672 B2 | 6/2011 | Salahieh et al. |
| 7,972,378 B2 | 7/2011 | Tabor et al. |
| 7,981,151 B2 | 7/2011 | Rowe |
| 7,993,392 B2 | 8/2011 | Righini et al. |
| 8,016,877 B2 | 9/2011 | Seguin et al. |
| 8,048,153 B2 | 11/2011 | Salahieh et al. |
| 8,052,750 B2 | 11/2011 | Tuval et al. |
| 8,070,800 B2 | 12/2011 | Lock et al. |
| 8,070,802 B2 | 12/2011 | Lamphere et al. |
| 8,075,615 B2 | 12/2011 | Eberhardt et al. |
| 8,080,054 B2 | 12/2011 | Rowe |
| 8,092,520 B2 | 1/2012 | Quadri |
| 8,109,996 B2 | 2/2012 | Stacchino et al. |
| 8,118,866 B2 | 2/2012 | Herrmann et al. |
| 8,136,218 B2 | 3/2012 | Millwee et al. |
| 8,137,398 B2 | 3/2012 | Tuval et al. |
| 8,157,852 B2 | 4/2012 | Bloom et al. |
| 8,167,934 B2 | 5/2012 | Styrc et al. |
| 8,182,528 B2 | 5/2012 | Salahieh et al. |
| 8,182,530 B2 | 5/2012 | Huber |
| 8,216,301 B2 | 7/2012 | Bonhoeffer et al. |
| 8,219,229 B2 | 7/2012 | Cao et al. |
| 8,220,121 B2 | 7/2012 | Hendriksen et al. |
| 8,221,493 B2 | 7/2012 | Boyle et al. |
| 8,226,710 B2 | 7/2012 | Nguyen et al. |
| 8,236,045 B2 | 8/2012 | Benichou et al. |
| 8,246,675 B2 | 8/2012 | Zegdi |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,287,584 B2 | 10/2012 | Salahieh et al. |
| 8,303,653 B2 | 11/2012 | Bonhoeffer et al. |
| 8,313,525 B2 | 11/2012 | Tuval et al. |
| 8,323,335 B2 | 12/2012 | Rowe et al. |
| 8,353,953 B2 | 1/2013 | Giannetti et al. |
| 8,403,983 B2 | 3/2013 | Quadri et al. |
| 8,414,644 B2 | 4/2013 | Quadri et al. |
| 8,414,645 B2 | 4/2013 | Dwork et al. |
| 8,444,689 B2 | 5/2013 | Zhang |
| 8,449,599 B2 | 5/2013 | Chau et al. |
| 8,454,685 B2 | 6/2013 | Hariton et al. |
| 8,460,368 B2 | 6/2013 | Taylor et al. |
| 8,470,023 B2 | 6/2013 | Eidenschink et al. |
| 8,475,521 B2 | 7/2013 | Suri et al. |
| 8,475,523 B2 | 7/2013 | Duffy |
| 8,479,380 B2 | 7/2013 | Malewicz et al. |
| 8,486,137 B2 | 7/2013 | Suri et al. |
| 8,491,650 B2 | 7/2013 | Wiemeyer et al. |
| 8,500,798 B2 | 8/2013 | Rowe et al. |
| 8,511,244 B2 | 8/2013 | Holecek et al. |
| 8,512,401 B2 | 8/2013 | Murray, III et al. |
| 8,518,106 B2 | 8/2013 | Duffy et al. |
| 8,562,663 B2 | 10/2013 | Mearns et al. |
| 8,579,963 B2 | 11/2013 | Tabor |
| 8,579,964 B2 | 11/2013 | Lane et al. |
| 8,579,965 B2 | 11/2013 | Bonhoeffer et al. |
| 8,585,755 B2 | 11/2013 | Chau et al. |
| 8,585,756 B2 | 11/2013 | Bonhoeffer et al. |
| 8,591,570 B2 | 11/2013 | Revuelta et al. |
| 8,597,348 B2 | 12/2013 | Rowe et al. |
| 8,617,236 B2 | 12/2013 | Paul et al. |
| 8,640,521 B2 | 2/2014 | Righini et al. |
| 8,647,381 B2 | 2/2014 | Essinger et al. |
| 8,652,145 B2 | 2/2014 | Maimon et al. |
| 8,652,201 B2 | 2/2014 | Oberti et al. |

(56) References Cited

U.S. PATENT DOCUMENTS

| | | |
|---|---|---|
| 8,652,203 B2 | 2/2014 | Quadri et al. |
| 8,668,733 B2 | 3/2014 | Haug et al. |
| 8,673,000 B2 | 3/2014 | Tabor et al. |
| 8,679,174 B2 | 3/2014 | Ottma et al. |
| 8,679,404 B2 | 3/2014 | Liburd et al. |
| 8,685,086 B2 | 4/2014 | Navia et al. |
| 8,721,708 B2 | 5/2014 | Seguin et al. |
| 8,721,714 B2 | 5/2014 | Kelley |
| 8,728,154 B2 | 5/2014 | Alkhatib |
| 8,728,155 B2 | 5/2014 | Montorfano et al. |
| 8,740,974 B2 | 6/2014 | Lambrecht et al. |
| 8,740,976 B2 | 6/2014 | Tran et al. |
| 8,747,458 B2 | 6/2014 | Tuval et al. |
| 8,747,459 B2 | 6/2014 | Nguyen et al. |
| 8,747,460 B2 | 6/2014 | Tuval et al. |
| 8,758,432 B2 | 6/2014 | Solem |
| 8,764,818 B2 | 7/2014 | Gregg |
| 8,771,344 B2 | 7/2014 | Tran et al. |
| 8,771,345 B2 | 7/2014 | Tuval et al. |
| 8,771,346 B2 | 7/2014 | Tuval et al. |
| 8,778,020 B2 | 7/2014 | Gregg et al. |
| 8,784,478 B2 | 7/2014 | Tuval et al. |
| 8,784,481 B2 | 7/2014 | Alkhatib et al. |
| 8,790,387 B2 | 7/2014 | Nguyen et al. |
| 8,795,356 B2 | 8/2014 | Quadri et al. |
| 8,795,357 B2 | 8/2014 | Yohanan et al. |
| 8,808,356 B2 | 8/2014 | Braido et al. |
| 8,828,078 B2 | 9/2014 | Salahieh et al. |
| 8,828,079 B2 | 9/2014 | Thielen et al. |
| 8,834,564 B2 | 9/2014 | Tuval et al. |
| 8,845,718 B2 | 9/2014 | Tuval et al. |
| 8,870,948 B1 | 10/2014 | Erzberger et al. |
| 8,870,950 B2 | 10/2014 | Hacohen |
| 8,876,893 B2 | 11/2014 | Dwork et al. |
| 8,876,894 B2 | 11/2014 | Tuval et al. |
| 8,876,895 B2 | 11/2014 | Tuval et al. |
| 8,911,455 B2 | 12/2014 | Quadri et al. |
| 8,926,693 B2 | 1/2015 | Duffy et al. |
| 8,926,694 B2 | 1/2015 | Costello |
| 8,945,209 B2 | 2/2015 | Bonyuet et al. |
| 8,951,299 B2 | 2/2015 | Paul et al. |
| 8,961,593 B2 | 2/2015 | Bonhoeffer et al. |
| 8,961,595 B2 | 2/2015 | Alkhatib |
| 8,974,524 B2 | 3/2015 | Yeung et al. |
| 8,979,922 B2 | 3/2015 | Jayasinghe et al. |
| 8,986,372 B2 | 3/2015 | Murry, III et al. |
| 8,986,375 B2 | 3/2015 | Garde et al. |
| 8,992,608 B2 | 3/2015 | Haug et al. |
| 8,998,979 B2 | 4/2015 | Seguin et al. |
| 8,998,980 B2 | 4/2015 | Shipley et al. |
| 9,005,273 B2 | 4/2015 | Salahieh et al. |
| 9,011,521 B2 | 4/2015 | Haug et al. |
| 9,011,523 B2 | 4/2015 | Seguin |
| 9,011,524 B2 | 4/2015 | Eberhardt |
| 9,028,545 B2 | 5/2015 | Taylor |
| 9,034,032 B2 | 5/2015 | McLean et al. |
| 9,034,033 B2 | 5/2015 | McLean et al. |
| 9,039,757 B2 | 5/2015 | McLean et al. |
| 9,055,937 B2 | 6/2015 | Rowe et al. |
| 9,066,801 B2 | 6/2015 | Kovalsky et al. |
| 9,078,749 B2 | 7/2015 | Lutter et al. |
| 9,078,751 B2 | 7/2015 | Naor |
| 9,084,676 B2 | 7/2015 | Chau et al. |
| 9,125,738 B2 | 9/2015 | Figulla et al. |
| 9,138,312 B2 | 9/2015 | Tuval et al. |
| 9,161,834 B2 | 10/2015 | Taylor et al. |
| 9,173,737 B2 | 11/2015 | Hill et al. |
| 9,186,249 B2 | 11/2015 | Rolando et al. |
| 9,220,594 B2 | 12/2015 | Braido et al. |
| 9,241,790 B2 | 1/2016 | Lane et al. |
| 9,248,014 B2 | 2/2016 | Lane et al. |
| 9,289,291 B2 | 3/2016 | Gorman, III et al. |
| 9,289,296 B2 | 3/2016 | Braido et al. |
| 9,331,328 B2 | 5/2016 | Eberhardt et al. |
| 9,339,382 B2 | 5/2016 | Tabor et al. |
| 9,351,831 B2 | 5/2016 | Braido et al. |
| 9,351,832 B2 | 5/2016 | Braido et al. |
| 9,364,321 B2 | 6/2016 | Alkhatib et al. |
| 2001/0007956 A1 | 7/2001 | Letac et al. |
| 2002/0016623 A1 | 2/2002 | Kula et al. |
| 2002/0032481 A1 | 3/2002 | Gabbay |
| 2002/0045929 A1 | 4/2002 | Diaz |
| 2002/0052644 A1 | 5/2002 | Shaolian et al. |
| 2003/0105517 A1 | 6/2003 | White et al. |
| 2003/0120333 A1 | 6/2003 | Ouriel et al. |
| 2003/0130729 A1 | 7/2003 | Paniagua et al. |
| 2003/0176914 A1 | 9/2003 | Rabkin et al. |
| 2003/0199971 A1 | 10/2003 | Tower et al. |
| 2003/0220683 A1 | 11/2003 | Minasian et al. |
| 2004/0117009 A1 | 6/2004 | Cali et al. |
| 2004/0133273 A1 | 7/2004 | Cox |
| 2004/0186561 A1 | 9/2004 | McGuckin et al. |
| 2004/0210304 A1 | 10/2004 | Seguin et al. |
| 2004/0210307 A1 | 10/2004 | Khairkhahan |
| 2004/0215325 A1 | 10/2004 | Penn et al. |
| 2004/0225353 A1 | 11/2004 | McGuckin et al. |
| 2004/0236411 A1 | 11/2004 | Sarac et al. |
| 2005/0033398 A1 | 2/2005 | Seguin |
| 2005/0075727 A1 | 4/2005 | Wheatley |
| 2005/0090887 A1 | 4/2005 | Pryor |
| 2005/0096738 A1 | 5/2005 | Cali et al. |
| 2005/0107872 A1 | 5/2005 | Mensah et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137691 A1 | 6/2005 | Salahieh et al. |
| 2005/0137693 A1 | 6/2005 | Haug et al. |
| 2005/0159811 A1 | 7/2005 | Lane |
| 2005/0182486 A1 | 8/2005 | Gabbay |
| 2005/0216079 A1 | 9/2005 | MaCoviak |
| 2005/0234546 A1 | 10/2005 | Nugent et al. |
| 2005/0283231 A1 | 12/2005 | Haug et al. |
| 2006/0020327 A1 | 1/2006 | Lashinski et al. |
| 2006/0052867 A1 | 3/2006 | Revuelta et al. |
| 2006/0058872 A1 | 3/2006 | Salahieh et al. |
| 2006/0095115 A1 | 5/2006 | Bladillah et al. |
| 2006/0173537 A1 | 8/2006 | Yang et al. |
| 2006/0195183 A1 | 8/2006 | Navia et al. |
| 2006/0212110 A1 | 9/2006 | Osborne et al. |
| 2006/0241745 A1 | 10/2006 | Solem |
| 2006/0259135 A1 | 11/2006 | Navia et al. |
| 2006/0265056 A1 | 11/2006 | Nguyen et al. |
| 2006/0287717 A1 | 12/2006 | Rowe et al. |
| 2006/0293745 A1 | 12/2006 | Carpentier et al. |
| 2007/0010876 A1 | 1/2007 | Salahieh et al. |
| 2007/0043435 A1 | 2/2007 | Seguin et al. |
| 2007/0050021 A1 | 3/2007 | Johnson |
| 2007/0100432 A1 | 5/2007 | Case et al. |
| 2007/0129794 A1 | 6/2007 | Realyvasquez |
| 2007/0142906 A1 | 6/2007 | Figulla et al. |
| 2007/0213813 A1 | 9/2007 | Von Segesser et al. |
| 2007/0255394 A1 | 11/2007 | Ryan |
| 2008/0021546 A1 | 1/2008 | Patz et al. |
| 2008/0071366 A1 | 3/2008 | Tuval et al. |
| 2008/0082164 A1 | 4/2008 | Friedman |
| 2008/0082165 A1 | 4/2008 | Wilson et al. |
| 2008/0097581 A1 | 4/2008 | Shanley |
| 2008/0147179 A1 | 6/2008 | Cai et al. |
| 2008/0147183 A1 | 6/2008 | Styrc |
| 2008/0161911 A1 | 7/2008 | Revuelta et al. |
| 2008/0177381 A1 | 7/2008 | Navia et al. |
| 2008/0183273 A1 | 7/2008 | Mesana et al. |
| 2008/0208328 A1 | 8/2008 | Antocci et al. |
| 2008/0228254 A1 | 9/2008 | Ryan |
| 2009/0005863 A1 | 1/2009 | Goetz et al. |
| 2009/0138079 A1 | 5/2009 | Tuval et al. |
| 2009/0171456 A1 | 7/2009 | Kveen et al. |
| 2009/0182413 A1 | 7/2009 | Burkart et al. |
| 2009/0188964 A1 | 7/2009 | Orlov |
| 2009/0270972 A1 | 10/2009 | Lane |
| 2009/0276040 A1 | 11/2009 | Rowe et al. |
| 2009/0281618 A1 | 11/2009 | Hill et al. |
| 2009/0287296 A1 | 11/2009 | Manasse |
| 2009/0292350 A1 | 11/2009 | Eberhardt et al. |

(56) References Cited

U.S. PATENT DOCUMENTS

| | | |
|---|---|---|
| 2009/0306768 A1 | 12/2009 | Quadri |
| 2010/0114305 A1 | 5/2010 | Kang et al. |
| 2010/0191326 A1 | 7/2010 | Alkhatib |
| 2010/0217382 A1 | 8/2010 | Chau et al. |
| 2010/0249894 A1 | 9/2010 | Oba et al. |
| 2010/0249911 A1 | 9/2010 | Alkhatib |
| 2010/0256723 A1 | 10/2010 | Murray |
| 2010/0305685 A1 | 12/2010 | Millwee et al. |
| 2011/0004296 A1 | 1/2011 | Lutter et al. |
| 2011/0029067 A1 | 2/2011 | McGuckin, Jr. et al. |
| 2011/0208297 A1 | 8/2011 | Tuval et al. |
| 2011/0208298 A1 | 8/2011 | Tuval et al. |
| 2011/0224785 A1 | 9/2011 | Hacohen |
| 2011/0264196 A1 | 10/2011 | Savage et al. |
| 2011/0313515 A1 | 12/2011 | Quadri et al. |
| 2012/0022639 A1 | 1/2012 | Hacohen et al. |
| 2012/0041550 A1 | 2/2012 | Salahieh et al. |
| 2012/0059454 A1 | 3/2012 | Millwee et al. |
| 2012/0078360 A1 | 3/2012 | Rafiee |
| 2012/0101571 A1 | 4/2012 | Thambar et al. |
| 2012/0101572 A1 | 4/2012 | Kovalsky et al. |
| 2012/0123529 A1 | 5/2012 | Levi et al. |
| 2012/0215303 A1 | 8/2012 | Quadri et al. |
| 2012/0271398 A1 | 10/2012 | Essinger et al. |
| 2012/0290062 A1 | 11/2012 | McNamara et al. |
| 2012/0310328 A1 | 12/2012 | Olson et al. |
| 2013/0006294 A1 | 1/2013 | Kashkarov et al. |
| 2013/0035759 A1 | 2/2013 | Gross et al. |
| 2013/0053950 A1 | 2/2013 | Rowe et al. |
| 2013/0131788 A1 | 5/2013 | Quadri et al. |
| 2013/0144378 A1 | 6/2013 | Quadri et al. |
| 2013/0211508 A1 | 8/2013 | Lane et al. |
| 2013/0253635 A1 | 9/2013 | Straubinger et al. |
| 2013/0253642 A1 | 9/2013 | Brecker |
| 2013/0310928 A1 | 11/2013 | Morriss et al. |
| 2013/0331929 A1 | 12/2013 | Mitra et al. |
| 2013/0338766 A1 | 12/2013 | Hastings et al. |
| 2013/0345786 A1 | 12/2013 | Behan |
| 2014/0018912 A1 | 1/2014 | Delaloye et al. |
| 2014/0025163 A1 | 1/2014 | Padala et al. |
| 2014/0039611 A1 | 2/2014 | Lane et al. |
| 2014/0052237 A1 | 2/2014 | Lane et al. |
| 2014/0052242 A1 | 2/2014 | Revuelta et al. |
| 2014/0100651 A1 | 4/2014 | Kheradvar et al. |
| 2014/0100653 A1 | 4/2014 | Savage et al. |
| 2014/0142694 A1 | 5/2014 | Tabor et al. |
| 2014/0163668 A1 | 6/2014 | Rafiee |
| 2014/0172077 A1 | 6/2014 | Bruchman et al. |
| 2014/0172083 A1 | 6/2014 | Bruchman et al. |
| 2014/0194981 A1 | 7/2014 | Menk et al. |
| 2014/0207231 A1 | 7/2014 | Hacohen et al. |
| 2014/0214153 A1 | 7/2014 | Ottma et al. |
| 2014/0214154 A1 | 7/2014 | Nguyen et al. |
| 2014/0214155 A1 | 7/2014 | Kelley |
| 2014/0214160 A1 | 7/2014 | Naor |
| 2014/0222136 A1 | 8/2014 | Geist et al. |
| 2014/0222139 A1 | 8/2014 | Nguyen et al. |
| 2014/0222142 A1 | 8/2014 | Kovalsky et al. |
| 2014/0230515 A1 | 8/2014 | Tuval et al. |
| 2014/0236288 A1 | 8/2014 | Lambrecht et al. |
| 2014/0257467 A1 | 9/2014 | Lane et al. |
| 2014/0277390 A1 | 9/2014 | Ratz et al. |
| 2014/0277402 A1 | 9/2014 | Essinger et al. |
| 2014/0277422 A1 | 9/2014 | Ratz et al. |
| 2014/0277427 A1 | 9/2014 | Ratz et al. |
| 2014/0296973 A1 | 10/2014 | Bergheim et al. |
| 2014/0296975 A1 | 10/2014 | Tegels et al. |
| 2014/0303719 A1 | 10/2014 | Cox et al. |
| 2014/0309728 A1 | 10/2014 | Dehdashtian et al. |
| 2014/0309732 A1 | 10/2014 | Solem |
| 2014/0324160 A1 | 10/2014 | Benichou et al. |
| 2014/0324164 A1 | 10/2014 | Gross et al. |
| 2014/0330368 A1 | 11/2014 | Gloss et al. |
| 2014/0330371 A1 | 11/2014 | Gloss et al. |
| 2014/0330372 A1 | 11/2014 | Weston et al. |
| 2014/0336754 A1 | 11/2014 | Gurskis et al. |
| 2014/0343669 A1 | 11/2014 | Lane et al. |
| 2014/0343670 A1 | 11/2014 | Bakis et al. |
| 2014/0343671 A1 | 11/2014 | Yohanan et al. |
| 2014/0350663 A1 | 11/2014 | Braido et al. |
| 2014/0350666 A1 | 11/2014 | Righini |
| 2014/0350668 A1 | 11/2014 | Delaloye et al. |
| 2014/0358223 A1 | 12/2014 | Rafiee et al. |
| 2014/0364939 A1 | 12/2014 | Deshmukh et al. |
| 2014/0364943 A1 | 12/2014 | Conklin |
| 2014/0371842 A1 | 12/2014 | Marquez et al. |
| 2014/0371844 A1 | 12/2014 | Dale et al. |
| 2014/0371845 A1 | 12/2014 | Tuval et al. |
| 2014/0371847 A1 | 12/2014 | Madrid et al. |
| 2014/0371848 A1 | 12/2014 | Murray, III et al. |
| 2014/0379067 A1 | 12/2014 | Nguyen et al. |
| 2014/0379068 A1 | 12/2014 | Thielen et al. |
| 2014/0379077 A1 | 12/2014 | Tuval et al. |
| 2015/0005863 A1 | 1/2015 | Para |
| 2015/0012085 A1 | 1/2015 | Salahieh et al. |
| 2015/0018938 A1 | 1/2015 | Von Segesser et al. |
| 2015/0018944 A1 | 1/2015 | O'Connell et al. |
| 2015/0039083 A1 | 2/2015 | Rafiee |
| 2015/0045880 A1 | 2/2015 | Hacohen |
| 2015/0142103 A1 | 5/2015 | Vidlund |
| 2015/0148731 A1 | 5/2015 | McNamara et al. |
| 2015/0157457 A1 | 6/2015 | Hacohen |
| 2015/0157458 A1 | 6/2015 | Thambar et al. |
| 2015/0173897 A1 | 6/2015 | Raanani et al. |
| 2015/0196390 A1 | 7/2015 | Ma et al. |
| 2015/0209141 A1 | 7/2015 | Braido et al. |
| 2015/0272737 A1 | 10/2015 | Dale et al. |
| 2015/0327994 A1 | 11/2015 | Morriss et al. |
| 2015/0328001 A1 | 11/2015 | McLean et al. |
| 2015/0335424 A1 | 11/2015 | McLean et al. |
| 2015/0335429 A1 | 11/2015 | Morriss et al. |
| 2015/0351903 A1 | 12/2015 | Morriss et al. |
| 2015/0351906 A1 | 12/2015 | Hammer et al. |
| 2015/0359629 A1 | 12/2015 | Ganesan et al. |
| 2016/0000591 A1 | 1/2016 | Lei et al. |
| 2016/0030169 A1 | 2/2016 | Shahriari |
| 2016/0030170 A1 | 2/2016 | Alkhatib et al. |
| 2016/0030171 A1 | 2/2016 | Quijano et al. |
| 2016/0038281 A1 | 2/2016 | Delaloye et al. |
| 2016/0074160 A1 | 3/2016 | Christianson et al. |
| 2016/0106537 A1 | 4/2016 | Christianson et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0143732 A1 | 5/2016 | Glimsdale |
| 2016/0158003 A1 | 6/2016 | Wallace et al. |
| 2016/0213473 A1 | 7/2016 | Hacohen et al. |
| 2016/0235529 A1 | 8/2016 | Ma et al. |

FOREIGN PATENT DOCUMENTS

| | | |
|---|---|---|
| DE | 102006052564 B3 | 12/2007 |
| EP | 1255510 A1 | 11/2002 |
| EP | 1259194 A1 | 11/2002 |
| EP | 1281375 A2 | 2/2003 |
| EP | 1472996 A1 | 11/2004 |
| EP | 1734903 A1 | 12/2006 |
| EP | 2124826 A1 | 12/2009 |
| EP | 2237746 A2 | 10/2010 |
| EP | 2285317 A1 | 2/2011 |
| EP | 2308425 A1 | 4/2011 |
| EP | 2319458 A1 | 5/2011 |
| EP | 2496182 A1 | 9/2012 |
| EP | 2566416 A1 | 3/2013 |
| EP | 2745805 A1 | 6/2014 |
| EP | 2749254 A1 | 7/2014 |
| EP | 2777617 A1 | 9/2014 |
| EP | 2815723 A1 | 12/2014 |
| EP | 2815725 A1 | 12/2014 |
| EP | 2898858 A1 | 7/2015 |
| EP | 2926766 B1 | 2/2016 |
| EP | 2985006 A1 | 2/2016 |
| GB | 126447 A | 5/1919 |
| GB | 1315844 A | 5/1973 |

(56) References Cited

FOREIGN PATENT DOCUMENTS

| | | | |
|---|---|---|---|
| GB | 2398245 A | 8/2004 | |
| JP | 2002540889 A | 12/2002 | |
| JP | 2008541865 A | 11/2008 | |
| WO | 1997049355 A1 | 12/1997 | |
| WO | 0061034 A1 | 10/2000 | |
| WO | 03092554 A1 | 11/2003 | |
| WO | 2005011534 A1 | 2/2005 | |
| WO | 2006070372 A2 | 7/2006 | |
| WO | 2006085225 A1 | 8/2006 | |
| WO | 2006089236 A1 | 8/2006 | |
| WO | 2006127765 A1 | 11/2006 | |
| WO | 2007025028 A1 | 3/2007 | |
| WO | 2007058857 A2 | 5/2007 | |
| WO | 2007123658 A1 | 11/2007 | |
| WO | 2008013915 A2 | 1/2008 | |
| WO | 2008070797 A2 | 6/2008 | |
| WO | 2008103722 A2 | 8/2008 | |
| WO | 2008150529 A1 | 12/2008 | |
| WO | 2009026563 A2 | 2/2009 | |
| WO | 2009033469 A1 | 3/2009 | |
| WO | 2009045331 A1 | 4/2009 | |
| WO | 2009053497 A1 | 4/2009 | |
| WO | 2009094500 A1 | 7/2009 | |
| WO | 2009134701 A2 | 11/2009 | |
| WO | 2010008549 A1 | 1/2010 | |
| WO | 2010037141 A1 | 4/2010 | |
| WO | 2010040009 A1 | 4/2010 | |
| WO | 2010057262 A1 | 5/2010 | |
| WO | 2011025945 A1 | 3/2011 | |
| WO | 2011057087 A1 | 5/2011 | |
| WO | 2011111047 A2 | 9/2011 | |
| WO | 2011137531 A1 | 11/2011 | |
| WO | 2012177942 A2 | 12/2012 | |
| WO | 2013028387 A2 | 2/2013 | |
| WO | 2013075215 A1 | 5/2013 | |
| WO | 2013120181 A1 | 8/2013 | |
| WO | 2013175468 A2 | 11/2013 | |
| WO | 2013192305 A2 | 12/2013 | |
| WO | 2014018432 A2 | 1/2014 | |
| WO | 2014099655 A1 | 6/2014 | |
| WO | 2014100394 A1 | 6/2014 | |
| WO | 2014110019 A1 | 7/2014 | |
| WO | 2014110171 A2 | 7/2014 | |
| WO | 2014121042 A1 | 8/2014 | |
| WO | 2014139545 A1 | 9/2014 | |
| WO | 2014145338 A1 | 9/2014 | |
| WO | 2014149865 A1 | 9/2014 | |
| WO | 2014163706 A1 | 10/2014 | |
| WO | 2014164364 A1 | 10/2014 | |
| WO | 2014194178 A1 | 12/2014 | |
| WO | 2014204807 A1 | 12/2014 | |
| WO | 2014205064 A1 | 12/2014 | |
| WO | 2015077274 A1 | 5/2015 | |
| WO | 2015148241 A1 | 10/2015 | |
| WO | 2015179423 A1 | 11/2015 | |
| WO | 2016016899 A1 | 2/2016 | |

OTHER PUBLICATIONS

Kronemyer, Bob, "CardiAQ Valve Technologies: Percutaneous Mitral Valve Replacement," Start Up—Windhover Review of Emerging Medical Ventures, vol. 14, Issue No. 6, Jun. 2009, pp. 48-49.

Bavaria, Joseph E. M.D.: "CardiAQ Valve Technologies: Transcatheter Mitral Valve Implantation," Sep. 21, 2009.

Ostrovsky, Gene, "Transcatheter Mitral Valve Implantation Technology from CardiAQ," medGadget, Jan. 15, 2010, available at: http://www.medgadget.com/2010/01/transcatheter_mitral_valve_implantation_technology_from_cardiaq.html.

Berreklouw, Eric, PhD, et al., "Sutureless Mitral Valve Replacement With Bioprostheses and Nitinol Attachment Rings: Feasibility in Acute Pig Experiments," The Journal of Thoracic and Cardiovascular Surgery, vol. 142, No. 2, Aug. 2011 in 7 pages, Applicant believes this may have been available online as early as Feb. 7, 2011.

Boudjemline, Younes, et al., "Steps Toward the Percutaneous Replacement of Atrioventricular Valves," JACC, vol. 46, No. 2, Jul. 19, 2005:360-5.

Chiam, Paul T.L., et al., "Percutaneous Transcatheter Aortic Valve Implantation: Assessing Results, Judging Outcomes, and Planning Trials," JACC: Cardiovascular Interventions, The American College of Cardiology Foundation, vol. 1, No. 4, Aug. 2008:341-50.

Condado, Jose Antonio, et al., "Percutaneous Treatment of Heart Valves," Rev Esp Cardio. 2006;59(12):1225-31, Applicant believes this may have been available as early as Dec. 2006.

Vu, Duc-Thang, et al., "Novel Sutureless Mitral Valve Implantation Method Involving a Bayonet Insertion and Release Mechanism: A Proof of Concept Study in Pigs," The Journal of Thoracic and Cardiovascular Surgery, vol. 143, No. 4, 985-988, Apr. 2012, Applicant believes this may have been available online as early as Feb. 13, 2012.

Fanning, Jonathon P., et al., "Transcatheter Aortic Valve Implantation (TAVI): Valve Design and Evolution," International Journal of Cardiology 168 (2013) 1822-1831, Applicant believes this may have been available as early as Oct. 3, 2013.

Spillner, J. et al., "New Sutureless 'Atrial-Mitral-Valve Prosthesis' for Minimally Invasive Mitral Valve Therapy," Textile Research Journal, 2010, in 7 pages, Applicant believes this may have been available as early as Aug. 9, 2010.

Karimi, Houshang, et al., "Percutaneous Valve Therapies," SIS 2007 Yearbook, Chapter 11, pp. 1-11.

Leon, Martin B., et al., "Transcatheter Aortic Valve Replacement in Patients with Critical Aortic Stenosis: Rationale, Device Descriptions, Early Clinical Experiences, and Perspectives," Semin. Thorac. Cardiovasc. Surg. 18:165-174, 2006 in 10 pages, Applicant believes this may have been available as early as the Summer of 2006.

Lutter, Georg, et al., "Off-Pump Transapical Mitral Valve Replacement," European Journal of Cardio-thoracic Surgery 36 (2009) 124-128, Applicant believes this may have been available as early as Apr. 25, 2009.

Ma, Liang, et al., "Double-Crowned Valved Stents for Off-Pump Mitral Valve Replacement," European Journal of Cardio-thoracic Surgery 28 (2005) 194-199, Applicant believes this may have been available as early as Aug. 2005.

Pluth, James R., M.D., et al., "Aortic and Mitral Valve Replacement with Cloth-Covered Braunwald-Cutter Prosthesis, A Three-Year Follow-up," The Annals of Thoracic Surgery, vol. 20, No. 3, Sep. 1975, pp. 239-248.

Seidel, Wolfgang, et al., "A Mitral Valve Prosthesis and a Study of Thrombosis on Heart Valves in Dogs," JSR—vol. II, No. 3—May 1962, submitted for publication Oct. 9, 1961.

Engager System, Precise Valve Positioning, Transcatheter Aortic Valve Implantation System, Transcatheter Aortic Valve Replacement—TAVR I Medtronic Engager, http://www.medtronic-engager.com/home/transcatheter-aortic-valve-repl., 2014 Medtronic, Inc. in 2 pages. Applicant believes this may have been available online as early as Aug. 25, 2013.

Webb, John G., et al., "Transcatheter Aortic Valve Implantation: The Evolution of Prostheses, Delivery Systems and Approaches," Archives of Cardiovascular Disease (2012) 105, 153-159. Applicant believes this may have been available as early as Mar. 16, 2012.

Sondergaard, Lars, et al., "Transcatheter Mitral Valve Implantation: CardiAQ™," Applicant believes this may have been presented at TCT 2013.

Sondergaard, Lars, et al., "Transcatheter Mitral Valve Implantation: CardiAQ™," Applicant believes this may have been presented at EuroPCR 2013.

Sondergaard, Lars, "CardiAQ TMVR FIH—Generation 2," Applicants believe this may have been presented in 2014 at the TVT symposium.

CardiAQ Valve Technologies, "Innovations in Heart Valve Therapy," In3 San Francisco, Jun. 18, 2008, PowerPoint presentation in 19 slides.

Ratz, J. Brent, "LSI EMT Spotlight," May 15, 2009.

Ratz, J. Brent, "In3 Company Overview," Jun. 24, 2009.

"Company Overview," at TVT on Jun. 25, 2009.

(56) References Cited

OTHER PUBLICATIONS

Ruiz, Carlos E., "Overview of Novel Transcatheter Valve Technologies," Applicant believes this may have been presented on May 27, 2010 at EuroPCR.
"Update," Applicant believes this may have been presented on Jun. 6, 2010 at TVT.
Mack, Michael, M.D., "Antegrade Transcatheter Mitral valve Implantation: A Short-term Experience in Swine Model," Applicant believes this may have been presented on May 2011 at TVT.
Mack, Michael, M.D., "Antegrade Transcatheter Mitral valve Implantation: On-Going Experience in Swine Model," Applicant believes this may have been presented on Nov. 2011 at TCT.
Fitzgerald, Peter J. M.D., "Tomorrow's Technology: Percutaneous Mitral Valve Replacement, Chordal Shortening, and Beyond," Transcatheter Valve Therapies (TVT) Conference. Seattle, WA. Applicant believes this may have been available as early as Jun. 7, 2010.
Quadri, Arshad M.D., "Transcatheter Mitral Valve Implantation (TMVI) (An Acute In Vivo Study)," Applicant believes this may have been presented on Sep. 22, 2010 at TCT.
Masson, Jean-Bernard, et al., "Percutaneous Treatment of Mitral Regurgitation," Circulation: Cardiovascular Interventions, 2:140-146, Applicant believes this may have been available as early as Apr. 14, 2009.
Horvath et al.: "Transapical Aortic Valve Replacement under Real-time Magnetic Resonance Imaging Guidance: Experimental Results with Balloon—Expandable and Self-Expanding Stents," http://www.ncbi.nlm.nih.gov/pmc/articles/PMC3038190/. Jun. 2011.
Treede et al.: "Transapical transcatheter aortic valve implantation using the JenaValve™ system: acute and 30-day results of the multicentre CE-mark study." http://ejcts.oxfordjournals.org/content/41/6/e131.long. Apr. 16, 2012.
Taramasso et al.: "New devices for TAVI: technologies and initial clinical experiences" http://www.nature.com/nrcardio/journal/v11/n3/full/nrcardio.2013.221.html?message-global=remove#access. Jan. 21, 2014.
Van Mieghem, et al., "Anatomy of the Mitral Valvular Complez and Its Implications for Transcatheter Interventions for Mitral Regurgitation," J. Am. Coll. Cardiol., 56:617-626 (Aug. 17, 2010).
Wayback Machine, Cleveland Clinic Lerner Research Institute, Transcatheter Mitral Stent/Valve Prosthetic, https://web.archive.org/web/20130831094624/http://mds.clevelandclinic.org/Portfolio.aspx?n=331, indicated as archived on Aug. 31, 2013.
Grube, E. et al, "Percutaneous aortic valve replacement for severe aortic stenosis in high-risk patients using the second- and current third-generation self-expanding CoreValve prosthesis: device success and 30-day clinical outcome." J Am Coll Cardiol. Jul. 3, 2007;50(1):69-76. Epub Jun. 6, 2007.
Piazza, Nicoló, MD, et al., "Anatomy of the Aortic Valvar Complex and Its Implications for Transcatheter Implantation of the Aortic Valve," Contemporary Reviews in Interventional Cardiology, Circ. Cardiovasc. Intervent., 2008;1:74-81, Applicant believes this may have been available as early as Aug. 2008.

Feldman, Ted, MD. "Prospects for Percutaneous Valve Therapies," Circulation 2007;116:2866-2877. Applicant believes that this may be available as early as Dec. 11, 2007.
Backer, Ole De, MD, et al., "Percutaneous Transcatheter Mitral Valve Replacement—An Overview of Devices in Preclinical and Early Clinical Evaluation," Contemporary Reviews in Interventional Cardiology, Circ Cardiovasc Interv. 2014;7:400-409, Applicant believes this may have been available as early as Jun. 2014.
Preston-Maher, Georgia L., et al., "A Technical Review of Minimally Invasive Mitral Valve Replacements," Cardiovascular Engineering and Technology, vol. 6, No. 2, Jun. 2015, pp. 174-184. Applicant believes this may have been available as early as Nov. 25, 2014.
BioSpace, "CardiAQ Valve Technologies (CVT) Reports Cardiovascular Medicine Milestone: First-in-Humannonsurgical Percutaneous Implantation of a Bioprosthetic Mitral Heart Valve," Jun. 14, 2012, p. 1, http://www.biospace.com/News/cardiaq-valve-technologies-cvt-reports/263900.
BioSpace, "CardiAQ Valve Technologies (CVT) Reports First-in-Human Percutaneous Transfemoral, Transseptal Implantation With Its Second Generation Transcatheter Bioprosthetic Mitral Heart Valve," Jun. 23, 2015, p. 1, http://www.biospace.com/News/cardiaq-valve-technologies-cvt-reports-first- in/382370.
"CardiAQTM Valve Technologies reports Successful First-in-Human Trans-Apical implantation of its Second Generation Transcatheter Mitral Valve," CardiAQ Valve Technologies Press Release, May 20, 2014.
Dave Fornell, "Transcatheter Mitral Valve replacement Devices in Development," Diagnostic and Interventional Cardiology, Dec. 30, 2014, p. 3, <http://www.dicardiology.com/article/transcatheter-mitral-valve-replacement-devices-development>.
The Journal of the American College of Cardiology, "Transapical Mitral Implantation of the Tiara Bioprosthesis Pre-Clinical Results," Feb. 2014, <http://interventions.onlinejacc.org/article.aspx?articleid=1831234>.
Ratz, J. Brent et al., "Any experiences making an expandable stent frame?" Arch-Pub.com, Architecture Forums: Modeling, Multiple forum postings from Feb. 3, 2009 to Feb. 4, 2009, http://www.arch-pub.com.
Neovasc corporate presentation, Oct. 2009, available at http://www.neovasc.com/investors/documents/Neovasc-Corporate-Presentation-October-2009.pdf.
NJ350: Vote for Your Favorite New Jersey Innovations, Jun. 27, 2014, http://www.kilmerhouse.com/2014/06/nj350-vote-for-your-favorite-new-jersey-innovations/.
Mack, Michael M.D., "Advantages and Limitations of Surgical Mitral Valve Replacement; Lessons for the Transcatheter Approach," Applicant believes this may have been available as early as Jun. 7, 2010. Applicant believes this may have been presented at the Texas Cardiovascular Innovative Ventures (TCIV) Conference in Dallas, TX on Dec. 8, 2010.
Bavaria, Joseph E. M.D. et al.: "Transcatheter Mitral Valve Implantation: The Future Gold Standard for MR?," Applicant requests the Examiner to consider this reference to be prior art as of Dec. 2010.

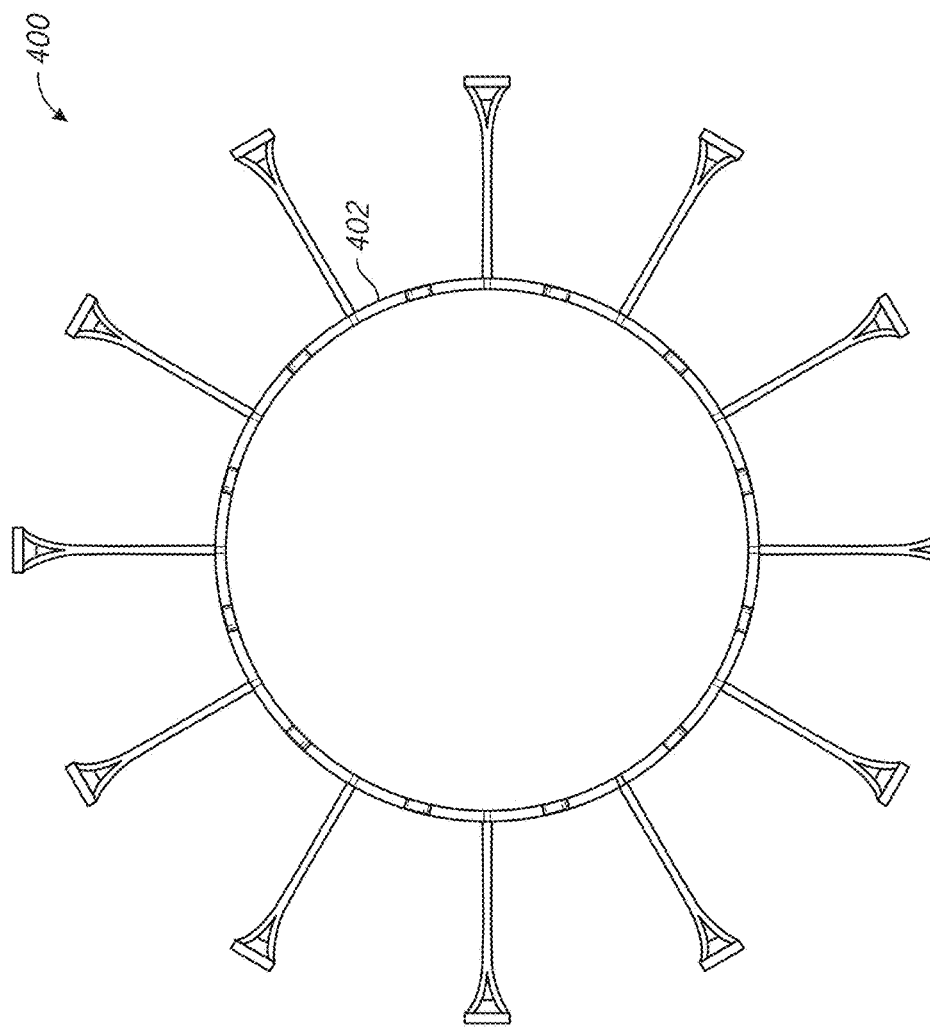

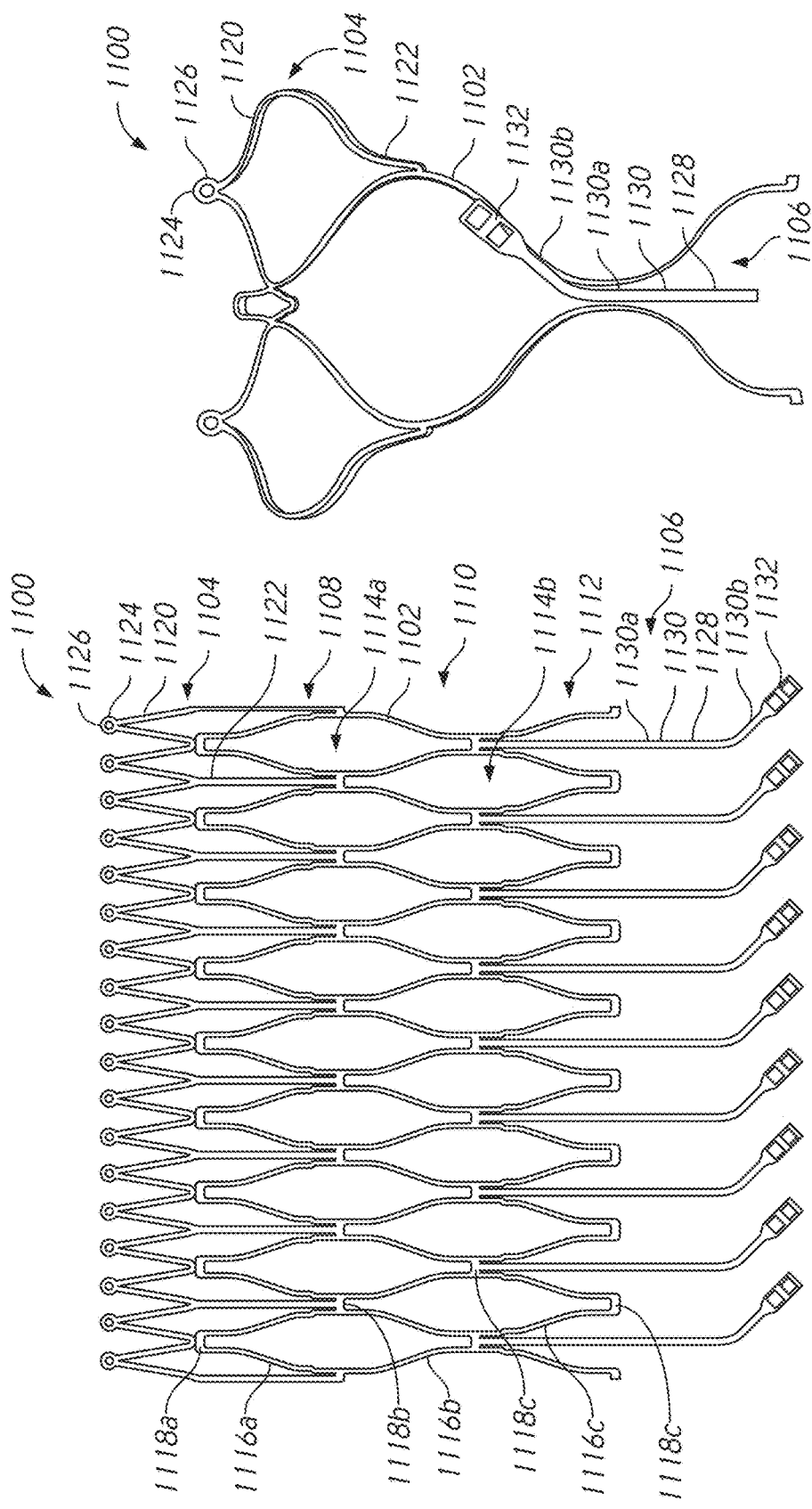

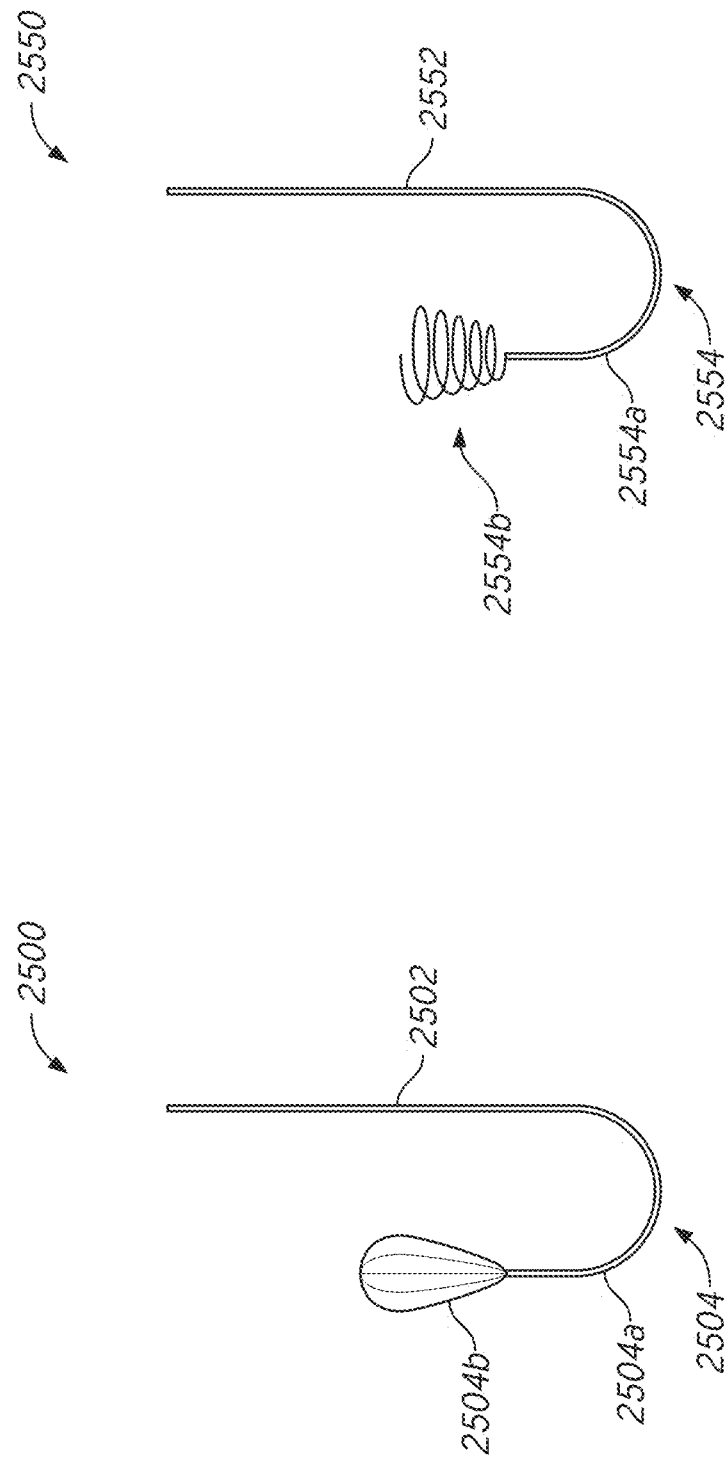

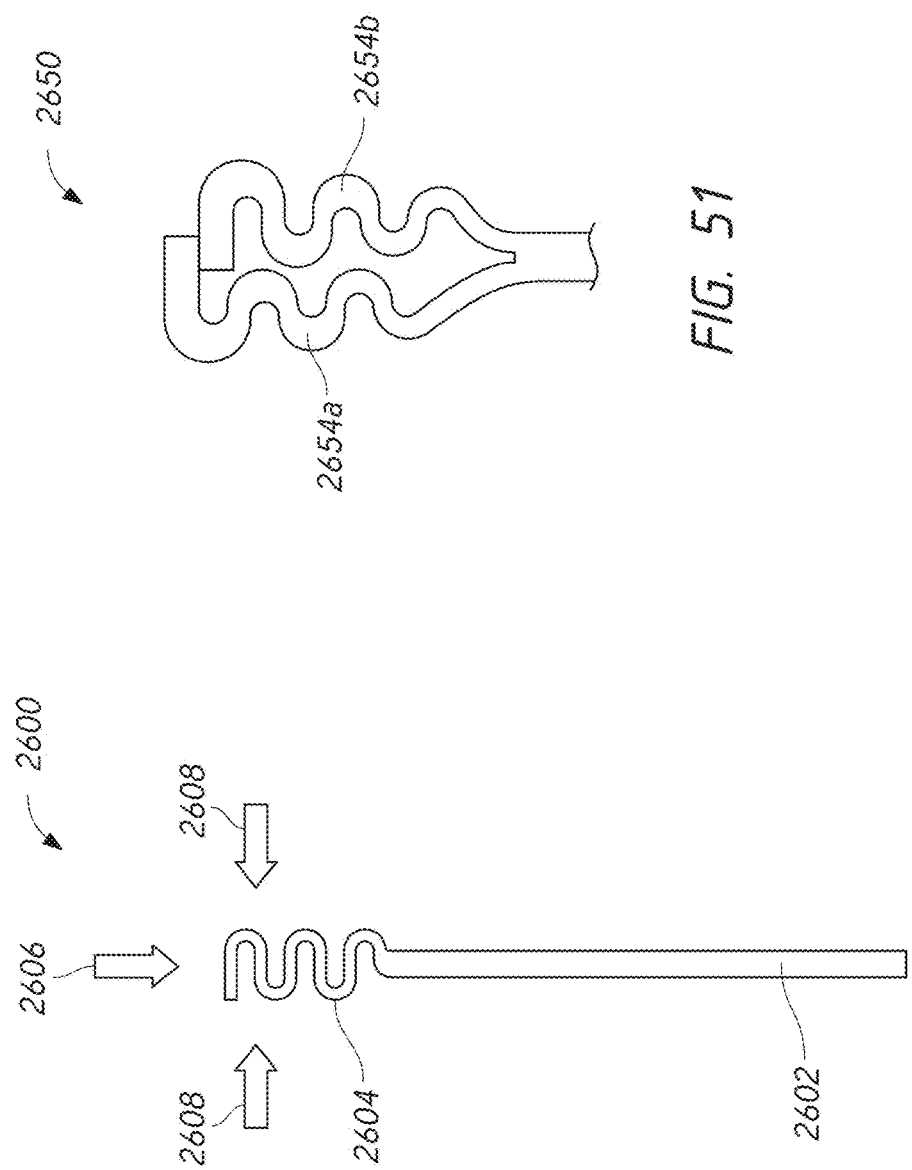

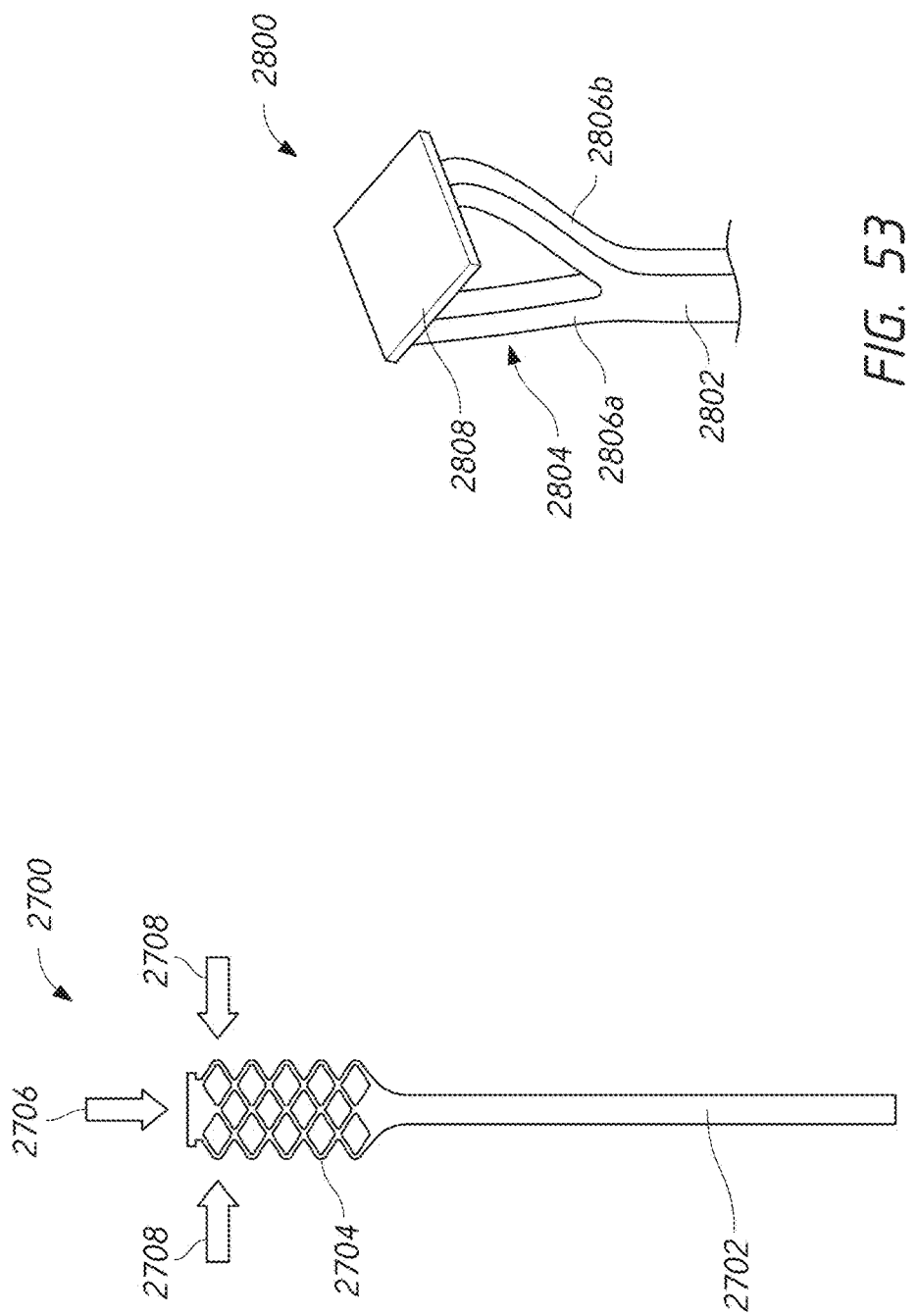

MULTI-PORTION REPLACEMENT HEART VALVE PROSTHESIS

CROSS-REFERENCE TO RELATED APPLICATIONS

This application claims priority to U.S. Provisional App. No. 62/380,061 filed Aug. 26, 2016, titled MULTI-PORTION REPLACEMENT HEART VALVE PROSTHESIS, the entirety of which is hereby incorporated herein by reference in its entirety and is to be considered a part of this specification.

BACKGROUND

Field

Certain embodiments disclosed herein relate generally to prostheses for implantation within a lumen or body cavity. In particular, certain embodiments relate to expandable prostheses such as replacement heart valves, such as for the mitral valve, that are configured to be secured to intralumenal tissue and prevent paravalvular leakage.

Background

Human heart valves, which include the aortic, pulmonary, mitral and tricuspid valves, function essentially as one-way valves operating in synchronization with the pumping heart. The valves allow blood to flow downstream, but block blood from flowing upstream. Diseased heart valves exhibit impairments such as narrowing of the valve or regurgitation, which inhibit the valves' ability to control blood flow. Such impairments reduce the heart's blood-pumping efficiency and can be a debilitating and life threatening condition. For example, valve insufficiency can lead to conditions such as heart hypertrophy and dilation of the ventricle. Thus, extensive efforts have been made to develop methods and apparatuses to repair or replace impaired heart valves.

Prostheses exist to correct problems associated with impaired heart valves. For example, mechanical and tissue-based heart valve prostheses can be used to replace impaired native heart valves. More recently, substantial effort has been dedicated to developing replacement heart valves, particularly tissue-based replacement heart valves that can be delivered with less trauma to the patient than through open heart surgery. Replacement valves are being designed to be delivered through minimally invasive procedures and even percutaneous procedures. Such replacement valves often include a tissue-based valve body that is connected to an expandable frame that is then delivered to the native valve's annulus.

These replacement valves are often intended to at least partially block blood flow. However, a problem occurs when blood flows around the valve on the outside of the prosthesis. For example, in the context of replacement heart valves, paravalvular leakage has proven particularly challenging. An additional challenge relates to the ability of such prostheses to be secured relative to intralumenal tissue, e.g., tissue within any body lumen or cavity, in an atraumatic manner. Yet another challenge arises when trying to reduce the likelihood of thrombosis within parts of the replacement valves.

SUMMARY

Embodiments of the present disclosure are directed to a prosthesis, such as but not limited to a replacement heart valve.

In some embodiments, a replacement heart valve prosthesis can include an expandable frame. The expandable frame can radially expand and contract for deployment within a native heart valve. The expandable frame can have a longitudinal axis between upper and lower ends. The expandable frame can include a first frame portion. The first frame portion can include a first frame body. The first frame body can include a first upper region, a first intermediate region, and/or a first lower region. The first frame portion can include a first anchoring feature. When the prosthesis is in an expanded configuration, the first anchoring feature can extend radially outwardly from the first lower region and/or at least a portion of the first anchoring feature can extend towards the first upper region.

The expandable frame can include a second frame portion positioned radially outward of the first frame body. The second frame portion can include a second frame body. The second frame body can include a second upper region, a second intermediate region, and/or a second lower region. When the prosthesis is in an expanded configuration, at least a portion of the second upper region can extend radially outwardly from the first upper region and/or the second lower region can be positioned radially between the first anchoring feature and the first frame body. When the prosthesis is in an expanded configuration and deployed within the native heart valve, the second intermediate portion can be positioned within a native valve annulus.

The replacement heart valve prosthesis can include a valve body positioned within an interior of the first frame portion. The valve body can include a plurality of leaflets which can allow flow in a first direction and prevent flow in a second opposite direction.

When the prosthesis is in an expanded configuration, the second intermediate region can be generally cylindrical. When the prosthesis is in an expanded configuration, the second intermediate region can be generally non-cylindrical. When the prosthesis is in an expanded configuration, a portion of the second intermediate region between the upper and lower ends of the second intermediate region can have a diameter greater than at least one of the upper and lower ends of the second intermediate region. The second intermediate region can be sized such that, when the prosthesis is deployed and expanded within the native heart valve, the second intermediate region can exert a radially outward force on the native valve annulus. When the prosthesis is in an expanded configuration, the second lower region can be inclined and/or curved radially inward towards the longitudinal axis. When the prosthesis is in an expanded configuration, at least a portion of the second upper region can extend towards the first lower region. When the prosthesis is in an expanded configuration, at least a portion of the second upper region can extend towards the first lower region in a direction generally parallel to the longitudinal axis. The second frame portion and the first anchoring feature can be sized such that, when the prosthesis is deployed and expanded within the native heart valve, native valve leaflets and/or the native valve annulus can be pinched between the second frame portion and the first anchoring feature.

When the prosthesis is in an expanded configuration, at least a portion of the first anchoring feature can extend upwards towards the first upper region. The first anchoring feature can include a first plurality of anchors. When the prosthesis is in an expanded configuration, tips of anchors of the first plurality of anchors can extend in a direction generally parallel to the longitudinal axis. When the prosthesis is in an expanded configuration, tips of anchors of the first plurality of anchors can extend in a direction generally perpendicular to the longitudinal axis. When the prosthesis is in an expanded configuration, at least a portion of tips of anchors of the first plurality of anchors can extend radially inwardly towards the longitudinal axis. When the prosthesis is in an expanded configuration, at least a portion of tips of anchors of the first plurality of anchors extend radially outwardly away from the longitudinal axis. When the prosthesis is deployed and expanded within a native mitral valve, at least some of the anchors of the first plurality of anchors can contact a native mitral valve annulus on a ventricular side. When the prosthesis is in an expanded configuration, at least a portion of anchors of the first plurality of anchors is angled in a circumferential direction and/or curved in a circumferential direction.

The second frame portion can include a second anchoring feature. At least a portion of the second anchoring feature can extend from at least one of the second upper region and the second intermediate region. The second anchoring feature can include a second plurality of anchors. Anchors of the second plurality of anchors can be V-shaped. When the prosthesis is in an expanded configuration, anchors of the second plurality of anchors can extend in a direction generally parallel to the second upper region. When the prosthesis transitions from an expanded configuration to a collapsed configuration, ends of the anchors of the second plurality of anchors can move radially outwardly and upwardly. When the prosthesis transitions from an expanded configuration to a collapsed configuration, ends of the anchors of the second plurality of anchors can move radially outwardly and downwardly.

The prosthesis can include a skirt extending around at least a portion of the prosthesis. At least a portion of the skirt can extend along an exterior of the second frame portion. At least a portion of the skirt can extend along an interior of the second frame portion. At least a portion of the skirt can extend along an interior of the second frame portion is attached to the valve body. At least a portion of the skirt can extend along an exterior of the second intermediate region. At least a portion of the skirt can extend along an exterior of the second upper region. At least a portion of the skirt can extend along an interior of the second upper region. At least a portion of the skirt is spaced apart from the second upper region.

The valve body can include a liner. The liner can extend from an arcuate edge of the plurality of leaflets towards an upper end of the first frame body. An upper end of the liner can be positioned at or proximate an upper end of the first frame body. An upper end of the liner can be positioned at or proximate an uppermost end of an arcuate edge of the plurality of leaflets.

The valve body can include one or more intermediate components. The one or more intermediate components can be positioned between the first frame body and the valve leaflets.

The first frame portion and the second frame portion can be separate components. The first frame portion can include a plurality of first eyelets. The second frame portion can include a plurality of second eyelets. Each of the plurality of first eyelets can correspond with each of the plurality of second eyelets. The first frame portion and the second frame portion can be coupled at each of the plurality of first and second eyelets. The first and second frame portions can be tautly secured at one or more attachment points such that relative movement at the one or more attachment points is inhibited. The first and second frame portions can be loosely secured at one or more attachment points such that the first and second frame portions are movable relative to each other at the one or more attachment points. The first and second frame portions can be coupled via the skirt.

The inner frame portion and the outer frame portion form a monolithic component.

The first frame body can include one or more rows of cells. At least one row of cells can include an upper and lower portion formed from a plurality of undulating struts and a middle portion formed from one or more eyelets. The first frame body can include a foreshortening portion. The second frame body can include one or more rows of cells. The second frame body can include a foreshortening portion. One or more portions of the first frame body can form a cylindrical shape, a bulbous shape, and/or a frustoconical shape.

In some embodiments, a replacement heart valve prosthesis can include an expandable frame. The expandable frame can radially expand and contract for deployment within a native heart valve. The expandable frame can have a longitudinal axis between upper and lower ends. The expandable frame can include a frame body. The frame body can include an upper region, an intermediate region, and/or a lower region.

The expandable frame can include an upper anchoring feature, an intermediate anchoring feature, and/or a lower anchoring feature. The upper anchoring feature can extend from the upper region of the frame body. The intermediate anchoring feature can extend from the intermediate region of the frame body. The lower anchoring feature can extend from the lower region of the frame body. When the frame is in an expanded configuration, at least a portion of the upper anchoring feature can be positioned radially outward of the frame body, at least a portion of the intermediate anchoring feature can be positioned radially outward of the frame body, and/or at least a portion of the lower anchoring feature can be positioned radially outward of the frame body.

The replacement heart valve prosthesis can include a valve body positioned within an interior of the first frame portion. The valve body can include a plurality of leaflets which can allow flow in a first direction and prevent flow in a second opposite direction.

The intermediate anchoring feature can be sized such that, when the prosthesis is deployed and expanded within the native heart valve, the second anchoring feature exerts a radially outward force on a native valve annulus. When the prosthesis is in an expanded configuration, at least a portion of the intermediate anchoring feature can be positioned radially between the frame body and the lower anchoring feature. The intermediate anchoring feature and the lower anchoring feature can be sized such that, when the prosthesis is deployed and expanded within the native heart valve, native valve leaflets and/or a native valve annulus can be pinched between the intermediate anchoring feature and the lower anchoring feature. The intermediate anchoring feature can include a braided mesh.

The frame body and the intermediate anchoring feature can be separate components. The frame body and the intermediate anchoring feature can form a monolithic component.

When the prosthesis is in an expanded configuration, at least a portion of the upper anchoring feature can extend radially outward away from the longitudinal axis. When the prosthesis is in an expanded configuration, at least a portion of the upper anchoring feature can extend radially inward towards the longitudinal axis. The upper anchoring feature can include an upper plurality of anchors.

When the prosthesis is in an expanded configuration, at least a portion of the lower anchoring feature can extend radially outward away from the longitudinal axis. When the prosthesis is in an expanded configuration, at least a portion of the lower anchoring feature can extend upwardly towards the upper anchoring feature. The lower anchoring feature can be attached to the frame body above a lower end of the lower region. The lower anchoring feature can include a lower plurality of anchors. When the prosthesis is in an expanded configuration, tips of anchors of the lower plurality of anchors extend in a direction generally parallel to the longitudinal axis. When the prosthesis is in an expanded configuration, tips of anchors of the lower plurality of anchors can extend in a direction generally perpendicular to the longitudinal axis. When the prosthesis is in an expanded configuration, at least a portion of tips of anchors of the lower plurality of anchors can extend radially inwardly towards the longitudinal axis. When the prosthesis is in an expanded configuration, at least a portion of tips of anchors of the lower plurality of anchors can extend radially outwardly away from the longitudinal axis. Anchors of the lower plurality of anchors can be sized such that, when the prosthesis is deployed and expanded within a native mitral valve, at least some of the anchors of the lower plurality of anchors can contact a native mitral valve annulus on a ventricular side. At least a portion of anchors of the lower plurality of anchors can be angled in a circumferential direction and/or curved in a circumferential direction.

The replacement heart valve prosthesis can include a skirt extending around at least a portion of the prosthesis. At least a portion of the skirt can extend radially outward of an exterior of the upper anchoring feature. At least a portion of the skirt can extend radially inward of an interior of the upper anchoring feature. At least a portion of the skirt can extend radially outward of an exterior of the intermediate anchoring feature. At least a portion of the skirt can extend between the intermediate anchoring feature and the lower anchoring feature. At least a portion of the skirt can be coupled to the upper region of the frame. At least a portion of the skirt can be coupled to the frame below the intermediate anchoring feature and above the lower anchoring feature. At least a portion of the skirt can be coupled to the valve body. At least a portion of the skirt can be coupled to a liner of the valve body.

The frame body can include one or more rows of cells. The first frame body can include a foreshortening portion.

In some embodiments, a replacement heart valve prosthesis can include an expandable frame. The expandable frame can radially expand and contract for deployment within a native heart valve. The expandable frame can have a longitudinal axis between upper and lower ends. The expandable frame can include a frame body. The frame body can include an upper region, an intermediate region, and/or a lower region. The expandable frame can include an anchoring feature. The anchoring feature can extend from the upper region of the frame body. The upper anchoring feature can include an anchor body formed from a wire mesh. When the prosthesis is in an expanded configuration, at least a portion of the anchor body can extend radially outwardly of the frame body.

The anchor body can be formed from a braided tube. The anchor body can conform to the shape of the native heart valve. When the prosthesis is deployed and expanded within a native mitral valve, at least a portion of the anchor body can be positioned intra-annularly and can exert a radially outward force on a native mitral valve annulus. When the prosthesis is deployed and expanded within a native mitral valve, at least a portion of the anchor body can be positioned in a left atrium and can extend over an atrial surface of a native valve annulus. When the prosthesis is deployed and expanded within a native mitral valve, at least a portion of the anchor body can be positioned in a left ventricle and can exert a radial outward force on native leaflets. The anchoring feature can include one or more barbs.

The anchoring feature can include one or more arms extending from the upper region of the frame body and/or the anchor body. The one or more arms can be formed from a wire mesh. When the prosthesis is in an expanded configuration, the one or more arms can extend radially outwardly from the frame body. When the prosthesis is in an expanded configuration, the one or more arms can extend upwardly away from the frame body. When the prosthesis is deployed and expanded within a native mitral valve, the one or more arms can contact portions of an atrial wall.

In some embodiments, a replacement heart valve prosthesis can include an expandable frame. The expandable frame can radially expand and contract for deployment within a native heart valve. The expandable frame can have a longitudinal axis between upper and lower ends. The expandable frame can include a first frame portion. The first frame portion can include a first frame body. The first frame body can include a first upper region, a first intermediate region, and/or a first lower region. The first frame portion can include a first anchoring feature. When the prosthesis is in an expanded configuration, the first anchoring feature can be attached to the first frame body at a base along the first distal region and/or at least a portion of the first anchoring feature can extend towards the first upper region.

The expandable frame can include a second frame portion positioned radially outward of the first frame body. The second frame portion can include a second frame body. The second frame body can include a second upper region, a second intermediate region, and/or a second lower region. When the prosthesis is in an expanded configuration, at least a portion of the second lower region is positioned below the base, at least a portion of the second lower region is positioned radially between the first anchoring feature, and/or the second lower region extends radially outwardly from the first lower region. When the prosthesis is in an expanded configuration and deployed within the native heart valve, the second intermediate portion can be positioned within a native valve annulus.

The replacement heart valve prosthesis can include a valve body positioned within an interior of the first frame portion. The valve body can include a plurality of leaflets which can allow flow in a first direction and prevent flow in a second opposite direction.

When the prosthesis is in an expanded configuration, the second intermediate region can be generally cylindrical. When the prosthesis is in an expanded configuration, the second intermediate region is generally non-cylindrical. The second intermediate region can be sized such that, when the prosthesis is deployed and expanded within the native heart valve, the second intermediate region exerts a radially outward force on the native valve annulus. The second frame portion and the first anchoring feature can be sized such that, when the prosthesis is deployed and expanded within the native heart valve, at least one of native valve leaflets and the native valve annulus are pinched between the second frame portion and the first anchoring feature.

The first anchoring feature can include a first plurality of anchors. When the prosthesis is in an expanded configuration, tips of anchors of the first plurality of anchors can extend in a direction generally parallel to the longitudinal axis. The first plurality of anchors can be sized such that, when the prosthesis is deployed and expanded within a native mitral valve, at least some of the anchors of the first plurality of anchors contact a native mitral valve annulus on a ventricular side.

The second frame portion can include a second anchoring feature. The second anchoring feature can include a second plurality of anchors. Anchors of the second plurality of anchors can be V-shaped. When the prosthesis transitions from an expanded configuration to a collapsed configuration, anchors of the second plurality of anchors can extend radially outwardly and upwardly. When the prosthesis transitions from an expanded configuration to a collapsed configuration, anchors of the second plurality of anchors can extend radially outwardly and downwardly.

The replacement heart valve can include a skirt extending around at least a portion of the prosthesis. At least a portion of the skirt can extend along an exterior of the second frame portion. At least a portion of the skirt can extend along an interior of the second frame portion.

The valve body can include one or more intermediate components. The one or more intermediate components can be positioned between the first frame body and the valve leaflets.

The first frame portion and the second frame portion can be separate components. The first frame portion can include a plurality of first eyelets. The second frame portion can include a plurality of second eyelets. Each of the plurality of first eyelets can correspond with each of the plurality of second eyelets. The first frame portion and the second frame portion can be coupled at each of the plurality of first and second eyelets.

The first frame portion and the second frame portion can form a monolithic component.

The first frame body can include one or more rows of cells. One or more portions of the first frame body can form a cylindrical shape, a bulbous shape, and/or a frustoconical shape.

In some embodiments, a replacement heart valve prosthesis can include a valve body including three flexible leaflets. The flexible leaflets can be made from pericardium. The prosthesis can include a self-expanding, metallic support structure surrounding and supporting the valve body. The support structure can be sized for deployment in a native mitral valve.

The support structure can include a valve frame having an upper portion, an intermediate portion, and a lower portion. The support structure can include a plurality of anchors which can be coupled to the lower portion of the valve frame. Each of the anchors can extend radially outwardly and/or upwardly.

The support structure can include a sealing frame. The sealing frame can be coupled to and disposed radially outwardly of the valve frame. The sealing frame can have an upper portion, an intermediate portion and a lower portion. A clearance can be provided between the sealing frame and the valve frame. The plurality of anchors can have ends disposed radially outwardly of the sealing frame.

The upper portion of the sealing frame can be coupled to the upper portion of the valve frame. The upper portion of the sealing frame can be sutured to the upper portion of the valve frame. The sealing frame can be more flexible than the valve frame for conforming to a mitral valve annulus. The support structure can be adapted to capture native mitral valve leaflets between the sealing frame and the anchors.

The intermediate portion of the sealing frame can have a diameter in the range of about 35 mm to 55 mm. At least a portion of the sealing frame can be covered by fabric. The lower portion of the sealing frame can have a larger diameter than the upper portion of the sealing frame. The intermediate portion of the sealing frame can have a larger diameter than the lower portion of the sealing frame.

The sealing frame can be convex. At least a portion of the sealing frame can be generally frustoconical. For example, the upper portion and/or lower portion of the sealing frame can be generally frustonical. At least a portion of the sealing frame can be generally cylindrical. For example, at least the intermediate portion of the sealing frame can be generally cylindrical.

The valve frame can be bulbous. The intermediate portion of the valve frame can have a diameter which is less than the diameter of the intermediate portion of the sealing frame. The diameter of the intermediate portion of the valve frame can be in the range of about 28 mm to about 32 mm.

The anchoring features can be axially and/or radially biased or compressible. Tips of the anchoring features can be formed from one or more wires. The wires can be looped to form a generally three-dimensional teardrop shape. The wires may be spiraled to form a generally three-dimensional conical shape. Tips of the anchoring features can have a serpentine shape. Tips of the anchoring features can be formed from one or more foreshortening cells.

BRIEF DESCRIPTION OF THE DRAWINGS

These and other features, aspects and advantages are described below with reference to the drawings, which are intended to illustrate embodiments of prostheses including embodiments of various components of these prostheses.

FIG. 10 is a top view of the inner frame of FIG. 2.

FIG. 26 is a flat, cutting pattern for another embodiment of a frame having a circumferentially curved anchoring feature.

FIG. 27 is a side view of a portion of the frame of FIG. 26 in an expanded configuration.

FIG. 48 is a side-oriented schematic view of an embodiment of an anchoring feature.

FIG. 49 is a side-oriented schematic view of another embodiment of an anchoring feature.

FIG. 50 is a side-oriented schematic view of an embodiment of an anchoring feature.

FIG. 51 is a side-oriented schematic view of another embodiment of an anchoring feature.

FIG. 52 is a side-oriented schematic view of an embodiment of an anchoring feature.

FIG. 53 is a side-oriented schematic view of another embodiment of an anchoring feature.

DETAILED DESCRIPTION

Figure 1:
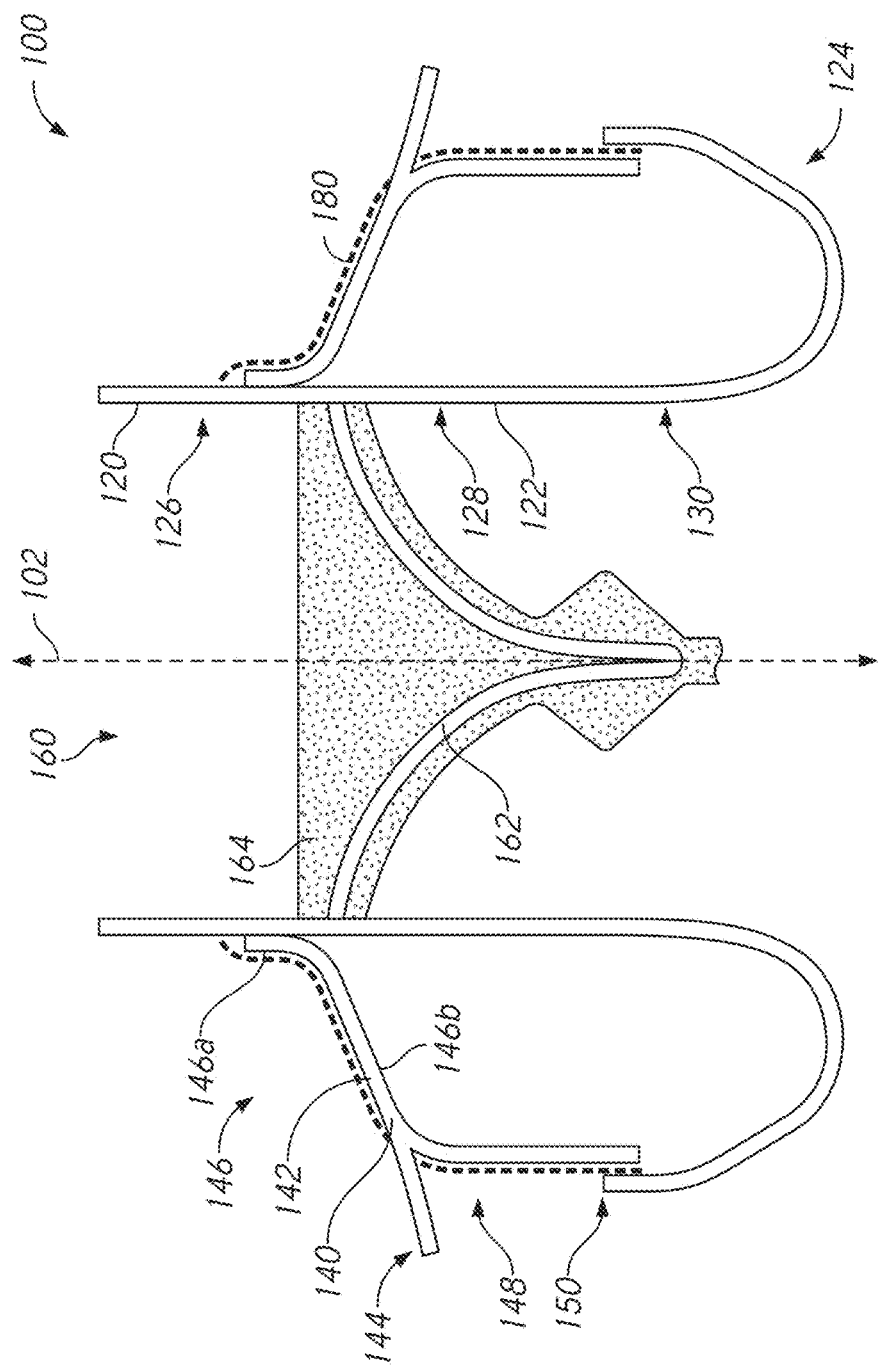
FIG. 1 is a side-oriented cross-sectional schematic view of an embodiment of a prosthesis having an inner frame, an outer frame, a valve body, and a skirt.
Figure 2:
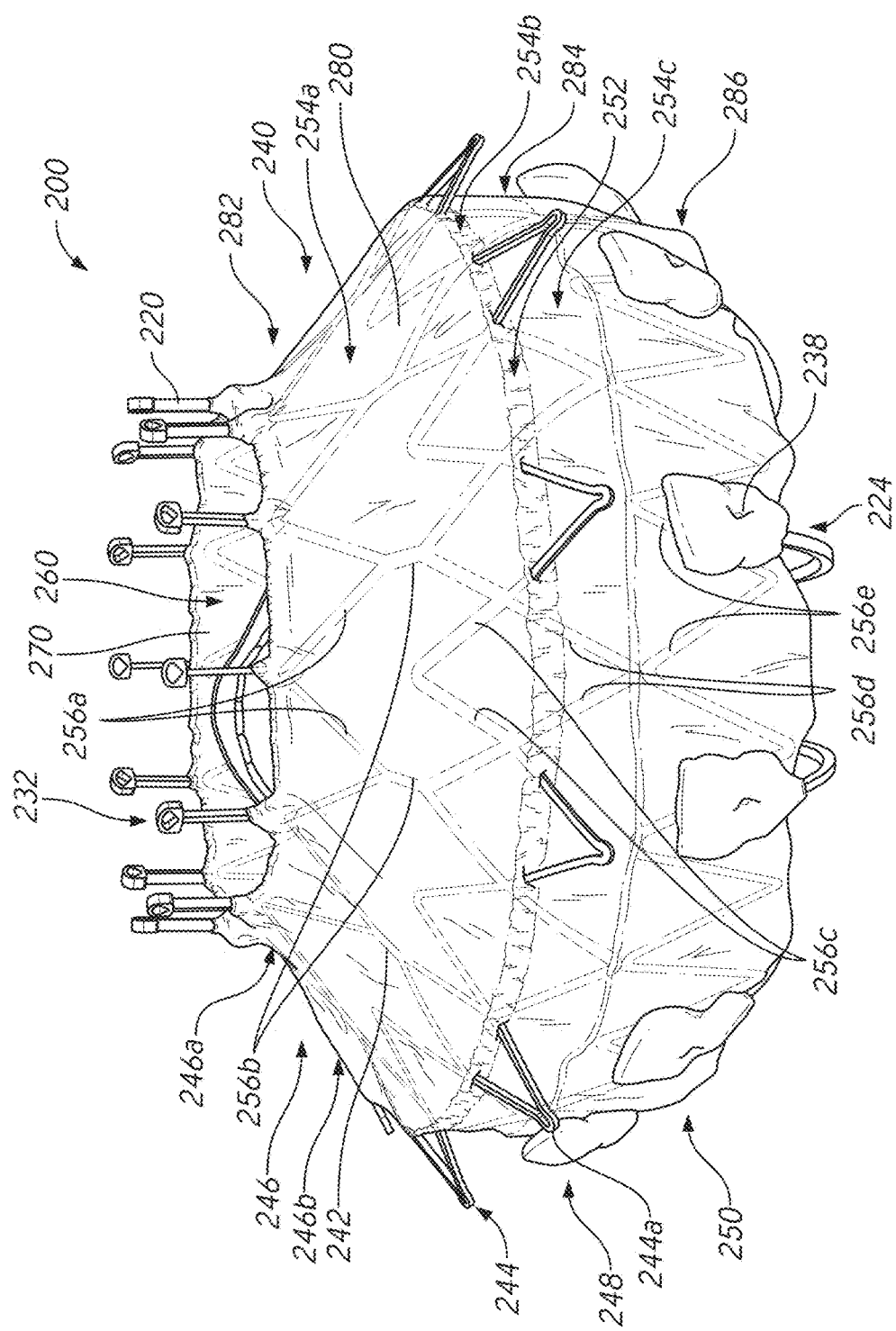
FIG. 2 is a top-oriented perspective view of another embodiment of a prosthesis having an inner frame, an outer frame, a valve body, and a skirt.
Figure 3:
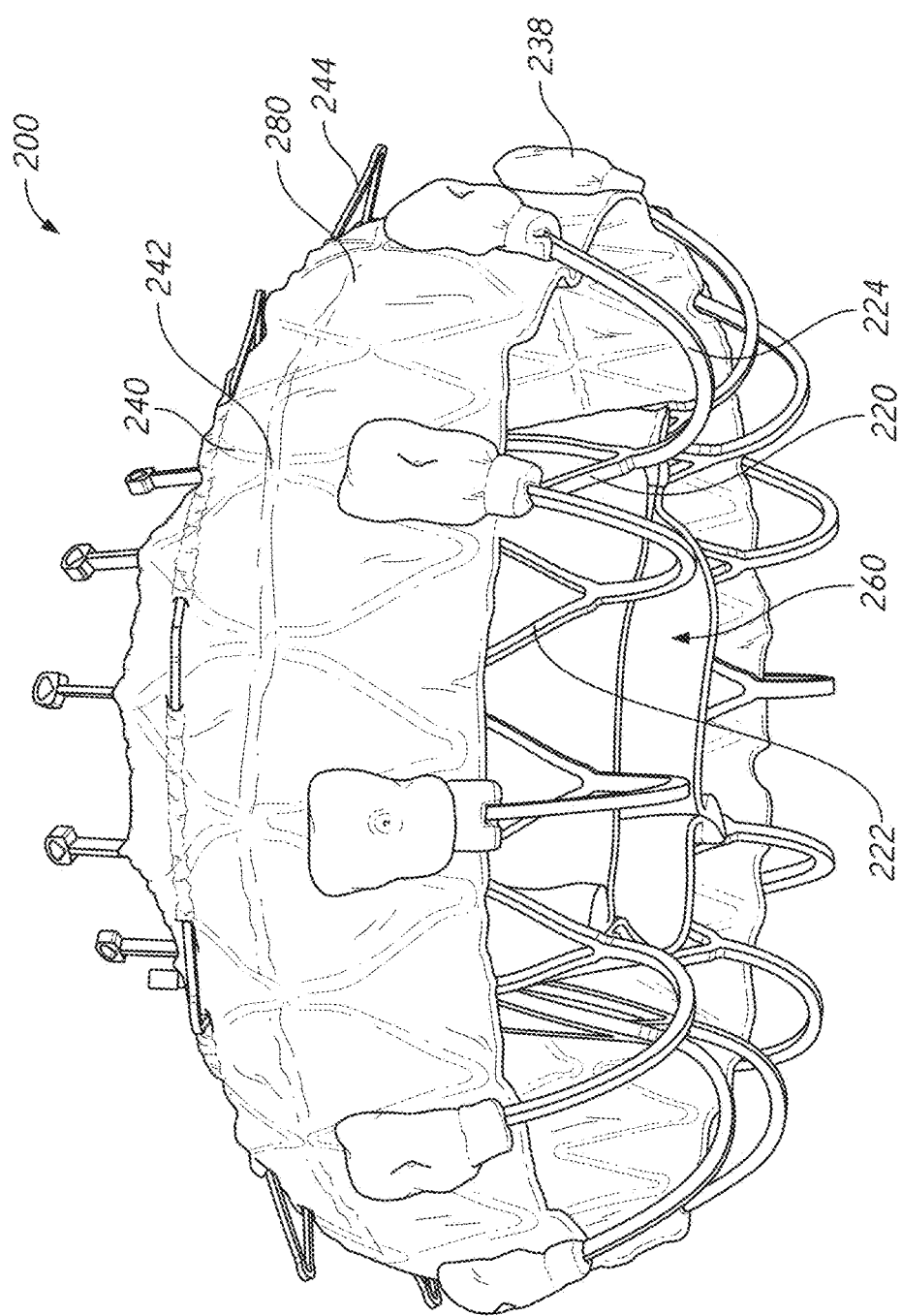
FIG. 3 is a bottom-oriented perspective view of the prosthesis of FIG. 2.
Figure 4:
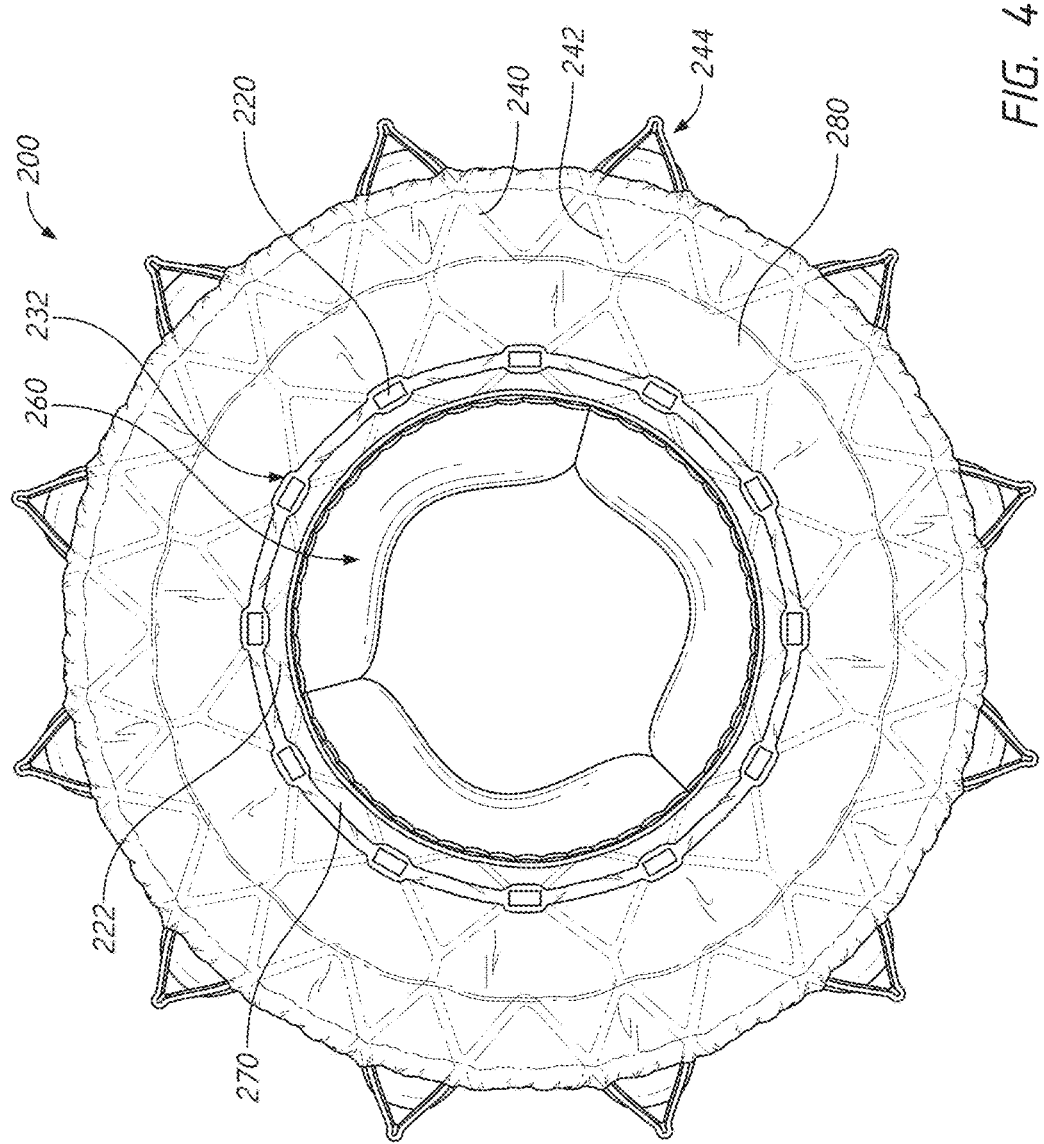
FIG. 4 is a top view of the prosthesis of FIG. 2

The present specification and drawings provide aspects and features of the disclosure in the context of several embodiments of prostheses, replacement heart valves, and methods that are configured for use in the vasculature of a patient, such as for replacement of natural heart valves in a patient. These embodiments may be discussed in connection with replacing specific valves such as the patient's mitral valve. However, it is to be understood that the features and concepts discussed herein can be applied to replacing other types of valves including, but not limited to, the aortic valve, the pulmonary valve, and the tricuspid valve. Moreover, it is to be understood that the features and concepts discussed herein can be applied to products other than heart valve implants. For example, the controlled positioning, deployment, and/or securing features described herein can be applied to medical implants, for example other types of expandable prostheses, for use elsewhere in the body, such as within a vein, or the like. In addition, particular features of a prosthesis should not be taken as limiting, and features of any one embodiment discussed herein can be combined with features of other embodiments as desired and when appropriate.

Certain terminology may be used in the following description for the purpose of reference only, and thus are not intended to be limiting. For example, terms such as "upper", "lower", "upward", "downward", "above", "below", "top", "bottom" and similar terms refer to directions in the drawings to which reference is made. Terms such as "proximal", "distal", "radially outward", "radially inward", "outer", "inner", and "side", describe the orientation and/or location of portions of the components or elements within a consistent but arbitrary frame of reference which is made clear by reference to the text and the associated drawings describing the components or elements under discussion. Such terminology may include the words specifically mentioned above, derivatives thereof, and words of similar import. Similarly, the terms "first", "second", and other such numerical terms referring to structures neither imply a sequence or order unless clearly indicated by the context.

In some embodiments, the term "proximal" may refer to the parts of the prostheses, or components thereof, which are located closer to the operator of the device and system (e.g., the clinician implanting the prosthesis). The term "distal" may refer to the parts of the prostheses, or components thereof, which are located further from the operator of the device and system (e.g., the clinician implanting the prosthesis). However, it is to be understood that this terminology may be reversed depending on the delivery technique utilized (e.g., a transapical approach as compared to a transseptal approach). In some situations, the prosthesis, or components thereof, may be oriented such that an upper end is a proximal portion and a lower end is a distal portion.

In some situations, the prosthesis, or components thereof, the upper end may be an inflow end and the lower end may be an outflow end. For example, a valve body used with the prosthesis can allow flow from the upper end to the lower end. However, it is to be understood that the inflow end and the outflow end may be reversed. For example, the valve body used with the prosthesis can allow flow from the lower end to the upper end.

A longitudinal axis of the prosthesis, or components thereof, may be defined as the central axis that extends through the center of the prosthesis or component between the upper and lower ends of the prosthesis or component (e.g., the prosthesis, the outer frame, and/or the inner frame). The prostheses described herein may be replacement valves that can be designed to replace a damaged or diseased native heart valve such as a mitral valve, as discussed above. It should be understood that the prostheses are not limited to being a replacement valve.

As will be described in further detail below, the prostheses can include an inner frame and/or an outer frame. In some embodiments, the inner frame can be a valve frame designed to support a valve body. In some embodiments, the outer frame can be a sealing frame designed to form a seal about a periphery of the outer frame. For example, the outer frame can engage tissue of a body cavity about a periphery of the outer frame and form a seal with said tissue. In some embodiments described herein, the outer frame can be attached to the inner frame at one or more stationary couplings such that the outer frame is fixed to the inner frame at one or more locations. It is to be understood that the outer frame can be attached to the inner frame via one or more movable couplings such as, but not limited to, rails. This can beneficially allow the outer frame to be adjusted relative to the inner frame to better conform to the anatomy of a patient's body cavity.

The inner frame and/or outer frame may be described as having an upper region, an intermediate region, and a lower region. In some situations, such as those in which the prostheses are positioned within a native mitral valve, the upper region can be generally positioned supra-annularly (i.e., above the plane of the annulus), the intermediate region can be generally positioned intra-annularly (i.e., within the plane of the annulus), and the lower region can be positioned sub-annularly (i.e., below the plane of the annulus). However, it is to be understood that in some situations, the positioning of the inner frame and/or outer frame relative to the annulus can differ. Moreover, it is to be understood that in some embodiments, the inner frame and/or outer frame can omit one or more of the upper region, the intermediate region, and/or the lower region.

While certain combinations of inner frames and outer frames are described herein, it is to be understood that the inner frames and outer frames can be interchanged. This can beneficially allow the prosthesis to be configured in a manner which better suits the native anatomy of the patient. Moreover, while the inner frames and outer frames can be attached prior to delivery into the patient, it is to be understood that the inner frames and outer frames can be delivered separately into the patient and subsequently attached in the patient's body. This can beneficially reduce the crimp profile when delivering the frames to the body cavity. The prostheses described herein can be used as a standalone device. For example, the prosthesis can be deployed at a native mitral valve and be sized and shaped appropriately to replace the function of the native mitral valve. However, it is to be understood that the prostheses described herein can be used with other devices. For example, one or more clips can be used to hold together native leaflets of a heart valve. This can advantageously allow a smaller prosthesis to be utilized at the native mitral valve.

Embodiments of Replacement Valves and Frames

With reference to FIG. 1, an embodiment of a prosthesis 100 in an expanded configuration is illustrated. The prosthesis 100 can include an inner frame 120, an outer frame 140, a valve body 160, and a skirt 180. A longitudinal axis 102 of the prosthesis 100 may be defined as the central axis that extends through the center of the prosthesis 100 between the upper and lower ends of the prosthesis 100. In some situations, the prosthesis 100 may be oriented such that an upper end of the prosthesis 100 is a proximal portion and a lower end of the prosthesis 100 is a distal portion. The illustrated prosthesis 100, as well as other prostheses described herein, may include components which are self-expanding or balloon expandable. For example, in some embodiments, the inner frame 120 and/or outer frame 140 can be self-expanding. The prosthesis 100, as well as other prostheses described herein, may be a replacement valve that can be designed to replace a damaged or diseased native heart valve such as a mitral valve, as discussed above. It should be understood that the prosthesis 100, as well as other prostheses described herein, are not limited to being a replacement valve.

With reference first to the inner frame 120 illustrated in FIG. 1, the inner frame 120 can provide a structure to which various components of the prosthesis 100 can be attached. The inner frame 120 can include an inner frame body 122 and an inner frame anchoring feature 124. The inner frame body 122 can have an upper region 126, an intermediate region 128, and a lower region 130. As shown, the inner frame body 122 can have a generally cylindrical shape such that the diameters of the upper region 126, the intermediate region 128, and the lower region 130 are generally equivalent. However, it is to be understood that the diameters of the upper region 126, the intermediate region 128, and/or the lower region 130 can be different. For example, in some embodiments, a diameter of the intermediate region 128 can be larger than the upper region 126 and the lower region 130 such that the frame body 122 has a generally bulbous shape. In some embodiments, the diameter of the lower region 130 can be larger than the diameter of the upper region 126. In other embodiments, the diameter of the upper region 126 can be larger than the diameter of the lower region 130. Moreover, although the inner frame body 122 has been described and illustrated as being cylindrical or having circular cross-sections, it is to be understood that all or a portion of the inner frame body 122 can have a non-circular cross-section such as, but not limited to, a D-shape, an oval or an otherwise ovoid cross-sectional shape.

In some situations, such as those in which the prosthesis 100 is positioned within a native mitral valve, the upper region 126 can be generally positioned supra-annularly (i.e., above the plane of the annulus), the intermediate region 128 can be generally positioned intra-annularly (i.e., within the plane of the annulus), and the lower region 130 can be positioned sub-annularly (i.e., below the plane of the annulus). However, it is to be understood that in some situations, the positioning of the inner frame 120 relative to the annulus can differ. Moreover, it is to be understood that in some embodiments, the inner frame 120 can omit one or more of the upper region 126, the intermediate region 128, and/or the lower region 130.

As shown in the illustrated embodiment, the inner frame anchoring feature 124 can extend generally downwardly and/or radially outwardly at or proximate a lower end of the lower region 130 of the inner frame body 122. The inner frame anchoring feature 124 can extend upwardly towards an end of the inner frame anchoring feature 124. As will be discussed in further detail below, components of the inner frame 120, such as the inner frame anchoring feature 124, can be used to attach or secure the prosthesis 100 to a native valve. For example, in some situations, the inner frame anchoring feature 124 can be used to attach or secure the prosthesis 100 to a native mitral valve. In such an embodiment, the inner frame anchoring feature 124 can be positioned to contact or engage a native mitral valve annulus on a ventricular side, tissue beyond the native valve annulus on a ventricular side, native leaflets on a ventricular side, and/or other tissue at or around the implantation location during one or more phases of the cardiac cycle, such as systole and/or diastole. When positioned within the native mitral valve, the inner frame anchoring feature 124 can beneficially eliminate, inhibit, or limit upward movement of the prosthesis 100 when subject to upwardly directed forces such as those which are applied on the prosthesis 100 during systole.

The inner frame 120 can be formed from many different materials including, but not limited to a shape-memory metal such as Nitinol. The inner frame 120 can be formed from a plurality of struts forming open cells. In some embodiments, the inner frame 120 can have a relatively rigid construction as compared to other components of the prosthesis 100 including, but not limited to, the outer frame 140. This can be achieved, for example, by the dimensions of the struts and by the configuration of the struts. The relatively rigid construction can more strongly resist deformation when subject to stress. This can be beneficial during certain portions of the cardiac cycle, such as systole, during which the inner frame 120 may be subject to significant stresses on the inner frame anchoring feature 124. The relatively rigid construction can also be beneficial when a valve body 160 is positioned within the inner frame 120 to maintain the shape of the valve body 160. Moreover, the relatively rigid construction can be beneficial when the inner frame 120 is used for a valve-in-valve procedure wherein a supplemental prosthesis is positioned within the inner frame 120. However, although the inner frame 120 has been described as having a relatively rigid construction, it is to be understood that in some embodiments the inner frame 120 can have a construction relatively flexible construction. For example, the inner frame 120 can have a constructions which is about as flexible as, or more flexible than, other components of the prosthesis 100, such as the outer frame 140.

The inner frame 120 can share characteristics, such as structure and/or functionality, which are the same as, or at least similar to, those of other frames described herein such as, but not limited to, frames 220, 400, 520a-k, 620, 720, 820, 920, 1000, 1100, 1202, 1520, 1620, 1700, 1920, 2020, 2220, 2320, 2420, 2910, 3010, 3110, 3210 discussed below. The inner frame 120, and any other frame described herein, may include features and concepts similar to those disclosed in U.S. Pat. Nos. 8,403,983, 8,414,644, and 8,652,203, U.S. Publication Nos. 2011/0313515, 2014/0277390, 2014/0277427, 2014/0277422, and 2015/0328000, and U.S. application Ser. No. 15/653,390, entitled REPLACEMENT HEART VALVE PROSTHESIS, filed on Jul. 18, 2017, the entireties of each of which are hereby incorporated by reference and made a part of this specification. This is inclusive of the entire disclosure and is not in any way limited to the disclosure of the associated frames. Moreover, although the inner frame 120 has been described as including an inner frame body 122 and an inner frame anchoring feature 124, it is to be understood that the inner frame 120 need not include all components. For example, in some embodiments, the inner frame 120 can include the inner frame body 122 while omitting the inner frame anchoring feature 124. Moreover, although the inner frame body 122 and the inner frame anchoring feature 124 have been illustrated as being unitarily or monolithically formed, it is to be understood that in some embodiments the inner frame body 122 and the inner frame anchoring feature 124 can be formed separately. In such embodiments, the separate components can be attached using any of the fasteners and/or techniques described herein. For example, the inner frame anchoring feature 124 can be formed separately from the inner frame body 122 and can be attached to the inner frame body 122.

With reference next to the outer frame 140 illustrated in FIG. 1, the outer frame 140 can provide a structure to which various components of the prosthesis 100 can be attached. The outer frame 140 can be attached to the inner frame 120 using any of the fasteners and/or techniques described herein including, but not limited to, mechanical fasteners, such as sutures, staples, screws, rivets, interfacing members (e.g., tabs and slots which can be on the inner frame 120 and the outer frame 140), and any other type of mechanical fastener as desired, chemical fasteners such as adhesives and any other type of chemical fastener as desired, fastening techniques such as welding, soldering, sintering, and any other type of fastening technique as desired, and/or a combination of such fasteners and techniques. The inner frame 120 and the outer frame 140 can be indirectly attached via an intermediate component, such as the skirt 180.

The outer frame 140 can be attached to the inner frame 120 at one or more attachment points. As will be described in further detail, the outer frame 140 can be tautly attached to the inner frame 120 such that little to no relative movement between the outer frame 140 and the inner frame 120 occurs at the one or more attachment points. In other embodiments, the outer frame 140 can be loosely attached to the inner frame 120 such that some relative movement between the outer frame 140 and the inner frame 120 can occur at the one or more attachment points. Although the outer frame 140 is illustrated as a separate component from the inner frame 120, it is to be understood that the frames 120, 140 can be unitarily or monolithically formed.

As shown in the illustrated embodiment, the outer frame 140 can include an outer frame body 142 and an outer frame anchoring feature 144. The outer frame body 142 can have an upper region 146, an intermediate region 148, and a lower region 150. In some situations, such as those in which the prosthesis 100 is positioned within a native mitral valve, the upper region 146 can be generally positioned supra-annularly, the intermediate region 148 can be generally positioned intra-annularly, and the lower region 150 can be positioned sub-annularly. However, it is to be understood that in some situations, the positioning of the outer frame 140 relative to the annulus can differ. Moreover, it is to be understood that in some embodiments, the outer frame 140 can omit one or more of the upper region 146, the intermediate region 148, and/or the lower region 150.

When in an expanded configuration such as a fully expanded configuration, the outer frame body 142 can have an enlarged shape with the intermediate region 148 and the lower region 150 being larger than the upper region 146. The enlarged shape of the outer frame body 142 can advantageously allow the outer frame body 142 to engage a native valve annulus, native valve leaflets, or other tissue of the body cavity, while spacing the upper end from the heart or vessel wall. This can help reduce undesired contact between the prosthesis 100 and the heart or vessel, such as the atrial and ventricular walls of the heart.

The upper region 146 of the outer frame body 122 can include a generally longitudinally-extending section 146a and an outwardly-extending section 146b. The longitudinally-extending section 146a can be generally concentric with the inner frame body 122. The outwardly-extending section 146b can extend radially outwardly away from the longitudinal axis 102 of the prosthesis 100. The outwardly-extending section 146b can extend in a direction that is more perpendicular to the longitudinal axis 102 than parallel and/or in a downward direction from the longitudinally-extending section 146a. However, it is to be understood that the outwardly-extending section 146b can extend generally perpendicularly to the longitudinal axis 102 and/or in an upward direction from the longitudinally-extending section 146a. Moreover, it is to be understood that the longitudinally-extending section 146a can be omitted such that the upper region 146 extends radially outwardly at the upper end of the upper region 146.

The intermediate region 148 of the outer frame body 142 can extend generally downwardly from the outwardly-extending section 146b of the upper region 146. As shown, the intermediate region 148 can have a generally constant diameter from an upper end of the intermediate region 148 to a lower end of the intermediate region 148 such that the intermediate region 148 forms a generally cylindrical shape. However, it is to be understood that the diameters of the upper end, the lower end, and/or the portion therebetween can be different. For example, a diameter of the portion between the upper end and the lower end can be larger than the upper end and the lower end such that the intermediate region 148 has a generally bulbous shape. In some embodiments, the diameter of the lower end can be larger than the diameter of the upper end. In other embodiments, the diameter of the upper end can be larger than the diameter of the lower end.

The lower region 150 of the outer frame body 142 can extend generally downwardly from the lower end of the intermediate region 148. As shown, the lower region 150 of the outer frame body 142 can have a generally constant diameter from an upper end of the lower region 150 to a lower end of the lower region 150 such that the lower region 150 forms a generally cylindrical shape. However, it is to be understood that the diameters of the upper end, the lower end, and/or the portion therebetween can be different. For example, in some embodiments, the diameter of the upper end of the lower region 150 can be greater than the diameter of the lower end of the lower region 150 such that the lower region 150 extends radially inwardly towards the longitudinal axis 102 of the prosthesis 100. In some embodiments, the diameter of the lower end can be larger than the diameter of the upper end.

As shown, the diameters of the intermediate region 148 and the lower region 150 are generally equivalent such that the intermediate region 148 and the lower region 150 together form a generally cylindrical shape. However, it is to be understood that the diameters of the intermediate region 148 and the lower region 150 can be different. For example, the diameter of the lower region 150 can be less than the diameter of the intermediate region 148. Moreover, although the outer frame body 142 has been described and illustrated as being cylindrical or having circular cross-sections, it is to be understood that all or a portion of the outer frame body 142 can be have a non-circular cross-section such as, but not limited to, a D-shape, an oval or an otherwise ovoid cross-sectional shape.

With continued reference to the outer frame 140 illustrated in FIG. 1, the outer frame anchoring feature 144 can extend outwardly relative to the longitudinal axis 102 of the prosthesis 100. The outer frame anchoring feature 144 can extend at or proximate the juncture between the upper region 146 and the intermediate region 148 of the outer frame body 142. The outer frame anchoring feature 144 can extend in a direction that is more perpendicular to the longitudinal axis 102 than parallel and/or can extend in a downward direction from the longitudinally-extending section 146a. As shown, the outer frame anchoring feature 144 can extend in a direction generally aligned with the outwardly-extending section 146b of the upper region 146. However, it is to be understood that the outer frame anchoring feature 144 can extend generally perpendicularly to the longitudinal axis 102 and/or in an upward direction.

Figure 45:
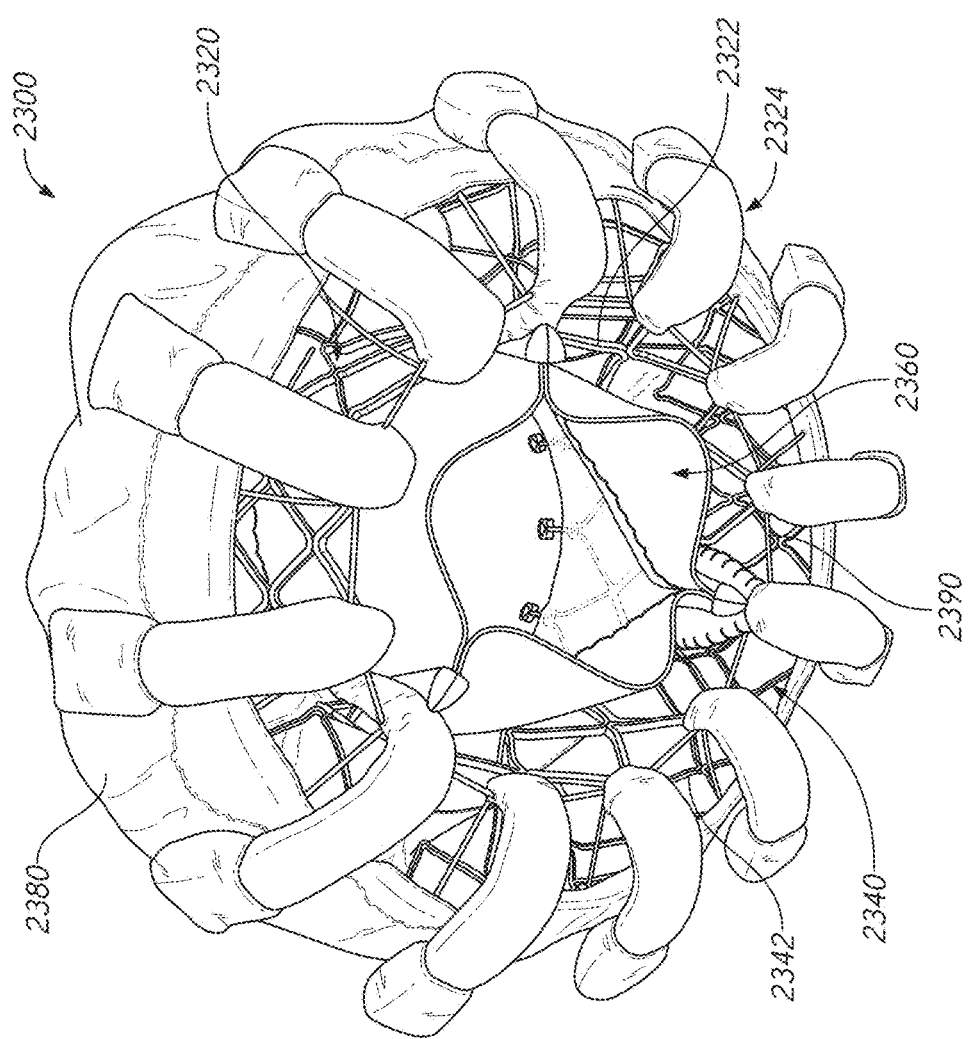
FIG. 45 is a bottom-oriented perspective view of another embodiment of a prosthesis having an inner frame, an outer frame, a valve body, and a skirt.

As will be discussed in further detail below, components of the outer frame 140, such as the outer frame body 142 can be used to attach or secure the prosthesis 100 to a native valve, such as a native mitral valve. For example, the intermediate region 148 of the outer frame body 142 and/or the outer anchoring feature 144 can be positioned to contact or engage a native valve annulus, tissue beyond the native valve annulus, native leaflets, and/or other tissue at or around the implantation location during one or more phases of the cardiac cycle, such as systole and/or diastole. In situations where the outer frame body 142 is positioned within a native mitral valve, the outer frame body 142 can beneficially eliminate, inhibit, or limit downwardly directed forces such as those which are applied on the prosthesis 100 during diastole and/or upwardly directed forces such as those which are applied on the prosthesis 100 during systole. As another example, the outer frame body 142 can be sized and positioned relative to the inner frame anchoring feature 124 such that tissue of the body cavity positioned between the outer frame body 142 and the inner frame anchoring feature 124, such as native valve leaflets and/or a native valve annulus, can be engaged or pinched to further secure the prosthesis 100 to the tissue. For example, the lower region 150 of the outer frame body 142 can be positioned at or proximate a tip or end of the inner frame anchoring feature 124. As shown, the lower region 150 of the outer frame body 142 is positioned such that at least a portion is positioned radially inward of and below the inner frame anchoring feature 124. In some embodiments, a portion of the outer frame 140, such as the lower region 150, can be attached to the inner frame body 122 via one or more tethers or sutures (as shown in FIG. 45) to limit the outward extension of the outer frame 140 relative to the inner frame body 122. This can beneficially maintain a portion of the outer frame 140 between the inner frame body 122 and the inner frame anchoring feature 124. Although the inner frame anchoring feature 124 is shown extending from the inner frame body 122, it is to be understood that such an anchoring feature can extend from the outer frame body 140.

Use of an inner frame 120 and an outer frame 140 can be beneficial for the design of the prosthesis in that the inner frame 120 can be designed to suit the structure of the valve body 160 and the outer frame 140 can be designed to suit the anatomy of the body cavity in which the prosthesis 100 is to be used. For example, the valve body 160 can be cylindrical and have a smaller diameter than the body cavity. In such an embodiment, the inner frame 120 can advantageously have a smaller shape and/or size to support the valve body 160 while the outer frame 140 can have a larger shape and/or size to secure the prosthesis 100 to the body cavity. Moreover, in embodiments in which the outer frame 140 is larger than the inner frame 120, the shape of the outer frame 140 can beneficially enhance hemodynamic performance. For example, the shape of the outer frame 140 with a larger, generally cylindrical intermediate region 148 can allow for significant washout on an underside of the valve body 160. This washout can beneficially reduce the risk of thrombosis or clot formation under and around the valve body 160.

The outer frame 140 can be formed from many different materials including, but not limited to, a shape-memory metal such as Nitinol. The outer frame 140 can be formed from a plurality of struts forming open cells. In some embodiments, the outer frame 140 can have a more flexible construction as compared to other components of the prosthesis 100 such as, but not limited to, the inner frame 120. This can be achieved, for example, by the dimensions of the struts and by the configuration of the struts. For example, fewer struts, thinner struts, and/or a different material for the struts can be used. The more flexible construction can allow the outer frame 140 to better conform to the anatomy of the body cavity, such a native valve annulus and/or native leaflets. This can be beneficial for anchoring against the body cavity and/or forming a seal against the body cavity. However, it is to be understood that in some embodiments the outer frame 140 can have a construction which is about as rigid as, or more rigid than, other components of the prosthesis 100, such as the inner frame 120.

The outer frame 140 can share characteristics, such as structure and/or functionality, which are the same as, or at least similar to, those of other frames described herein such as, but not limited to, frames 240, 300, 540a-k, 560h, 1204, 1540, 1640, 1800, 1940, 2040, 2100, 2240, 2340, 2440, 2920, 3020, 3120, 3220 discussed below. The outer frame 140, and any other frame described herein, may include features and concepts similar to those disclosed in U.S. Pat. Nos. 8,403,983, 8,414,644, and 8,652,203, U.S. Publication Nos. 2011/0313515, 2014/0277390, 2014/0277427, 2014/0277422, and 2015/0328000, and U.S. application Ser. No. 15/653,390, entitled REPLACEMENT HEART VALVE PROSTHESIS, filed on Jul. 18, 2017, the entireties of each of which have been incorporated by reference. Moreover, although the outer frame 140 has been described as including an outer frame body 142 and an outer frame anchoring feature 144, it is to be understood that the outer frame 140 need not include all components. For example, in some embodiments, the outer frame 140 can include the outer frame body 142 while omitting the outer frame anchoring feature 144. Moreover, although the outer frame body 142 and the outer frame anchoring feature 144 have been illustrated as being unitarily or monolithically formed, it is to be understood that in some embodiments the outer frame body 142 and the outer frame anchoring feature 144 can be formed separately. In such embodiments, the separate components can be attached using any of the fasteners and techniques described herein. For example, the outer frame anchoring feature 144 can be formed separately from the outer frame body 142 and can be attached to the outer frame body 142.

With reference next to the valve body 160 illustrated in FIG. 1, the valve body 160 can be attached to the inner frame 120 within an interior of the inner frame 120. The valve body 160 can function as a one-way valve to allow blood flow in a first direction through the valve body 160 and inhibit blood flow in a second direction through the valve body 160. For example, in situations where the upper end of the prosthesis 100 is a proximal end and the lower end of the prosthesis 100 is a distal end, the valve body 160 can allow blood flow in a proximal-to-distal direction and inhibit blood flow in a distal-to-proximal direction. The valve body 160 can include a plurality of valve leaflets 162, for example three leaflets 162, which are joined at commissures. The leaflets 162 can be formed from biocompatible materials including, but not limited to, pericardium and/or synthetic materials.

The valve body 160 can include a liner 164. The liner 164 can be used to assist with fluid flow through and/or around the prosthesis 100, such as through and around the inner frame 120 and the valve leaflets 162. The liner 164 can surround at least a portion of the valve leaflets 162 and be connected to one or more of the valve leaflets 162. For example, as shown in the illustrated embodiment, the one or more valve leaflets 162 can be attached to the liner 164 along an arcuate or fixed edge of the valve leaflets 162. The liner 164 can extend from the arcuate or fixed edge of the leaflet 162 and extend upwardly towards an upper end of the inner frame 120.

The valve body 160 can share characteristics, such as structure and/or functionality, which are the same as, or at least similar to, those of other valve bodies described herein such as, but not limited to, valve bodies 260, 660, 760, 870, 970, 1560, 1660, 1960, 2060, 2260, 2360, 2460, discussed below. Moreover, although the valve body 160 has been described as including a plurality of leaflets 162 and a liner 164, it is to be understood that the valve body 160 need not include all features. For example, in some embodiments, the valve body 160 can include the plurality of valve leaflets 162 while omitting the liner 164. It is to be understood that other types of valves can be utilized in conjunction with, or in lieu of, the valve body 160. For example, the valve can be a mechanical valve such as a ball and cage.

With continued next to the skirt 180 illustrated in FIG. 1, the skirt 180 can be attached to the inner frame 120 and/or outer frame 140. As shown, the skirt 180 can be positioned around and secured to a portion of, or the entirety of, the exterior of the inner frame 120 and/or outer frame 140. The skirt 180 can also be secured to a portion of the valve body 160. The skirt 180 can follow the contours of the outer frame 140, such as the contours of the upper region 146, the intermediate region 148, and/or the lower region 150. In some embodiments, the skirt 180 can be used to attach the outer frame 140 to the inner frame 120. Although not shown, it is to be understood that the skirt 180 can be positioned around and secured to a portion of, or the entirety of, an interior of the inner frame 120 and/or the outer frame 140. Moreover, it is to be understood that while the skirt 180 can follow the contours of portions of the inner frame 120 and the outer frame 140, at least a portion of the skirt 180 can be spaced apart from at least a portion of both the inner frame 120 and the outer frame 140. In some embodiments, the skirt 180 can be spaced apart from the upper region 146 of the outer frame 140. For example, the skirt 180 can be positioned below the upper region 146. In such an embodiment, the spaced-apart portion of the skirt 180 can be loose such that the skirt 180 is movable relative to the upper region 146 or can be taut such that the skirt 180 is generally fixed in position.

The skirt 180 can be annular and can extend entirely circumferentially around the inner frame 120 and/or outer frame 140. The skirt 180 can prevent or inhibit backflow of fluids, such as blood, around the prosthesis 100. For example, with the skirt 180 positioned annularly around an exterior of the inner frame 120 and/or outer frame 140, the skirt 180 can create an axial barrier to fluid flow exterior to the inner frame 120 and/or outer frame 140 when deployed within a body cavity such as a native valve annulus. The skirt 180 can encourage tissue in-growth between the skirt 180 and the natural tissue of the body cavity. This may further help to prevent leakage of blood flow around the prosthesis 100 and can provide further securement of the prosthesis 100 to the body cavity. In some embodiments, the skirt 180 can be tautly attached to the inner frame 120 and/or outer frame 140 such that the skirt 180 is generally not movable relative to the inner frame 120 and/or outer frame 140. In some embodiments, the skirt 180 can be loosely attached to the inner frame 120 and/or outer frame 140 such that the skirt 180 is movable relative to the inner frame 120 and/or outer frame 140.

The skirt 180 can share characteristics, such as structure and/or functionality, which are the same as, or at least similar to, those of other skirts described herein such as, but not limited to, skirts 280, 780, 890, 990, 1580, 1590, 1680, 1690, 1980, 1990, 2080, 2280, 2380, 2480, 2490, discussed below.

Although the prosthesis 100 has been described as including an inner frame 120, an outer frame 140, a valve body 160, and a skirt 180, it is to be understood that the prosthesis 100 need not include all components. For example, in some embodiments, the prosthesis 100 can include the inner frame 120, the outer frame 140, and the valve body 160 while omitting the skirt 180. Moreover, although the components of the prosthesis 100 have been described and illustrated as separate components, it is to be understood that one or more components of the prosthesis 100 can be integrally or monolithically formed. For example, in some embodiments, the inner frame 120 and the outer frame 140 can be integrally or monolithically formed as a single component.

With reference next to FIGS. 2-6, an embodiment of a prosthesis 200 in an expanded configuration, or components of the prosthesis 200, are illustrated. The prosthesis 200 can include an inner frame 220, an outer frame 240, a valve body 260, and a skirt 280. A longitudinal axis of the prosthesis 200 may be defined as the central axis that extends through the center of the prosthesis 200 between the upper and lower ends of the prosthesis 200. In some situations, the prosthesis 200 may be oriented such that an upper end of the prosthesis 200 is a proximal portion and a lower end of the prosthesis 200 is a distal portion.

With reference first to the outer frame 240 illustrated in FIGS. 2-5, the outer frame 240 can include an outer frame body 242 and an outer frame anchoring feature 244. The outer frame 240 can share characteristics, such as structure and/or functionality, which are the same as, or at least similar to, those of outer frame 140 described above in connection with FIG. 1.

The outer frame body 242 can have an upper region 246, an intermediate region 248, and a lower region 250. As shown, when in an expanded configuration such as the fully expanded configuration, the outer frame body 242 can have an enlarged shape with an intermediate region 248 and a lower region 250 being larger than the upper region 246. The enlarged shape of the outer frame body 242 can advantageously allow the outer frame body 242 to engage a native valve annulus, native valve leaflets, or other body cavity, while spacing the inlet and outlet from the heart or vessel wall. This can help reduce undesired contact between the prosthesis 200 and the heart or vessel, such as the atrial and ventricular walls of the heart.

The upper region 246 of the outer frame body 242 can include a generally longitudinally-extending section 246a and an outwardly-extending section 246b. The longitudinally-extending section 246a can be generally concentric with the inner frame 220. The outwardly-extending section 246b can extend radially outwardly away from the longitudinal axis of the prosthesis 200. In some embodiments, the outwardly-extending section 246b can extend in a direction that is more perpendicular to the longitudinal axis 202 than parallel and/or can extend in a downward direction from the longitudinally-extending section 246a. However, it is to be understood that the outwardly-extending section 246b can extend generally perpendicularly to the longitudinal axis and/or in an upward direction from the longitudinally-extending section 246a. Moreover, it is to be understood that the longitudinally-extending section 246a can be omitted.

In some embodiments, the outwardly-extending section 246b can form an angle of between about 20 degrees to about 70 degrees with a plane orthogonal to the longitudinal axis of the prosthesis 200, an angle of between about 30 degrees to about 60 degrees with a plane orthogonal to the longitudinal axis of the prosthesis 200, an angle of between about 40 degrees to about 50 degrees with a plane orthogonal to the longitudinal axis of the prosthesis 200, an angle of about 45 degrees with a plane orthogonal to the longitudinal axis of the prosthesis 200, any subrange within these ranges, or any other angle as desired. In some embodiments, the outwardly-extending section 246b can form an angle of less than 70 degrees with a plane orthogonal to the longitudinal axis of the prosthesis 200, an angle of less than 55 degrees with a plane orthogonal to the longitudinal axis of the prosthesis 200, an angle of less than 40 degrees with a plane orthogonal to the longitudinal axis of the prosthesis 200, an angle of less than 25 degrees with a plane orthogonal to the longitudinal axis of the prosthesis 200, or less than any other angle as desired The intermediate region 248 of the outer frame body 242 can extend generally downwardly from the outwardly-extending section 246b of the upper region 246. As shown, the intermediate region 248 can have a generally constant diameter from an upper end of the intermediate region 248 to a lower end of the intermediate region 248 such that the intermediate region 248 forms a generally cylindrical shape. However, it is to be understood that the diameters of the upper end, the lower end, and/or the portion therebetween can be different. For example, in some embodiments, a diameter of the portion between the upper and lower ends can be larger than diameters of the upper and lower ends such that the intermediate region 248 has a generally bulbous shape (as shown, for example, in connection with frame 300 illustrated in FIGS. 7-8). In some embodiments, the diameter of the lower end can be larger than the diameter of the upper end. In other embodiments, the diameter of the upper end can be larger than the diameter of the lower end.

The general uniformity of the diameter of the intermediate region 248 from the upper end to the lower end, in conjunction with the axial dimension between the upper end and the lower end (i.e., the "height" of the intermediate region 248), provides for a significantly large circumferential area upon which a native valve annulus, or other body cavity, can be engaged. This can beneficially improve securement of the outer frame 240 to the native valve annulus or other body cavity. This can also improve sealing between the outer frame 240 and the native valve annulus, or other body cavity, thereby reducing paravalvular leakage.

At the juncture between the upper region 246 and the intermediate region 248, the outer frame body 242 can include a bend 252. The bend 252 can be a bend about a circumferential axis such that the intermediate region 248 extends in a direction more parallel to the longitudinal axis of the prosthesis 200 than the outwardly-extending section 246b of the upper region 246. In some embodiments, the bend 252 can generally form an arc with an angle between about 20 degrees to about 90 degrees. For example, as shown in the illustrated embodiment, the arc can have an angle of about 45 degrees. In some embodiments, the bend 252 can form an arc with an angle between about 30 degrees to about 60 degrees. The radius of curvature of the arc may be constant such that the bend 252 forms a circular arc or may differ along the length of the bend 252.

The lower region 250 of the outer frame body 242 can extend generally downwardly from the lower end of the intermediate region 248. As shown, the lower region 250 of the outer frame body 242 can have a generally constant diameter from an upper end of the lower region 250 to a lower end of the lower region 250 such that the lower region 250 forms a generally cylindrical shape. However, it is to be understood that the diameters of the upper end, the lower end, and/or the portion therebetween can be different. For example, in some embodiments, the diameter of the upper end of the lower region 250 can be greater than the diameter of the lower end of the lower region 250 such that the lower region 250 extends radially inwardly towards the longitudinal axis of the prosthesis 200. In some embodiments, the diameter of the lower end can be larger than the diameter of the upper end.

As shown, the diameters of the intermediate region 248 and the lower region 250 are generally equivalent such that the intermediate region 248 and the lower region 250 together form a generally cylindrical shape. However, it is to be understood that the diameters of the intermediate region 248 and the lower region 250 can be different. For example, the diameter of the lower region 250 can be less than the diameter of the intermediate region 248. Moreover, although the outer frame body 242 has been described and illustrated as being cylindrical or having circular cross-sections, it is to be understood that all or a portion of the outer frame body 242 can be have a non-circular cross-section such as, but not limited to, a D-shape, an oval or an otherwise ovoid cross-sectional shape.

The outer frame body 242 in an expanded configuration can have a diameter at its widest portion of between about 30 mm to about 60 mm, between about 35 mm to about 55 mm, about 40 mm, any sub-range within these ranges, or any other diameter as desired. The outer frame body 242 in an expanded configuration can have a diameter at its narrowest portion between about 20 mm to about 40 mm, any sub-range within these ranges, or any other diameter as desired. In some embodiments, in an expanded configuration, the ratio of the diameter of the outer frame body 242 at its widest portion to the diameter of the frame body 242 at its narrowest portion can be about 3:1, about 5:2, about 2:1, about 3:2, about 4:3, any ratio within these ratios, or any other ratio as desired.

The outer frame body 242 can have an axially compact configuration relative to the radial dimension. The outer frame body 242 in an expanded configuration can have an the axial dimension between the upper and lower ends of the outer frame body 242 (i.e., the "height" of the outer frame body 242) of between about 10 mm to about 40 mm, between about 18 mm to about 30 mm, about 20 mm, any sub-range within these ranges, or any other height as desired. In some embodiments, the ratio of the diameter of the largest portion of the outer frame body 242 to the height of the outer frame body 242 when the frame is in its expanded configuration can be about 3:1, about 5:2, about 2:1, about 3:2, about 4:3, about 13:10, about 5:4, or about 1:1. Thus, in some embodiments the width at the largest portion of the outer frame body 242 can be greater than the height of the outer frame body 242.

With continued reference to the outer frame 240 illustrated in FIGS. 2-5, the outer frame body 242 can include a plurality of struts with at least some of the struts forming cells 254a-c. Any number of configurations of struts can be used, such as rings of undulating struts shown forming ellipses, ovals, rounded polygons, and teardrops, but also chevrons, diamonds, curves, and various other shapes. For reference, the struts in FIG. 2 have been highlighted to show the general configuration of these struts; however, it is to be understood that one or more of the struts may not actually be seen. For example, the skirt 280 can be formed from a non-transparent material and be positioned over the exterior of the outer frame body 242.

The upper row of cells 254a can have an irregular octagonal shape such as a "heart" shape. The cell 254a can be formed via a combination of struts. As shown in the illustrated embodiment, the upper portion of cells 254a can be formed from a set of circumferentially-expansible struts 256a having a zig-zag or undulating shape forming a repeating "V" shape. The circumferentially-expansible struts 256a can be inclined or curved radially outwardly away from the longitudinal axis of the prosthesis 200 such that an upper portion of the struts 256a are positioned closer to the longitudinal axis of the prosthesis 200 than the lower portion of the struts 256a. The middle portion of cells 254a can be formed from a set of struts 256b extending downwardly from bottom ends of each of the "V" shapes. The struts 256b can extend along with a plane parallel to and/or extending through the longitudinal axis of the prosthesis 200. The portion of the cells 254a extending upwardly from the bottom end of struts 256b may be considered to be a substantially non-foreshortening portion of the outer frame 240. As will be discussed in further detail below, foreshortening refers to the ability of the frame to longitudinally shorten as the frame radially expands.

The lower portion of cells 254a can be formed from a set of circumferentially-expansible struts 256c having a zig-zag or undulating shape forming a repeating "V" shape. The lower tips or ends of the circumferentially-expansible struts 256c can be at or proximate the junction of the upper region 246 and the intermediate region 248. In some embodiments, one or more of the upper ends or tips of the circumferentially-expansible struts 256c can be a "free" apex which is not connected to a strut. As shown in the illustrated embodiment, every other upper end or tip of circumferentially-expansible struts 256c is a free apex. However, it is to be understood that other configurations can be used. For example, every upper apex along the upper end can be connected to a strut.

As shown in the illustrated embodiment, the middle and/or lower rows of cells 254*b-c* can have a different shape from the cells 254*a* of the first row. The middle row of cells 254*b* can have a diamond or generally diamond shape. The cells 254*b-c* may be considered to be a substantially foreshortening portion of the outer frame 240. The diamond or generally diamond shape can be formed via a combination of struts. The upper portion of cells 254*b* can be formed from the set of circumferentially-expansible struts 256*c* such that cells 254*b* share struts with cells 254*a*. The lower portion of cells 254*b* can be formed from a set of circumferentially-expansible struts 256*d*. As shown in the illustrated embodiment, one or more of the circumferentially-expansible struts 256*d* can extend generally in a downward direction. The one or more circumferentially-expansible struts 256*d* can incorporate the bend 252 such that an upper portion of the struts 256*d* can be positioned closer to the longitudinal axis of the prosthesis 200 than the lower portion of the struts 256*d* are to the longitudinal axis of the prosthesis 200. In some embodiments, one or more of the circumferentially-expansible struts 256*d* can extend radially outwardly away from the longitudinal axis of the prosthesis 200. As will be discussed in further detail below, these radially outward portions of struts 256*d* can form part of the outer frame anchoring feature 244.

The lower row of cells 254*c* can have an irregular octagonal shape. The upper portion of cells 254*c* can be formed from the set of circumferentially-expansible struts 256*d* such that cells 254*c* share struts with cells 254*b*. The lower portion of cells 254*c* can be formed from a set of circumferentially-expansible struts 256*e*. Circumferentially-expansible struts 256*e* can extend generally in a downward direction. In some embodiments, the circumferentially-expansible struts 256*e* can extend radially inwardly towards the longitudinal axis of the prosthesis 200 (as shown, for example, in connection with frame 300 illustrated in FIGS. 7-8). The circumferentially-expansible struts 256*e* can be inclined or curved towards the longitudinal axis of the prosthesis 200.

While the struts 256*a-e* are generally described and illustrated as being straight segments, it is to be understood that some or all of the struts 256*a-e* may not form entirely straight segments. For example, the struts 256*a-e* can include some curvature such that the upper and/or lower apices are curved.

As shown in the illustrated embodiment, there can be a row of twelve cells 254*a*, a row of twenty-four cells 254*b*, and a row of twelve cells 254*c*. While each of the cells 254*a-c* are shown as having the same shape as other cells 254*a-c* of the same row, it is to be understood that the shapes of cells 254*a-c* within a row can differ. Moreover, it is to be understood that any number of rows of cells can be used and any number of cells may be contained in the rows. In some embodiments, the number of cells can correspond to the number of anchors or anchor tips forming the outer frame anchoring feature 244. As shown, the number of cells in the upper row of cells 254*a* and the lower row of cells 254*c* can have a 1:1 correspondence with the number of anchors in the outer frame anchoring feature 244 (i.e., twelve cells in each row of cells 254*a*, 254*c* and twelve anchors for the anchoring features 244). The number of cells in the middle row of cells 254*b* can have a 2:1 correspondence with the number of anchors in the outer frame anchoring feature 244 (i.e., twenty-four cells in cells 254*b* and twelve anchors for the anchoring features 244). It is to be understood that other ratios of numbers of cells per row to number of anchors per anchoring feature can be used such as, but not limited to, 3:1, 4:1, 5:1, 6:1, and other ratios as desired. In some embodiments, all three rows of cells 254*a-c* can have the same number of cells. Moreover, it is to be understood that fewer or greater numbers of rows of cells can be used.

The geometry of cells 254*a-c* can allow the cells 254*a-c* to foreshorten as the outer frame 240 is expanded. As such, one or more of cells 254*a-c* can allow the outer frame 240 to foreshorten as the outer frame 240 is expanded. Foreshortening of the outer frame 240 can be used to secure the prosthesis to intralumenal tissue in a body cavity such as tissue at or adjacent a native valve including, but not limited to, a native valve annulus and/or leaflets. For example, expansion of the outer frame 240 can allow the outer frame 240 to exert a radially outward force against the tissue at or adjacent the native valve, such as the native valve annulus and/or leaflets.

With continued reference to the outer frame 240 illustrated in FIGS. 2-5, the outer frame anchoring feature 244 can extend outwardly relative to the longitudinal axis of the prosthesis 200. The outer frame anchoring feature 244 can extend at or proximate the juncture between the upper region 246 and the intermediate region 248 of the outer frame body 242. As shown, the outer frame anchoring feature 244 can be formed from one or more anchors extending from the frame body 242 in a direction radially outward from a longitudinal axis of the outer frame 240 and/or in a direction generally toward a lower end of the outer frame 240. The anchors of the outer frame anchoring feature 244 can be attached to the outer frame body 242 at one or more attachment points. For example, the anchors of the outer frame anchoring feature 244 can be formed from two struts of circumferentially-expansible struts 256*d* which are oriented radially outwardly and jointed together at a tip or end 244*a*. The individual anchors can form a generally "V" shape.

In some embodiments, the outer frame anchoring feature 244 can extend in a direction that is more perpendicular to the longitudinal axis of the prosthesis 200 than parallel. As shown, the outer frame anchoring feature 244 can extend in a downward direction generally parallel to the outwardly-extending section 246*b*. In some embodiments, the outer frame anchoring feature 144 can extend generally perpendicularly to the longitudinal axis 102 and/or in an upward direction.

In some embodiments, the lower row of cells 254*c* can be omitted. For example, the struts 256*e* can extend downwardly along a plane parallel to the longitudinal axis. These struts can extend between anchors of the inner frame anchoring feature 224. This can advantageously allow the outer frame 240 to extend further downwardly which can beneficially allow a skirt, such as skirt 280, to extend further downwardly and increase the effective sealing area. For example, in situations where the outer frame 240 is retained in a collapsed configuration and the inner frame anchoring feature 224 is released, the struts would not intersect with the individual anchors of the inner frame anchoring feature 224 regardless of the length of the struts. This can allow the individual anchors of the inner frame anchoring feature 224 to transition from a collapsed configuration to an expanded configuration without contacting the outer frame 240 when the outer frame 240 is retained in a collapsed configuration.

Figure 6:
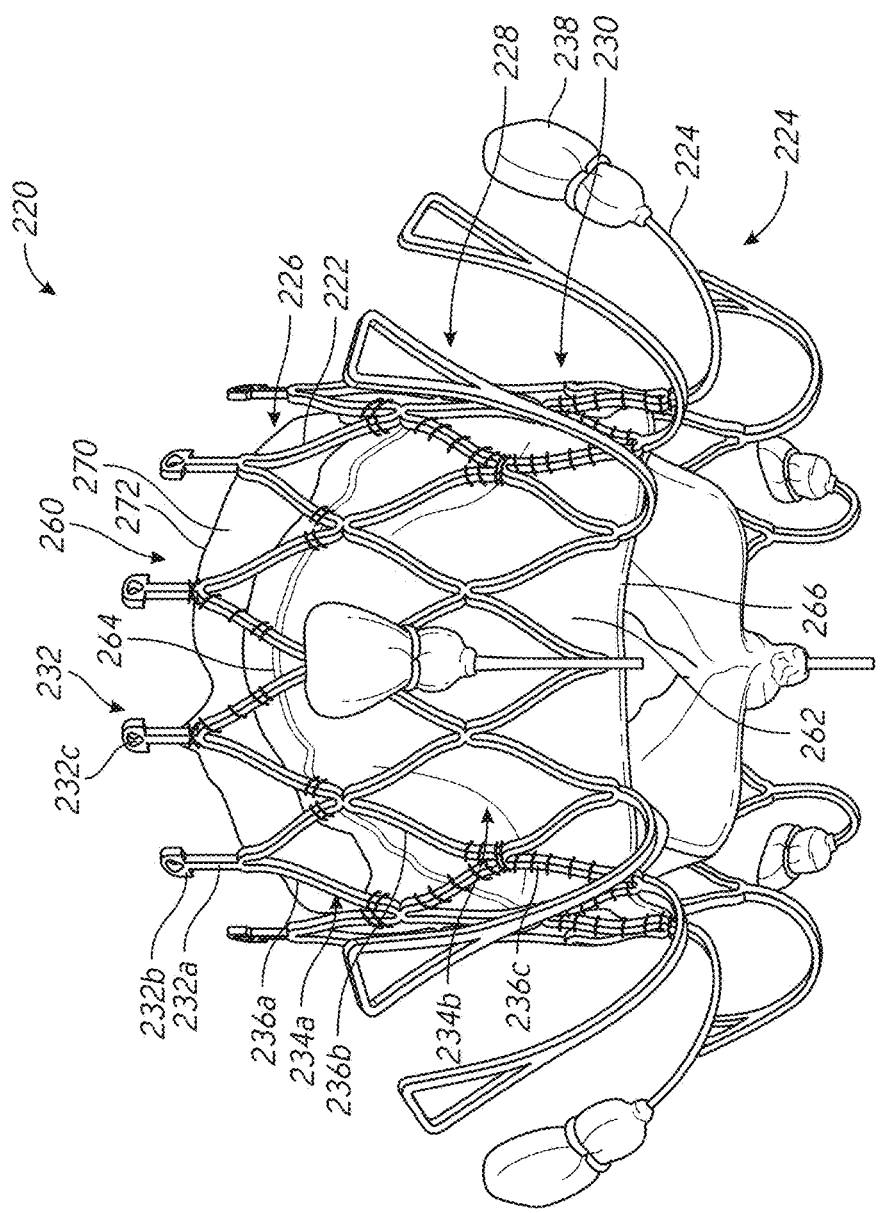
FIG. 6 is a bottom-oriented perspective view of the inner frame and valve body of FIG. 2.

With reference next to FIG. 6, the inner frame 220 and valve body 260 of prosthesis 200 are illustrated. The inner frame 220 can include an inner frame body 222 and an inner frame anchoring feature 224. As shown, the inner frame body 222 can have an upper region 226, an intermediate region 228, and a lower region 230. As shown, the inner frame body 222 can have a generally cylindrical shape such that the diameters of the upper region 226, the intermediate region 228, and the lower region 230 are generally equivalent. However, it is to be understood that the diameters of the upper region 226, the intermediate region 228, and/or the lower region 230 can be different. For example, in some embodiments, a diameter of the intermediate region 228 can be larger than the upper region 226 and the lower region 230 such that the inner frame body 222 has a generally bulbous shape. In some embodiments, the diameter of the lower region 230 can be larger than the diameter of the upper region 226. In other embodiments, the diameter of the upper region 226 can be larger than the diameter of the lower region 230.

The diameter of the upper region 226, intermediate region 228, and/or lower region 230 of the inner frame body 222 may be chosen such that the inner frame body 222 is adequately spaced from the body cavity when the prosthesis 200 is positioned within the body cavity. For example, in embodiments where the prosthesis 200 is positioned within the native mitral valve, the inner frame body 222 may have a diameter which is less than the diameter of the native mitral valve annulus. In situations where the native mitral valve annulus is about 40 mm in diameter, the diameter of the inner frame body 222 can be about 30 mm. Accordingly, the diameter of the inner frame body 222 may be about 75% of the diameter of the native mitral valve annulus.

In some embodiments, the diameter of the inner frame body 222 may be between about 40% to about 90% of the diameter of the native valve annulus, between about 60% to about 85%, of the diameter of the native valve annulus, between about 70% to about 80% of the diameter of the native valve annulus, any other sub-range between these ranges, or any other percentage as desired. In some embodiments, the diameter of the inner frame body 222 can be in the range of about 20 mm to about 40 mm when expanded, in the range of about 25 mm to about 35 mm when expanded, in the range of about 28 mm to about 32 mm when expanded, any other sub-range within these ranges when expanded, or any other diameter when expanded as desired. Although the inner frame body 222 has been described and illustrated as being cylindrical or having circular cross-sections, it is to be understood that all or a portion of the inner frame body 222 can be have a non-circular cross-section such as, but not limited to, a D-shape, an oval or an otherwise ovoid cross-sectional shape.

In other embodiments, the diameter of portions of the inner frame body 222 such as the upper region 226, intermediate region 228, and/or lower region 230 may be chosen such that the inner frame body 222 is positioned at the periphery of the body cavity. For example, in embodiments where the prosthesis 200 is positioned within the native mitral valve, the inner frame body 222 may have a diameter which is about equal to the diameter of the native mitral valve annulus.

With continued reference to the inner frame 220 illustrated in FIG. 6, the inner frame body 222 can include a plurality of struts with at least some of the struts forming cells 234a-b. Any number of configurations of struts can be used, such as rings of undulating struts shown forming ellipses, ovals, rounded polygons, and teardrops, but also chevrons, diamonds, curves, and various other shapes.

The upper row of cells 234a and the lower row of cells 234b can have a diamond or generally diamond shape. The rows of cells 234a-b can be formed via a combination of struts. As shown in the illustrated embodiment, the upper row of cells 234a can be formed from a first set of circumferentially-expansible struts 236a and a second set of circumferentially-expansible struts 236b. The lower row of cells 236b can be formed from the second set of circumferentially-expansible struts 236b and a third set of circumferentially-expansible struts 236c. The first, second, and third sets of struts 236a-c can have a zig-zag or undulating shape forming a repeating "V" shape. While the struts 236a-c are generally described and illustrated as being straight segments, it is to be understood that some or all of the struts 236a-c may not form entirely straight segments. For example, the struts 236a-c can include some curvature such that the upper and/or lower apices are curved.

As shown in the illustrated embodiment, the upper row of cells 234a and the lower row of cells 234b extend in a direction generally parallel to the longitudinal axis of the prosthesis 200. There can be a row of twelve cells 234a and a row of twelve cells 234b. While each of the cells 234a-b are shown as having the same shape as other cells 234a-b of the same row, it is to be understood that the shapes of cells 234a-b within a row can differ. Moreover, it is to be understood that any number of rows of cells can be used and any number of cells may be contained in the rows. In some embodiments, the number of cells can correspond to the number of anchors or anchor tips forming the inner frame anchoring feature 224. As shown, the number of cells in the upper row of cells 234a and the lower row of cells 234b can have a 1:1 correspondence with the number of anchors in the outer frame anchoring feature 224 (i.e., twelve cells in each row of cells 234a-b and twelve anchors for the anchoring features 224). It is to be understood that other ratios of numbers of cells per row to number of anchors per anchoring feature can be used such as, but not limited to, 3:1, 4:1, 5:1, 6:1, and other ratios as desired. In some embodiments, both rows of cells 234a-b can have different numbers of cells. Moreover, it is to be understood that fewer or greater numbers of rows of cells can be used.

The geometry of cells 234a-b can allow the cells 234a-b to foreshorten as the inner frame 220 is expanded. As such, one or more of cells 234a-b can allow the inner frame 220 to foreshorten as the inner frame 220 is expanded. As will be discussed in further detail, foreshortening of the inner frame 220 can be used to secure the prosthesis to intralumenal tissue in a body cavity such as tissue at or adjacent a native valve including, but not limited to, a native valve annulus and/or leaflets. For example, expansion of the inner frame 220 can allow the inner frame anchoring feature 224 to extend radially outward and draw closer to tissue of the body cavity, such as a native valve annulus and/or leaflets, to engage tissue of the body cavity.

With continued reference to the inner frame 220 illustrated in FIG. 6, the inner frame anchoring feature 224 can have ends or tips 224a positioned radially outwardly relative to the longitudinal axis of the prosthesis 200. The inner frame anchoring feature 224 can extend at or proximate a lower end of the lower region 230 of the inner frame body 222. As shown, the inner frame anchoring feature 224 can be formed from a plurality of individual anchors extending from the frame body 222. The anchors can extend downwardly from one or more attachment points to the frame body 222 including, but not limited to, lower apices of cells 234b. The anchors can bend to extend generally radially outwardly of the longitudinal axis of the prosthesis 200. As shown in the illustrated embodiment, the anchors can extend upwardly towards an end or tip 224a.

As shown in the illustrated embodiment, the tips or ends 224a extend upwardly in a direction generally parallel to the longitudinal axis of the prosthesis 200. In some embodiments, the tip or end 224a of anchoring feature 224 can extend generally perpendicular to the longitudinal axis of the prosthesis 200. This can beneficially increase the tissue contact area of the tip 224a of the anchor. This increased tissue contact area can beneficially reduce the stress applied by the tip 224a to tissue thereby reducing the amount of pressure and potential for trauma to the tissue. In some embodiments, the tip or ends 224a of the anchoring feature 224 extend radially inward towards the longitudinal axis and/or radially outward away from the longitudinal axis.

The tips or ends 224a, 244a as described above can advantageously provide atraumatic surfaces that may be used to contact or engage intralumenal tissue without causing unnecessary or undesired trauma to tissue. For example, the tips or ends 224a, 244a can form flat, substantially flat, curved or other non-sharp surfaces to allow the tips to engage and/or grasp tissue, without necessarily piercing or puncturing through tissue. A looped end or looped anchor may assist the frame in not getting caught up on structures at or near the treatment location. For example, each loop can be configured so that when the prosthesis 200 is deployed in-situ and the anchoring features 224, 244 expands away from the frame bodies 222, 242, the movement of each loop from a delivered position to a deployed position avoids getting caught on the papillary muscles. As shown in the illustrated embodiment, the inner frame anchoring feature 224 can include a lacrosse-head-shaped tip or end 224a. The outer frame anchoring feature 244 can include tips or ends 244a having a "U" shape or rounded shape.

As shown in the illustrated embodiment, the anchoring features 224, 244 can include twelve individual anchors; however, it is to be understood that a greater number or lesser number of individual anchors can be used. For example, the number of individual anchors can be chosen as a multiple of the number of commissures for the valve body 260. As such, for a prosthesis 200 with a valve body 260 having three commissures, the inner frame anchoring feature 224 and/or the outer frame anchoring feature 244 can have three individual anchors (1:1 ratio), six individual anchors (2:1 ratio), nine individual anchors (3:1 ratio), twelve individual anchors (4:1 ratio), fifteen individual anchors (5:1 ratio), or any other multiple of three. It is to be understood that the number of individual anchors need not correspond to the number of commissures of the valve body 260. Moreover, while the prosthesis 200 includes anchoring features 224, 244 with twelve anchors each, it is to be understood that a greater number of anchors or a lesser number of anchors can be used. In some embodiments, instead of a 1:1 correspondence between the number of anchors in the inner frame anchoring feature 224 and the outer frame anchoring feature 244 (i.e., twelve anchors each), other ratios can be used. For example, a 1:2 or a 1:3 correspondence between the anchors, are possible such that the inner frame anchoring feature 224 or the outer frame anchoring feature 244 have fewer anchors than the other anchoring feature.

With continued reference to the inner frame 220 illustrated in FIG. 6, the inner frame anchoring feature 224 can include covers and/or cushions 238 to surround or partially surround at least a portion of the inner frame anchoring feature 224, such as the tips or ends 224a. The covers and/or cushions 238 can be similar to those described in U.S. Publication No. 2015/0328000, which has been incorporated by reference in its entirety. The covers and/or cushions 238 can either fit snuggly around the tips 224a of the inner frame anchoring feature 224 or can have extra padding so that the covers extend radially away from the inner frame body 222. As shown in the illustrated embodiment, covers and/or cushions 238 are attached to a subset of anchors of the inner frame anchoring feature 224 such that a cover and/or cushion 238 is used on every third anchor. In some embodiments, the outer frame anchoring feature 244 can include covers and/or cushions to surround or partially surround at least a portion of the outer frame anchoring feature 244, such as the tips or ends 244a.

It is to be understood that greater or fewer numbers of covers and/or cushions 238 can be used with anchors of the inner frame anchoring feature 224 and/or the outer frame anchoring feature 244. For example, a cover and/or cushion 238 can be used on every other anchor such that there is a 1:2 ratio of covers and/or cushions 238 to anchors. As another example, a cover and/or cushion 238 can be used on every anchor (as shown in FIGS. 2-5). In some embodiments, all of the anchors can have the covers and/or cushions with some of the anchors having less cushioning than others. In some embodiments, all of the anchors can have the padded covers. In other embodiments, all of the anchors can have the snuggly fitting cushions. In other embodiments, the configuration of the covers and/or cushions can differ between the inner frame anchoring feature 224 and the outer frame anchoring feature 244.

The cover and/or cushion 238 can be formed from a deformable material. When the top portion of the cover and/or cushion 238 is subject to pressure due to a downwardly directed force, the cover and/or cushion 238 can compress and expand laterally outward. Such a force may be exerted upon the cover and/or cushion 238 when the cover and/or cushion 238, for example, when the cover and/or cushion 238 contacts a ventricular side of the mitral valve annulus during systole. The compression and lateral expansion of cover and/or cushion 238 can increase the surface area of the cover and/or cushion 238 in contact with the tissue, thereby exerting less pressure on the tissue and reducing the potential for trauma.

With continued reference to the anchoring features 224, 244 illustrated in FIGS. 2-6, the tips or ends 224a of the inner frame anchoring feature 224 can be generally circumferentially aligned with respect to the tips or ends 244a of the outer frame anchoring feature 244 meaning that the tips or ends 224a of the inner frame anchoring feature 224 are aligned, in a circumferential direction, with the tips or ends 244a of the outer frame anchoring feature 244. In other embodiments (not shown), the tips or ends 224a of the inner frame anchoring feature 224 and the tips or ends 244a of the outer frame anchoring feature 244 can be circumferentially offset or staggered meaning that the tips or ends 224a of the inner frame anchoring feature 224 are not aligned, in a circumferential direction, with the tips or ends 244a of the outer frame anchoring feature 244.

Preferably, each of the anchoring features 224, 244 are positioned or extend generally radially outwardly from the prosthesis 200 so that the anchor tips or ends 224a, 244a are generally spaced away or radially outward from the rest of the frame bodies 222, 242 and from the one or more attachment points or bases of the anchors of the anchoring features 224, 244. For example, the anchor tips 224a, 244a may be located radially outward from the intermediate region 248 and/or lower region 250 of the outer frame body 242, with the tips 224a, 244a being axially spaced from one another.

As shown in the illustrated embodiment, at least some of the anchoring features, such as anchoring feature 244, can extend to a radial distance from an exterior surface of the intermediate region 248 and/or lower region 250 of the outer frame body 242 that is about 110% or more of the expanded diameter of the intermediate region 248 of the outer frame body 242 at the plane of tips 244a. At least some of the anchoring features, such as anchoring feature 224, can extend to a radial distance from an exterior surface of the intermediate region 248 of the outer frame body 242 that is slightly greater than the expanded diameter of the intermediate region 248 and/or the lower region 250 of the outer frame body 242 at the plane of tips 224a. As shown, the tips 224a can be positioned such that the tips 224a contact an exterior of the outer frame body 242. As will be discussed in further detail below, this can beneficially pinch or grasp tissue of the body cavity therebetween. For example, in instances where the prosthesis 200 is used at a native mitral valve, native leaflets and/or portions of the native mitral valve annulus can be pinched or grasped between the anchoring feature 224 and the intermediate region 248 and/or lower region 250 of the outer frame body 242.

In some embodiments, all of the anchors of the inner frame anchoring feature 224 and/or all of the anchors of the outer frame anchoring feature 244 extend at least to this radial distance. In other embodiments, fewer than all of the anchors of the inner frame anchoring feature 224 and/or all of the anchors of the outer frame anchoring feature 244 extend to this radial distance. The outermost diameter of the inner frame anchoring feature 224 and/or the outer frame anchoring feature 244 may be greater than the diameter of frame bodies 222, 224 as described above and may be in the range of about 35 mm to about 70 mm when expanded, in the range of about 35 mm to about 60 mm when expanded, in the range of about 40 mm to about 60 mm when expanded, in the range of about 45 mm to about 50 mm when expanded, any sub-range within these ranges when expanded, or any other diameter as desired.

As shown, the inner frame anchoring feature 224 can be positioned to be not as far radially outward as the outer frame anchoring feature 244. However, it is to be understood that in other embodiments, the inner frame anchoring feature 224 and the outer frame anchoring feature 244 can extend radially outward from the longitudinal axis of the prosthesis 200 to about the same radial dimension or the outer frame anchoring feature 244 can be positioned to be not as far radially outward as the inner frame anchoring feature 224. Such configurations may be advantageous in positioning and securing the prosthesis in a native valve annulus or other body location.

In some embodiments, individual anchors can extend radially outwardly from the frame at an anchor base and terminate at an anchor tip. The individual anchors can be connected to the frame at one of many different locations including apices, junctions, other parts of struts, etc. Moreover, the anchors forming the anchoring features 224, 244 can comprise first, second, third, or more spaced apart bending stages along the length of each anchor. Further details that may be incorporated and/or interchanged with the features described herein are disclosed in U.S. Publication Nos. 2014/0277422, 2014/0277427, 2014/0277390, and 2015/0328000, and U.S. application Ser. No. 15/653,390, entitled REPLACEMENT HEART VALVE PROSTHESIS, filed on Jul. 18, 2017, which have been incorporated by reference herein.

One or both anchoring features 224, 244 can contact or engage a native valve annulus, such as the native mitral valve annulus, tissue beyond the native valve annulus, native leaflets, and/or other tissue at or around the implantation location during one or more phases of the cardiac cycle, such as systole and/or diastole. In some embodiments, one or both anchoring features 224, 244 do not contact or engage, or only partially contact or engage, a native valve annulus, such as the native mitral valve annulus, tissue beyond the native valve annulus, native leaflets, and/or other tissue at or around the implantation location during one or more phases of the cardiac cycle, such as systole and/or diastole. However, it is to be understood that in some embodiments, when the prosthesis 200 is used for a replacement mitral valve prosthesis, during diastole and/or systole, both the inner frame anchoring feature 224 and the outer frame anchoring feature 244 can be sized to contact or engage the native mitral valve annulus.

The anchoring features 224, 244 and anchor tips 224a, 244a are preferably located along the prosthesis 200 with at least part of the foreshortening portion positioned between the anchoring features 224, 244 so that a portion of the anchoring features 224, 244 will move closer together with expansion of the prosthesis 200. This can allow the anchoring features 224, 244 to close in on opposite sides of the native mitral annulus to thereby secure the prosthesis at the mitral valve. In some embodiments, the anchoring features 224, 244 can be positioned such that the anchoring features 224, 244 do not contact opposing portions of the native mitral annulus at the same time. For example, when the prosthesis 200 is used for a replacement mitral valve prosthesis, during at least systole, in some embodiments the inner frame anchoring feature 224 is sized to contact or engage the native mitral valve annulus whereas the outer frame anchoring feature 244 is sized to be spaced from the native mitral valve annulus. This can be beneficial when outer frame anchoring feature 244 is used to provide stabilization and help align the prosthesis. In some embodiments, the anchoring features 224, 244 can be positioned such that the anchoring features 224, 244 grasp opposite side of the native mitral annulus.

While the anchoring features 224, 244 have been illustrated as extending from the lower end of the lower region 230 of the inner frame body 222 and at a junction between the upper region 246 and the intermediate region 248 of the outer frame body 242 respectively, it is to be understood that the anchoring features 224, 244 can be positioned along any other portion of the prosthesis 200 as desired. Moreover, while two anchoring features 224, 244 have been included in the illustrated embodiment, it is to be understood that a greater number or lesser number of sets of anchoring features can be utilized.

With reference back to the inner frame 220 illustrated in FIG. 6, the inner frame 220 can include a set of locking tabs 232 extending the at or proximate an upper end of the upper region 226 of the inner frame body 222 such as upper apices of cells 234a. As shown, the inner frame 220 can include twelve locking tabs 232, however, it is to be understood that a greater number or lesser number of locking tabs can be used. The locking tabs 232 can extend generally upwardly from the upper region 226 of the inner frame body 222 in a direction generally aligned with the longitudinal axis of the prosthesis 200. As shown in the illustrated embodiment, the locking tabs 232 can include a longitudinally-extending strut 232a. At an upper end of the strut 232a, the locking tab 232 can include an enlarged head 232b. As shown, the enlarged head 232b can have a semi-circular or semi-elliptical shape forming a "mushroom" shape with the strut 232a. The locking tab 232 can include an eyelet 232c which can be positioned through the enlarged head 232b. It is to be understood that the locking tab 232 can include an eyelet at other locations, or can include more than a single eyelet.

The locking tab 232 can be advantageously used with multiple types of delivery systems. For example, the shape of the struts 232a and the enlarged head 232b can be used to secure the inner frame 220 to a "slot" based delivery system. The eyelets 232c can be used to secure the inner frame 220 to a "tether" based delivery system such as those which utilize sutures, wires, or fingers to control delivery of the inner frame 220 and the prosthesis 200. This can advantageously facilitate recapture and repositioning of the inner frame 220 and the prosthesis 200 in situ. In some embodiments, the prosthesis 220 can be used with the delivery systems described herein, including but not limited to, those described in U.S. Pat. Nos. 8,414,644 and 8,652,203 and U.S. Publication Nos. 2015/0238315, the entireties of each of which are hereby incorporated by reference and made a part of this specification.

While the locking tabs 232 have been described as being attached to the inner frame body 222, it is to be understood that the locking tabs 232 can be attached to other portions of the prosthesis 200 such as, but not limited to, the outer frame body 242. For example, in some embodiments, the locking tabs 232 can extend from an upper end of an upper region 246 of the outer frame body 242. Moreover, it is to be understood that portions of, or the entirety of, the locking tabs 232 can be omitted. For example, in some embodiments, the strut 232a can be omitted such that the enlarged head 232b and eyelet 232c are positioned at an upper end of the upper region 226 of the inner frame body 222, such as at upper apices of cell 234a.

Figure 5:
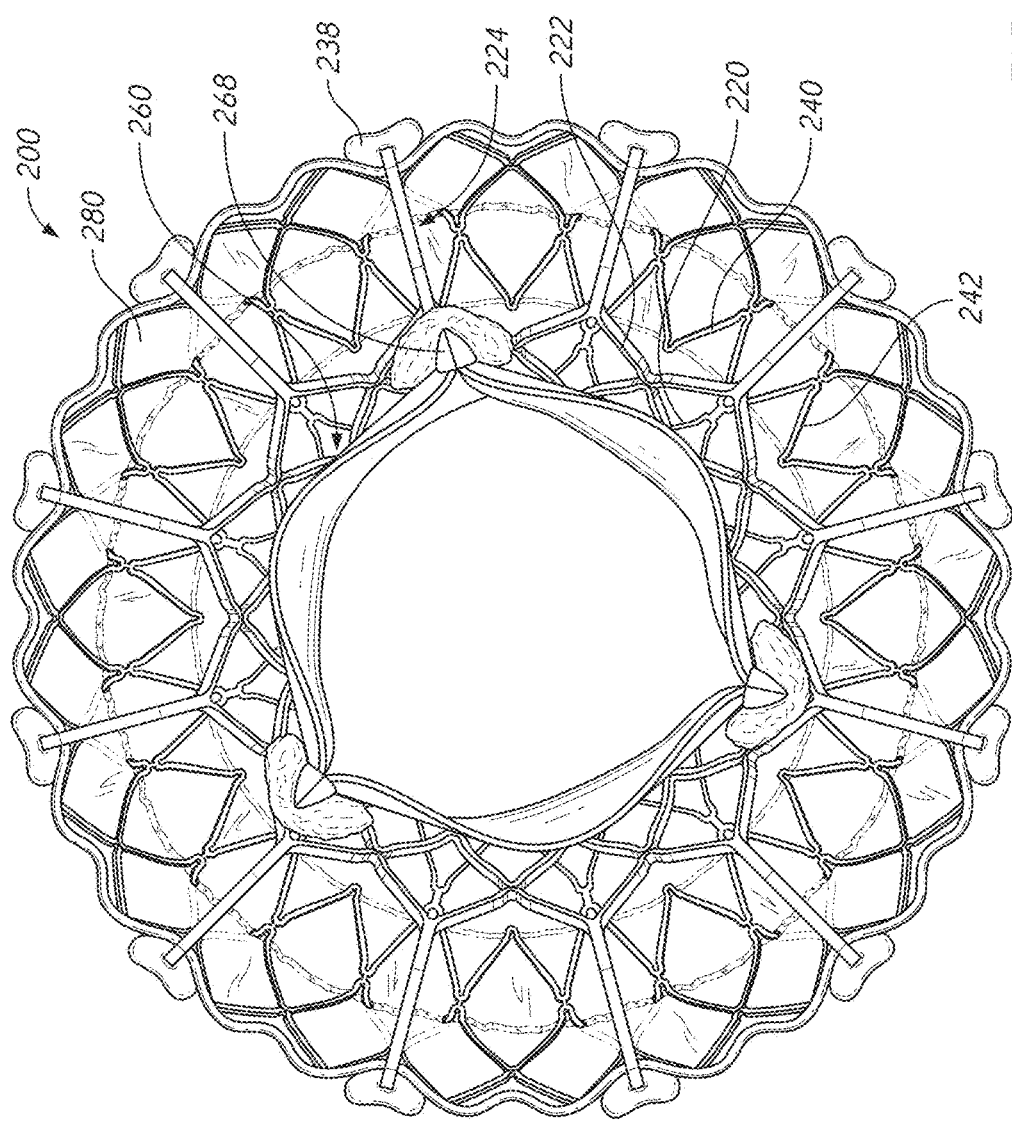
FIG. 5 is a bottom view of the prosthesis of FIG. 2.

With reference next to the valve body 260 illustrated in FIG. 6, the valve body 260 can be positioned within the inner frame 220. The valve body 260 can be a replacement heart valve which includes a plurality of valve leaflets 262. The valve leaflets 262 can include a first edge 264, second edge 266, and tabs 268 (as shown in FIG. 5) for attaching the valve leaflets 262 together at commissures of the valve body 260. The tabs 268 can be used to secure the valve leaflets 262 to the inner frame 220. The first edge 264 can be an arcuate edge and can be generally fixed in position relative to the frame 220. The second edge 266 can be a freely moving edge which can allow the valve body 260 to open and close.

The plurality of valve leaflets 262 can function in a manner similar to the native mitral valve, or to any other valves in the vascular system as desired. The plurality of valve leaflets 262 can open in a first position and then engage one another to close the valve in a second position. The plurality of valve leaflets 262 can be made to function as a one way valve such that flow in one direction opens the valve and flow in a second direction opposite the first direction closes the valve. For example, as shown in the illustrated embodiment, the valve body 260 can open allow to blood to flow through the valve body 260 in a direction from an upper end to a lower end. The valve body 260 can close to inhibit blood flow through the valve body 260 in a direction from the lower end to the upper end. In situations where the prosthesis 200 is oriented such that an upper end is a proximal end and a lower end is a distal end, the valve body 260 can be positioned such that the valve body 260 can open to allow blood to flow through the valve body 260 in a proximal-to-distal direction and close to inhibit blood flow in a distal-to-proximal direction. The valve body 260 can be constructed so as to open naturally with the beating of the heart. For example, the valve body 260 can open during diastole and close during systole. The valve body 260 can replace a damaged or diseased native heart valve such as a diseased native mitral valve.

The valve body 260 can include a liner 270. The liner 270 can be used to assist with fluid flow through and/or around the prosthesis 200, such as through and around the inner frame 220 and the valve leaflets 262. The liner 270 can surround at least a portion of the valve leaflets 262 and be connected to one or more of the valve leaflets 262. For example, as shown in the illustrated embodiment, the one or more valve leaflets 262 can be attached to the liner 270 along the first edge 264 of the valve leaflets 262.

As shown in the illustrated embodiment, the liner 270 can be positioned within the interior of the inner frame 220 and can form an inner wall of the prosthesis 200. For example, the liner 270 can be positioned such that the liner 270 is radially inward, relative to the longitudinal axis of the prosthesis 200, from the struts 236a-c of the inner frame 220. In this manner, the fluid pathway towards the valve leaflets 262 can be relatively smooth. It is also contemplated that the liner 270 can at least be partially positioned along an exterior of the inner frame 220 and/or outer frame 240 such that at least a portion of the liner 270 is radially outward, relative to the longitudinal axis of the prosthesis 200, from struts of the inner frame 220 and/or outer frame 240. As shown in the illustrated embodiment, the liner 270 can be positioned along an upper or inlet side of the inner frame 220. The liner 270 can extend from the first edge 264 of the valve leaflets 262 towards the upper end of the inner frame 220. The liner 270 can also extend below the first edge 264 of the valve leaflet 262 towards the lower end of the inner frame 220. The liner 270 can also be made to move with foreshortening portions of the inner frame 220.

In some embodiments, the liner 270 can extend the entire length of the inner frame 220 or the inner frame body 222. In other embodiments, it can extend along only part of the length of the inner frame body 222 as shown. In some embodiments, the ends of the valve leaflets 262 can coincide with ends of the liner 270. In addition, one or more of the ends of the inner frame body 222 can coincide with the ends of the liner 270. As shown in the illustrated embodiment, an end 272 of the liner 270 can be positioned between the upper end of the inner frame 220 and the valve leaflets 262. The end 272 of the liner 270 can extend above an upper end of the inner frame body 222 and extend along a portion of the locking tabs 232. In some embodiments, the end 272 of the liner 270 can be positioned at or proximate an uppermost portion of the first or arcuate edge 264 of the valve leaflet 262 below the upper end of the inner frame body 222.

Other shapes and configurations can also be used for the valve body 260. In some embodiments, the liner 270 may extend along the length of the leaflets, but is not connected to them. In the illustrated embodiment, the liner 270 is attached to the inner frame 220 and at least a portion of the leaflets 262, such as the first or arcuate edge 264, is attached to the liner 270. Portions of the valve leaflets 262, such as the portions of the first edge 264 and/or tabs 268, can also be attached to the inner frame 220. The liner 270 and/or the valve leaflets 262 can be attached to the inner frame 220 or to each other using any of the fasteners and/or techniques described herein including, but not limited to, mechanical fasteners, such as sutures, staples, screws, rivets, interfacing members (e.g., tabs and slots), and any other type of mechanical fastener as desired, chemical fasteners such as adhesives and any other type of chemical fastener as desired, fastening techniques such as welding, soldering, sintering, and any other type of fastening technique as desired, and/or a combination of such fasteners and techniques.

The liner 270 can be constructed in multiple different ways. The liner 270 can be made a layer of resilient material, such as such as knit polyester (e.g., polyethylene terephthalate (PET), polyvalerolactone (PVL)) or any other biocompatible material such as those which are wholly or substantially fluid impermeable, flexible, stretchable, deformable, and/or resilient. In some embodiments, the liner 270 can be made from a material that is more flexible than the valve leaflet material. The upper and/or lower end, such as end 272, of the liner 270 can be straight, curved, or have any other desired configuration. For example, as shown in the illustrated embodiment, the liner 270 can have a straight edge forming the end 272. In other embodiments, the end 272 can be patterned to generally correspond to the undulations at one end of the inner frame 220. The liner 270 can be formed of one piece or multiple pieces.

In another embodiment of the liner 270, the end can extend past the inner frame 220 and can be wrapped around it. Thus, the liner 270 can extend from the interior of the inner frame 220 to the exterior of the inner frame 220. The liner 270 can extend completely around the inner frame 220 for ¼, ⅓, ½, or more of the length of inner frame 220.

With reference next to the skirt 280 illustrated in FIGS. 2-5, the skirt 280 can be positioned around and secured to at least a portion of the exterior of the prosthesis 200 such as, but not limited to, the inner frame 220 and/or the outer frame 240. The skirt 280 can be annular and can extend entirely circumferentially around the prosthesis 200. The skirt 280 can prevent or inhibit backflow of fluids around the prosthesis 200. For example, with the skirt 280 positioned annularly around an exterior of the prosthesis 200, the skirt 280 can create an axial barrier to fluid flow exterior to the prosthesis 200 when deployed within a body cavity. As shown, the skirt 280 can seal against at least a portion of tissue surrounding the body cavity. In addition, the skirt 280 can encourage tissue in-growth between the flap assembly 280 and natural tissue of the body cavity. This may further help to prevent leakage of blood flow around the prosthesis 200.

The skirt 280 can have an upper region 282, an intermediate region 284, and a lower region 286. The upper region 282 of the skirt 280 can extend along a portion of the exterior of the outer frame 240 such as the upper region 246 of the outer frame 240. The intermediate region 284 of the skirt 280 can extend along a portion of the exterior of the outer frame 240 such as the intermediate region 248 of the outer frame 240. The lower region 286 of the skirt 280 can extend along a portion of the exterior of the outer frame 240 such as the lower region 250 of the outer frame 240. While the skirt 280 is shown extending along the exterior of the outer frame 240, it is to be understood that portions of, or the entirety of, the skirt 280 can extend along an interior of the outer frame. It is also to be understood that while the skirt 280 is shown tautly attached to the outer frame 240, a portion of, or the entirety of, the skirt 280 can be loosely attached such that a portion of, or the entirety of, the skirt 280 is movable relative to the outer frame 240.

The upper end of the skirt 280 can be positioned at or proximate an upper end of the outer frame body 242 and/or an upper end of the inner frame body 222. In some embodiments, the upper end of the skirt 280 can be attached to the end 272 of the liner 270 using any of the fasteners and/or techniques described herein including, but not limited to, mechanical fasteners, such as sutures, staples, screws, rivets, interfacing members (e.g., tabs and slots), and any other type of mechanical fastener as desired, chemical fasteners such as adhesives and any other type of chemical fastener as desired, fastening techniques such as welding, soldering, sintering, and any other type of fastening technique as desired, and/or a combination of such fasteners and techniques. The lower end of the lower region 286 of the skirt 280 can be positioned at or proximate a lower end of the lower region 250 of the outer frame body 242. The skirt 280 may be attached to the outer frame 240 and/or inner frame 220 using any fasteners and/or techniques described herein. For example, portions of the skirt 280 can be attached to struts and/or anchoring features of the outer frame 240 and/or inner frame 220 via sutures.

As shown in the illustrated embodiment, the lower end of the lower region 286 of the skirt 280 can be provided with a generally straight edge with extends circumferentially around the outer frame body 242 and/or inner frame body 222. It is to be understood that other configurations, such as a curved edge, can also be used as desired. In some embodiments, the lower end of the lower region 286 of the skirt 280 can follow the shape of the struts along the lower end of the lower region 250 of the outer frame body 242.

In some embodiments, the skirt 280 can be formed from a material such as knit polyester (e.g., polyethylene terephthalate (PET), polyvalerolactone (PVL)) or any other biocompatible material such as those which are wholly or substantially fluid impermeable, flexible, stretchable, deformable, and/or resilient. The skirt 280 and/or the liner 270 may be made from the same or similar materials. As shown in the illustrated embodiment, the skirt 280 can be formed as separate components. The components can be attached together using any of the fasteners and/or techniques described herein including, but not limited to, mechanical fasteners, such as sutures, staples, screws, rivets, interfacing members (e.g., tabs and slots), and any other type of mechanical fastener as desired, chemical fasteners such as adhesives and any other type of chemical fastener as desired, fastening techniques such as welding, soldering, sintering, and any other type of fastening technique as desired, and/or a combination of such fasteners and techniques. For example, the upper region 282 can be a first component and the intermediate region 284 and/or lower region 286 can be a second component. In other embodiments, skirt 280 can be integrally or monolithically formed. For example, in some embodiments, the upper region 282 of the skirt 280 and the intermediate region 284 and/or lower region 286 can be integrally or monolithically formed as a single component.

In some embodiments, the outer frame 240 can be attached to the inner frame 220 at one or more attachment points using any of the fasteners and/or techniques described herein including, but not limited to, mechanical fasteners, such as sutures, staples, screws, rivets, interfacing members (e.g., tabs and slots which can be on the inner frame 220 and the outer frame 240), and any other type of mechanical fastener as desired, chemical fasteners such as adhesives and any other type of chemical fastener as desired, fastening techniques such as welding, soldering, sintering, and any other type of fastening technique as desired, and/or a combination of such fasteners and techniques.

The outer frame 240 can be attached to the inner frame 220 by attaching the skirt 280 to the inner frame 220 and/or portions of the valve body 260, such as the liner 270 using any mechanism or technique described herein. In some embodiments, the outer frame 240 can be tautly attached to the inner frame 220 such that little to no relative movement between the outer frame 240 and the inner frame 220 occurs at the one or more attachment points of the outer frame 240 to the inner frame 220. For example, the outer frame 240 can be tautly attached to the inner frame 220 and/or the skirt 280 can be attached to the inner frame 220 and/or valve body 260 with little to no slack. In other embodiments, the outer frame 240 can be loosely attached to the inner frame 220 such that some relative movement between the outer frame 240 and the inner frame 220 occurs at the one or more attachment points of the outer frame 240 to the inner frame 220. For example, the outer frame 240 can be loosely attached to the inner frame 220 and/or the skirt 280 can be attached to the inner frame 220 and/or valve body 260 with slack to permit relative movement between the outer frame 240 and the inner frame 240.

Figure 7:
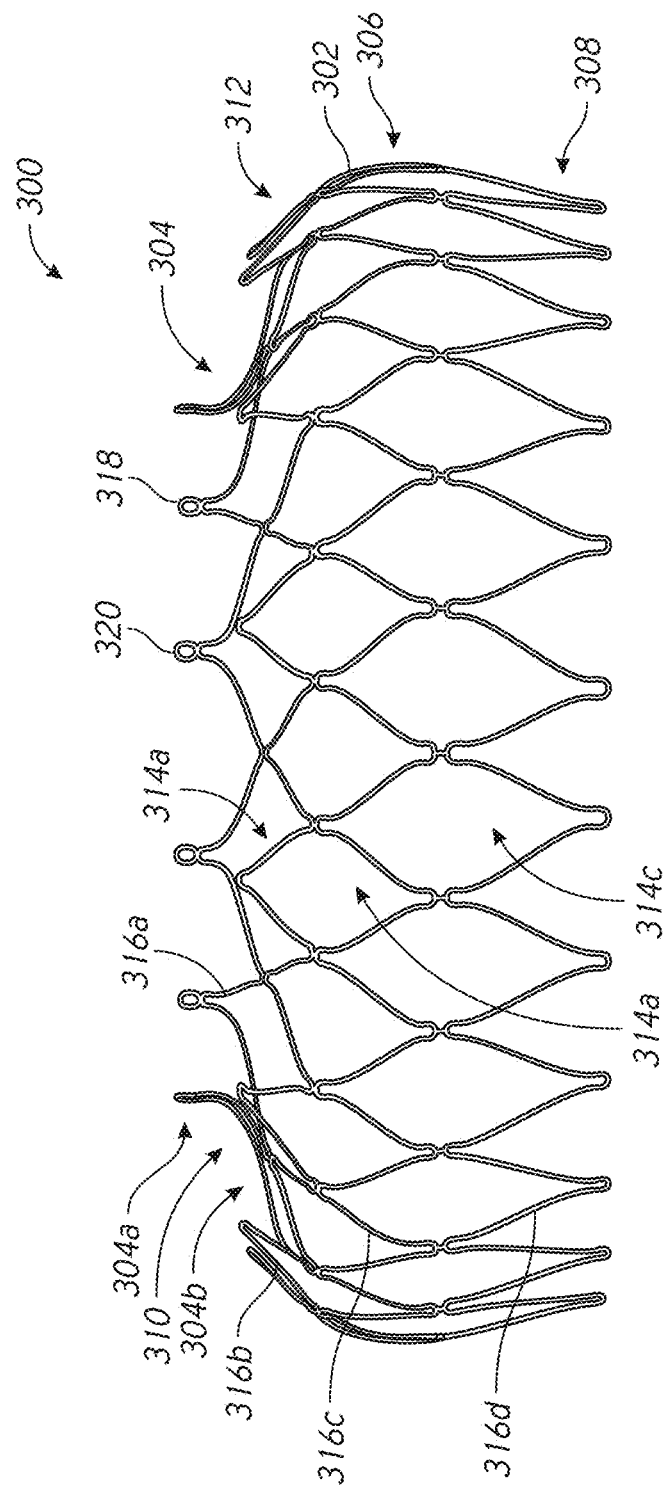
FIG. 7 is a side view of a front-half of another embodiment of an outer frame.
Figure 8:
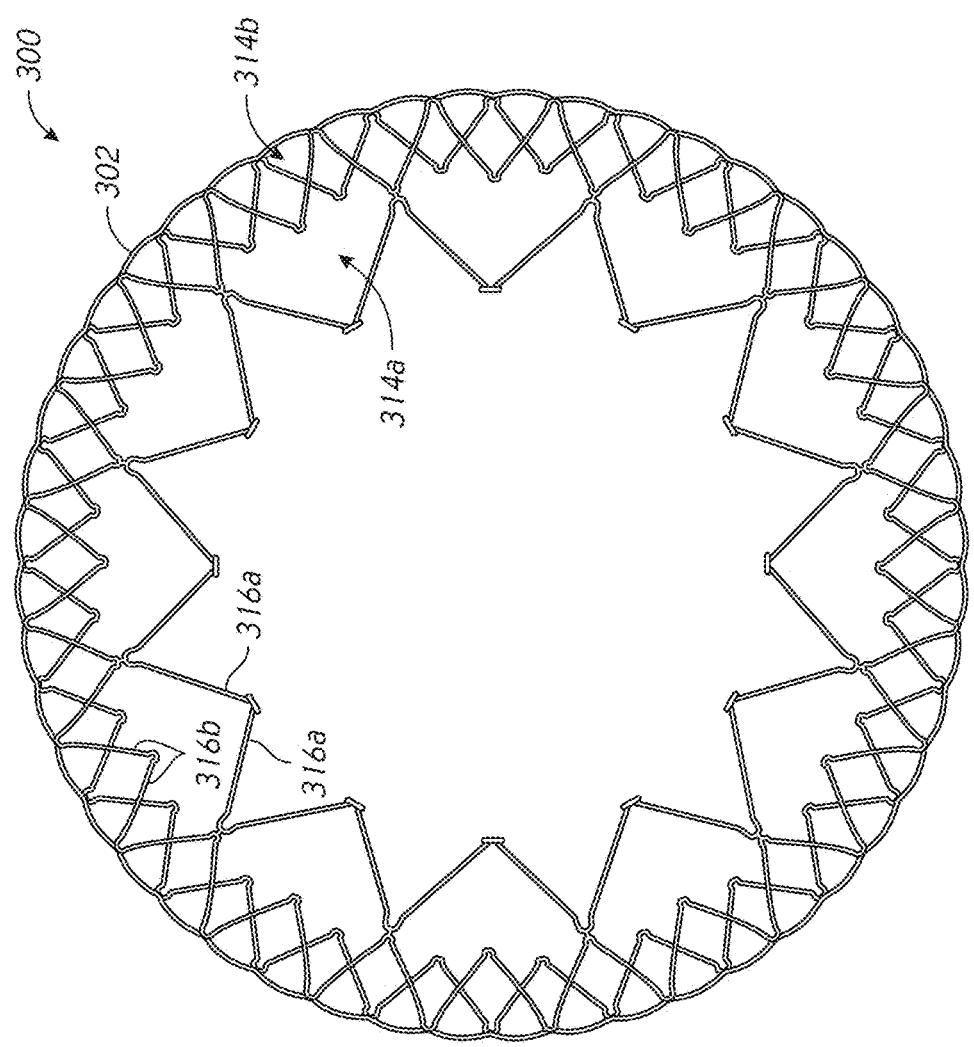
FIG. 8 is a top view of the outer frame of FIG. 2.

With reference next to FIGS. 7-8, an embodiment of an outer frame 300 in an expanded configuration is illustrated. The outer frame 300 can include an outer frame body 302. A longitudinal axis of the outer frame 300 may be defined as the central axis that extends through the center of the outer frame 300 between the upper and lower ends of the outer frame 300. As shown, the outer frame body 302 can have an upper region 304, an intermediate region 306, and a lower region 308.

When in an expanded configuration such as in a fully expanded configuration, the outer frame body 302 can have a bulbous shape with the intermediate region 306 being larger than the upper region 304 and the lower region 308. The bulbous shape of the outer frame body 302 can advantageously allow the outer frame body 302 to engage a native valve annulus, native valve leaflets, or other body cavity, while spacing the inlet and outlet from the heart or vessel wall. This can help reduce undesired contact between the prosthesis in which the outer frame 300 is used and the heart or vessel, such as the atrial and ventricular walls of the heart. The bulbous shape can further enhance securement of the outer frame body 302 to the body cavity. For example, in some embodiments, the bulbous shape can allow the intermediate region 306 to extend further radially outward compared to an anchoring feature, such as lower frame anchoring features 124, 224. In this manner, the intermediate region 306 can exert a greater radial force on tissue of the body cavity and/or can more completely conform to the tissue of the body cavity, such as the native valve annulus and/or native leaflets.

The upper region 304 of the outer frame body 302 can include a generally longitudinally-extending section 304a and an outwardly-extending section 304b. The outwardly-extending section 304b can extend radially outwardly away from the longitudinal axis of the outer frame 300. In some embodiments, the outwardly-extending section 246b can extend in a direction that is more perpendicular to the longitudinal axis 202 than parallel and/or in a downward direction from the longitudinally-extending section 304a. However, it is to be understood that the outwardly-extending section 304b can extend generally perpendicularly to the longitudinal axis and/or in an upward direction from the longitudinally-extending section 304a. Moreover, it is to be understood that the longitudinally-extending section 304a can be omitted.

At the juncture between the longitudinally-extending section 304a and the outwardly-extending section 304b, the outer frame body 302 can include a bend 310. The bend 310 can be about a circumferential axis such that the outwardly-extending section 304b extends in a direction more perpendicular to the longitudinal axis of the outer frame 300 than the longitudinally-extending section 304a. In some embodiments, the bend 310 can generally form an arc with an angle between about 20 degrees to about 90 degrees. For example, as shown in the illustrated embodiment, the arc can have an angle of about 60 degrees. In some embodiments, the bend 310 can form an arc with an angle between about 30 degrees to about 60 degrees. The radius of curvature of the arc may be constant such that the bend 310 forms a circular arc or may differ along the length of the bend 310.

In some embodiments, the outwardly-extending section 304b can form an angle of between about 20 degrees to about 70 degrees with a plane orthogonal to the longitudinal axis of the outer frame 300, an angle of between about 30 degrees to about 60 degrees with a plane orthogonal to the longitudinal axis of the outer frame 300, an angle of between about 40 degrees to about 50 degrees with a plane orthogonal to the longitudinal axis of the outer frame 300, an angle of about 30 degrees with a plane orthogonal to the longitudinal axis of the outer frame 300, any subrange within these ranges, or any other angle as desired. In some embodiments, the outwardly-extending section 304b can form an angle of less than 70 degrees with a plane orthogonal to the longitudinal axis of the outer frame 200, an angle of less than 55 degrees with a plane orthogonal to the longitudinal axis of the outer frame 300, an angle of less than 40 degrees with a plane orthogonal to the longitudinal axis of the outer frame 300, an angle of less than 25 degrees with a plane orthogonal to the longitudinal axis of the outer frame 300, or less than any other angle as desired.

The intermediate region 306 of the outer frame body 302 can extend generally downwardly from the outwardly-extending section 304b of the upper region 304. As shown, the intermediate region 306 can have a generally bulbous shape with a greater diameter along a portion between the upper and lower ends of the intermediate region 306. However, it is to be understood that the diameters of the upper end, the lower end, and/or the portion therebetween can be the same such that the intermediate region 306 forms a generally cylindrical shape. In some embodiments, the diameter of the lower end can be larger than the diameter of the upper end. In other embodiments, the diameter of the upper end can be larger than the diameter of the lower end.

Although the outer frame body 302 has been described and illustrated as having a circular cross-sections, it is to be understood that all or a portion of the outer frame body 302 can be have a non-circular cross-section such as, but not limited to, a D-shape, an oval or an otherwise ovoid cross-sectional shape.

At the juncture between the upper region 304 and the intermediate region 306, the outer frame body 302 can include a bend 312. The bend 312 can be about a circumferential axis such that the intermediate region 306 extends in a direction more parallel to the longitudinal axis of the outer frame 300 than the outwardly-extending section 304b of the upper region 304. In some embodiments, the bend 312 can generally form an arc with an angle between about 20 degrees to about 90 degrees. For example, as shown in the illustrated embodiment, the arc can have an angle of about 60 degrees. In some embodiments, the bend 312 can form an arc with an angle between about 30 degrees to about 60 degrees. The radius of curvature of the arc may be constant such that the bend 312 forms a circular arc or may differ along the length of the bend 312.

The lower region 308 of the outer frame body 302 can extend generally downwardly from the lower end of the intermediate region 306. As shown, the lower region 308 of the outer frame body 302 can have a decreasing diameter from an upper end of the lower region 308 to a lower end of the lower region 308 such that the lower region 308 is inclined or curved radially inwards towards the longitudinal axis of the outer frame 300. This radially inward incline or curve of the lower region 308 can facilitate capture of native valve leaflets between the outer frame 300 and other portions, such as an anchoring feature, of the prosthesis in which the outer frame 300 is used. Moreover, this radially inward inclined or curve of the lower region 308 can reduce or inhibit potential trauma to tissue of the body cavity, such as the native leaflets and/or native valve annulus. For example, the curvature and/or inclination of the lower region 308 can be chosen to better conform to the curvature of tissue positioned between the outer frame 300 and an anchoring feature of another portion of a prosthesis in which the outer frame 300 is used.

The lower region 308 can be curved and/or inclined towards the longitudinal axis of the frame 300 such that the lower ends of the lower region 308 can extend in a direction that is between about 20 degrees to about 80 degrees with respect to a plane parallel to the longitudinal axis of the frame 300, between about 25 degrees to about 70 degrees with respect to a plane parallel to the longitudinal axis of the frame 300 between about 30 degrees to about 60 degrees with respect to a plane parallel to the longitudinal axis of the frame 300, about 30 degrees with respect to a plane parallel to the longitudinal axis of the frame 300. The lower region 308 can be curved and/or inclined towards the longitudinal axis of the frame 300 such that the lower ends of the lower region 308 can extend in a direction generally perpendicular to the longitudinal axis of the frame 300.

In some embodiments, the outer frame body 302 in an expanded configuration can have a diameter at its widest portion of between about 30 mm to about 60 mm, between about 35 mm to about 55 mm, about 40 mm, any sub-range within these ranges, or any other diameter as desired. In some embodiments, the outer frame body 302 in an expanded configuration can have a diameter at its narrowest portion between about 20 mm to about 40 mm, any sub-range within these ranges, or any other diameter as desired. In some embodiments, the outer frame body 302 in an expanded configuration can have a diameter at a lower end of the lower region 308 between about 20 mm to about 40 mm, any sub-range within these ranges, or any other diameter as desired. In some embodiments, in an expanded configuration, the ratio of the diameter of the outer frame body 302 at its widest portion to the diameter of the frame body 302 at its narrowest portion can be about 3:1, about 5:2, about 2:1, about 3:2, about 4:3, any ratio within these ratios, or any other ratio as desired.

The outer frame body 302 can have an axially compact configuration relative to the radial dimension. In some embodiments, the outer frame body 302 in an expanded configuration can have an the axial dimension between the upper and lower ends of the outer frame body 302 (i.e., the "height" of the outer frame body 302) of between about 10 mm to about 40 mm, between about 18 mm to about 30 mm, about 20 mm, any sub-range within these ranges, or any other height as desired. For example, the ratio of the diameter of the largest portion of the outer frame body 302 to the height of the outer frame body 302 when the frame is in its expanded configuration can be about 3:1, about 5:2, about 2:1, about 3:2, about 4:3, about 13:10, about 5:4, or about 1:1. Thus, in some embodiments the width at the largest portion of the outer frame body 302 can be greater than the height of the outer frame body 302.

With continued reference to the outer frame 300 illustrated in FIGS. 7-8, the outer frame body 302 can include a plurality of struts with at least some of the struts forming cells 314a-c. Any number of configurations of struts can be used, such as rings of undulating struts shown forming ellipses, ovals, rounded polygons, and teardrops, but also chevrons, diamonds, curves, and various other shapes.

The upper row of cells 314a can have an irregular hexagonal shape such as the illustrated "heart" shape. The cell 314a can be formed via a combination of struts. As shown in the illustrated embodiment, the upper portion of cells 314a can be formed from a set of circumferentially-expansible struts 316a having a zig-zag or undulating shape forming a repeating "V" shape. The circumferentially-expansible struts 316a can be inclined or curved radially outwards away from the longitudinal axis of the outer frame 300 such that an upper portion of the struts 316a is positioned closer to the longitudinal axis of the outer frame 300 than the lower portion of the struts 316a. As shown in the illustrated embodiment, the circumferentially-expansible struts can incorporate bend 310 of the outer frame body 302.

The lower portion of cells 314a can be formed from a set of circumferentially-expansible struts 316b having a zig-zag or undulating shape forming a repeating "V" shape. The lower tips or ends of the circumferentially-expansible struts 316b can be at or proximate the junction of the upper region 304 and the intermediate region 306. As shown in the illustrated embodiment, the circumferentially-expansible struts can incorporate part of bend 312 of the outer frame body 302. One or more of the upper ends or tips of the circumferentially-expansible struts 316b can be a "free" apex which is not connected to a strut. For example, as shown in the illustrated embodiment, every other upper end or tip of circumferentially-expansible struts 316b is a free apex. However, it is to be understood that other configurations can be used. For example, every upper apex along the upper end can be connected to a strut.

The middle and/or lower rows of cells 314b-c can have a different shape from the cells 314a of the first row. The middle row of cells 314b and the lower row of cells 314c can have a diamond or generally diamond shape. The diamond or generally diamond shape can be formed via a combination of struts. The upper portion of cells 314b can be formed from the set of circumferentially-expansible struts 316b such that cells 314b share struts with cells 314a. The lower portion of cells 314b can be formed from a set of circumferentially-expansible struts 316c. As shown in the illustrated embodiment, one or more of the circumferentially-expansible struts 316c can extend generally in a downward direction and can incorporate part of bend 312 of the outer frame body 302. For example, the one or more circumferentially-expansible struts 316c can be curved such that an upper portion of the struts 316c are positioned closer to the longitudinal axis of the outer frame 300 than a portion of the struts 316c positioned between the upper and lower ends of the struts 316c. In some embodiments, one or more of the circumferentially-expansible struts 316c can extend radially outward from the longitudinal axis of the outer frame 300.

The upper portion of cells 314c can be formed from the set of circumferentially-expansible struts 316c such that cells 314c share struts with cells 314b. The lower portion of cells 314c can be formed from a set of circumferentially-expansible struts 316d. Circumferentially-expansible struts 316d can extend generally in a downward direction. As shown in the illustrated embodiment, the circumferentially-expansible struts 316e can be inclined or curved towards the longitudinal axis of the outer frame 300 such that an upper portion of the struts 316d can be positioned closer to the longitudinal axis of the outer frame 300 than the lower portion of the struts 316d. In some embodiments, the circumferentially-expansible struts 316d can extend in a direction generally parallel to the longitudinal axis of the outer frame 300.

As shown in the illustrated embodiment, there can be a row of twelve cells 314a, a row of twenty-four cells 314b, and a row of twenty-four cells 314c. While each of the cells 314a-c are shown as having the same shape as other cells 314a-c of the same row, it is to be understood that the shapes of cells 314a-c within a row can differ. Moreover, it is to be understood that any number of rows of cells can be used and any number of cells may be contained in the rows. In some embodiments, the number of cells can correspond to the number of anchors or anchor tips forming the anchoring features of the prosthesis in which the outer frame 300 is used such as, but not limited to, a 1:1 correspondence, a 2:1 correspondence, a 3:1 correspondence, a 4:1 correspondence, a 5:1 correspondence, a 6:1 correspondence, and other ratios as desired. In some embodiments, all three rows of cells 314a-c can have the same the number of cells. Moreover, it is to be understood that fewer or greater numbers of rows of cells can be used.

The geometry of cells 314a-c can allow the cells 314a-c to foreshorten as the outer frame 300 is expanded. As such, one or more of cells 314a-c can allow the outer frame 300 to foreshorten as the outer frame 300 is expanded. Foreshortening of the outer frame 300 can be used to secure the prosthesis to intralumenal tissue in a body cavity such as a native valve including, but not limited to, a native valve annulus and/or leaflets. For example, expansion of the outer frame 300 can allow the outer frame 300 to exert a radially outward force against the tissue at or adjacent the native valve, such as the native valve annulus and/or leaflets.

As shown in the illustrated embodiment, the outer frame 300 can include tabs 318 extending from a portion of the frame 300 such as an upper end of the frame body 302. The tabs 318 can include an eyelet 320. The tab 318 can be advantageously used to couple the outer frame 300 to an inner frame, such as inner frames 120, 220, of the prosthesis in which the outer frame 300 is used. For example, a suture can be passed through the eyelet 320 for coupling to an inner frame. In some embodiments, the tabs 318 can be used to couple to other components of a prosthesis in which the outer frame 300 is used such as, but not limited to, a valve body and/or a skirt.

In some embodiments, the tab 318 can be advantageously used to couple the outer frame 300 with multiple types of delivery systems. For example, the shape of the tab 318 can be used to secure the outer frame 300 to a "slot" based delivery system. The eyelets 320 can be used to secure the outer frame 300 to a "tether" based delivery system such as those which utilize sutures, wires, or fingers to control delivery of the outer frame 300 and the prosthesis. This can advantageously facilitate recapture and repositioning of the outer frame 300 and the prosthesis in situ. In some embodiments, the outer frame 300 and prosthesis can be used with the delivery systems described herein, including but not limited to, those described in U.S. Pat. Nos. 8,414,644 and 8,652,203 and U.S. Publication Nos. 2015/0238315, the entireties of each of which have been incorporated by reference herein. In some embodiments, a tab can be positioned at an end of a strut similar to locking tabs 232.

Figure 9:
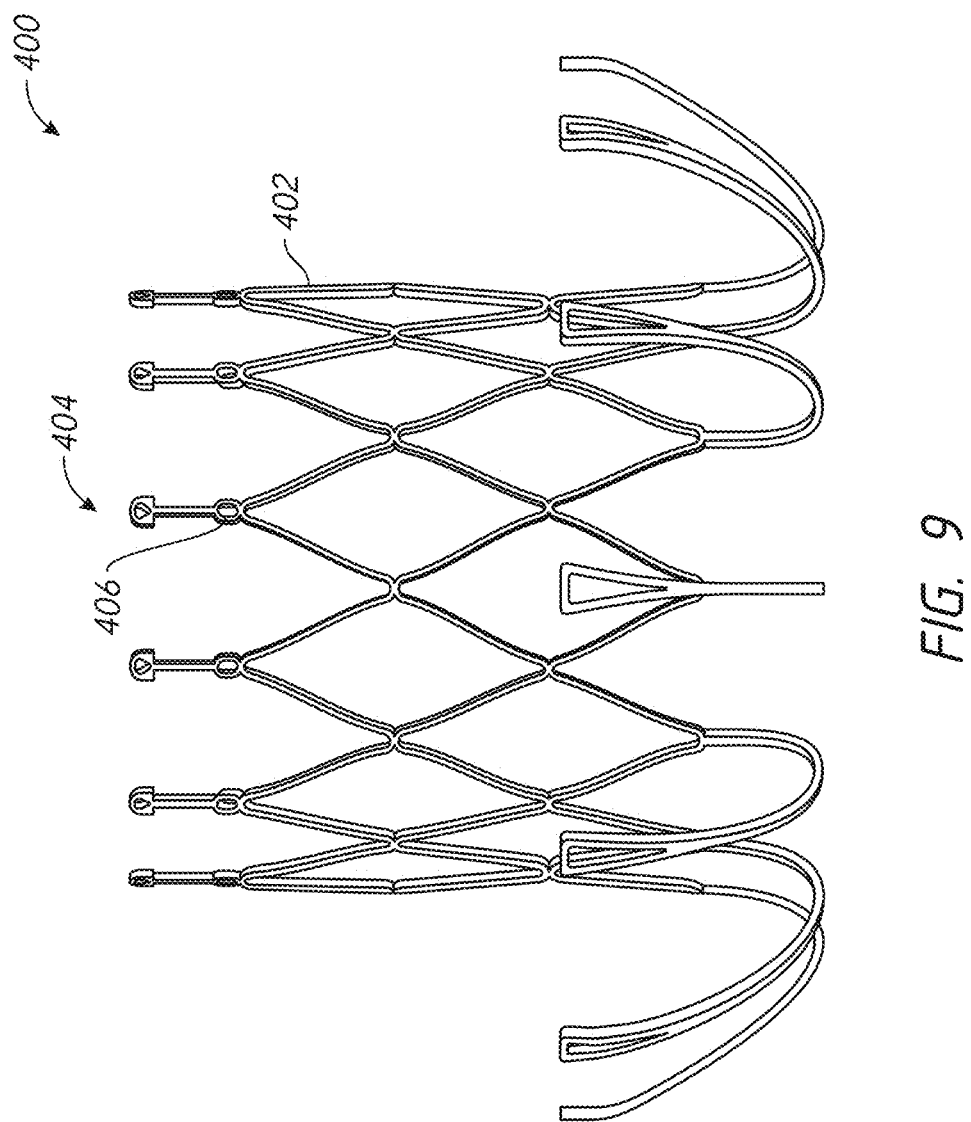
FIG. 9 is a side view of a front-half of another embodiment of an inner frame.

With reference next to FIGS. 9-10, an embodiment of an inner frame 400 in an expanded configuration is illustrated. The inner frame 400 can include an inner frame body 402. The inner frame 400 can share characteristics, such as structure and/or functionality, which are the same as, or at least similar to, those of inner frame 220 described above in connection with FIGS. 2-6. As such, reference should be made to the description of inner frame 220 above.

As shown in the illustrated embodiment, the inner frame 400 can include tabs 404 extending from a portion of the inner frame 400, such as an upper end of the frame body 402. The inner frame 400 can include an eyelet 406. The eyelet 406 can be advantageously used to couple the inner frame 400 to an outer frame, such as outer frames 120, 220, 300, of the prosthesis in which the inner frame 400 is used. For example, a suture can be passed through the eyelet 406 for coupling to an eyelet 320 of the outer frame 300. In some embodiments, the eyelet 406 can be used to couple to other components of a prosthesis in which the inner frame 400 is used such as, but not limited to, a valve body and/or a skirt.

In some embodiments, the tab 404 can be advantageously used to couple the inner frame 400 with multiple types of delivery systems. For example, the shape of the tab 404 can be used to secure the inner frame 400 to a "slot" based delivery system. The eyelets 406 can be used to secure the inner frame 400 to a "tether" based delivery system such as those which utilize sutures, wires, or fingers to control delivery of the inner frame 400 and the prosthesis. This can advantageously facilitate recapture and repositioning of the inner frame 400 and the prosthesis in situ. In some embodiments, the inner frame 400 and prosthesis can be used with the delivery systems described herein, including but not limited to, those described in U.S. Pat. Nos. 8,414,644 and 8,652,203 and U.S. Publication Nos. 2015/0238315, the entireties of each of which have been incorporated by reference herein. In such embodiments, the tab 404 may be omitted to advantageously the axial dimension between the upper end and the lower end of the inner frame 400 (i.e., the "height" of the inner frame 400).

Figure 33:
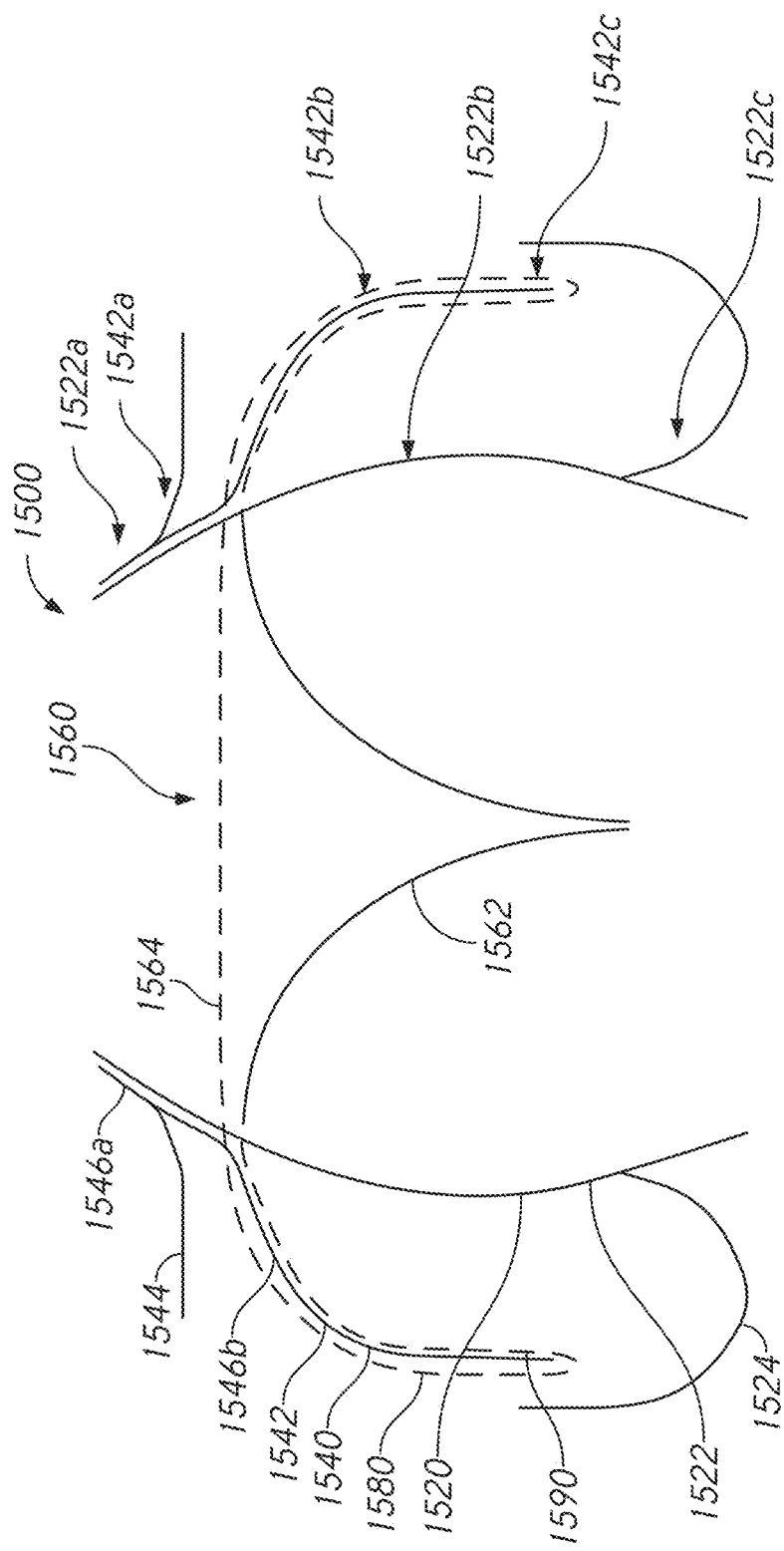
FIG. 33 is a side-oriented cross-sectional schematic view of another embodiment of a prosthesis having an inner frame, an outer frame, a valve body, and a skirt.

With reference next to FIG. 33, an embodiment of a prosthesis 1500 in an expanded configuration is illustrated. The prosthesis 1500 can include an inner frame 1520, an outer frame 1540, a valve body 1560, and one or more skirts, such as an outer skirt 1580 and an inner skirt 1590. The prosthesis 1500 can share characteristics, such as structure and/or functionality, which are the same as, or at least similar to, those of other prostheses described herein such as, but not limited to prosthesis 100.

With reference first to the inner frame 1520, the inner frame 1520 can include an inner frame body 1522 and an inner frame anchoring feature 1524. The inner frame body 1522 can have an upper region 1522a, an intermediate region 1522b, and a lower region 1522c. As shown, the inner frame body 1522 can have a generally bulbous shape such that the diameters of the upper region 1522a and the lower region 1522c are less than the diameter of the intermediate region 1522b. The diameter of the upper region 1522a can be less than the diameter of the lower region 1522c. This can beneficially allow the use of a smaller valve body 1560 within the inner frame 1520 while allowing the inner frame body 1522 to have a larger diameter proximate the connection between the inner frame body 1522 and the inner frame anchoring feature 1524. This larger diameter can reduce the radial distance between the connection and the tip or end of the inner frame anchoring feature 1524. This can beneficially enhance fatigue resistance of the inner frame anchoring feature 1524 by reducing the length of the cantilever.

While the illustrated inner frame body 1522 is bulbous, it is to be understood that the diameters of the upper region 1522a, the intermediate region 1522b, and/or the lower region 1522c can be the same such that the inner frame body 1522 is generally cylindrical along one or more regions. Moreover, while the illustrated embodiment includes a lower region 1522a having a greater diameter than the upper region 1522c, it is to be understood that the diameters of the upper and lower regions 1522a, 1522c can be the same or the diameter of the upper region 1522a can be greater than the diameter of the lower region 1522c. Moreover, although the inner frame body 1522 has been described and illustrated as being cylindrical or having circular cross-sections, it is to be understood that all or a portion of the inner frame body 1522 can have a non-circular cross-section such as, but not limited to, a D-shape, an oval or an otherwise ovoid cross-sectional shape.

With reference next to the outer frame 1540 illustrated in FIG. 33, the outer frame 1540 can be attached to the inner frame 1520 using any of the fasteners and/or techniques described herein. Although the outer frame 1540 is illustrated as a separate component from the inner frame 1520, it is to be understood that the frames 1520, 1540 can be unitarily or monolithically formed.

As shown in the illustrated embodiment, the outer frame 1540 can include an outer frame body 1542 and an outer frame anchoring feature 1544. The outer frame body 1542 can have an upper region 1542a, an intermediate region 1542b, and a lower region 1542c. When in an expanded configuration such as a fully expanded configuration, the outer frame body 1542 can have an enlarged shape with the intermediate region 1542b and the lower region 1542c being larger than the upper region 1542a. The enlarged shape of the outer frame body 1542 can advantageously allow the outer frame body 1542 to engage a native valve annulus, native valve leaflets, or other tissue of the body cavity, while spacing the upper end from the heart or vessel wall.

The upper region 1542a of the outer frame body 1542 can include a first section 1546a and a second section 1546b. The first section 1546a can be sized and/or shaped to generally match the size and/or shape of the inner frame 1520. For example, the first section 1546a can have a curvature which matches a curvature of the upper region 1522a of the inner frame body 1522. The second section 1546b can extend radially outwardly away from the inner frame 1520. As shown in the illustrated embodiment, the transition between the first section 1546a and the second section 1546b can incorporate a bend such that the second section 1546b extends radially outwardly at a greater angle relative to the longitudinal axis.

The intermediate region 1542b of the outer frame body 1542 can extend generally downwardly from the outwardly-extending section 1546b of the upper region 1542a. As shown, the intermediate region 1542b can have a generally constant diameter from an upper end to a lower end such that the intermediate region 1542b forms a generally cylindrical shape. The lower region 1542c of the outer frame body 1542 can extend generally downwardly from the lower end of the intermediate region 1542b. As shown, the lower region 1542c of the outer frame body 1542 can have a generally constant diameter from an upper end to a lower end such that the lower region 1542c forms a generally cylindrical shape. As shown, the diameters of the intermediate region 1542b and the lower region 1542c are generally equivalent such that the intermediate region 1542b and the lower region 1542c together form a generally cylindrical shape.

While the intermediate and lower regions 1542b, 1542c have been described as cylindrical, it is to be understood that the diameters of the upper end, the lower end, and/or the portion therebetween can be different. For example, a diameter of the portion between the upper end and the lower end can be larger than the upper end and the lower end such that the intermediate region 1542b and/or lower region 1542c forms a generally bulbous shape. In some embodiments, the diameter of the lower end can be larger than the diameter of the upper end. In other embodiments, the diameter of the upper end can be larger than the diameter of the lower end. Moreover, although the outer frame body 1542 has been described and illustrated as being cylindrical or having circular cross-sections, it is to be understood that all or a portion of the outer frame body 1542 can be have a non-circular cross-section such as, but not limited to, a D-shape, an oval or an otherwise ovoid cross-sectional shape.

With continued reference to the outer frame 1540 illustrated in FIG. 33, the outer frame anchoring feature 1544 can extend outwardly relative to the longitudinal axis of the prosthesis 1500. As shown in the illustrated embodiment, the outer frame anchoring feature 1544 is attached to the outer frame body 1542 along the upper region 1542a. The outer frame anchoring feature 1544 can be attached to the outer frame body 1542 such that, when transitioning from a collapsed configuration to an expanded configuration, the tip or end of the outer frame anchoring feature 1544 moves radially outwardly and upwardly.

In some embodiments, the outer frame anchoring feature 1544 can be attached to the outer frame body 1542 along a portion having a larger diameter, such as the intermediate region 1542b and/or the second section 1546b. This can beneficially increase the radial extent of the outer frame anchoring feature 1544 while maintaining the same anchor length. Moreover, in some embodiments, the outer frame anchoring feature 1544 can be attached to the outer frame body 1542 such that, when transitioning from a collapsed configuration to an expanded configuration, the tip or end of the outer frame anchoring feature 1544 moves radially outwardly and downwardly. This can beneficially facilitate alignment of the prosthesis 1500. For example, in the event that a portion of the prosthesis 1500 is positioned too far into the ventricle, the outer frame anchoring features 1544 can contact tissue of the native mitral valve and exert a force to elevate at least that portion of the prosthesis 1500. In some embodiments, the outer frame anchoring feature 1544 can include one or more individual anchors to allow the individual anchors to operate independently of other anchors. In some embodiments, the outer frame anchoring feature 1544 can be relatively flexible. For example, the outer frame anchoring feature 1544 can incorporate anchors having the serpentine shape of anchoring feature 2600 described in connection with FIG. 50.

The outer frame 1540, such as the outer frame body 1542 can be used to attach or secure the prosthesis 1500 to a native valve, such as a native mitral valve. For example, the intermediate region 1542b of the outer frame body 1542 and/or the outer anchoring feature 1544 can be positioned to contact or engage a native valve annulus, tissue beyond the native valve annulus, native leaflets, and/or other tissue at or around the implantation location during one or more phases of the cardiac cycle, such as systole and/or diastole. As another example, the outer frame body 1542 can be sized and positioned relative to the inner frame anchoring feature 1524 such that tissue of the body cavity positioned between the outer frame body 1542 and the inner frame anchoring feature 1524, such as native valve leaflets and/or a native valve annulus, can be engaged or pinched to further secure the prosthesis 1500 to the tissue.

With continued reference to the prosthesis 1500 illustrated in FIG. 33, the valve body 1560 is attached to the inner frame 1520 within an interior of the inner frame body 1522. The valve body 1560 functions as a one-way valve to allow blood flow in a first direction through the valve body 1560 and inhibit blood flow in a second direction through the valve body 1560.

The valve body 1560 can include a plurality of valve leaflets 1562, for example three leaflets 1562, which are joined at commissures. The valve body 1560 can include one or more intermediate components 1564. The intermediate components 1564 can be positioned between a portion of, or the entirety of, the leaflets 1562 and the inner frame 1520 such that at least a portion of the leaflets 1542 are coupled to the frame 1520 via the intermediate component 1564. In this manner, a portion of, or the entirety of, the portion of the valve leaflets 1562 at the commissures and/or an arcuate edge of the valve leaflets 1562 are not directly coupled or attached to the inner frame 1520 and are indirectly coupled or "float" within the inner frame 1520. For example, a portion of, or the entirety of, the portion of the valve leaflets 1562 proximate the commissures and/or the arcuate edge of the valve leaflets 1562 can be spaced radially inward from an inner surface of the inner frame 1520. By using one or more intermediate components 1564, the valve leaflets 1562 can be attached to non-cylindrical frames 1520 and/or frames 1520 having a diameter larger than that of the diameter of the valve leaflets 1562. Further details on floating valve concepts can be found in U.S. application Ser. No. 15/653,390, entitled REPLACEMENT HEART VALVE PROSTHESIS, filed on Jul. 18, 2017, the entirety of which has been incorporated herein by reference.

With reference next to the outer skirt 1580 illustrated in FIG. 33, the outer skirt 1580 can be attached to the inner frame 1520 and/or outer frame 1540. As shown, the outer skirt 1580 can be positioned around and secured to a portion of, or the entirety of, the exterior of the outer frame 1540. The skirt 1580 can also be secured to a portion of the valve body 1560 such as, but not limited to, the intermediate components 1564. For example, the skirt 1580 can be attached to an inflow region of the intermediate components 1564. As shown, the outer skirt 1580 can follow the contours of the outer frame 1540; however, it is to be understood that at least a portion of the skirt 1580 can be spaced apart from at least a portion of both the inner frame 1520 and the outer frame 1540.

With reference next to the inner skirt 1590 illustrated in FIG. 33, the inner skirt 1590 can be attached to the valve body 1560 and the outer skirt 1580. As shown, a first end of the inner skirt 1590 can be coupled to the valve body 1560 along portions of the valve body 1560 which are proximate the inner frame 1520. A second end of the inner skirt 1590 can be attached to the lower region of the outer skirt 1580. In so doing, a smooth surface can be formed under each of the leaflets. This can beneficially enhance hemodynamics by allowing blood to more freely circulate and reducing areas of stagnation. In some embodiments, the inner skirt 1590 can beneficially reduce contact between the outer frame body 1542 and the inner frame body 1522.

Although the prosthesis 1500 has been described as including an inner frame 1520, an outer frame 1540, a valve body 1560, and skirts 1580, 1590, it is to be understood that the prosthesis 1500 need not include all components. For example, in some embodiments, the prosthesis 1500 can include the inner frame 1520, the outer frame 1540, and the valve body 1560 while omitting the skirt 1580. Moreover, although the components of the prosthesis 1500 have been described and illustrated as separate components, it is to be understood that one or more components of the prosthesis 1500 can be integrally or monolithically formed. For example, in some embodiments, the inner frame 1520 and the outer frame 1540 can be integrally or monolithically formed as a single component.

Figure 34:
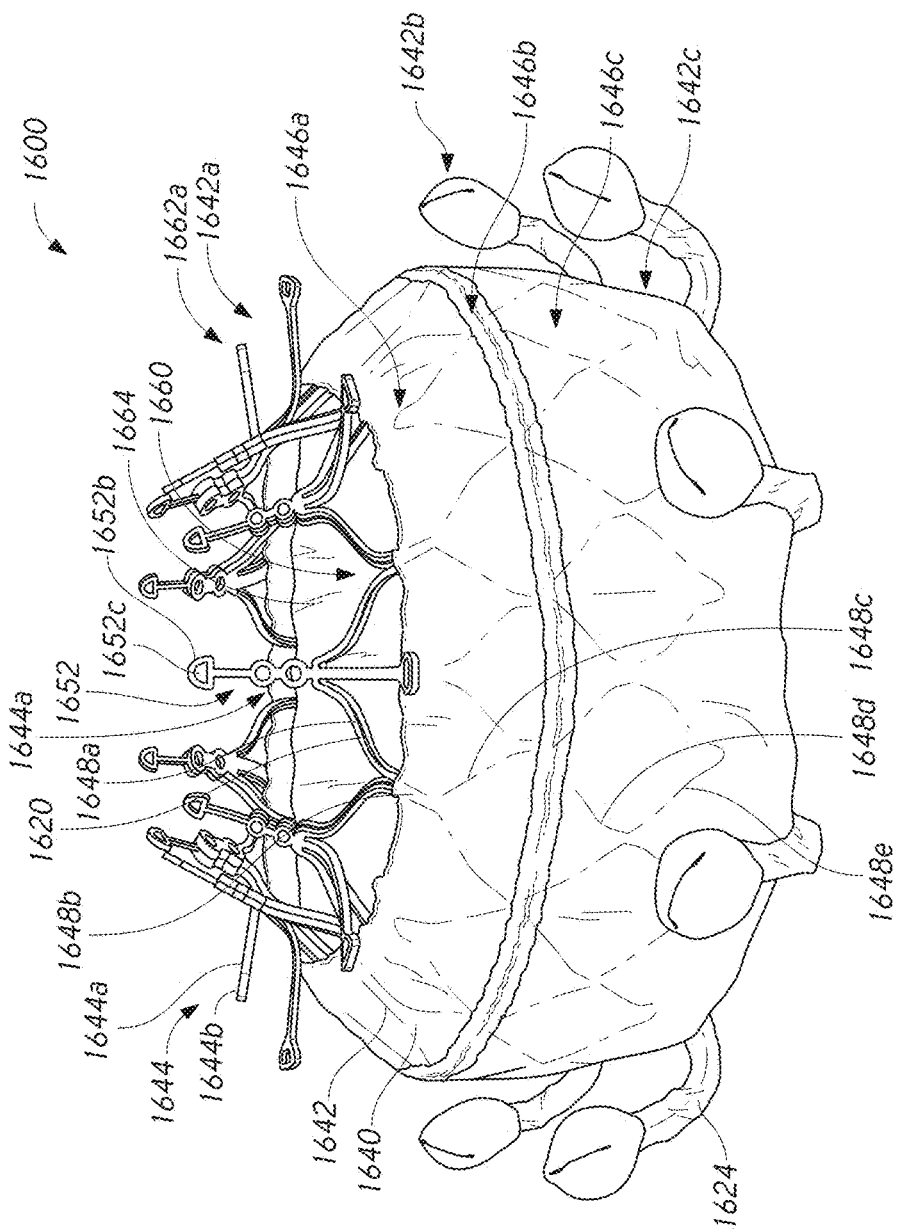
FIG. 34 is a top-oriented perspective view of another embodiment of a prosthesis having an inner frame, an outer frame, a valve body, and a skirt.
Figure 35:
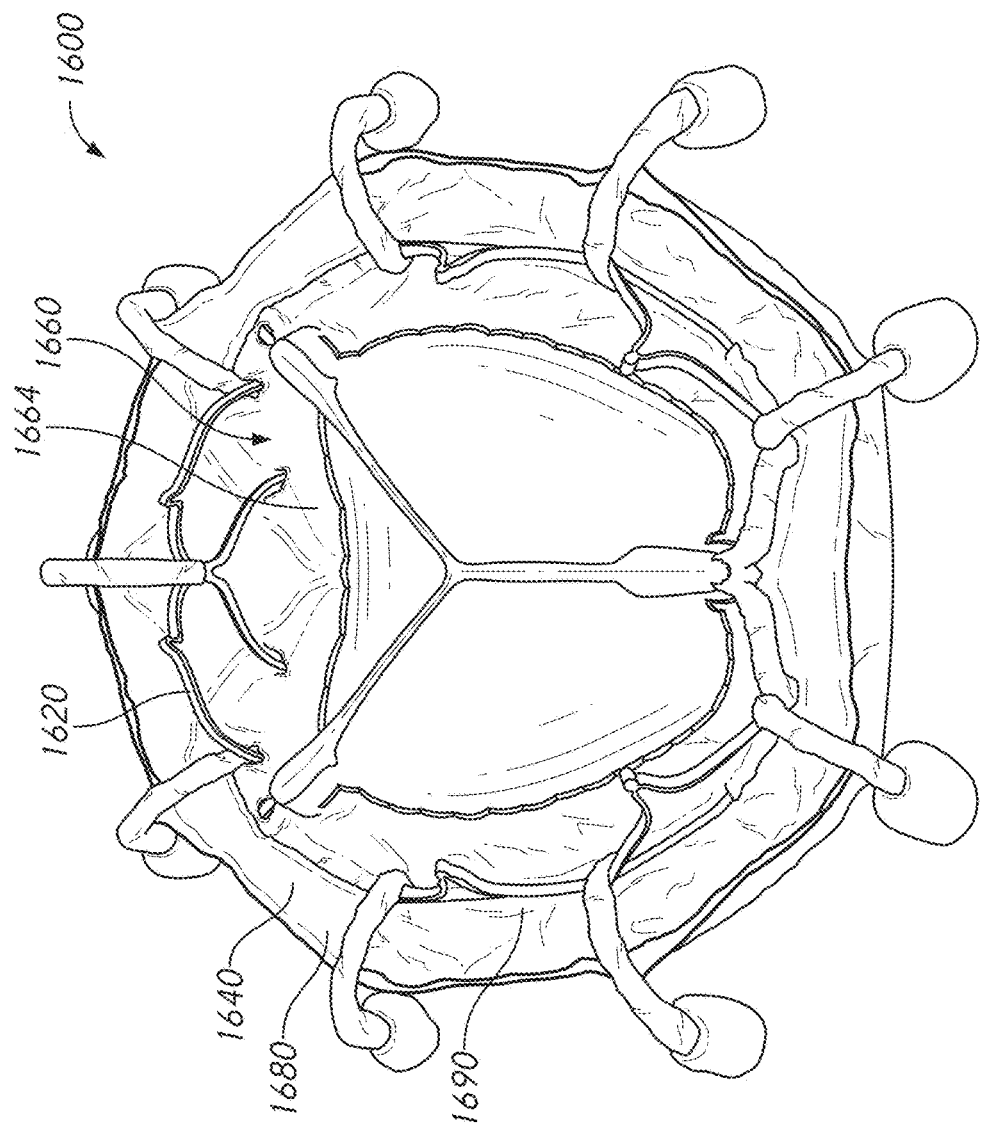
FIG. 35 is a bottom view of the prosthesis of FIG. 34.

With reference next to FIGS. 34-35, an embodiment of a prosthesis 1600 in an expanded configuration is illustrated. The prosthesis 1600 can include an inner frame 1620, an outer frame 1640, a valve body 1660, and one or more skirts, such as an outer skirt 1680 and an inner skirt 1690. The prosthesis 1600 can share characteristics, such as structure and/or functionality, which are the same as, or at least similar to, those of other prostheses described herein such as, but not limited to prostheses 100, 1500.

With reference first to the outer frame 1640 illustrated in FIGS. 34-35, the outer frame 1640 can be attached to the inner frame 1620 using any of the fasteners and/or techniques described herein. Although the outer frame 1640 is illustrated as a separate component from the inner frame 1620, it is to be understood that the frames 1620, 1640 can be unitarily or monolithically formed.

As shown in the illustrated embodiment, the outer frame 1640 can include an outer frame body 1642 and an outer frame anchoring feature 1644. The outer frame body 1642 can have an upper region 1642a, an intermediate region 1642b, and a lower region 1642c. At least a portion of the upper region 1642a of the outer frame body 1642 can be sized and/or shaped to generally match the size and/or shape of an upper region 1622a the inner frame 1620. As shown in the illustrated embodiment, the upper region 1642a of the outer frame body 1642 can include one or more struts which generally match the size and/or shape of struts of the inner frame 1620. This can locally reinforce a portion of the prosthesis 1600 by effectively increasing the wall thickness of the combined struts. Further details on reinforcing portions of the prosthesis can be found in U.S. application Ser. No. 15/653,390, entitled REPLACEMENT HEART VALVE PROSTHESIS, filed on Jul. 18, 2017, the entirety of which has been incorporated herein by reference.

When in an expanded configuration such as in a fully expanded configuration, the outer frame body 1642 can have a shape similar to that of outer frame body 1542 described above in connection with FIG. 33. As shown, the intermediate region 1642b and the lower region 1642c can have a diameter which is larger than the diameter of the upper region 1642a. The upper region 1642a of the outer frame body 1642 can have a decreasing diameter from a lower end to an upper end such that the upper region 1642a is inclined or curved radially inwards towards the longitudinal axis of the prosthesis 1600. Although the outer frame body 1642 has been described and illustrated as being cylindrical or having circular cross-sections, it is to be understood that all or a portion of the outer frame body 1642 can be have a non-circular cross-section such as, but not limited to, a D-shape, an oval or an otherwise ovoid cross-sectional shape.

With continued reference to the outer frame 1600 illustrated in FIG. 34, the outer frame body 1642 can include a plurality of struts with at least some of the struts forming cells 1646a-c. Any number of configurations of struts can be used, such as rings of undulating struts shown forming ellipses, ovals, rounded polygons, and teardrops, but also chevrons, diamonds, curves, and various other shapes.

The upper row of cells 1646a can have an irregular octagonal shape such as a "heart" shape. This larger shape can provide additional space for outer frame anchoring feature 1644. This additional space can beneficially allow the outer frame 1640 to retain a smaller profile when crimped. The cell 1646a can be formed via a combination of struts. As shown in the illustrated embodiment, the upper portion of cells 1646a can be formed from a set of circumferentially-expansible struts 1648a having a zig-zag or undulating shape forming a repeating "V" shape. The struts 1648a can extend radially outwardly from an upper end to a lower end. These struts can generally match the size and/or shape of struts of the inner frame 1620.

The middle portion of cells 1646a can be formed from a set of struts 1648b extending downwardly from bottom ends of each of the "V" shapes. The struts 1648b can extend radially outwardly from an upper end to a lower end. The portion of the cells 1646a extending upwardly from the bottom end of struts 1648b may be considered to be a substantially non-foreshortening portion of the outer frame 1640.

The lower portion of cells 1646a can be formed from a set of circumferentially-expansible struts 1648c having a zig-zag or undulating shape forming a repeating "V" shape. As shown in the illustrated embodiment, the struts 1648c can incorporate a curvature such that the lower end of struts 1648c extend more parallel with the longitudinal axis than the upper end of the struts 1648c. One or more of the upper ends or tips of the circumferentially-expansible struts 1648c can be a "free" apex which is not connected to a strut. For example, as shown in the illustrated embodiment, every other upper end or tip of circumferentially-expansible struts 1648b is a free apex. However, it is to be understood that other configurations can be used. For example, every upper apex along the upper end can be connected to a strut.

The middle and/or lower rows of cells 1646b-c can have a different shape from the cells 1646a of the first row. The middle row of cells 1646b and the lower row of cells 1646c can have a diamond or generally diamond shape. The diamond or generally diamond shape can be formed via a combination of struts.

The upper portion of cells 1646b can be formed from the set of circumferentially-expansible struts 1648c such that cells 1646b share struts with cells 1646a. The lower portion of cells 1646b can be formed from a set of circumferentially-expansible struts 1648d. As shown in the illustrated embodiment, one or more of the circumferentially-expansible struts 1648d can extend generally in a downward direction generally parallel to the longitudinal axis of the outer frame 1640.

The upper portion of cells 1646c can be formed from the set of circumferentially-expansible struts 1648d such that cells 1646c share struts with cells 1646b. The lower portion of cells 1646c can be formed from a set of circumferentially-expansible struts 1648e. Circumferentially-expansible struts 1648e can extend generally in a downward direction.

As shown in the illustrated embodiment, there can be a row of nine cells 1646a and a row of eighteen cells 1646b-c. While each of the cells 1646a-c are shown as having the same shape as other cells 1646a-c of the same row, it is to be understood that the shapes of cells 1646a-c within a row can differ. Moreover, it is to be understood that any number of rows of cells can be used and any number of cells may be contained in the rows.

With continued reference to FIGS. 34-35, the outer frame 1640 can include an outer frame anchoring feature 1644. The outer frame anchoring feature 1644 can include one or more individual anchors 1644a having tips or ends 1644b. As shown, the outer frame anchoring feature 1644 includes nine anchors; however, it is to be understood that a fewer or greater number of anchors can be used. For example, the outer frame anchoring feature 1644 can include three anchors 1644a.

As shown, the anchors 1644a extend from an upper portion of cells 1646a, such as an upper apex of cells 1646a. The anchors 1644a can extend downwardly. The anchors 1644a can be attached to the outer frame body 1642 such that, when transitioning from a collapsed configuration to an expanded configuration, the tip or end 1644b of the anchors 1644a moves radially outwardly and upwardly.

In some embodiments, one or more anchors 1644a can be attached to the outer frame body 1642 along struts 1648c. For example, the anchors 1644a can extend from one or more of the free apices. The anchors 1644a can be attached to the outer frame body 1642 such that, when transitioning from a collapsed configuration to an expanded configuration, the tip or end 1644b of the anchors 1644a moves radially outwardly and downwardly. This can beneficially facilitate alignment of the prosthesis 1600.

As shown in the illustrated embodiment, the outer frame 1600 can include a set of eyelets 1650. The upper set of eyelets 1650 can extend from an upper region 1642a of the outer frame body 1642. As shown, the upper set of eyelets 1650 can extend from an upper portion of cells 1646a, such as the upper apices of cells 1646a. The upper set of eyelets 1650 can be used to attach the outer frame 1640 to the inner frame 1620. For example, in some embodiments, the inner frame 1620 can include one or more eyelets which correspond to the eyelets 2150. In such embodiments, the inner frame 1620 and outer frame 1640 can be attached together via eyelets 1650 and corresponding eyelets on the inner frame 1620. For example, the inner frame 1620 and outer frame 1640 can be sutured together through said eyelets or attached via other means, such as mechanical fasteners (e.g., screws, rivets, and the like).

As shown, the set of eyelets 1650 can include two eyelets extending in series from each "V" shaped strut. This can reduce the likelihood that the outer frame 1640 twists along an axis of the eyelet. However, it is to be understood that some "V" shaped struts may not include an eyelet. Moreover, it is to be understood that a fewer or greater number of eyelets can extend from a "V" shaped strut.

The outer frame 1640 can include a set of locking tabs 1652 extending from at or proximate an upper end of the upper region 1642a. As shown, the locking tabs 1652 can extend upwardly from the set of eyelets 1650. The outer frame 1640 can include twelve locking tabs 1652, however, it is to be understood that a greater number or lesser number of locking tabs can be used. The locking tabs 1652 can include a longitudinally-extending strut 1652a. At an upper end of the strut 1652a, the locking tab 1652 can include an enlarged head 1652b. As shown, the enlarged head 1652b can have a semi-circular or semi-elliptical shape forming a "mushroom" shape with the strut 1652a. The locking tab 1652 can include an eyelet 1652c which can be positioned through the enlarged head 1652b. It is to be understood that the locking tab 1652 can include an eyelet at other locations, or can include more than a single eyelet.

The locking tab 1652 can be advantageously used with multiple types of delivery systems. For example, the shape of the struts 1652a and the enlarged head 1652b can be used to secure the outer frame 1640 to a "slot" based delivery system. The eyelets 1652c and/or eyelets 1650 can be used to secure the outer frame 1640 to a "tether" based delivery system such as those which utilize sutures, wires, or fingers to control delivery of the outer frame 1640 and the prosthesis 1600. This can advantageously facilitate recapture and repositioning of the outer frame 1640 and the prosthesis 1600 in situ. In some embodiments, the prosthesis 1600 can be used with the delivery systems described herein, including but not limited to, those described in U.S. Pat. Nos. 8,414,644 and 8,652,203 and U.S. Publication Nos. 2015/0238315, the entireties of each of which are hereby incorporated by reference and made a part of this specification.

The outer frame 1640, such as the outer frame body 1642 can be used to attach or secure the prosthesis 1600 to a native valve, such as a native mitral valve. For example, the intermediate region 1642*b* of the outer frame body 1642 and/or the outer anchoring feature 1644 can be positioned to contact or engage a native valve annulus, tissue beyond the native valve annulus, native leaflets, and/or other tissue at or around the implantation location during one or more phases of the cardiac cycle, such as systole and/or diastole. As another example, the outer frame body 1642 can be sized and positioned relative to the inner frame anchoring feature 1624 such that tissue of the body cavity positioned between the outer frame body 1642 and the inner frame anchoring feature 1624, such as native valve leaflets and/or a native valve annulus, can be engaged or pinched to further secure the prosthesis 1600 to the tissue. As shown, the inner frame anchoring feature 1624 includes nine anchors; however, it is to be understood that a fewer or greater number of anchors can be used. In some embodiments, the number of individual anchors can be chosen as a multiple of the number of commissures for the valve body 1660. For example, for a valve body 1660 have three commissures, the inner frame anchoring feature 1624 can have three individual anchors (1:1 ratio), six individual anchors (2:1 ratio), nine individual anchors (3:1 ratio), twelve individual anchors (4:1 ratio), fifteen individual anchors (5:1 ratio), or any other multiple of three. In some embodiments, the number of individual anchors does not correspond to the number of commissures of the valve body 1660.

With continued reference to the prosthesis 1600 illustrated in FIGS. 34-35, the valve body 1660 is attached to the inner frame 1620 within an interior of the inner frame body 1622. The valve body 1660 functions as a one-way valve to allow blood flow in a first direction through the valve body 1660 and inhibit blood flow in a second direction through the valve body 1660.

The valve body 1660 can include a plurality of valve leaflets 1662, for example three leaflets 1662, which are joined at commissures. The valve body 1660 can include one or more intermediate components 1664. The intermediate components 1664 can be positioned between a portion of, or the entirety of, the leaflets 1662 and the inner frame 1620 such that at least a portion of the leaflets 1642 are coupled to the frame 1620 via the intermediate component 1664. In this manner, a portion of, or the entirety of, the portion of the valve leaflets 1662 at the commissures and/or an arcuate edge of the valve leaflets 1662 are not directly coupled or attached to the inner frame 1620 and are indirectly coupled or "float" within the inner frame 1620. Further details on floating valve concepts can be found in U.S. application Ser. No. 15/653,390, entitled REPLACEMENT HEART VALVE PROSTHESIS, filed on Jul. 18, 2017, the entirety of which is incorporated herein by reference.

With reference next to the outer skirt 1680 illustrated in FIG. 34, the outer skirt 1680 can be attached to the inner frame 1620 and/or outer frame 1640. As shown, the outer skirt 1680 can be positioned around and secured to a portion of, or the entirety of, the exterior of the outer frame 1640. The inner skirt 1690 can be attached to the valve body 1660 and the outer skirt 1680. As shown, a first end of the inner skirt 1690 can be coupled to the valve body 1660 along portions of the valve body 1660 which are proximate the inner frame 1620. A second end of the inner skirt 1690 can be attached to the lower region of the outer skirt 1680. In so doing, a smooth surface can be formed along under each of the leaflets. This can beneficially enhance hemodynamics by allowing blood to more freely circulate and reducing areas of stagnation.

Although the prosthesis 1600 has been described as including an inner frame 1620, an outer frame 1640, a valve body 1660, and skirts 1680, 1690, it is to be understood that the prosthesis 1600 need not include all components. For example, in some embodiments, the prosthesis 1600 can include the inner frame 1620, the outer frame 1640, and the valve body 1660 while omitting the skirt 1680. Moreover, although the components of the prosthesis 1600 have been described and illustrated as separate components, it is to be understood that one or more components of the prosthesis 1600 can be integrally or monolithically formed. For example, in some embodiments, the inner frame 1620 and the outer frame 1640 can be integrally or monolithically formed as a single component.

Figure 36:
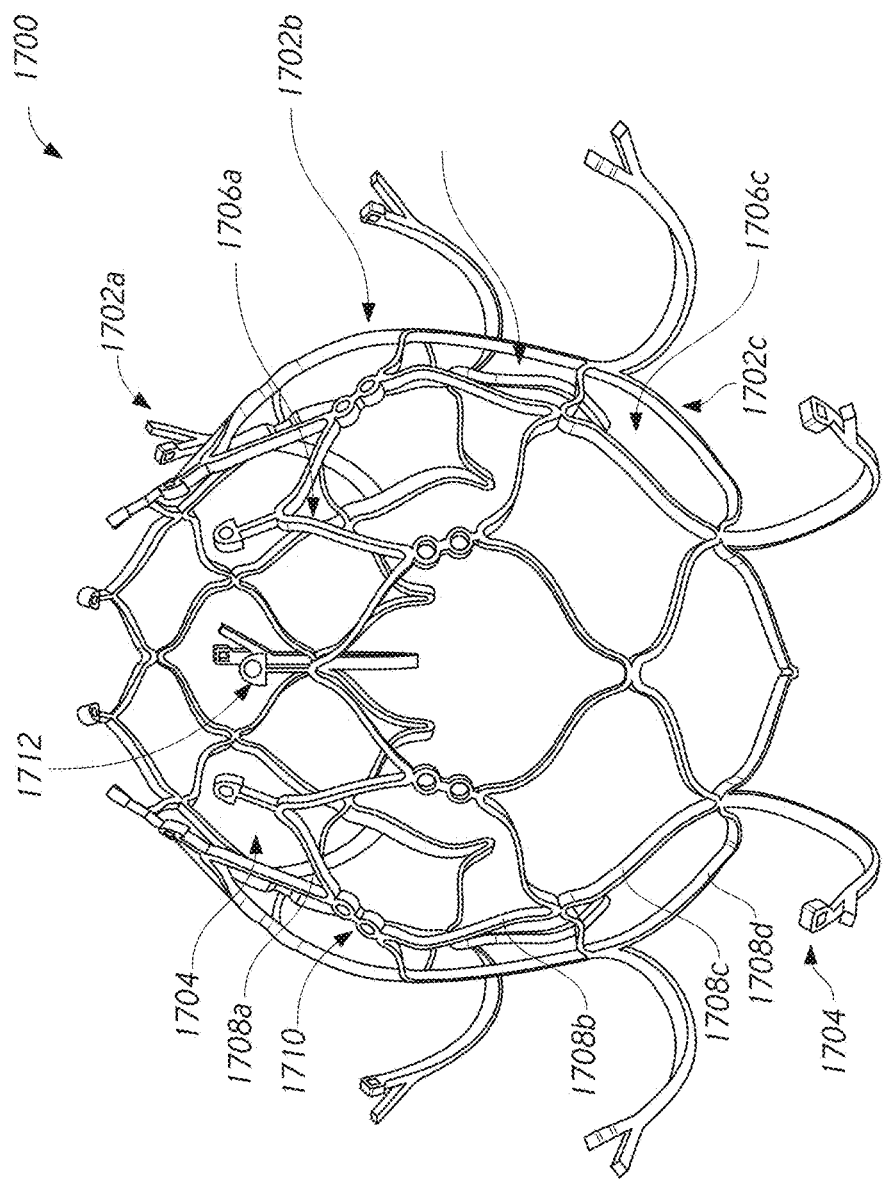
FIG. 36 is a top-oriented perspective view of another embodiment of an inner frame.

With reference next to FIG. 36, an embodiment of an inner frame 1700 in an expanded configuration is illustrated. The inner frame 1700 can include an inner frame body 1702, an inner frame anchoring feature 1704 and/or a set of locking tabs 1712. The locking tabs 1812 can include features similar to other locking tabs described herein. As shown in the illustrated embodiment, the tips or ends of the inner frame anchoring feature 1704 can incorporate two or more prongs which extend in different directions. This can beneficially increase a tissue contact surface for the tips or ends particularly when used with a cover or cushion.

The inner frame body 1702 can have an upper region 1702*a*, an intermediate region 1702*b*, and a lower region 1702*c*. The inner frame body 1702 can have a shape similar to that described above in connection with inner frame bodies 1520 and 1620. As shown, the inner frame body 1702 can have a generally bulbous shape such that the diameters of the upper region 1702*a* and the lower region 1702*c* are less than the diameter of the intermediate region 1702*b*. The diameter of the upper region 1702*a* can be less than the diameter of the lower region 1702*c*.

While the illustrated inner frame body 1702 is bulbous, it is to be understood that the diameters of the upper region 1702*a*, the intermediate region 1702*b*, and/or the lower region 1702*c* can be the same such that the inner frame body 1702 is generally cylindrical along one or more regions. Moreover, while the illustrated embodiment includes a lower region 1702*a* having a greater diameter than the upper region 1702*c*, it is to be understood that the diameters of the lower and upper regions 1702*a*, 1702*c* can be the same or the diameter of the upper region 1702*a* can be greater than the diameter of the lower region 1702*c*. Moreover, although the inner frame body 1702 has been described and illustrated as being cylindrical or having circular cross-sections, it is to be understood that all or a portion of the inner frame body 1702 can have a non-circular cross-section such as, but not limited to, a D-shape, an oval or an otherwise ovoid cross-sectional shape.

The inner frame body 1702 can include a plurality of struts with at least some of the struts forming cells 1706*a-c*. Any number of configurations of struts can be used, such as rings of undulating struts shown forming ellipses, ovals, rounded polygons, and teardrops, but also chevrons, diamonds, curves, and various other shapes.

The upper row of cells 1706*a* can have an elongated hexagonal shape. The cell 1706*a* can be formed via a combination of struts. As shown in the illustrated embodiment, the upper portion of cells 1706*a* can be formed from a set of circumferentially-expansible struts 1708*a* having a zig-zag or undulating shape forming a repeating "V" shape. The struts 1708a can extend radially outwardly from an upper end to a lower end.

The middle portion of cells 1706a can be formed from a set of eyelets 1710 extending downwardly from bottom ends of each of the "V" shapes. The eyelets 1710 can extend radially outwardly from an upper end to a lower end. The eyelets 1710 can be used to attach various components to the inner frame 1700. In some embodiments, the eyelets 1710 can be used to attach the inner frame 1700 to an outer frame. For example, the outer frame may be similar to outer frame 1640 having eyelets 1650. Such an attachment location can be lower than that illustrated in connection with prosthesis 1600. This can allow the use of a more axially compact outer frame. In some embodiments, the eyelets 1710 can be utilized to attach a valve body to the inner frame 1700.

The portion of the cells 1706a extending upwardly from the bottom end of eyelets 1710 may be considered to be a substantially non-foreshortening portion of the inner frame 1700. Although eyelets 1710 are used, it is to be understood that a strut can be utilized in lieu of or in combination with eyelets 1710.

The lower portion of cells 1706a can be formed from a set of circumferentially-expansible struts 1708b having a zig-zag or undulating shape forming a repeating "V" shape. As shown in the illustrated embodiment, the struts 1708b can incorporate a curvature such that the lower end of struts 1708b extend more parallel with the longitudinal axis than the upper end of the struts 1708b.

The middle and/or lower rows of cells 1706b-c can have a different shape from the cells 1706a of the first row. The middle row of cells 1706b and the lower row of cells 1706c can have a diamond or generally diamond shape. The diamond or generally diamond shape can be formed via a combination of struts.

The upper portion of cells 1706b can be formed from the set of circumferentially-expansible struts 1708b such that cells 1706b share struts with cells 1706a. The lower portion of cells 1706b can be formed from a set of circumferentially-expansible struts 1708c. As shown in the illustrated embodiment, one or more of the circumferentially-expansible struts 1708c can extend generally in a downward direction generally parallel to the longitudinal axis of the outer frame 1640.

The upper portion of cells 1706c can be formed from the set of circumferentially-expansible struts 1708c such that cells 1706c share struts with cells 1706b. The lower portion of cells 1706c can be formed from a set of circumferentially-expansible struts 1708d. Circumferentially-expansible struts 1708d can extend generally in a downward direction and/or radially inward direction.

As shown in the illustrated embodiment, there can be nine cells in each row of cells 1706a-c. While each of the cells 1706a-c are shown as having the same shape as other cells 1706a-c of the same row, it is to be understood that the shapes of cells 1706a-c within a row can differ. Moreover, it is to be understood that any number of rows of cells can be used and any number of cells may be contained in the rows.

Figure 37:
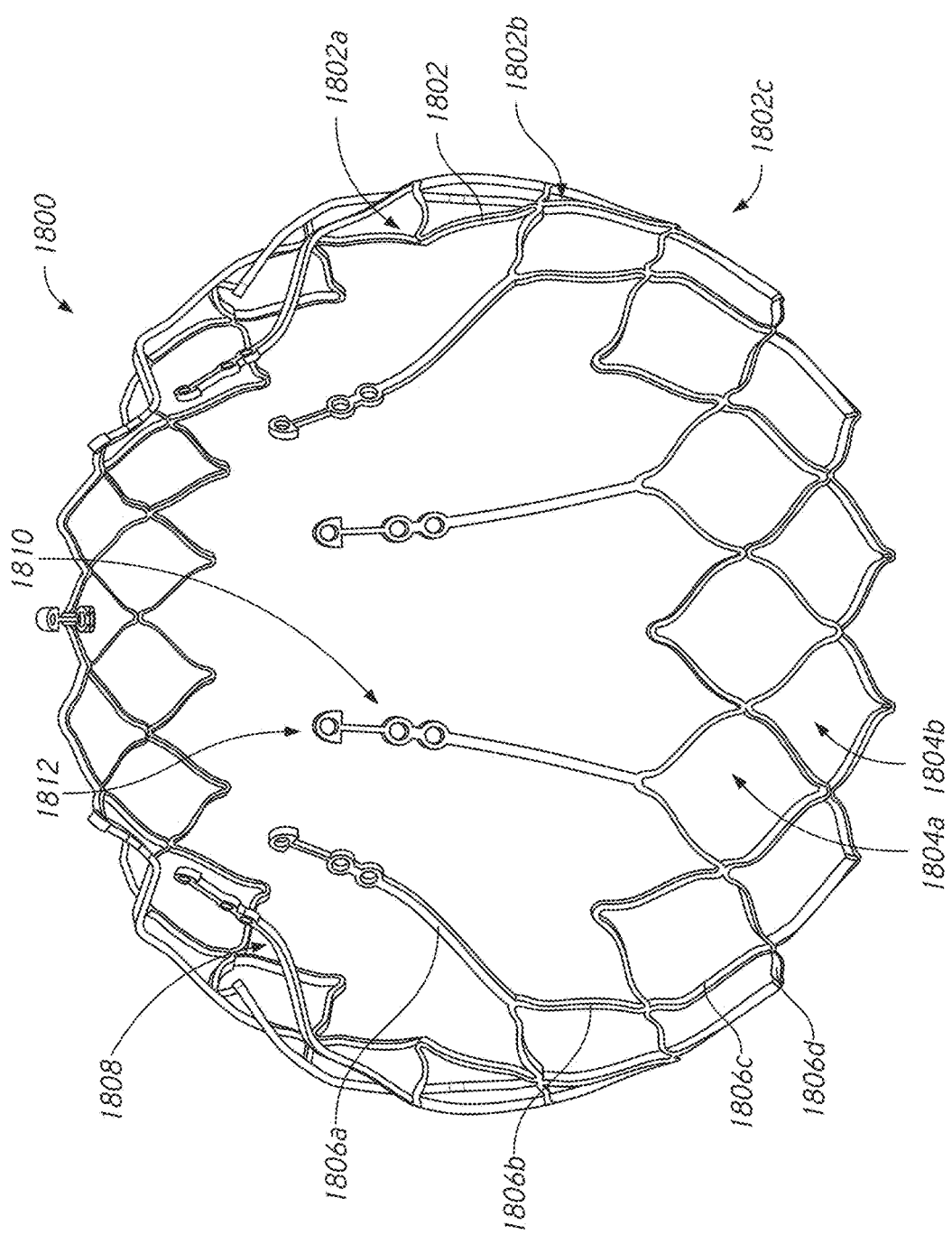
FIG. 37 is a top-oriented perspective view of another embodiment of an outer frame.

With reference next to FIG. 37, an embodiment of an outer frame 1800 in an expanded configuration is illustrated. The outer frame 1800 can include an outer frame body 1802 and/or locking tabs 1812. The locking tabs 1812 can include features similar to other locking tabs described herein.

When in an expanded configuration such as in a fully expanded configuration, the outer frame body 1802 can have a shape similar to that of outer frames 1540 and 1640 described above in connection with FIGS. 33 and 34-35. As shown, the intermediate region 1802b and the lower region 1802c can have a diameter which is larger than the diameter of the upper region 1802a. The upper region 1802a of the outer frame body 1802 can increase in diameter from an upper end to a lower end such that the upper region 1802a is inclined or curved radially outwards away from the longitudinal axis of the outer frame 1800. Although the outer frame body 1802 has been illustrated as having a circular cross-sections, it is to be understood that all or a portion of the outer frame body 1802 can be have a non-circular cross-section such as, but not limited to, a D-shape, an oval or an otherwise ovoid cross-sectional shape.

The outer frame body 1802 can include a plurality of struts with at least some of the struts forming cells 1804a-b. Any number of configurations of struts can be used, such as rings of undulating struts shown forming ellipses, ovals, rounded polygons, and teardrops, but also chevrons, diamonds, curves, and various other shapes.

The upper region 1802a can include an elongate strut 1806a. The elongate strut 1806a can extend radially outwardly from the longitudinal axis of the outer frame 1802. The elongate strut 1806a can incorporate a bend 1808 to orient an upper portion of the strut 1806a in a direction more parallel with the longitudinal axis. The use of an elongate strut 1806a can reduce the change in axial length when the outer frame 1800 transitions from a collapsed configuration to an expanded configuration.

In some embodiments, the elongate strut 1806a can beneficially dampen radial displacements and/or forces experienced by other portions of the outer frame body 1800. For example, the elongate strut 1806a can dampen radial displacements and/or forces due to compression of the intermediate and/or lower regions 1802b, 1802c during phases of the cardiac cycle. In situations where the outer frame 1800 is positioned within a native mitral valve, these compressive forces can be cyclically imparted by the native mitral valve annulus during phases of the cardiac cycle. Dampening of such displacements and/or forces by the elongate strut 1806a can reduce forces applied on an inner frame which may cause undesirable movement and/or deformation of the inner frame. The amount of dampening can be chosen by adjusting the width, length, taper, materials, and other characteristics of the elongate strut 1806a.

The upper row of cells 1804a can have a diamond or generally diamond shape. As shown in the illustrated embodiment, the upper portion of cells 1804a can be formed from a set of circumferentially-expansible struts 1806b having a zig-zag or undulating shape forming a repeating "V" shape. One or more of the upper ends or tips of the circumferentially-expansible struts 1806b can be a "free" apex which is not connected to a strut. For example, as shown in the illustrated embodiment, every other upper end or tip of circumferentially-expansible struts 1806b is a free apex. However, it is to be understood that other configurations can be used. For example, every upper apex along the upper end can be connected to a strut. The lower portion of cells 1804a can be formed from a set of circumferentially-expansible struts 1806c having a zig-zag or undulating shape forming a repeating "V" shape. Although the outer frame 1800 is shown without an anchoring feature, it is to be understood that an anchoring feature may be incorporated into the outer frame 1800 in a manner similar to those described in connection with other outer frames described herein. For example, an anchoring feature may extend from one or more of the free apices of the circumferentially-expansible struts 1806b.

The upper portion of cells 1804*b* can be formed from the set of circumferentially-expansible struts 1806*c* such that cells 1804*b* share struts with cells 1804*a*. The lower portion of cells 1804*b* can be formed from a set of circumferentially-expansible struts 1806*d*.

As shown in the illustrated embodiment, there can be a row of eighteen cells 1804*a-b*. While each of the cells 1804*a-b* are shown as having the same shape as other cells 1804*a-b* of the same row, it is to be understood that the shapes of cells 1804*a-b* within a row can differ. Moreover, it is to be understood that any number of rows of cells can be used and any number of cells may be contained in the rows.

As shown in the illustrated embodiment, the outer frame 1800 can include a set of eyelets 1810. The eyelets 1810 can extend from an upper region 1802*a* of the outer frame body 1802. As shown, the eyelets 1810 can extend from an upper end of struts 1806*a*. In some embodiments, the eyelets 1810 can be used to attach the outer frame 1800 to an inner frame. For example, the inner frame may be similar to inner frame 1620 and/or 1700 having eyelets 1710. This can allow the use of a more axially compact outer frame. In some embodiments, the eyelets 1710 can be utilized to attach a valve body to the inner frame 1700. In some embodiments, the upper set of eyelets 1810 can be used to attach the outer frame 1800 to a delivery system. For example, sutures or tethers of a delivery system can be attached or passed through the eyelets 1810.

Figure 38A:
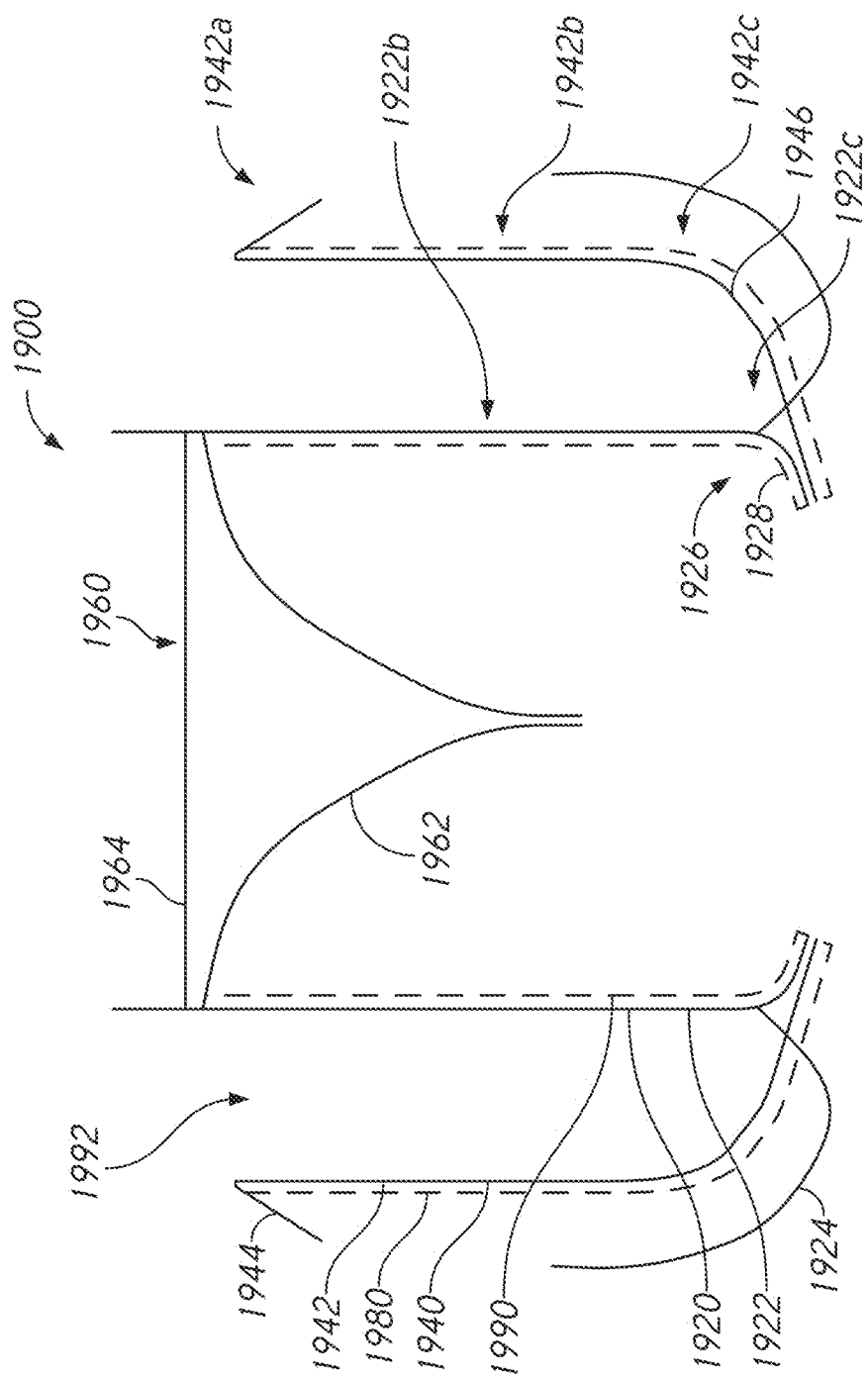
FIG. 38A is a side-oriented cross-sectional schematic view of another embodiment of a prosthesis having an inner frame, an outer frame, a valve body, and a skirt.

With reference next to FIG. 38A, an embodiment of a prosthesis 1900 in an expanded configuration is illustrated. The prosthesis 1900 can include an inner frame 1920, an outer frame 1940, a valve body 1960, and one or more skirts, such as outer skirt 1980 and inner skirt 1990. The prosthesis 1900 can share characteristics, such as structure and/or functionality, which are the same as, or at least similar to, those of other prostheses described herein.

With reference first to the inner frame 1920, the inner frame 1920 can include an inner frame body 1922 and an inner frame anchoring feature 1924. The inner frame body 1922 can have an upper region 1922*a*, an intermediate region 1922*b*, and a lower region 1922*c*. As shown, the inner frame body 1922 can have a generally cylindrical shape. The inner frame body 1922 can include a bend 1926 along a lower region 1922*c* of the inner frame body 1920 such that a region 1928 of the inner frame body 1920 tapers radially inwardly towards the longitudinal axis of the prosthesis 1900. The shape of region 1928 can match the shape of a portion of the outer frame 1940.

While the illustrated inner frame body 1922 is generally cylindrical, it is to be understood that the diameters of the upper region 1922*a*, the intermediate region 1922*b*, and/or the lower region 1922*c* can be different. For example, in some embodiments, a diameter of the intermediate region 1922*a* can be larger than the upper region 1922*b* and the lower region 1922*c* such that the frame body 1922 has a generally bulbous shape. Moreover, although the inner frame body 1922 has been described and illustrated as being cylindrical or having circular cross-sections, it is to be understood that all or a portion of the inner frame body 1922 can have a non-circular cross-section such as, but not limited to, a D-shape, an oval or an otherwise ovoid cross-sectional shape.

With reference next to the outer frame 1940 illustrated in FIG. 38A, the outer frame 1940 can be attached to the inner frame 1920 using any of the fasteners and/or techniques described herein. Although the outer frame 1940 is illustrated as a separate component from the inner frame 1920, it is to be understood that the frames 1920, 1940 can be unitarily or monolithically formed.

As shown in the illustrated embodiment, the outer frame 1940 can include an outer frame body 1942 and an outer frame anchoring feature 1944. The outer frame body 1942 can have an upper region 1942*a*, an intermediate region 1942*b*, and a lower region 1942*c*. When in an expanded configuration such as a fully expanded configuration, the outer frame body 1942 can have an enlarged shape with the upper region 1942*a* and the intermediate region 1942*b* being larger than the lower region 1942*c*. The enlarged shape of the outer frame body 1942 can advantageously allow the outer frame body 1942 to engage a native valve annulus, native valve leaflets, or other tissue of the body cavity, while spacing the upper end from the heart or vessel wall.

As shown in the illustrated embodiment, the lower region 1942*c* of the outer frame body 1942 can be attached to the lower region 1922*c* of the inner frame body 1922. This can provide significant advantages particularly with respect to the geometry of the prosthesis 1900 when the prosthesis 1900 is in a crimped or collapsed configuration. For example, in embodiments where the outer frame body 1942 is capable of foreshortening, any increase in the axial length of the outer frame body 1942 as the outer frame body 1942 is crimped occurs upwardly relative to the lower regions 1922*c*, 1942*c* from which the frame bodies are attached. In this manner, regardless of the axial length of the outer frame body 1942 in the crimped or collapsed configuration, the outer frame body 1942 can be prevented from extending over the inner frame anchoring features 1922 when crimped or collapsed.

The lower region 1942*c* of the outer frame body 1942 can include a region 1946. The region 1946 can extend radially inwardly towards the longitudinal axis of the prosthesis 1900. As shown in the illustrated embodiment, a portion of region 1946 can be sized and/or shaped to generally match the size and/or shape of the region 1928 of inner frame 1920. This can advantageously enhance securement of the outer frame 1940 to the inner frame 1920 by providing a greater area over which the outer frame 1940 can be attached to the inner frame 1920. Moreover, by bending the region 1928 of inner frame 1920 to match the shape of region 1946 of the outer frame 1940, the fatigue resistance of the outer frame 1940 can be enhanced as the lower end of outer frame 1940 need not be significantly bent to match the geometry of the inner frame 1920.

The intermediate region 1942*b* of the outer frame body 1942 can extend generally upwardly from the lower region 1942*c*. As shown, the intermediate region 1942*b* can have a generally constant diameter from an upper end to a lower end such that the intermediate region 1942*b* forms a generally cylindrical shape. The upper region 1942*a* of the outer frame body 1942 can extend generally upwardly from the lower end of the intermediate region 1942*b*. As shown, the upper region 1942*a* of the outer frame body 1942 can have a generally constant diameter from an upper end to a lower end such that the upper region 1942*a* forms a generally cylindrical shape. While, the diameters of the intermediate region and the upper region 1942*a* are generally equivalent such that the intermediate region and the upper region 1942*b*, 1942*a* together form a generally cylindrical shape, it is to be understood that the diameters of the upper end, the lower end, and/or the portion therebetween can be different.

For example, a diameter of the portion between the upper end and the lower end can be larger than the upper end and the lower end such that the intermediate region and/or lower region 1942*b*, 1942*a* forms a generally bulbous shape. In some embodiments, the diameter of the lower end can be larger than the diameter of the upper end. In other embodiments, the diameter of the upper end can be larger than the diameter of the lower end.

As another example, the diameter of the upper end of the upper region 1942a can be greater than the diameter of the lower end of the upper region 1942a such that the upper region 1942a extends radially outwardly away from the longitudinal axis of the prosthesis 1900. This can advantageously enhance securement and/or stability when the prosthesis 1900 is positioned within a native valve, such as the native mitral valve. For example, when the prosthesis 1900 is positioned within a native mitral valve, the upper region 1942a can extend radially outwardly over an atrial side of the native mitral valve annulus. This can inhibit movement of the prosthesis 1900 into the left ventricle during phases of the cardiac cycle (e.g., diastole). In some embodiments, the upper end can increase to a diameter which is similar to, or greater than, a diameter formed around the tips or ends 1924b of inner frame anchoring feature 1924. In some embodiments, the upper region 1942a can extend generally perpendicularly to the intermediate region 1942b to form a flange.

Moreover, although the outer frame body 1942 has been described and illustrated as being cylindrical or having circular cross-sections, it is to be understood that all or a portion of the outer frame body 1942 can be have a non-circular cross-section such as, but not limited to, a D-shape, an oval or an otherwise ovoid cross-sectional shape.

With continued reference to the outer frame 1940 illustrated in FIG. 38A, the outer frame anchoring feature 1944 can extend outwardly relative to the longitudinal axis of the prosthesis 1900. As shown in the illustrated embodiment, the outer frame anchoring feature 1944 is attached to the outer frame body 1942 along the upper region 1942a. The outer frame anchoring feature 1944 can be attached to the outer frame body 1942 such that, when transitioning from a collapsed configuration to an expanded configuration, the tip or end of the outer frame anchoring feature 1944 moves radially outwardly and downwardly; however, it is to be understood that the outer frame anchoring feature 1944 can be attached to the outer frame body 1942 such that, when transitioning from a collapsed configuration to an expanded configuration, the tip or end of the outer frame anchoring feature 1944 moves radially outwardly and upwardly. The radial extent of the outer frame anchor feature 1944 can be generally the same as the radial extend of the inner frame anchoring feature 1924. Although the anchoring feature 1944 is shown attached to the outer frame body 1942, it is to be understood that the anchoring feature 1944 can be attached to the inner frame body 1922. Moreover, it is to be understood that the anchoring feature 1944 can be one or more barbs or penetrating structures. The barbs may be angled upwardly, angled downwardly, and/or perpendicular. Although shown extending along an upper region of the outer frame body 1942, it is to be understood that such barbs or other penetrating structures may extend along other regions of the outer frame body 1942.

Similar to other prostheses described herein, components of the outer frame 1940, can be used to attach or secure the prosthesis 1900 to a native valve, such as a native mitral valve. For example, the intermediate region 1942b of the outer frame body 1942 and/or the outer anchoring feature 1944 can be positioned to contact or engage a native valve annulus, tissue beyond the native valve annulus, native leaflets, and/or other tissue at or around the implantation location during one or more phases of the cardiac cycle, such as systole and/or diastole. As another example, the outer frame body 1942 can be sized and positioned relative to the inner frame anchoring feature 1924 such that tissue of the body cavity positioned between the outer frame body 1942 and the inner frame anchoring feature 1924, such as native valve leaflets and/or a native valve annulus, can be engaged or pinched to further secure the prosthesis 1900 to the tissue. As shown in the illustrated embodiment, the profile of the outer frame 1940 can generally match the profile of the inner frame anchoring feature 1924. This can beneficially enhance sealing along the outer frame 1940 when tissue, such as a leaflet, is captured between the outer frame 1940 and the inner frame anchoring feature 1924. This can also beneficially enhance sealing along the outer frame 1940 even if tissue, such as a leaflet, is not captured between the outer frame 1940 and the inner frame anchoring feature.

Figure 38B:
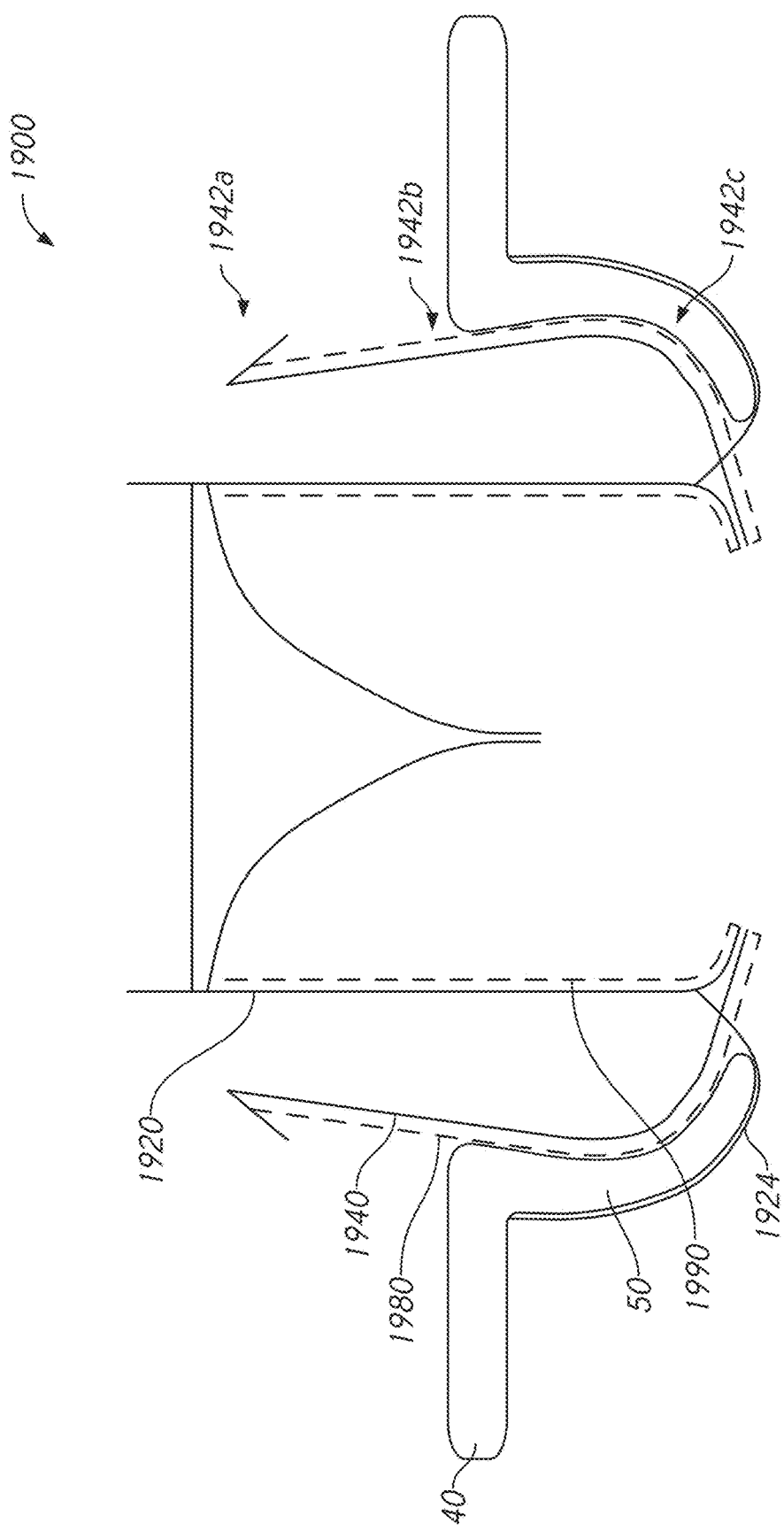
FIG. 38B is a side-oriented cross-sectional schematic view of the prosthesis of FIG. 38A in a native mitral valve.

The shape of the illustrated outer frame body 1942 can enhance securement of the prosthesis 1900. For example, as shown in FIG. 38B, in some instances where the prosthesis 1900 is positioned within the native mitral valve, the outer frame 1940 can compress in a manner such that the region above the annulus 40 bends further radially inwardly than a region below the annulus 40. This can allow the outer frame 1940 to impart a force on the native leaflets and/or native mitral valve annulus 40 in at least a direction towards the atrium. This application of force can result in a counter-force which can tend to push the outer frame 1940, and the prosthesis 1900, towards the ventricle. In embodiments where the inner frame anchoring feature 1924 contacts the annulus 40, this can reduce the systolic loads applied to the inner frame anchoring feature 1924 during systole. This can beneficially reduce and distribute fatigue loads on the inner frame anchoring feature 1924. Moreover, this counter-force can reduce the likelihood that the prosthesis 1900 shifts towards the atrium during systole.

However, it is to be understood that the outer frame 1900 can take on other shapes. For example, in some instances where the prosthesis 1900 is positioned within the native mitral valve, the outer frame 1940 can compress in a manner such that the region below the annulus 40 bends further radially inwardly than a region above the annulus 40. This can allow the outer frame 1940 to impart a force on the native leaflets and/or native mitral valve annulus 40 in at least a direction towards the ventricle. This application of force can result in a counter-force which can tend to push the outer frame 1940, and the prosthesis 1900, towards the atrium. In embodiments where the inner frame anchoring feature 1924 contacts the annulus, this can increase the force applied by the inner frame anchoring feature 1924 to the annulus. Moreover, this counter-force can reduce the likelihood that the prosthesis 1900 shifts towards the left ventricle during stages of the cardiac cycle.

The shape of the illustrated outer frame body 1942 can facilitate positioning of the inner frame anchoring feature 1924 during partial deployment of the prosthesis 1900. During this stage of deployment, the inner frame anchoring feature 1924 can be released while the upper end of the outer frame body 1942 is retained within the delivery system. Since the larger diameter portion of the outer frame body 1942 is proximate the upper region 1942a of the outer frame body 1942 and the lower region 1942c is attached to the inner frame 1920, the outer frame body 1942 can be substantially constrained from expanding. In this manner, the outer frame body 1942 can be maintained in a smaller profile during partial deployment. The smaller profile of the outer frame body 1942 can increase the gap between the inner frame anchoring feature 1924 and the outer frame body 1942 during partial deployment which can facilitate placement of the inner frame anchoring feature 1924 at a target tissue location and/or capture of native valve tissue between the inner frame anchoring feature 1924 and the outer frame body 1942.

With continued reference to the prosthesis 1900 illustrated in FIG. 38A, the valve body 1960 is attached to the inner frame 1920 within an interior of the inner frame body 1922. The valve body 1960 functions as a one-way valve to allow blood flow in a first direction through the valve body 1960 and inhibit blood flow in a second direction through the valve body 1960. As shown in the illustrated embodiment, the valve body 1960 can include a plurality of leaflets 1962 and/or a liner 1964. The liner 1964 can be positioned between at least the upper edges of the leaflets 1962 to an inflow end of the inner frame 1960. In some instances, the leaflets 1962 can be attached to the liner 1964 which is attached to the inner frame 1960.

With reference next to the skirts 1980, 1990 illustrated in FIG. 38A, the outer skirt 1980 can be attached to the inner frame 1920 and/or outer frame 1940. As shown, the outer skirt 1980 can be positioned around and secured to a portion of, or the entirety of, the exterior of the outer frame 1940. As shown, the outer skirt 1980 can follow the contours of the outer frame 1940; however, it is to be understood that at least a portion of the skirt 1980 can be spaced apart from at least a portion of both the inner frame 1920 and the outer frame 1940. The inner skirt 1990 can be attached to the valve body 1960 and the outer skirt 1980. As shown, a first end of the inner skirt 1990 can be coupled to the valve body 1960 along portions of the valve body 1960 which are proximate the inner frame 1920. A second end of the inner skirt 1990 can be attached to the lower region of the outer skirt 1980. Although described as separate structures, it is to be understood that the outer skirt 1980 and the inner skirt 1990 can be monolithically formed. Moreover, it is to be understood that the liner 1964 and the inner skirt 1990 can be monolithically formed.

The outer skirt 1980 can extend to a location below the connection between the inner frame body 1922 and the inner frame anchoring feature 1924. This can advantageously provide a greater surface area upon which the outer skirt 1980 can form a seal with tissue of the native valve, such as the native mitral valve. Moreover, the inward taper of the outer skirt 1980 can better conform to the native anatomy, such as the native mitral valve leaflets, when parts of the native anatomy are positioned between the inner frame anchoring feature 1924 and the outer frame 1940. This can further enhance sealing along the outer skirt 1980.

Although the outer skirt 1980 is shown extending along an exterior of the outer frame body 1942, it is to be understood that the outer skirt 1980 can extend along an interior of the outer frame body 1942. This can allow the outer frame body 1942 to directly contact tissue of the body cavity. In embodiments where the outer frame body 1942 includes struts and/or cells, the tissue can extend between the struts and/or cells. This can beneficially enhance securement of the prosthesis 1900 to the body cavity.

As shown in the illustrated embodiment, a cavity 1992 can be formed between the outer skirt 1980 and the inner skirt 1990 which opens upwardly. In instances where the prosthesis 1900 is positioned within the native mitral valve, the cavity 1992 can open towards the atrium. Accordingly, during systole, the cavity 1992 can be at a lower pressure than the ventricle. This can beneficially enhance sealing outer skirt 1980 since the native tissue, such as the native mitral valve leaflets, are forced towards the outer skirt 1980 due to a pressure differential between the ventricle and the cavity 1992.

In some embodiments, the cavity 1992 can be filed with material such as, but not limited to, silicone, saline, foam, hydrogel, knit polyesters such as polyethylene terephthalate (PET) and/or polyvalerolactone (PVL), other materials, and/or a combination of such materials. The filler material can be included in the cavity 1992 prior to the prosthesis 1900 being deployed. In some embodiments, the filler material can be added after the prosthesis 1900 has been at least partially deployed. For example, the filler material can be pre-formed into a cylindrical shape or ring can subsequently positioned within the cavity 1992 after the prosthesis 1900 has been deployed.

The filler material can be used to fill the cavity 1992 to reduce the open volume. In some embodiments, the filler material can promote tissue growth within the cavity. In some embodiments, the filler material can promote healing of tissue surrounding the prosthesis 1900. In some embodiments, the filler material can beneficially alter the structural characteristics of the outer frame 1940 and/or inner frame 1920. For example, the filler material can be used to reduce the compliancy of the outer frame 1940 along certain portions of the outer frame and/or to transmit forces applied to the outer frame 1940 to the inner frame 1920. This can beneficially allow the outer frame 2040 to exert a greater force along these regions.

In some embodiments, the cavity 1992 can include a cover (not shown) to partially or fully close the cavity 1992. An upper end of the outer skirt 1980 can be attached to the upper end of the inner skirt 1990 and/or liner 1964 such that the cover extends generally perpendicular to the longitudinal axis. However, it is to be understood that the cover can take other shapes. In some embodiments, the cover can extend downwardly and radially inwardly to funnel blood towards the inflow end of the inner frame 1920. In some embodiments, the cover can extend upwardly and radially inwardly. This can form a tapered shape which can facilitate recapture of the device.

In some embodiments, the cover can be at least partially permeable to allow the flow of blood into the cavity 1992 and/or sufficiently impermeable to inhibit larger particulates such as clots. For example, the cover can be formed from a mesh such as a cloth or wire mesh, a woven material, and/or a perforated material. This can facilitate the growth of tissue within the cavity 1992 and/or on the cover. For example, the cover can allow for endothelialization. This tissue growth can be enhanced in combination with the filler material noted above. In some embodiments, the cover can be formed from a substantially impermeable material to inhibit the flow of fluids into the cavity 1992. In some embodiments, this material can be the same material forming the skirt 2080 and/or the inner skirt 1990.

Although the prosthesis 1900 has been described as including an inner frame 1920, an outer frame 1940, a valve body 1960, and skirts 1980, 1990, it is to be understood that the prosthesis 1900 need not include all components. For example, in some embodiments, the prosthesis 1900 can include the inner frame 1920, the outer frame 1940, the valve body 1960, and the outer skirt 1980 while omitting the inner skirt 1990, particularly in instances where a cover is used. Moreover, although the components of the prosthesis 1900 have been described and illustrated as separate components, it is to be understood that one or more components of the prosthesis 1900 can be integrally or monolithically formed. For example, in some embodiments, the inner frame 1920 and the outer frame 1940 can be integrally or monolithically formed as a single component.

With reference next to FIGS. 39-42, an embodiment of a prosthesis 2000 in an expanded configuration, or components of the prosthesis 2000, are illustrated. The prosthesis 2000 can include an inner frame 2020, an outer frame 2040, a valve body 2060, and a skirt 2080. The prosthesis 1900 can share characteristics, such as structure and/or functionality, which are the same as, or at least similar to, those of other prostheses described herein such as prosthesis 1900.

Figure 39:
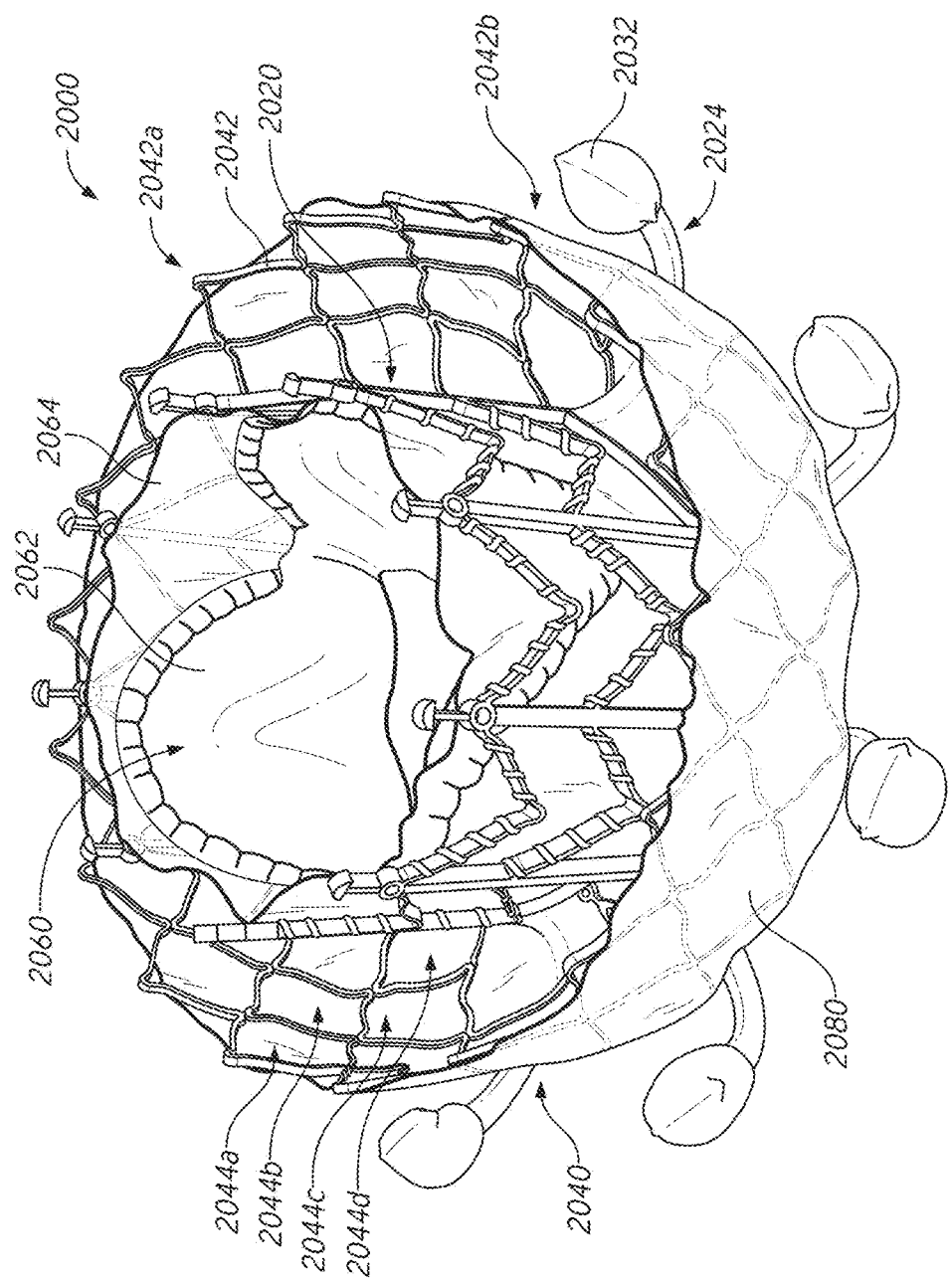
FIG. 39 is a top-oriented perspective view of another embodiment of a prosthesis having an inner frame, an outer frame, a valve body, and a skirt.
Figure 40:
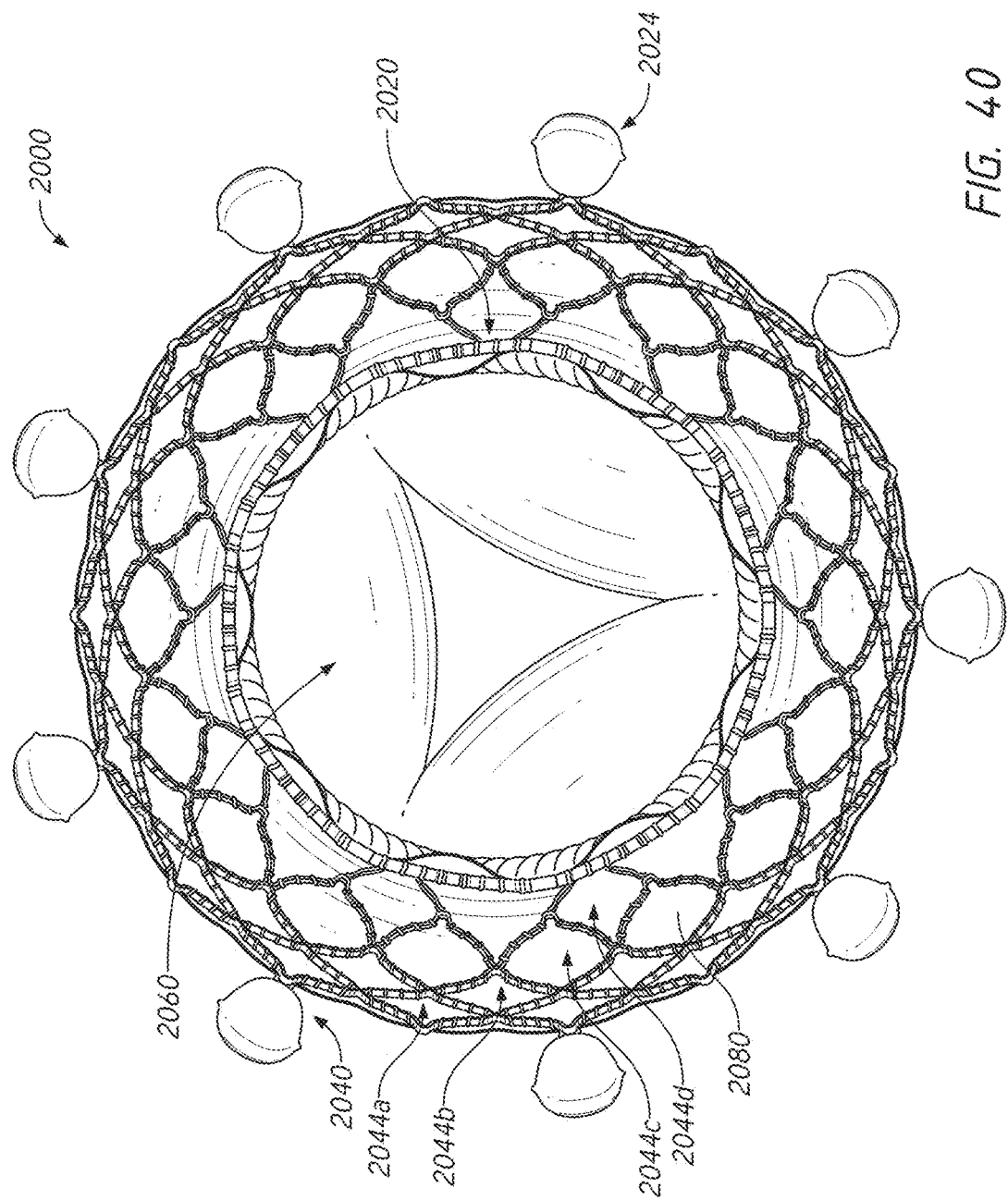
FIG. 40 is a top view of the prosthesis of FIG. 39.
Figure 41:
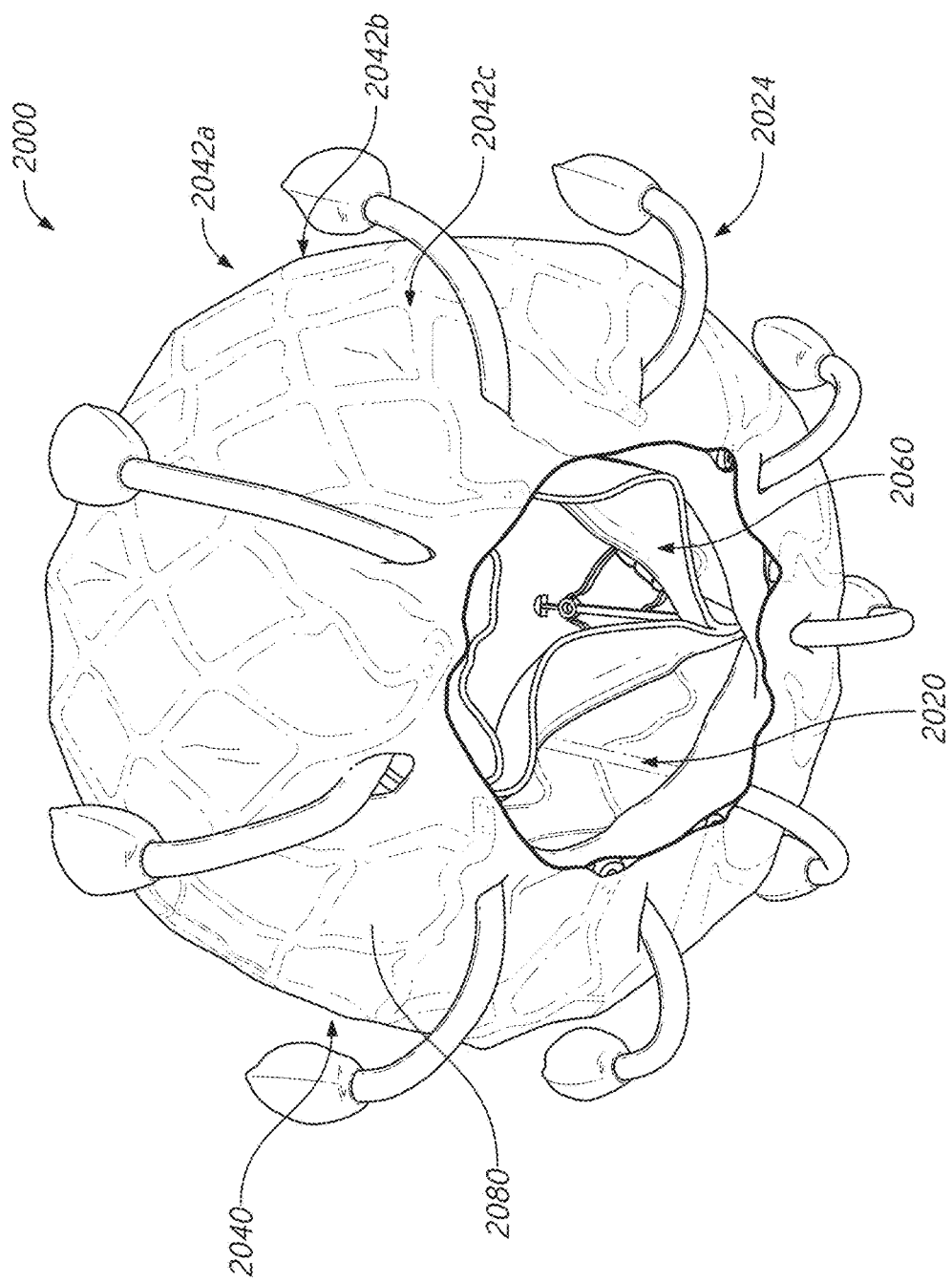
FIG. 41 is a bottom-oriented perspective view of the prosthesis of FIG. 39.

With reference first to the outer frame 2040 illustrated in FIGS. 39-41, the outer frame 2040 can include an outer frame body 2042. The outer frame body 2042 can have an upper region 2042a, an intermediate region 2042b, and a lower region 2042c. As shown, when in an expanded configuration such as the fully expanded configuration, the outer frame body 2042 can have an enlarged shape with an upper region 2042a and an intermediate region 2042b being larger than the lower region 2042c. The enlarged shape of the outer frame body 2040 can advantageously allow the outer frame body to engage a native valve annulus, native valve leaflets, or other body cavity, while spacing the inlet and outlet from the heart or vessel wall.

The lower region 2042c of the outer frame body 2042 can extend radially outwardly away from the longitudinal axis of the prosthesis 2000 and/or in an upward direction towards the upper region. As shown in the illustrated embodiment, the lower region 2042c can incorporate a bend or curve such that the angle of the lower region 2042c relative to the longitudinal axis decreases towards an upper end of the lower region 2042c. However, it is to be understood that in some embodiments, the lower region 2042c can extend substantially linearly.

The intermediate region 2042b of the outer frame body 2042 can extend generally upwardly from the lower region 2042c. As shown, the intermediate region 2042b can have a generally constant diameter from a lower end to an upper end such that the intermediate region 2042b forms a generally cylindrical shape. The upper region 2042a of the outer frame body 2042 can extend generally upwardly from the upper end of the intermediate region 2042b. As shown, the upper region 2042a of the outer frame body 2042 can have a generally constant diameter from a lower end to an upper end such that the upper region 2042a forms a generally cylindrical shape. However, it is to be understood that the diameters of the upper end, the lower end, and/or the portion therebetween of the intermediate region and/or upper region 2042b, 2042a can be different. For example, in some embodiments, a diameter of the portion between the upper and lower ends can be larger than diameters of the upper and lower ends such that the intermediate region and/or upper region 2042b, 2042a form a generally bulbous shape (as shown, for example, in connection with frame 300 illustrated in FIGS. 7-8). In some embodiments, the diameter of the lower end can be larger than the diameter of the upper end. In other embodiments, the diameter of the upper end can be larger than the diameter of the lower end.

Moreover, although the outer frame body 2042 has been described and illustrated as being cylindrical or having circular cross-sections, it is to be understood that all or a portion of the outer frame body 2042 can be have a non-circular cross-section such as, but not limited to, a D-shape, an oval or an otherwise ovoid cross-sectional shape.

With continued reference to the outer frame 2040 illustrated in FIGS. 39-41, the outer frame body 2042 can include a plurality of struts with at least some of the struts forming cells 2044a-d. Any number of configurations of struts can be used, such as rings of undulating struts shown forming ellipses, ovals, rounded polygons, and teardrops, but also chevrons, diamonds, curves, and various other shapes.

As shown in the illustrated embodiment, the cells 2044a-d can have a diamond or generally diamond shape. The cells 2044a-d can be considered to be a substantially foreshortening portion of the outer frame 2040. While the struts forming cells 2044a-d are generally illustrated as being straight segments, it is to be understood that some or all of the struts may not form entirely straight segments. For example, the struts can include some curvature such that the upper and/or lower apices are curved.

As shown in the illustrated embodiment, there can be three rows of eighteen cells 2044a-c and a row of nine cells 2044d. While each of the cells 2044a-d are shown as having the same shape as other cells 2044a-d of the same row, it is to be understood that the shapes of cells 2044a-d within a row can differ. Moreover, it is to be understood that any number of rows of cells can be used and any number of cells may be contained in the rows.

Figure 42:
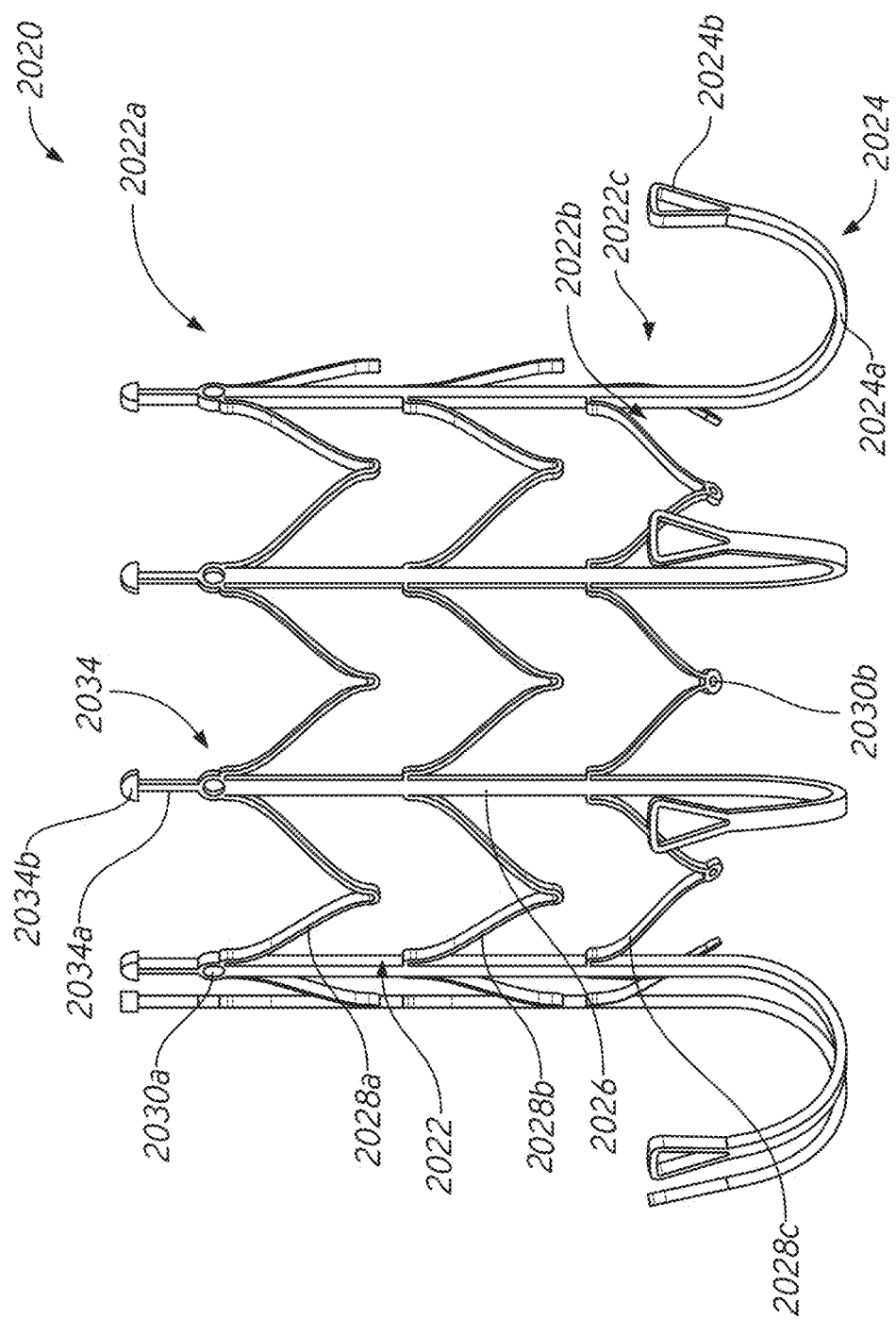
FIG. 42 is a side view of a front-half of the inner frame of FIG. 39.

With reference next to FIG. 42, the inner frame 2020 of prosthesis 2000 is illustrated. The inner frame 2020 can include an inner frame body 2022 and an inner frame anchoring feature 2024. As shown, the inner frame body 2022 can have an upper region 2022a, an intermediate region 2022b, and a lower region 2022c. As shown, the inner frame body 2022 can have a generally cylindrical shape such that the diameters of the upper region 2022a, the intermediate region 2022b, and the lower region 2022c are generally equivalent. However, it is to be understood that the diameters of the upper region 2022a, the intermediate region 2022b, and/or the lower region 2022c can be different. For example, in some embodiments, a diameter of the lower region 2022c can be larger than the upper region 2022a. In other embodiments, the diameter of the upper region 2022a can be larger than the diameter of the lower region 2022c.

The diameter of the upper region 2022a, intermediate region 2022b, and/or lower region 2022c of the inner frame body 2022 may be chosen such that the inner frame body 2022 is adequately spaced from the body cavity when the prosthesis 2000 is positioned within the body cavity. For example, in embodiments where the prosthesis 2000 is positioned within the native mitral valve, the inner frame body 2022 may have a diameter which is less than the diameter of the native mitral valve annulus. Although the inner frame body 2022 has been described and illustrated as being cylindrical or having circular cross-sections, it is to be understood that all or a portion of the inner frame body 2022 can be have a non-circular cross-section such as, but not limited to, a D-shape, an oval or an otherwise ovoid cross-sectional shape.

The inner frame body 2022 can be substantially non-foreshortening. This can advantageously allow the inner frame body 2022 to retain its axial length when the inner frame body 2022 transitions from a collapsed configuration to an expanded configuration. This can reduce the crimp length of the inner frame body 2022 which can facilitate positioning within a delivery system. As shown in the illustrated embodiment, the inner frame body 2022 can include longitudinally-extending struts 2026. The longitudinally-extending struts 2026 can extend in a direction generally parallel to the longitudinal axis of the prosthesis 2000. The longitudinally-extending struts 2026 can extend from an upper region 2022a of the inner frame body 2022 to a lower region 2022c of the inner frame body 2022. Although the longitudinally-extending struts 2026 extend in a direction generally parallel to the longitudinal axis of the prosthesis 2000, it is to be understood that at least a portion of these struts 2026 can extend in a direction transverse to the longitudinal axis.

As shown in the illustrate embodiment, the inner frame body 2022 can include nine longitudinally-extending struts 2026. It is to be understood that a fewer or greater number of struts can be used. The number of struts can be a multiple of the number of commissures of the valve body. For example, in instances where a valve body having three commissures is used, the inner frame body 2022 can include three, six, twelve, fifteen, or more struts.

A plurality of undulating struts can extend between the longitudinally-extending struts 2026. In some embodiments, the inner frame body 2022 can include one or more sets of struts which extend circumferentially around the inner frame body 2022. As shown, the inner frame body 2022 can include a first, second, and third set of struts 2028a-c extending circumferentially around the inner frame body 2022. Each of the sets of struts 2028a-c can have a zig-zag or undulating shape forming a repeating "V" shape. The tips of these "V" shapes can form a "U" shape. This can facilitate transitioning of the inner frame body 2022 between a collapsed configuration and an expanded configuration.

As shown, the first and second sets of struts 2028a-b can extend in a direction generally parallel to the longitudinal axis of the prosthesis 2000. As such, the first and second sets of struts 2028a-b can form a generally cylindrical shape. The third set of struts 2028c can extend radially inwardly towards the longitudinal axis of the prosthesis 2000. This radially inward shape can correspond to the shape of the lower region 2042c of the outer frame body 2042. This can advantageously facilitate attachment of the outer frame body 2042 to the inner frame body 2022 along the lower regions 2022c, 2042c.

The inner frame 2020 can include one or more eyelets to facilitate attachment of one or more components of the prosthesis 2000 to the inner frame 2020. As shown in the illustrated embodiment, the inner frame 2020 can include an upper and/or lower set of eyelets 2030a-b. The upper set of eyelets 2030a can be positioned along the upper region 2022a of the inner frame body 2022. As shown, the eyelets 2030a can be positioned at or proximate an upper end of the longitudinally-extending struts 2026.

The eyelets 2030a can be used to attach the inner frame 2020 to a delivery instrument, such as a suture or tether-based delivery instrument. For example, sutures or tethers can be attached to the eyelets 2030a. In some embodiments, the outer frame 2040 can include an upper set of eyelets (not shown) in lieu of, or in combination with, the upper eyelets 2030a. In embodiments with eyelets on both the inner frame 2020 and the outer frame 2040, a tether or suture can be passed through corresponding eyelets of the inner frame 2020 and the outer frame 2040. This tether or suture can draw the inner frame 2020 and the outer frame 2040 closer together when tightened. This can facilitate recapture of the prosthesis 2000.

The lower set of eyelets 2030b can be positioned along the lower region 2022c of the inner frame body 2022. As shown in the illustrated embodiment, the lower set of eyelets 2030b can be positioned along the lower row of struts 2028c. The eyelets 2030b can be utilized to facilitate securement of the outer frame 2040 to the inner frame 2020. For example, in some embodiments, the outer frame 2040 can include one or more eyelets which correspond to the eyelets 2030b. The inner frame 2020 and outer frame 2040 can be attached together via eyelets 2030b and corresponding eyelets on the outer frame 2040. For example, the inner frame 2020 and outer frame 2040 can be sutured together through said eyelets or attached via other means, such as mechanical fasteners (e.g., screws, rivets, and the like).

Although a single eyelet 2030b is shown extending from each "V" shaped strut, it is to be understood that some "V" shaped struts may not include an eyelet. Moreover, it is to be understood that multiple eyelets can extend from a "V" shaped strut. For example, two eyelets can extend in series. This can enhance the stability of the coupling between the inner frame 2020 and the outer frame 2040 by allowing a suture to pass through two adjacent eyelets. For example, this can reduce the likelihood that the outer frame 2040 twists along an axis of the eyelet.

With continued reference to the inner frame 2020 illustrated in FIG. 42, the inner frame anchoring feature 2024 can extend at or proximate a lower end of the lower region 2022c of the inner frame body 2022. The inner frame anchoring feature 2024 can be formed from a plurality of individual anchors 2024a extending from the frame body 2022. The anchors 2024a can extend downwardly from one or more attachment points to the inner frame body 2022 including, but not limited to, longitudinally-extending struts 2026. As shown, the anchors 2024a can be an extension of the longitudinally-extending struts 2026. This can beneficially enhance the structural integrity of the anchors 2024a. The anchors 2024a can bend to extend generally radially outwardly of the longitudinal axis of the prosthesis 2000. Although the anchors 2024a are shown extending from longitudinally-extending struts 2026, it is to be understood that the anchors 2024a can be connected to the inner frame body 2022 frame at one of many different locations including apices, junctions, other parts of struts, etc.

The anchors 2024a can extend upwardly towards an end or tip 2024b. The ends or tips 2024b can be positioned radially outwardly relative to the longitudinal axis of the prosthesis 2000. As shown, the ends or tips 2024b can extend upwardly in a direction generally parallel to the longitudinal axis of the prosthesis 2000; however, it is to be understood that the ends or tips 2024b can have other geometries as described herein. For example, the ends or tips can extend generally perpendicular to the longitudinal axis of the prosthesis 2000. Although the anchors 2024a are shown with a single bend, it is to be understood that one or more anchors can comprise first, second, third, or more spaced apart bending stages along the length of each anchor. Further details that may be incorporated and/or interchanged with the features described herein are disclosed in U.S. Publication Nos. 2014/0277422, 2014/0277427, 2014/0277390, and 2015/0328000, and U.S. application Ser. No. 15/653,390, entitled REPLACEMENT HEART VALVE PROSTHESIS, filed on Jul. 18, 2017, which have been incorporated by reference herein.

As shown in the illustrated embodiment, the inner frame anchoring feature 2024 can include nine individual anchors; however, it is to be understood that a greater number or lesser number of individual anchors can be used. For example, the number of individual anchors can be chosen as a multiple of the number of commissures for the valve body 2060. As such, for a prosthesis 2000 with a valve body 2060 having three commissures, the inner frame anchoring feature 2024 can have three individual anchors (1:1 ratio), six individual anchors (2:1 ratio), nine individual anchors (3:1 ratio), twelve individual anchors (4:1 ratio), fifteen individual anchors (5:1 ratio), or any other multiple of three. It is to be understood that the number of individual anchors need not correspond to the number of commissures of the valve body 2060.

With reference back to FIGS. 39-41, the inner frame anchoring feature 2024 can include covers and/or cushions 2032 to surround or partially surround at least a portion of the inner frame anchoring feature 2024, such as the tips or ends 2024*b*. The covers and/or cushions 2032 can be similar to cushions 238 and/or those described in U.S. Publication No. 2015/0328000, which has been incorporated by reference in its entirety. As shown in the illustrated embodiment, covers and/or cushions 2032 are attached to all anchors 2024*a*; however, it is to be understood that the covers and/or cushions 2032 can be utilized on a subset of anchors 2024*a*.

As shown in the illustrated embodiment, the radial extent of the tips or ends 2024*b* of the inner frame anchoring feature 2024 can be greater than the radial extent of the outer frame body 2042 at the plane of the tips or ends 2024*b*. The tips or ends 2024*b* can be positioned such that the tips or ends 2024*b* are spaced apart from an exterior of the outer frame body 2042. This can provide a gap in which tissue of the body cavity can be retained. For example, in instances where the prosthesis 2000 is positioned within a native mitral valve, the native mitral valve leaflets can be positioned between these gaps. It is to be understood that this gap between the tips or ends 2024*b* and the outer frame body 2042 can be reduced. For example, in some embodiments, the tips or ends 2024*b* can be positioned proximate, or contact, the exterior of the outer frame body 2042. This can beneficially increase the force applied by the prosthesis 2000 to pinch or grasp tissue of the body cavity therebetween.

With continued reference to FIGS. 39-41, the valve body 2060 can share characteristics, such as structure and/or functionality, which are the same as, or at least similar to, those of other valve bodies described herein. The valve body 2060 can include one or more leaflets 2062 and/or a liner 2064. The liner 2064 can be used to assist with fluid flow through and/or around the prosthesis 2000, such as through and around the inner frame 2020 and the valve leaflets 2062. The liner 2062 can surround at least a portion of the valve leaflets 2062 and be connected to one or more of the valve leaflets 2062. For example, as shown in the illustrated embodiment, the one or more valve leaflets 2062 can be attached to the liner 2064 along an upper edge of the valve leaflets 2062.

As shown in the illustrated embodiment, the liner 2064 can be positioned within the interior of the inner frame 2020 and can form an inner wall of the prosthesis 2000. It is also contemplated that the liner 2064 can at least be partially positioned along an exterior of the inner frame 2020 and/or outer frame 2040 such that at least a portion of the liner 2064 is radially outward, relative to the longitudinal axis of the prosthesis 2000, from struts of the inner frame 2020 and/or outer frame 2040. As shown in the illustrated embodiment, the liner 2064 can be positioned along an upper or inlet side of the inner frame 2020. The liner 2064 can extend above the upper edge of the valve leaflets 2062 towards the upper end of the inner frame 2020. As shown, the liner 2064 can also extend below the upper edge of the valve leaflet 2062 towards the lower end of the inner frame 2020.

With continued reference to FIGS. 39-41, the skirt 2080 can share characteristics, such as structure and/or functionality, which are the same as, or at least similar to, those of other skirts described herein. The skirt 2080 can be positioned around and secured to at least a portion of the exterior of the prosthesis 2000 such as, but not limited to, the inner frame 2020 and/or the outer frame 2040. The skirt 2080 can be annular and can extend entirely circumferentially around the prosthesis 2000. The skirt 2080 can prevent or inhibit backflow of fluids around the prosthesis 2000. For example, with the skirt 2080 positioned annularly around an exterior of the prosthesis 2000, the skirt 2080 can create an axial barrier to fluid flow exterior to the prosthesis 2000 when deployed within a body cavity. As shown, the skirt 2080 can seal against at least a portion of tissue surrounding the body cavity. In addition, the skirt 2080 can encourage tissue in-growth between the flap assembly 2080 and natural tissue of the body cavity. This may further help to prevent leakage of blood flow around the prosthesis 2000.

As shown in the illustrated embodiment, the skirt 2080 can extend along an exterior of the outer frame body 2042. This can increase the contact area between tissue of the body cavity and the skirt 2080. This can beneficially enhance sealing around the prosthesis 2000 by providing smooth, continuous contact along the periphery of the outer frame 2040 and the skirt 2080. In embodiments where the skirt 2080 is formed from a material which encourages tissue in-growth, this increased contact area can be beneficial.

While the skirt 2080 is shown extending along the exterior of the outer frame body 2042, it is to be understood that portions of, or the entirety of, the skirt 2080 can extend along an interior of the outer frame. This can allow tissue of the body cavity to contact and/or extend between struts forming the outer frame body 2042. For example, tissue of the body cavity can contact and/or extend between struts forming one or more of cells 2044*a-d*. This can beneficially enhance stability and/or securement of the prosthesis 2000 to tissue of the body cavity. It is also to be understood that while the skirt 2080 is shown tautly attached to the outer frame 2040, a portion of, or the entirety of, the skirt 2080 can be loosely attached such that a portion of, or the entirety of, the skirt 2080 is movable relative to the outer frame 2040.

The upper end of the skirt 2080 can be positioned at or proximate an upper end of the outer frame body 2042 and/or an upper end of the inner frame body 2022. The lower end of the skirt 2080 can be positioned at or proximate a lower end of the outer frame body 2042. The skirt 2080 may be attached to the outer frame 2040 and/or inner frame 2020 using any fasteners and/or techniques described herein. For example, portions of the skirt 2080 can be attached to struts and/or anchoring features of the outer frame 2040 and/or inner frame 2020 using any of the fasteners and/or techniques described herein including, but not limited to, mechanical fasteners, such as sutures, staples, screws, rivets, interfacing members (e.g., tabs and slots), and any other type of mechanical fastener as desired, chemical fasteners such as adhesives and any other type of chemical fastener as desired, fastening techniques such as welding, soldering, sintering, and any other type of fastening technique as desired, and/or a combination of such fasteners and techniques.

With reference back to the inner frame 2020 illustrated in FIG. 42, the inner frame 2020 can include a set of locking tabs 2034 extending at or proximate an upper end of the upper region 2022*a* of the inner frame body 2022. As shown, the locking tabs 2034 can extend at or proximate an upper end of the longitudinal struts 2030 and/or the upper set of eyelets 2030*a*. The locking tabs 2034 can extend upwardly in a direction generally aligned with the longitudinal axis of the prosthesis 2000. As shown in the illustrated embodiment, the locking tabs 2034 can include a longitudinally-extending strut 2034*a*. At an upper end of the strut 2034*a*, the locking tab 2034 can include an enlarged head 2034*b*. As shown, the enlarged head 2034*b* can have a semi-circular or semi-elliptical shape forming a "mushroom" shape with the strut 2034*a*. As shown, the inner frame 2020 can include nine locking tabs 2034; however, it is to be understood that a greater number or lesser number of locking tabs can be used.

Moreover, it is to be understood that portions of, or the entirety of, the locking tabs 2034 can be omitted.

The locking tabs 2034 can be advantageously used with multiple types of delivery systems. For example, the shape of the locking tabs 2034 can allow the prosthesis 2000 to be used with multiple delivery systems such as, but not limited to, a "slot" based delivery system and a "tether" based delivery system such as those which utilize sutures, wires, or fingers to control delivery. In some embodiments, the prosthesis 2000 can be used with the delivery systems described herein, including but not limited to, those described in U.S. Pat. Nos. 8,414,644 and 8,652,203 and U.S. Publication Nos. 2015/0238315, the entireties of each of which are hereby incorporated by reference and made a part of this specification.

Although the locking tabs 2034 are shown extending from the inner frame 2020, it is to be understood that locking tabs can extend from the outer frame 2040 in lieu of, or in addition to, the locking tabs 2034. Moreover, although the locking tabs are shown extending generally parallel to the longitudinal axis, it is to be understood that locking tabs, such as locking tabs 2034 or those on the outer frame, can extend at an angle relative to the longitudinal axis. This can beneficially allow the locking tabs to function as an upper set of anchors (similar to upper anchors 1944 discussed in connection with FIG. 38A).

Figure 43:
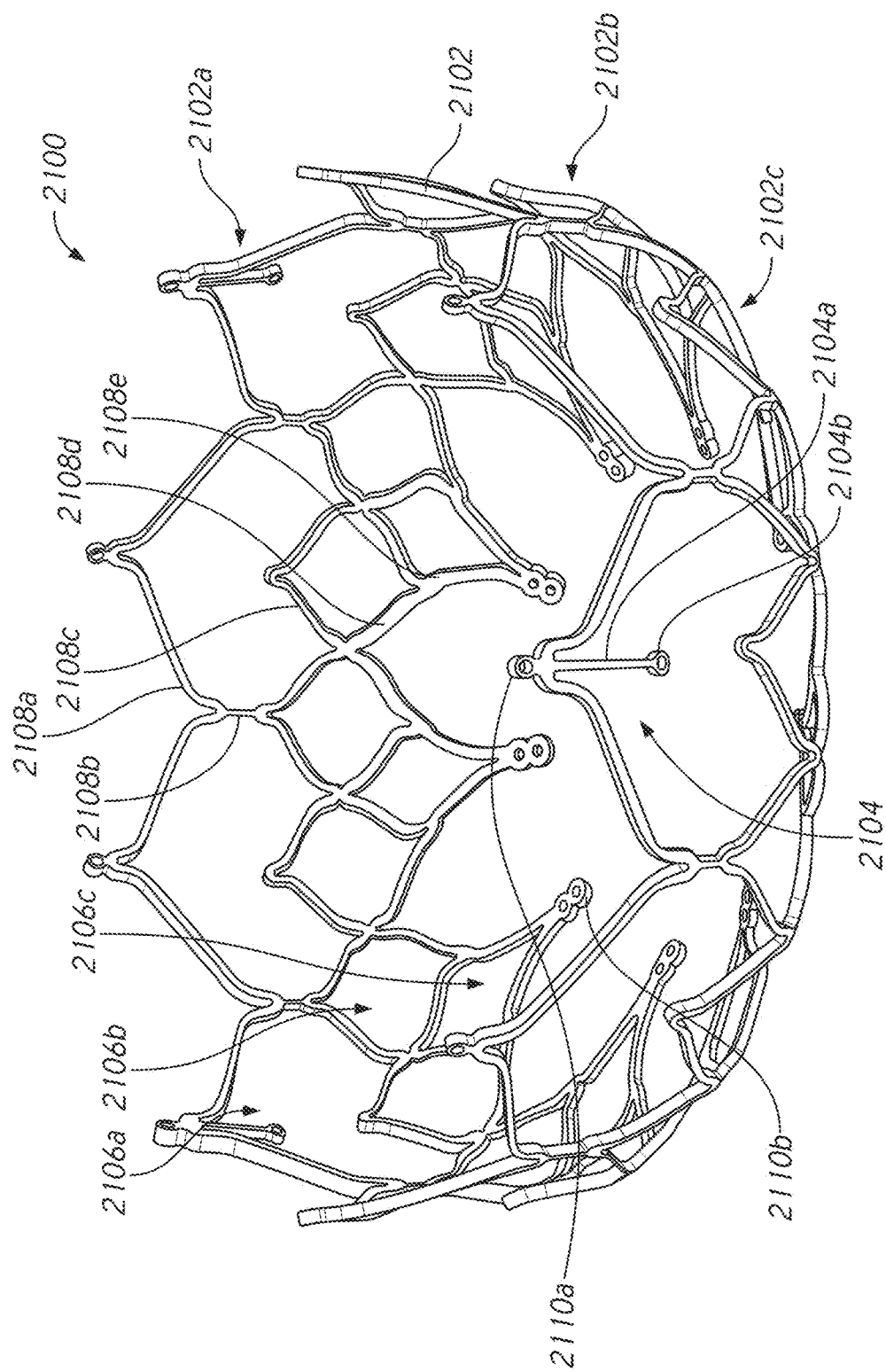
FIG. 43 is a top-oriented perspective view of another embodiment of an outer frame.

With reference next to FIG. 43, an embodiment of an outer frame 2100 in an expanded configuration is illustrated. The outer frame 2100 can include an outer frame body 2102 and/or an outer frame anchoring feature 2104. The outer frame 2100 can share characteristics, such as structure and/or functionality, which are the same as, or at least similar to, those of other outer frames described herein such as outer frames 1940 and 2040 described above in connection with FIGS. 38 and 39-41.

When in an expanded configuration such as in a fully expanded configuration, the outer frame body 2102 can have a shape similar to that of outer frame 1940 and 2040. As shown, the upper region 2102a and the intermediate region 2102b can have a diameter which is larger than the diameter of the lower region 2102c. The lower region 2102c of the outer frame body 2102 can have a decreasing diameter from an upper end of the lower region 2102c to a lower end of the lower region 2102c such that the lower region 2102c is inclined or curved radially inwards towards the longitudinal axis of the outer frame 2100. This radially inward incline or curve of the lower region 2102c can facilitate capture of native valve leaflets between the outer frame 2100 and other portions, such as an anchoring feature, of the prosthesis in which the outer frame 2100 is used. Moreover, this radially inward inclined or curve of the lower region 2102c can reduce or inhibit potential trauma to tissue of the body cavity, such as the native leaflets and/or native valve annulus. For example, the curvature and/or inclination of the lower region 2102c can be chosen to better conform to the curvature of tissue positioned between the outer frame 2100 and an anchoring feature of another portion of a prosthesis in which the outer frame 2100 is used.

Although the outer frame body 2102 has been illustrated as having circular cross-sections, it is to be understood that all or a portion of the outer frame body 2102 can be have a non-circular cross-section such as, but not limited to, a D-shape, an oval or an otherwise ovoid cross-sectional shape.

With continued reference to the outer frame 2100 illustrated in FIG. 43, the outer frame body 2102 can include a plurality of struts with at least some of the struts forming cells 2106a-c. Any number of configurations of struts can be used, such as rings of undulating struts shown forming ellipses, ovals, rounded polygons, and teardrops, but also chevrons, diamonds, curves, and various other shapes.

The upper row of cells 2106a can have an irregular octagonal shape such as a "heart" shape. This larger shape can provide additional space for outer frame anchoring feature 2104. This additional space can beneficially allow the outer frame 2100 to retain a smaller profile when crimped. The cell 2106a can be formed via a combination of struts. As shown in the illustrated embodiment, the upper portion of cells 2106a can be formed from a set of circumferentially-expansible struts 2108a having a zig-zag or undulating shape forming a repeating "V" shape.

The middle portion of cells 2106a can be formed from a set of struts 2108b extending downwardly from bottom ends of each of the "V" shapes. The struts 2108b can extend along with a plane parallel to and/or extending through the longitudinal axis of the prosthesis 2100. The portion of the cells 2106a extending upwardly from the bottom end of struts 2108b may be considered to be a substantially non-foreshortening portion of the outer frame 2100.

The lower portion of cells 2106a can be formed from a set of circumferentially-expansible struts 2108c having a zig-zag or undulating shape forming a repeating "V" shape. One or more of the upper ends or tips of the circumferentially-expansible struts 2108c can be a "free" apex which is not connected to a strut. For example, as shown in the illustrated embodiment, every other upper end or tip of circumferentially-expansible struts 2108b is a free apex. However, it is to be understood that other configurations can be used. For example, every upper apex along the upper end can be connected to a strut.

The middle and/or lower rows of cells 2106b-c can have a different shape from the cells 2106a of the first row. The middle row of cells 2106b and the lower row of cells 2106c can have a diamond or generally diamond shape. The diamond or generally diamond shape can be formed via a combination of struts.

The upper portion of cells 2106b can be formed from the set of circumferentially-expansible struts 2108c such that cells 2106b share struts with cells 2106a. The lower portion of cells 2106b can be formed from a set of circumferentially-expansible struts 2108d. As shown in the illustrated embodiment, one or more of the circumferentially-expansible struts 2108d can extend generally in a downward direction and extend radially inwardly towards the longitudinal axis of the outer frame 2100. For example, the one or more circumferentially-expansible struts 2108d can be curved such that an upper portion of the struts 2108d is positioned further from the longitudinal axis of the outer frame 2100 than the lower portion of the struts 2108d.

The upper portion of cells 2106c can be formed from the set of circumferentially-expansible struts 2108d such that cells 2106c share struts with cells 2106b. The lower portion of cells 2106c can be formed from a set of circumferentially-expansible struts 2108e. Circumferentially-expansible struts 2108e can extend generally in a downward direction. As shown in the illustrated embodiment, the circumferentially-expansible struts 2108e can be inclined or curved towards the longitudinal axis of the outer frame 2100 such that an upper portion of the struts 2108e is positioned further from the longitudinal axis of the outer frame 2100 than the lower portion of the struts 2108e. In some embodiments, the circumferentially-expansible struts 2108d can extend in a direction generally parallel to the longitudinal axis of the outer frame 2100.

As shown in the illustrated embodiment, there can be a row of nine cells 2106a, a row of eighteen cells 2106b, and a row of nine cells 2106c. While each of the cells 2106a-c are shown as having the same shape as other cells 2106a-c of the same row, it is to be understood that the shapes of cells 2106a-c within a row can differ. Moreover, it is to be understood that any number of rows of cells can be used and any number of cells may be contained in the rows.

With continued reference to FIG. 43, the outer frame 2100 can include an outer frame anchoring feature 2104. The outer frame anchoring feature 2104 can include one or more individual anchors 2104a having tips or ends 2104b. As shown, the outer frame anchoring feature 2104 includes three anchors; however, it is to be understood that a fewer or greater number of anchors can be used. For example, the outer frame anchoring feature 2104 can include nine anchors 2104a.

As shown, the anchors 2104a extend from an upper portion of cells 2106a, such as an upper apex of cells 2106a. The anchors 2104a can extend downwardly. The anchors 2104a can be attached to the outer frame body 2102 such that, when transitioning from a collapsed configuration to an expanded configuration, the tip or end 2104b of the anchors 2104a moves radially outwardly and upwardly.

In some embodiments, one or more anchors 2104a can be attached to the outer frame body 2102 along struts 2108c. For example, the anchors 2104a can extend from one or more of the free apices. The anchors 2104a can be attached to the outer frame body 2102 such that, when transitioning from a collapsed configuration to an expanded configuration, the tip or end 2104b of the anchors 2104a moves radially outwardly and downwardly. This can beneficially facilitate alignment of the prosthesis 2104a. Moreover, it is to be understood that the anchors 2104a and/or the tips or ends 2104b can be barbs or penetrating structures. The barbs may be angled upwardly, angled downwardly, and/or perpendicular. Although shown extending along an upper region of the outer frame body 2102, it is to be understood that such barbs or other penetrating structures may extend along other regions of the outer frame body 2102.

As shown in the illustrated embodiment, the outer frame 2100 can include an upper set of eyelets 2110a and/or a lower set of eyelets 2110b. The upper set of eyelets 2110a can extend from an upper region 2102a of the outer frame body 2102. As shown, the upper set of eyelets 2110a can extend from an upper portion of cells 2106a, such as the upper apices of cells 2106a. The upper set of eyelets 2110a can be used to attach the outer frame 2100 to a delivery system. For example, sutures or tethers of a delivery system can be attached or passed through the upper set of eyelets 2110a.

The lower set of eyelets 2110b can be positioned along the lower region 2102c of the outer frame body 2102. As shown, the lower set of eyelets 2110b can extend from an upper portion of cells 2106c, such as the lower apices of cells 2106c. The lower set of eyelets 2110b can be used to attach the outer frame 2100 to an inner frame of a prosthesis. For example, in some embodiments, the inner frame can include one or more eyelets which correspond to the eyelets 2110b. The inner frame and outer frame 2100 can be attached together via these eyelets. For example, the inner frame and outer frame 2040 can be sutured together through said eyelets or attached via other means, such as mechanical fasteners (e.g., screws, rivets, and the like).

As shown, the lower set of eyelets 2110b can include two eyelets extending in series from each "V" shaped strut. This can reduce the likelihood that the outer frame 2040 twists along an axis of the eyelet. However, it is to be understood that some "V" shaped struts may not include an eyelet. Moreover, it is to be understood that a fewer or greater number of eyelets can extend from a "V" shaped strut.

Figure 44:
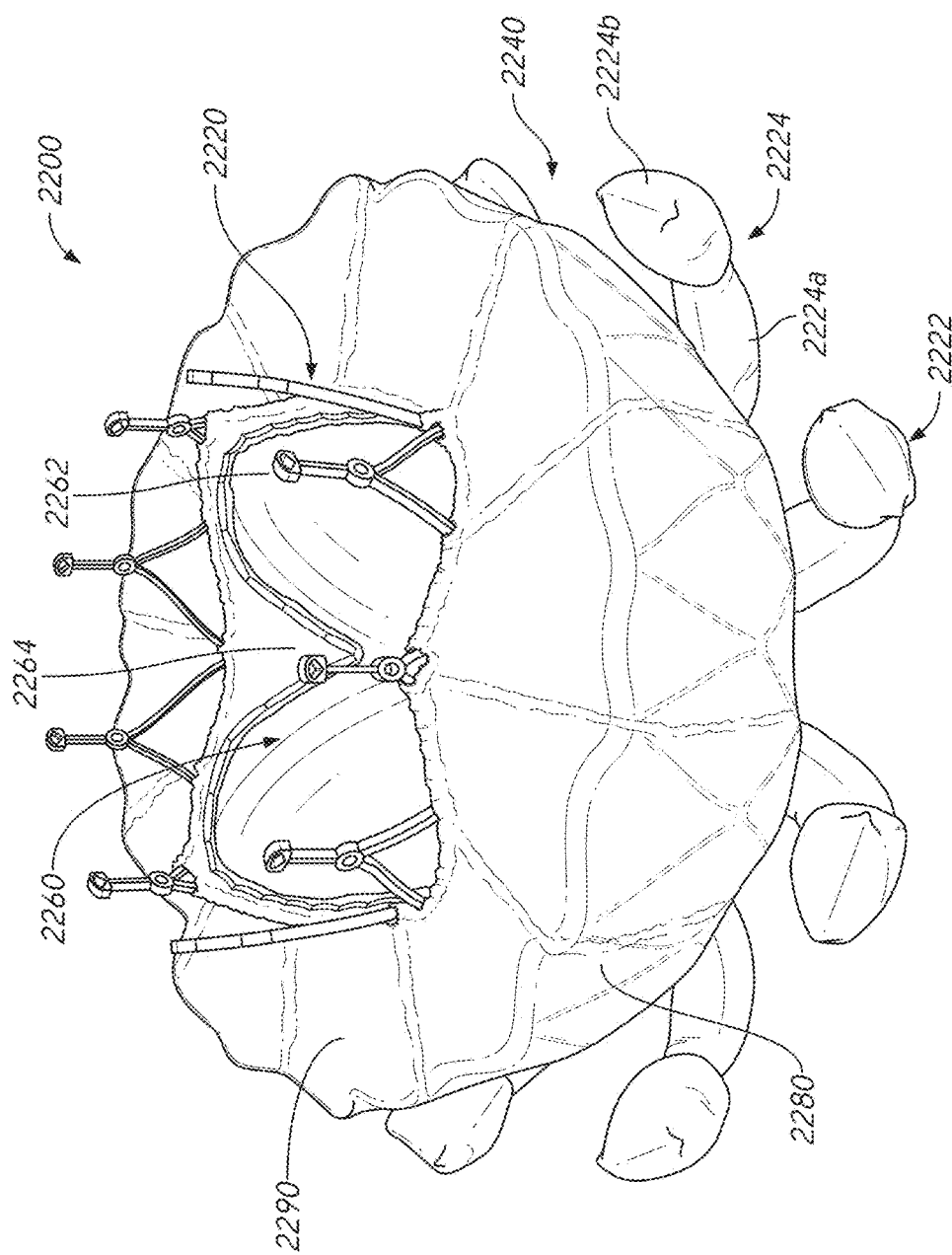
FIG. 44 is a top-oriented perspective view of another embodiment of a prosthesis having an inner frame, an outer frame, a valve body, and a skirt.

With reference next to FIG. 44, an embodiment of a prosthesis 2200 in an expanded configuration, or components of the prosthesis 2200, are illustrated. The prosthesis 2200 can include an inner frame 2220, an outer frame 2240, a valve body 2260, and a skirt 2280. The prosthesis 2200 can share characteristics, such as structure and/or functionality, which are the same as, or at least similar to, those of prostheses described herein such as prosthesis 1900 and 2000.

The prosthesis 2200 can include a cover 2290 to close the gap between the upper regions of the inner frame 2220 and the outer frame 2240. The cover 2290 can extend between the upper end of the outer skirt 2280 and the upper end of the leaflets 2262 and/or liner 2264 of the valve body 2260. As shown, the cover 2290 extends generally perpendicular to the longitudinal axis; however, it is to be understood that the cover 2290 can be transverse to the longitudinal axis. In some embodiments, the cover 2290 can extend downwardly and radially inwardly to funnel blood towards the inflow end of the inner frame 2220 and towards the leaflets. In some embodiments, the cover 2290 can extend upwardly and radially inwardly. This can form a tapered shape which can facilitate recapture of the device. As shown, the cover 2290 can be integrally formed with the skirt 2280; however, it is to be understood that the cover 2290 can be formed separately from the shirt 2280.

The prosthesis 2200 can include a cushion 2224 extending along the length of the inner frame anchoring feature 2222. The cushion 2224 can include a first section 2224a extending along a portion of an individual anchor and a second section 2224b extending along a tip or end of an individual anchor. The cushion 2224 can beneficially reduce trauma to tissue of the body cavity.

With reference next to FIG. 45, an embodiment of a prosthesis 2300 in an expanded configuration, or components of the prosthesis 2300, are illustrated. The prosthesis 2300 can include an inner frame 2320, an outer frame 2340, a valve body 2360, and a skirt 2380. The prosthesis 2300 can share characteristics, such as structure and/or functionality, which are the same as, or at least similar to, those of prostheses described herein.

The prosthesis 2300 can include sutures 2390 extending between the inner frame 2320 and the outer frame 2340. In some embodiments, the sutures 2390 can extend between the lower portion of the outer frame 2340 and the lower portion of the inner frame body 2322 and/or inner frame anchoring feature 2324. The sutures 2390 can be tensioned such that a radially inward force is applied on the outer frame 2340 and a radially outward force is applied on the inner frame 2320. This can beneficially enhance the structural integrity of the prosthesis 2300 by maintaining the outer frame 2340 and inner frame 2320 with an initial amount of strain. In embodiments utilizing materials with a generally linear modulus of elasticity, the pre-strained frame components can require a greater degree of force to further strain the frame components.

Moreover, the structural integrity of the prosthesis 2300 can be enhanced by tying movement of the outer frame 2340 and the inner frame 2320 together. For example, application of a downwardly-oriented force on anchoring feature 2342 can tend to move the inner frame anchoring feature 2342 in a downward and/or radially inward direction. By tying the outer frame 2340 and the inner frame 2320 together, the inner frame 2320 can pull the outer frame 2340 in the same direction. As such, the forces required to move the inner frame anchoring feature 2342 would be higher than if the inner frame anchoring feature 2342 moved independently of the outer frame 2340.

Figure 46:
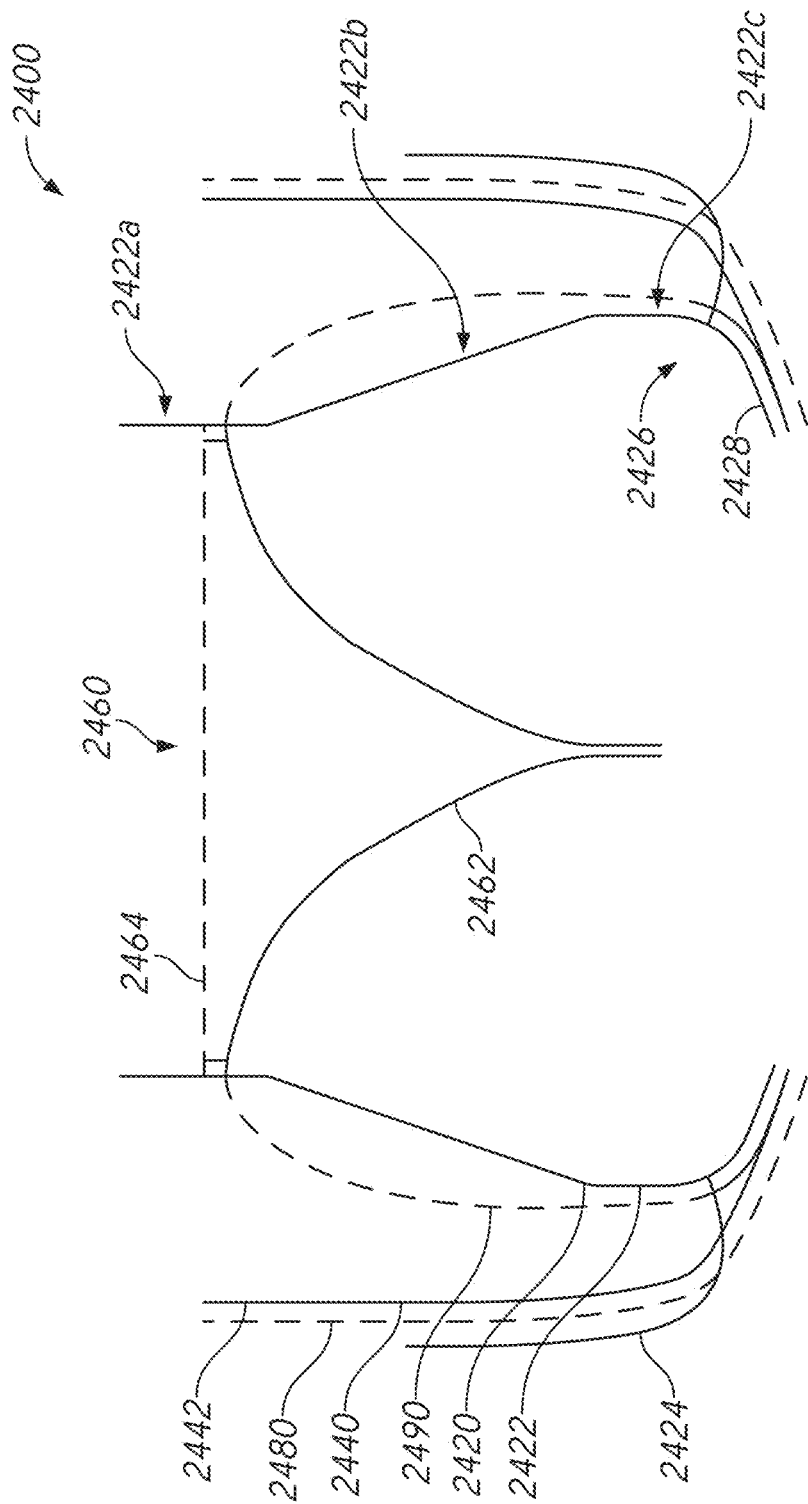
FIG. 46 is a side-oriented cross-sectional schematic view of another embodiment of a prosthesis having an inner frame, an outer frame, a valve body, and a skirt.
Figure 47:
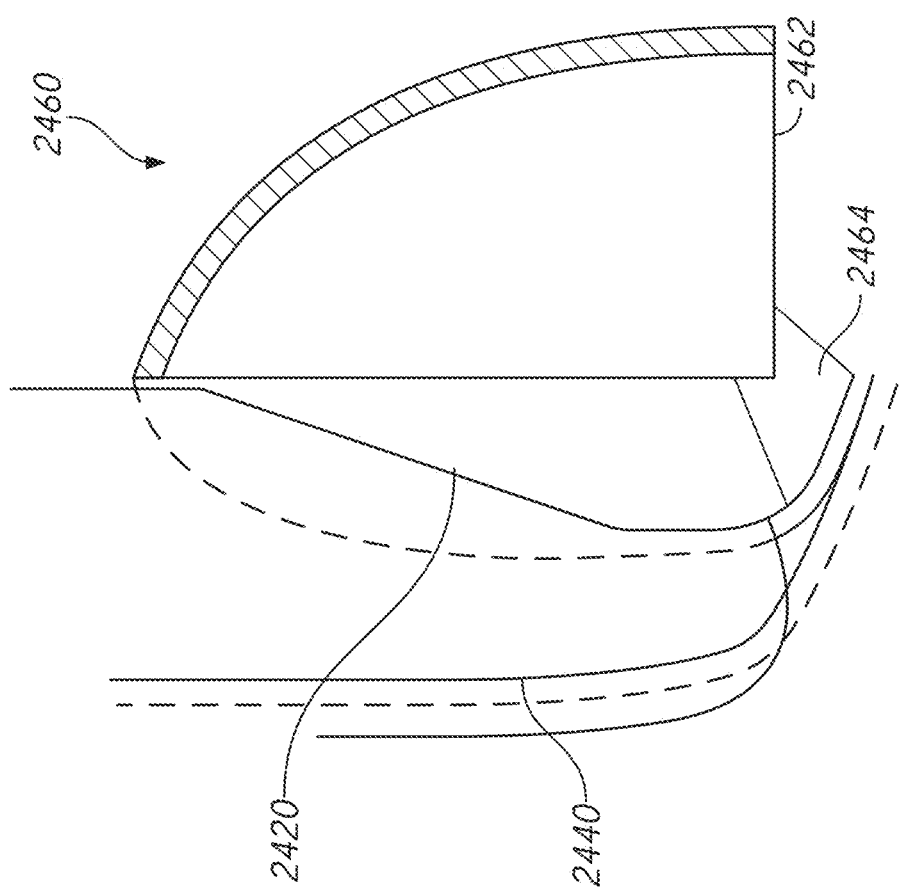
FIG. 47 is a side-oriented cross-sectional schematic view of the prosthesis of FIG. 46 illustrating the commissure of a leaflet.

With reference next to FIGS. 46-47, an embodiment of a prosthesis 2400 in an expanded configuration is illustrated. The prosthesis 2400 can include an inner frame 2420, an outer frame 2440, a valve body 2460, and one or more skirts, such as outer skirt 2480 and inner skirt 2490. The prosthesis 2400 can share characteristics, such as structure and/or functionality, which are the same as, or at least similar to, those of other prostheses described herein such as prostheses 1900, 2000, and 2200.

With reference first to the inner frame 2420, the inner frame 2420 can include an inner frame body 2422 and an inner frame anchoring feature 2424. As shown, the inner frame body 2422 can have a generally bulbous shape and/or frustoconical shape. The diameter of the upper region 2422a can be less than the diameter of the lower region 2422c. This can beneficially allow the use of a smaller valve body 2460 within the inner frame 2420 while allowing the inner frame body 2422 to have a larger diameter proximate the connection between the inner frame body 2422 and the inner frame anchoring feature 2424. This larger diameter can reduce the radial distance between the connection and the tip or end of the inner frame anchoring feature 2424. This can beneficially enhance fatigue resistance of the inner frame anchoring feature 2424 by reducing the length of the cantilever. Moreover, this can allow the inner frame anchoring feature 2424 to more closely match the geometry of the outer frame 2440. The larger diameter can also facilitate valve-in-valve functionality by providing a larger diameter portion in which a subsequent replacement valve may be received.

As shown in the illustrated embodiment, the intermediate region 2422b can have a frustoconical shape such that the diameter increases linearly from an upper end to a lower end of the intermediate region 2422b. However, it is to be understood that the intermediate region 2422b can incorporate a curvature. For example, the intermediate region 2422b can include a geometry similar to that of inner frame body 1522b described in connection with FIG. 33. The inner frame body 2422 can include a bend 2426 along a lower region 2422c of the inner frame body 2420 such that a region 2428 of the inner frame body 2420 tapers radially inwardly towards the longitudinal axis of the prosthesis 2400. The shape of region 2428 can match the shape of a portion of the outer frame 2440.

The radially inward bend can enhance the durability of the valve body 2460. As shown in FIG. 47, an intermediate component 2464 of the valve body 2460 can couple a commissure formed by leaflets 2464 to the inner frame body 2422. The intermediate component 2464 can extend from below the leaflets 2464. As such, when the valve body 2460 closes due to a flow of fluid in the upward direction, the intermediate component 2464 is pulled upwardly into tension as opposed to shear. This can be beneficial in instances where the intermediate component 2464 is more resistant to tension than shear as it can reduce the likelihood of the intermediate component 2464 tearing.

With continued reference to the prosthesis 2400 illustrated in FIG. 46, the valve body 2460 is attached to the inner frame 2420 within an interior of the inner frame body 2422. The valve body 2460 functions as a one-way valve to allow blood flow in a first direction through the valve body 2460 and inhibit blood flow in a second direction through the valve body 2460.

The valve body 2460 can include a plurality of valve leaflets 2462, for example three leaflets 2462, which are joined at commissures. The valve body 2460 can include one or more intermediate components 2464. The intermediate components 2464 can be positioned between a portion of, or the entirety of, the leaflets 2462 and the inner frame 2420 such that at least a portion of the leaflets 2462 are coupled to the frame 2420 via the intermediate component 2464. In this manner, a portion of, or the entirety of, the portion of the valve leaflets 2462 at the commissures and/or an arcuate edge of the valve leaflets 2462 are not directly coupled or attached to the inner frame 2420 and are indirectly coupled or "float" within the inner frame 2420. For example, a portion of, or the entirety of, the portion of the valve leaflets 2462 proximate the commissures and/or the arcuate edge of the valve leaflets 2462 can be spaced radially inward from an inner surface of the inner frame 2420. By using one or more intermediate components 2464, the valve leaflets 2462 can be attached to non-cylindrical frames 2420 and/or frames 2420 having a diameter larger than that of the diameter of the valve leaflets 2462. Further details on floating valve concepts can be found in U.S. application Ser. No. 15/653,390, entitled REPLACEMENT HEART VALVE PROSTHESIS, filed on Jul. 18, 2017, the entirety of which is incorporated herein by reference.

With reference next to the skirts 2480, 2490 illustrated in FIG. 46, the outer skirt 2480 can be attached to the inner frame 2420 and/or outer frame 2440. As shown, the outer skirt 2480 can be positioned around and secured to a portion of, or the entirety of, the exterior of the outer frame 2440. As shown, the outer skirt 2480 can follow the contours of the outer frame 2440; however, it is to be understood that at least a portion of the skirt 2480 can be spaced apart from at least a portion of both the inner frame 2420 and the outer frame 2440.

The inner skirt 2490 can be attached to the valve body 2460 and the outer skirt 2480. As shown, a first end of the inner skirt 2490 can be coupled to the valve body 2460 along portions of the valve body 2460 which are proximate the inner frame 2420. A second end of the inner skirt 2490 can be attached to the lower region of the outer skirt 2480. As shown, the inner skirt 2490 can be positioned radially outwardly of the inner frame 2420. The inner skirt 2490 can be detached from the inner frame 2490 along portions between the upper end and the lower end such that the inner skirt 2490. This can allow the inner skirt 2490 to form a shape which facilitate fluid flow around the underside of the valve body 2460. This can improve washout on the underside of the valve thereby beneficially reducing the risk of thrombosis or clot formation under and around the valve body 2460.

Although the inner skirt 2490 is shown positioned radially outwardly from the inner frame 2420, it is to be understood that the inner skirt 2490 can follow the contours of the inner frame 2420 and/or be positioned along an interior surface of the inner skirt 2490. In some embodiments, the inner frame 2490 can incorporate the shape of the illustrated inner skirt 2490.

Although the prosthesis 2400 has been described as including an inner frame 2420, an outer frame 2440, a valve body 2460, and skirts 2480, 2490, it is to be understood that the prosthesis 2400 need not include all components. For example, in some embodiments, the prosthesis 2400 can include the inner frame 2420, the outer frame 2440, and the valve body 2460 while omitting the skirt 2480. Moreover, although the components of the prosthesis 2400 have been described and illustrated as separate components, it is to be understood that one or more components of the prosthesis 2400 can be integrally or monolithically formed. For example, in some embodiments, the inner frame 2420 and the outer frame 2440 can be integrally or monolithically formed as a single component.

With reference next to FIGS. 11A-K, embodiments of prostheses 500*a-k* in expanded configurations are illustrated. The prostheses 500*a-k* can include inner frames 520*a-k* and outer frames 540*a-k*. The inner frames 520*a-k* can share characteristics, such as structure and/or functionality, which are the same as, or at least similar to, those of the inner frames described herein such as inner frames 120, 220, 400. The outer frames 540*a-k* can share characteristics, such as structure and/or functionality, which are the same as, or at least similar to, those of the outer frames described herein such as outer frames 140, 240, 300.

Figure 11A:
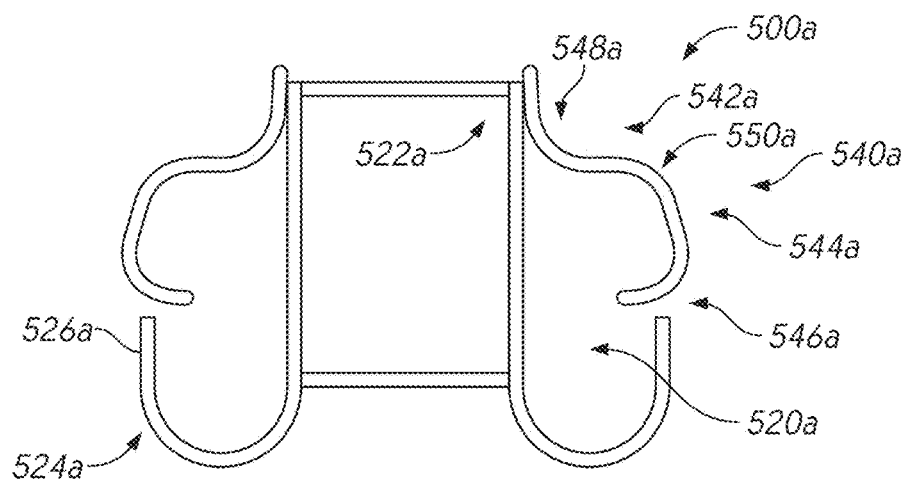
FIGS. 11A-11K are side-oriented schematic views of other embodiments of a prosthesis having an inner frame and an outer frame.

With reference first to the prosthesis 500*a* illustrated in FIG. 11A, outer frame 540*a* can include an upper region 542*a*, an intermediate region 544*a*, and a lower region 546*a*. The upper region 542*a* can include a longitudinally-extending section 548*a* and an outwardly-extending section 550*a*. The intermediate region 544*a* can extend from the outwardly-extending section 550*a*. As shown in the illustrated embodiment, the intermediate region 544*a* can extend in a direction generally parallel to a longitudinal axis of the prosthesis 500*a*. The lower region 546*a* can extend from the intermediate region 544*a*. The lower region 546*a* can bend to extend radially inward towards the longitudinal axis of the prosthesis 500*a*. In some embodiments, the lower region 546*a* can extend in a direction more perpendicular to the longitudinal axis of the prosthesis 500*a* than parallel. For example, the lower region 546*a* can extend in a direction generally perpendicular to the longitudinal axis of the prosthesis 500*a*.

Portions of the outer frame 540*a*, such as the upper region 542*a*, can be attached to the inner frame 520*a* at or proximate an upper region 522*a* of the inner frame 520*a*. As shown in the illustrated embodiment, the outer frame 540*a* can be sized such that a lower end of the outer frame 540*a* is at or proximate an upper end or tip 526*a* of anchoring feature 524*a*.

Figure 11B:
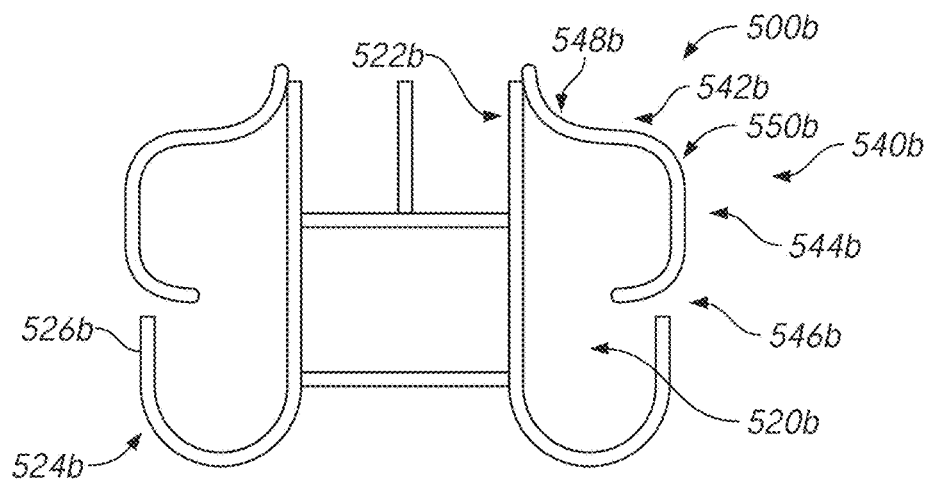

With reference next to the prosthesis 500*b* illustrated in FIG. 11B, outer frame 540*b* can include an upper region 542*b*, an intermediate region 544*b*, and a lower region 546*b*. The upper region 542*b* can include a longitudinally-extending section 548*b* and an outwardly-extending section 550*b*. The regions 542*b*, 544*b*, 546*b* and sections 548*b*, 550*b* can be similar, or the same, as regions 542*a*, 544*a*, 546*a* and sections 548*a*, 550*a* described above in connection with prosthesis 500*a* illustrated in FIG. 11A. Portions of the outer frame 540*b*, such as the upper region 542*b*, can be attached to the inner frame 520*b* at or proximate an upper region 522*b* of the inner frame 520*b*. As shown in the illustrated embodiment, the outer frame 540*b* can be sized such that a lower end of the outer frame 540*b* is above an upper end or tip 526*b* of anchoring feature 524*b*.

Figure 11C:
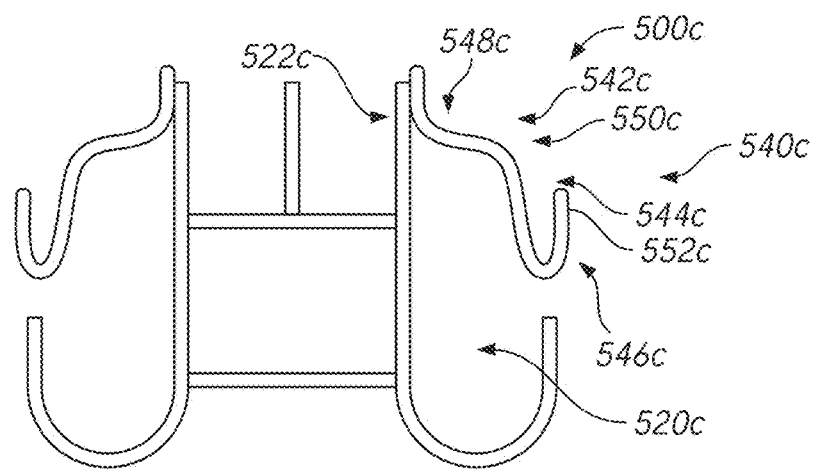

With reference next to the prosthesis 500*c* illustrated in FIG. 11C, outer frame 540*c* can include an upper region 542*c*, an intermediate region 544*c*, and a lower region 546*c*. Portions of the outer frame 540*c*, such as the upper region 542*c*, can be attached to the inner frame 520*c* at or proximate an upper region 522*c* of the inner frame 520*c*. The upper region 542*c* can include a longitudinally-extending section 548*c* and an outwardly-extending section 550*c*. The intermediate region 544*c* can extend from the outwardly-extending section 550*c*. As shown in the illustrated embodiment, the intermediate region 544*c* can extend in a direction generally parallel to a longitudinal axis of the prosthesis 500*c*. The lower region 546*c* can extend from the intermediate region 544*c*. As shown in the illustrated embodiment, the lower region 546*c* can bend to extend radially outwardly away from the longitudinal axis of the prosthesis 500*c*. The lower region 546*c* can continue to bend such that a tip or end 552*c* of the lower region 546*c* extends upwardly. For example, the tip or end 552*c* of the lower region 546*c* can extend upwardly in a direction generally parallel to the longitudinal axis of the prosthesis 500*c*.

In some embodiments, the lower region 546*c* can function similarly to anchoring features described herein such as, but not limited to, anchoring features 124, 224. The tips or ends 552*c* as described above can be positioned to contact or engage a native mitral valve annulus on a ventricular side, tissue beyond the native valve annulus on a ventricular side, native leaflets on a ventricular side, and/or other tissue at or around the implantation location during one or more phases of the cardiac cycle, such as systole and/or diastole. For example, the tips or ends 552*c* can be positioned to contact a ventricular side of the native mitral valve annulus and/or tissue beyond the ventricular side of the native valve annulus. In some embodiments, the tips or ends 552*c* can advantageously provide atraumatic surfaces that may be used to contact or engage intralumenal tissue without causing unnecessary or undesired trauma to tissue. For example, the tips or ends 552*c* can form flat, substantially flat, curved or other non-sharp surfaces to allow the tips to engage and/or grasp tissue, without necessarily piercing or puncturing through tissue. A looped end or looped anchor may assist the frame in not getting caught up on structures at or near the treatment location.

Figure 11D:
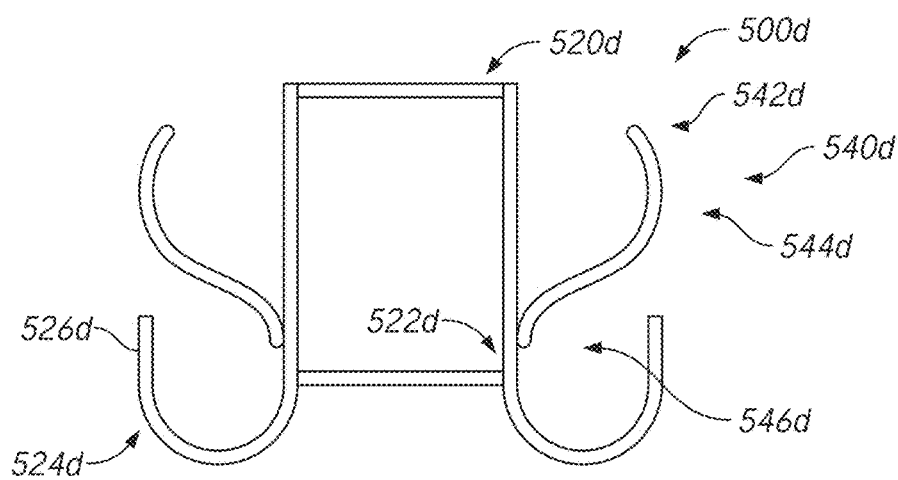

With reference next to the prosthesis 500*d* illustrated in FIG. 11D, outer frame 540*d* can include an upper region 542*d*, an intermediate region 544*d*, and a lower region 546*d*. As shown in the illustrated embodiment, the outer frame 540*d* can have a generally bulbous shape with a diameter of the intermediate region 544*d* being greater than the diameter of the upper region 542*d* and the diameter of the lower region 546*d*. Moreover, as shown in the illustrated embodiment, the diameter of the upper region 542*d* can be larger than the diameter of the lower region 546*d*.

Portions of the outer frame 540*d*, such as the lower region 546*d*, can be attached to the inner frame 520*d* at or proximate a lower region 522*d* of the inner frame 520*d*. As shown in the illustrated embodiment, the outer frame 540*d* can be sized such that an upper end of the outer frame 540*d* is at or proximate a plane orthogonal to the longitudinal axis of the prosthesis 500*d* which passes through the upper end of the inner frame 520*d*. The outer frame 540*d* can be sized such that a lower end of the outer frame 540*d* is axially below the tips or ends 526*d* of the inner frame anchoring feature 524*d*. The outer frame 540*d* can be sized such that a diameter of the widest portion of the outer frame 540*d* is greater than a widest portion of the inner frame anchoring feature 524*d*.

Figure 11E:
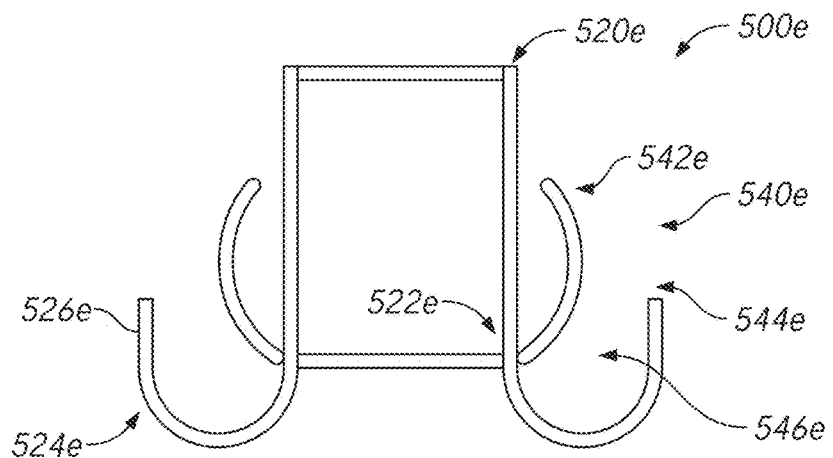

With reference next to the prosthesis 500*e* illustrated in FIG. 11E, outer frame 540*e* can include an upper region 542*e*, an intermediate region 544*e*, and a lower region 546*e*. As shown in the illustrated embodiment, the outer frame 540*e* can have a generally bulbous shape with a diameter of the intermediate region 544*e* being greater than the diameter of the upper region 542*e* and the diameter of the lower region 546*e*. Moreover, as shown in the illustrated embodiment, the diameter of the upper region 542*e* can be larger than the diameter of the lower region 546*e*.

Portions of the outer frame 540*e*, such as the lower region 546*e*, can be attached to the inner frame 520*e* at or proximate a lower region 522e of the inner frame 520e. As shown in the illustrated embodiment, the outer frame 540e can be sized such that an upper end of the outer frame 540e is below a plane orthogonal to the longitudinal axis of the prosthesis 500e which passes through the upper end of the inner frame 520e. The outer frame 540e can be sized such that a lower end of the outer frame 540e is axially below the tips or ends 526e of the inner frame anchoring feature 524e. The outer frame 540e can be sized such that a diameter of the widest portion of the outer frame 540e is less than a widest portion of the inner frame anchoring feature 524e. As shown in the illustrated embodiment, the tips 526e of the inner anchoring feature 524e can be at or proximate an intermediate region 544e of the outer frame 540e.

Figure 11F:
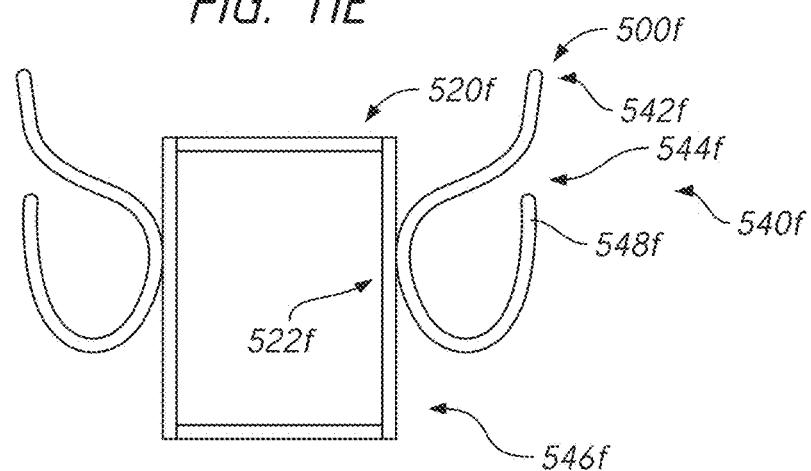

With reference next to the prosthesis 500f illustrated in FIG. 11F, outer frame 540f can include an upper region 542f, an intermediate region 544f, and a lower region 546f. Portions of the outer frame 540f, such as the intermediate region 544f and/or lower region 546f, can be attached to the inner frame 520f at or proximate an intermediate region 522f of the inner frame 520f.

The upper region 542f can extend downwardly in a direction generally parallel to a longitudinal axis of the prosthesis 500f. The intermediate region 544f can extend from the upper region 542f. As shown in the illustrated embodiment, the intermediate region 544f can extend in a direction radially inward towards the longitudinal axis of the prosthesis 500f. The lower region 546f can extend from the intermediate region 544f. As shown in the illustrated embodiment, the lower region 546f can bend to extend radially outwardly away from the longitudinal axis of the prosthesis 500f. In some embodiments, the lower region 546f can continue to bend such that a tip or end 548f of the lower region 546f extends upwardly. For example, the tip or end 548f of the lower region 546f can extend upwardly in a direction generally parallel to the longitudinal axis of the prosthesis 500f. In some embodiments, the tip or end 548f of the lower region 546f can extend axially such that it is positioned at or proximate the intermediate region 544f.

In some embodiments, the lower region 546f can function similarly to anchoring features described herein such as, but not limited to, anchoring features 124, 224. The tips or ends 548f as described above can be positioned to contact or engage a native mitral valve annulus on a ventricular side, tissue beyond the native valve annulus on a ventricular side, native leaflets on a ventricular side, and/or other tissue at or around the implantation location during one or more phases of the cardiac cycle, such as systole and/or diastole. For example, the tips or ends 548f can be positioned to contact a ventricular side of the native mitral valve annulus and/or tissue beyond the ventricular side of the native valve annulus. In some embodiments, the tips or ends 548f can advantageously provide atraumatic surfaces that may be used to contact or engage intralumenal tissue without causing unnecessary or undesired trauma to tissue. For example, the tips or ends 548f can form flat, substantially flat, curved or other non-sharp surfaces to allow the tips to engage and/or grasp tissue, without necessarily piercing or puncturing through tissue. A looped end or looped anchor may assist the frame in not getting caught up on structures at or near the treatment location.

Figure 11G:
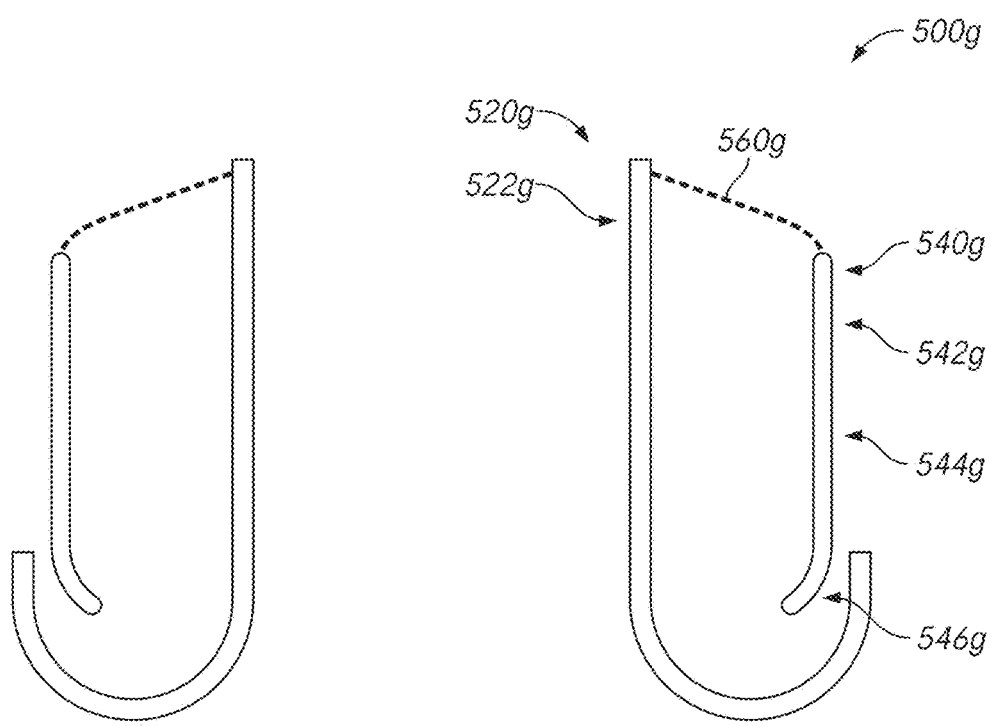

With reference next to the prosthesis 500g illustrated in FIG. 11G, outer frame 540g can include an upper region 542g, an intermediate region 544g, and a lower region 546g. Portions of the outer frame 540f, such as the upper region 544g, can be attached to the inner frame 520g at or proximate an upper region 522g of the inner frame 520g. As shown in the illustrated embodiment, the outer frame 540g can loosely attached to the inner frame 520g via a coupling 560g such that the entirety of the outer frame 540g is generally movable relative to the entirety of the inner frame 520g. For example, the coupling 560g can be a portion of a skirt attached to both the outer frame 540g and the inner frame 520g.

The upper region 542g can extend downwardly in a direction generally parallel to a longitudinal axis of the prosthesis 500g. The intermediate region 544g can extend from the upper region 542g. As shown in the illustrated embodiment, the intermediate region 544g can extend in a direction generally downwards such that the intermediate region 544g and the upper region 542g form a generally cylindrical portion. The lower region 546g can extend from the intermediate region 544g. As shown in the illustrated embodiment, the lower region 546g can bend to extend radially inward towards the longitudinal axis of the prosthesis 500g. In some embodiments, the lower region 546g can extend in a direction more perpendicular to the longitudinal axis of the prosthesis 500g than parallel. For example, the lower region 546g can extend in a direction generally perpendicular to the longitudinal axis of the prosthesis 500g.

Figure 11H:
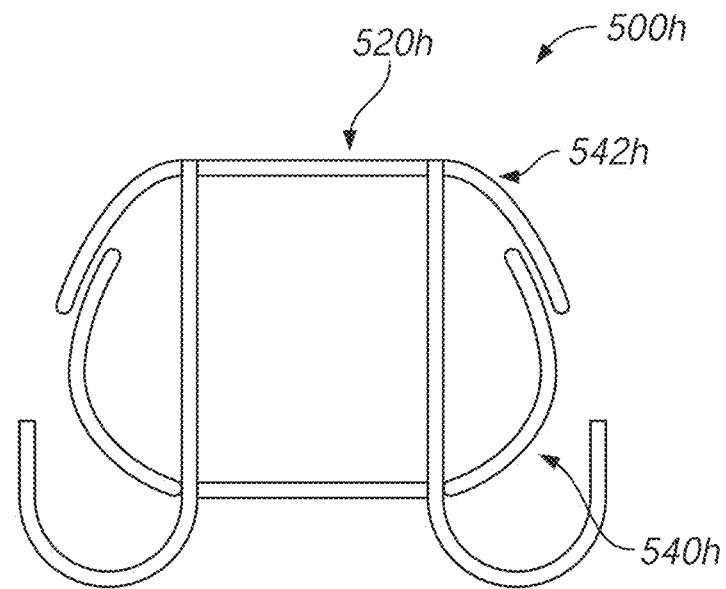

With reference next to the prosthesis 500h illustrated in FIG. 11H, the prosthesis 500h can include a lower outer frame 540h and an upper outer frame 560h. The prosthesis 500h can be similar to other prostheses described herein, such as prosthesis 500e described in connection with FIG. 11E. For example, the lower outer frame 540h can be similar to outer frame 540e described in connection with FIG. 11E. As shown in the illustrated embodiment, the lower and upper outer frames 540h, 560h can form a generally bulbous shape with a diameter of an intermediate region being greater than the diameter of the upper region and the diameter of the lower region. The lower outer frame 540h can be attached to the inner frame 520h along a lower region of the lower outer frame 540h. The upper outer frame 560h can be attached to the inner frame 520h along an upper region of the upper outer frame 540h.

The upper outer frame 560h can extend downwardly and extend radially outwardly. As shown, the upper end of the upper outer frame 560h can have a diameter which is less than the upper end of the lower outer frame 560h. The lower end of the upper outer frame 560h can have a diameter which is greater than the upper end of the lower outer frame 560h. As shown, the upper outer frame 560h can overlap with a portion of the lower outer frame 540h when at least when the prosthesis 500h is in a partially or fully expanded state.

The shape of the upper outer frame 560h can facilitate recapture of the prosthesis 500h. In some embodiments, the prosthesis 500h is sequentially deployed with the lower region of the prosthesis 500h being deployed before the upper region of the prosthesis 500h. For example, a sheath (not shown) maintaining the prosthesis 500h in a collapsed or crimped configuration can be retracted upwardly. The upper region of the prosthesis 500h can be retained in a collapsed or crimped configuration while the remaining portions of the prosthesis 500h are allowed to expand as shown, for example, in FIG. 56F. Should a user decide to recapture the prosthesis 500h to re-position or remove the prosthesis 500h, the user may advance the sheath downwardly over the prosthesis 500h. This process can be facilitated due to the shape and/or attachment of the upper end of the upper outer frame 560h. Moreover, as the sheath is advanced downwardly, the upper outer frame 560h can crimp or collapse over the lower outer frame 540*h* thereby crimping the lower outer frame 540*h*.

Figure 11I:
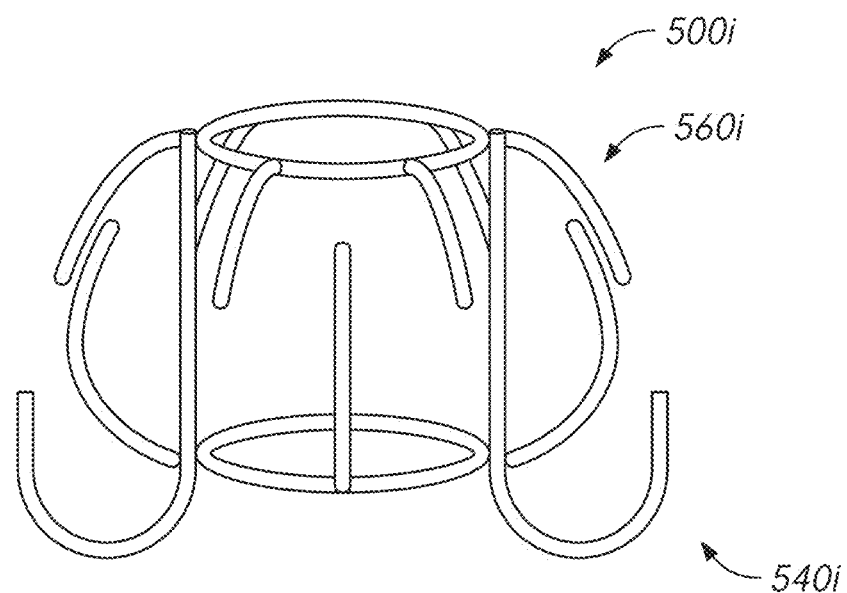

With reference next to the prosthesis 500*i* illustrated in FIG. 11I, the prosthesis 500*i* can include a lower outer frame 540*i* and an upper outer frame 560*i*. The prosthesis 500*i* can be similar to other prostheses described herein, such as prosthesis 500*h* described in connection with FIG. 11H. As shown, the upper outer frame 560*i* and the lower outer frame 540*i* can be formed from structures, such as struts, which do not overlap.

Figure 11J:
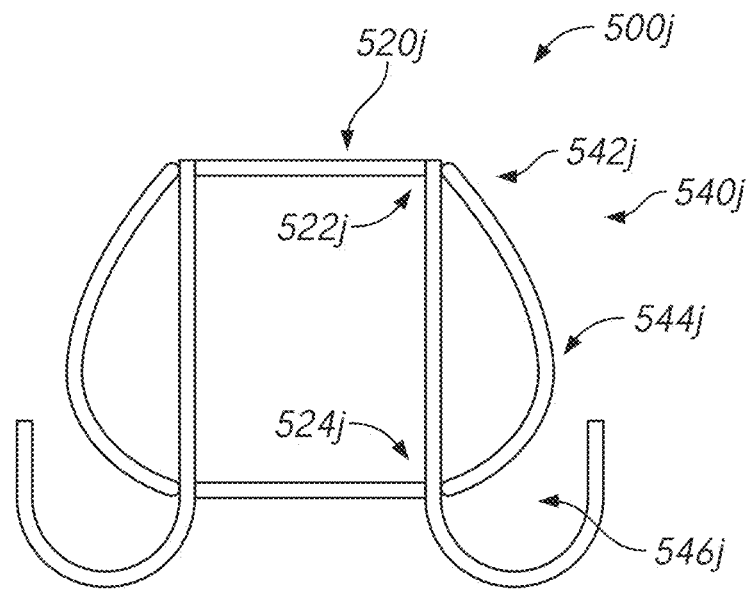

With reference next to the prosthesis 500*j* illustrated in FIG. 11J, outer frame 540*j* can include an upper region 542*j*, an intermediate region 544*j*, and a lower region 546*j*. As shown in the illustrated embodiment, the outer frame 540*j* can have a generally bulbous shape with a diameter of the intermediate region 544*j* being greater than the diameter of the upper region 542*j* and the diameter of the lower region 546*j*. Portions of the outer frame 540*j* such as the upper region 542*j* and/or the lower region 546*j*, can be attached to the inner frame 520*j* at or proximate an upper region 522*j* and/or lower region 524*j* of the inner frame 520*j*. The outer frame 540*j* may be formed from a plurality of struts and/or cells which can allow the outer frame to be crimped or collapsed to a configuration which generally matches the size and/or shape of the inner frame 520*j*. For example, when the outer frame 540*j* is in a collapsed configuration, the length of the outer frame 540*j* can generally match that of the inner frame 520*j*. When expanded, differences in cell structure between the upper region 542*j*, intermediate region 544*j*, and the lower region 546*j* can allow the regions to expand to different extents as shown. For example, in some embodiments, the intermediate region 544*j* can have a strut geometry which differs from the strut geometry of the upper and/or lower regions 542*j*, 546*j*.

The shape of the outer frame 540*j* can facilitate recapture of the prosthesis 500*j*. In some embodiments, the prosthesis 500*j* is sequentially deployed with the lower region of the prosthesis 500*h* being deployed before the upper region of the prosthesis 500*h*. For example, the upper region of the prosthesis 500*j* can be retained in a collapsed or crimped configuration while the remaining portions of the prosthesis 500*j* are allowed to expand as shown, for example, in FIG. 56F. Should a user decide to recapture the prosthesis 500*j* to re-position or remove the prosthesis 500*j*, the user may advance the sheath downwardly over the prosthesis 500*j*. This process can be facilitated due to the shape and/or attachment of the upper end of the outer frame 540*j*.

Figure 11K:
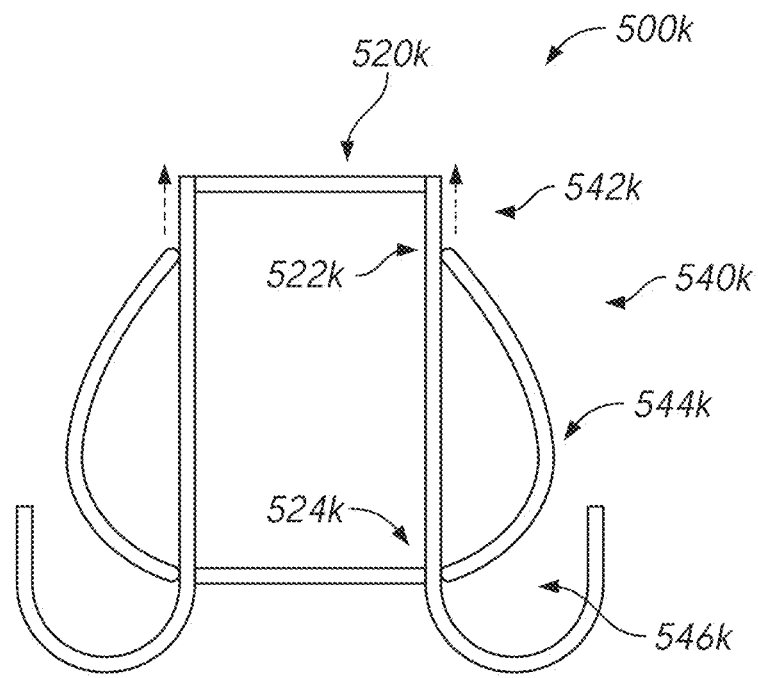

With reference next to the prosthesis 500*k* illustrated in FIG. 11*k*, outer frame 540*k* can include an upper region 542*k*, an intermediate region 544*k*, and a lower region 546*k*. As shown in the illustrated embodiment, the outer frame 540*k* can have a generally bulbous shape with a diameter of the intermediate region 544*k* being greater than the diameter of the upper region 542*k* and the diameter of the lower region 546*k*. The shape of the outer frame 540*k* can facilitate recapture of the prosthesis 500*k* for reasons similar to those described in connection with prosthesis 500*j* shown in FIG. 11J.

Portions of the outer frame 540*k* such as the upper region 542*k* and/or the lower region 546*k*, can be attached to the inner frame 520*k* at or proximate an upper region 522*k* and/or lower region 524*k* of the inner frame 520*k*. As shown, the coupling between the upper region 542*k* of the outer frame 540*k* and inner frame 520*k* can be movable. This can facilitate crimping of the outer frame 540*k* since the upper region 542*k* can move independently of the inner frame 520*k*. In some embodiments, the upper region 542*k* of the outer frame 540*k* can be coupled to the inner frame 520*k* via a track or rail to allow the upper region 542*k* to slide relative to the inner frame 520*k*. This can beneficially maintain the upper end of the outer frame 540*k* at a diameter which matches the diameter of the inner frame 520*k*. In some embodiments, the upper region 542*k* of the outer frame 540*k* can be coupled to the inner frame 520*k* via a coupling similar to the coupling 560*g* discussed in connection with FIG. 11G. For example, the coupling 560*g* can be a portion of a skirt. Although the coupling between the upper region 542*k* of the outer frame 540*k* and inner frame 520*k* has been described as movable, it is to be understood that the coupling between the lower region 546*k* of the outer frame 540*k* can be movably coupled to the inner frame 520*k* in lieu of, or in combination with, the movable coupling between the upper region 542*k* and the inner frame 520*k*.

Embodiments of Mesh Anchoring Features

In some embodiments, the prostheses described herein can incorporate a mesh or braided anchoring feature. It is to be understood that the mesh or braided anchoring features can be used in combination with other anchoring features described herein or as a replacement for one or more of the anchoring features described herein.

Figure 12:
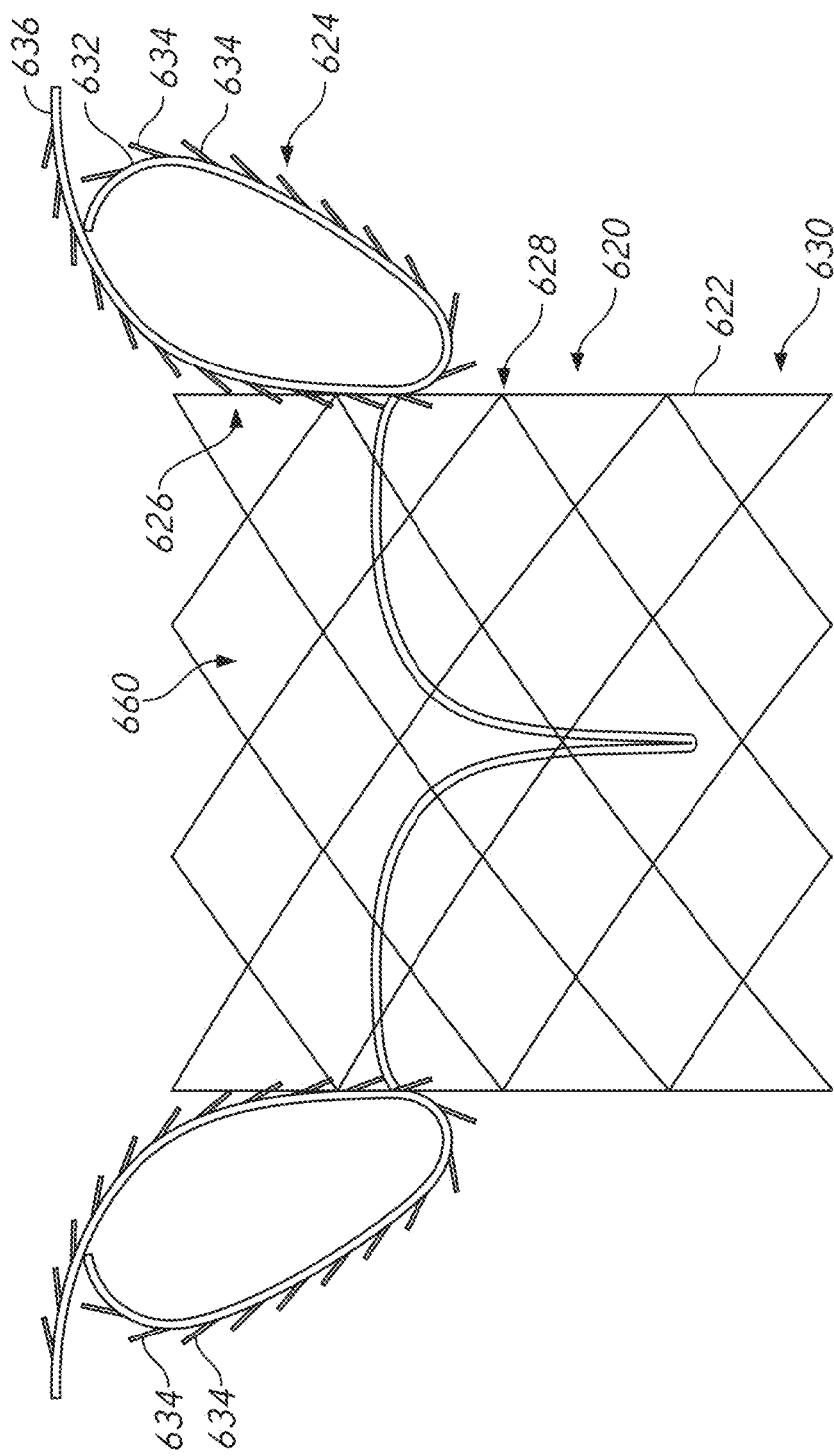
FIG. 12 is a side-oriented schematic view of an embodiment of a prosthesis having a frame body, a mesh anchoring feature, and a valve body.
Figure 14:
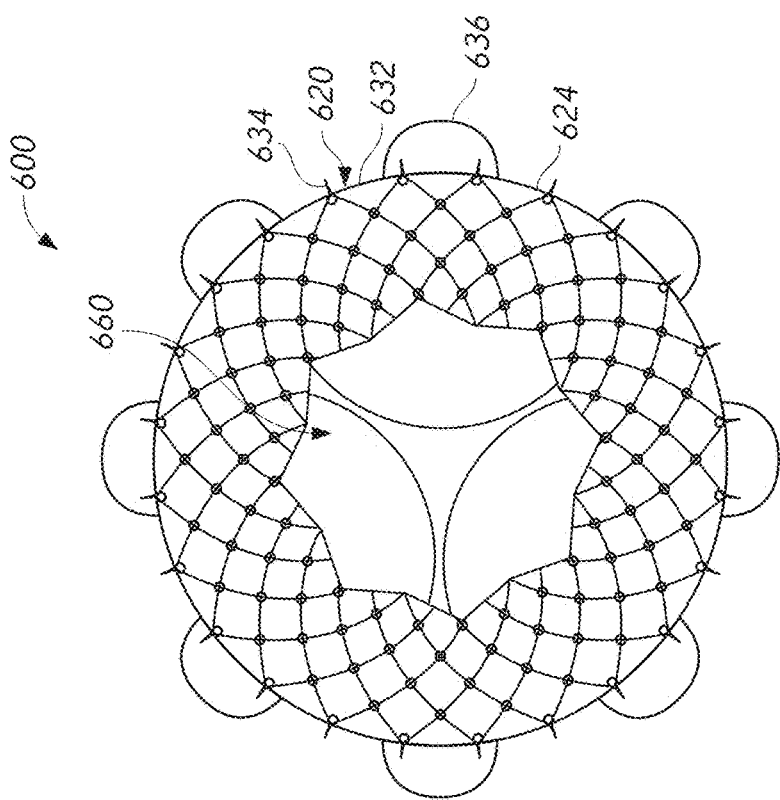
FIG. 14 is a bottom view of the prosthesis of FIG. 12.
Figure 13:
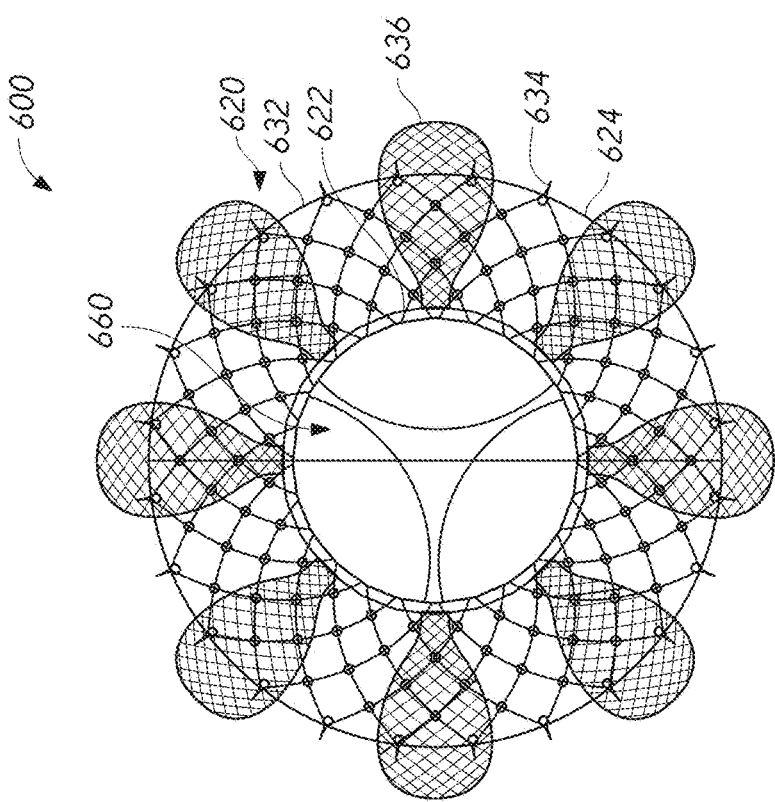
FIG. 13 is a top view of the prosthesis of FIG. 12.

With reference next to FIGS. 12-14, an embodiment of a prosthesis 600 in an expanded configuration is illustrated. The prosthesis 600 can include a frame 620 and a valve body 660. A longitudinal axis of the prosthesis 600 may be defined as the central axis that extends through the center of the prosthesis 600 between the upper and lower ends of the prosthesis 600. In some situations, the prosthesis 600 may be oriented such that an upper end of the prosthesis 600 is a proximal portion and a lower end of the prosthesis 600 is a distal portion. The valve body 660 can be similar to, or the same as, other valve bodies described herein such as, but not limited to, valve bodies 160, 260, 760, 870, 970. Accordingly, reference should be made to the discussion of such valve bodies.

As shown in the illustrated embodiment, the frame 620 can include a frame body 622 and an anchoring feature 624. The frame body 622 can include an upper region 626, an intermediate region 628, and a lower region 630. As shown, the frame body 622 can have a generally cylindrical shape such that the diameters of the upper region 626, the intermediate region 628, and the lower region 620 are generally constant. However, it is to be understood that the diameters of the upper region 626, the intermediate region 628, and/or the lower region 630 can be different. For example, in some embodiments, a diameter of the intermediate region 628 can be larger than the upper region 626 and the lower region 630 such that the frame body 622 has a generally bulbous shape. In some embodiments, the diameter of the lower region 630 can be larger than the diameter of the upper region 626. In other embodiments, the diameter of the upper region 626 can be larger than the diameter of the lower region 630. In some situations, the frame 620 may be oriented such that the upper region 626 is a proximal portion and the lower region 630 is a distal portion. Moreover, although the frame body 622 has been described and illustrated as being cylindrical, it is to be understood that all or a portion of the frame body 622 can be have a non-circular cross-section such as, but not limited to, a D-shape, an oval or an otherwise ovoid cross-sectional shape. The frame body 622 can share characteristics, such as structure and/or functionality, which are the same as, or at least similar to, those of frames described herein such as, but not limited to, inner frames 120, 220, 400, 520*a-g*.

As shown, the anchoring feature 624 can be positioned at or proximate the upper region 626 of the frame body 622.

However, it is to be understood that the anchoring feature 624 can be positioned along other regions of the frame body 622 such as the intermediate region 630 and/or the lower region 628 based on the configuration of the prosthesis 600 and the implantation location. The anchoring feature 624 can include a body portion 632 formed from a wire mesh. The body portion 632 can be positioned such that it is radially outward of the frame body 622. The body portion 632 can be relatively flexible, resilient, and/or malleable. For example, the construction of the body portion 632, such as the materials used and/or the geometry of the mesh, can be chosen to provide this flexibility, resilience, and/or flexibility. In some embodiments, the body portion 632 can be formed from a metal including, but not limited to, a shape memory metal such as Nitinol. The body portion 632 can take the form of a braided tube. In some embodiments, the body portion 632 can be formed separately from the other portions of the frame 620. The body portion 632 can be attached to the frame 620 using any of the fasteners and/or techniques described herein including, but not limited to, mechanical fasteners, such as sutures, staples, screws, rivets, interfacing members (e.g., tabs and slots which can be on the frame 620 and the body portion 632), and any other type of mechanical fastener as desired, chemical fasteners such as adhesives and any other type of chemical fastener as desired, fastening techniques such as welding, soldering, sintering, and any other type of fastening technique as desired, and/or a combination of such fasteners and techniques. The frame 620 and the body portion 632 can be indirectly attached via an intermediate component, such as a skirt. In other embodiments, the body portion 632 can be integrally or monolithically formed with other portions of the frame 620.

The flexibility, resiliency, and/or malleability of the body portion 632 can beneficially allow the body portion 632 to conform to the anatomy of the body cavity in which it is positioned, such as tissue of a native heart wall, a native valve annulus, and/or leaflets. In some situations, such as when the body portion 632 is positioned within a native mitral valve, the body portion 632 can conform to the shape of the mitral valve annulus such that an upper region of the body portion 632 extends over an atrial side of the native mitral valve annulus, an intermediate region of the body portion 632 conforms to the inner periphery of the native mitral valve annulus, and/or the lower region of the body portion 632 contacts portions of the leaflets. Moreover, the flexibility, resiliency, and/or malleability can beneficially allow the body portion 632 to be crimped to a smaller diameter during the delivery process, thereby allowing for the use of a smaller gauge delivery device.

The anchoring feature 624 can include one or more protrusions or barbs 634. The one or more protrusions 634 can be positioned along the body portion 632. As shown in the illustrated embodiment, the one or more protrusions 634 can advantageously enhance securement of the anchoring feature 624 to tissue of the body cavity in which the anchoring feature 624 is positioned, such as tissue of a native heart wall, a native valve annulus, and/or native leaflets. In some instances, the protrusions 634 can be oriented to inhibit or limit upward movement of the prosthesis 600. For example, in situations where the prosthesis 600 is positioned within a native mitral valve, the protrusions 634 can be oriented to inhibit or limit upward movement of the prosthesis 600 during systole. Moreover, the one or more protrusions 634 can beneficially encourage tissue ingrowth by activating the fibroblasts and inducing tissue proliferation. The length and directionality of the protrusions 634 can be chosen to reduce trauma yet provide adequate engagement with tissue and adequate tissue ingrowth.

The anchoring feature 624 can include one or more arms or paddles 636. As shown, the anchoring feature 624 can include eight arms or paddles 636, however, it is to be understood that the anchoring feature 624 can include a greater or fewer number of arms or paddles. The arms or paddles 636 can be attached at or proximate an upper region 626 of the frame body 622. The arms or paddles 638 can extend radially outward relative to the longitudinal axis of the prosthesis 600. As shown in the illustrated embodiment, the arms or paddles 636 can be positioned to extend above the body portion 632. The arms or paddles 636 can be formed from a wire mesh. The arms or paddles 636 can be relatively flexible, resilient, and/or malleable. For example, the construction of the arms or paddles 636, such as the materials used and/or the geometry of the mesh, can be chosen to provide this flexibility, resilience, and/or flexibility. The construction of the arms or paddles 636 can be chosen to provide adequate engagement with tissue while is use while reducing the forces exerted by the prosthesis 600 while in a collapsed or crimped configuration.

In some embodiments, the arms or paddles 636 can be formed from a metal including, but not limited to, a shape memory metal such as Nitinol. The arms or paddles 636 can be braided. In some embodiments, the arms or paddles 636 can be formed separately from the other portions of the frame 620 such as the body portion 632. The arms or paddles 636 can be attached to other portions of the frame 620 such as the body portion 632 using any of the fasteners and/or techniques described herein including, but not limited to, mechanical fasteners, such as sutures, staples, screws, rivets, interfacing members (e.g., tabs and slots which can be on the arms or paddles 636 and other portions of the frame 620), and any other type of mechanical fastener as desired, chemical fasteners such as adhesives and any other type of chemical fastener as desired, fastening techniques such as welding, soldering, sintering, and any other type of fastening technique as desired, and/or a combination of such fasteners and techniques. The arms or paddles 636 and other portions of the frame 620 can be indirectly attached via an intermediate component, such as a skirt. In other embodiments, the arms or paddles 636 can be integrally or monolithically formed with other portions of the frame 620 and/or body portion 632.

The flexibility, resiliency, and/or malleability of the arms or paddles 636 can beneficially allow the arms or paddles 636 to conform to the anatomy of the body cavity in which it is positioned, such as tissue of a native heart wall, a native valve annulus, and/or leaflets. In some situations, such as when the arms or paddles 636 are positioned within a native mitral valve, the arms or paddles 636 can conform to the shape of the atrial wall. Moreover, the flexibility, resiliency, and/or malleability can beneficially allow the body portion 632 to be crimped to a smaller diameter during the delivery process, thereby allowing for the use of a smaller gauge delivery device.

Although not shown, the frame body 622 can include an anchoring feature positioned below the anchoring feature 624. The anchoring feature can share characteristics, such as structure and/or functionality, which are the same as, or at least similar to, those of anchoring features described herein including, but not limited to, inner frame anchoring features 124, 224, 524d, 524e and lower frame anchoring features 726, 826, 926, 1106, 1220.

Figure 15:
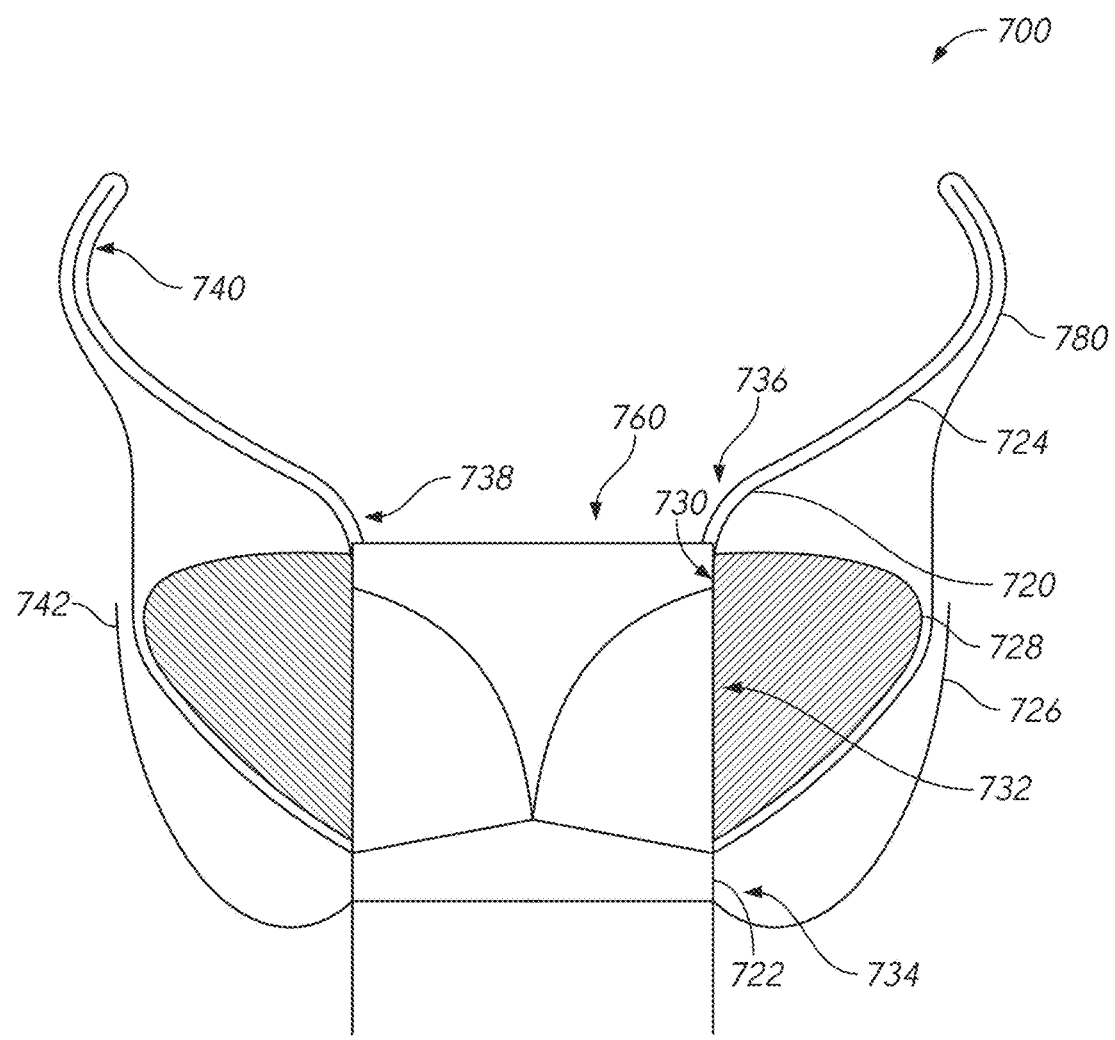
FIG. 15 is a side-oriented cross-sectional schematic view of an embodiment of a prosthesis having a frame, a mesh anchoring feature, a valve body, and a skirt.

With reference next to FIG. 15, an embodiment of a prosthesis 700 in an expanded configuration is illustrated. The prosthesis 700 can include a frame 720, a valve body 760, and a skirt 780. A longitudinal axis of the prosthesis 700 may be defined as the central axis that extends through the center of the prosthesis 700 between the upper and lower ends of the prosthesis 700. In some situations, the prosthesis 700 may be oriented such that an upper end of the prosthesis 700 is a proximal portion and a lower end of the prosthesis 700 is a distal portion. The valve body 760 can share characteristics, such as structure and/or functionality, which are the same as, or at least similar to, those of other valve bodies described herein such as, but not limited to, valve bodies 160, 260, 660, 870, 970.

The frame 720 can include a frame body 722, an upper anchoring feature 724, a lower anchoring feature 726, and an intermediate anchoring feature 728. The frame body 722 can include an upper region 730, an intermediate region 732, and a lower region 734. As shown, the frame body 722 can have a generally cylindrical shape such that the diameters of the upper region 730, the intermediate region 732, and the lower region 734 are generally constant. However, it is to be understood that the diameters of the upper region 730, the intermediate region 732, and/or the lower region 734 can be different. For example, in some embodiments, a diameter of the intermediate region 732 can be larger than the upper region 730 and the lower region 734 such that the frame body 722 has a generally bulbous shape. In some embodiments, the diameter of the lower region 734 can be larger than the diameter of the upper region 730. In other embodiments, the diameter of the upper region 730 can be larger than the diameter of the lower region 734. Moreover, although the frame body 722 has been described and illustrated as being cylindrical, it is to be understood that all or a portion of the frame body 722 can be have a non-circular cross-section such as, but not limited to, a D-shape, an oval or an otherwise ovoid cross-sectional shape. The frame body 722 can share characteristics, such as structure and/or functionality, which are the same as, or at least similar to, those of frame such as inner frames 120, 220, 400, 520a-g.

The upper anchoring feature 724 can extend radially outward from the longitudinal axis of the prosthesis 700. In this manner, upper anchoring feature 724 can create a flared or shoulder portion 736 of the frame 720. As shown in the illustrated embodiment, a portion of the upper anchoring feature 724 can extend radially outward via a bend 738 beginning at or proximate the upper end of the upper region 730 of the frame body 722. The bend 738 can be about a circumferential axis such that the upper anchoring feature 724 extends in a direction more perpendicular to the longitudinal axis of the prosthesis 700 than the frame body 722. In some embodiments, the bend 738 can generally form an arc with an angle between about 20 degrees to about 90 degrees. For example, as shown in the illustrated embodiment, the arc can have an angle of about 60 degrees. In some embodiments, the bend 738 can form an arc with an angle between about 30 degrees to about 70 degrees. The radius of curvature of the arc may be constant such that the bend 738 forms a circular arc or may differ along the length of the bend 738.

The upper anchoring feature 724 can include a second bend 740 above the bend 738. The bend 740 can be about a circumferential axis such that the portion of the upper anchoring feature 724 above the second bend 740 extends in a direction less perpendicular to the longitudinal axis of the prosthesis 700 than the portion of the upper anchoring feature 724 below the second bend 740. In some embodiments, the bend 740 can continue such that the end of the upper anchoring feature 724 extends in a direction radially towards the longitudinal axis of the prosthesis 700. In some embodiments, the second bend 740 can generally form an arc with an angle between about 20 degrees to about 90 degrees. For example, as shown in the illustrated embodiment, the arc can have an angle of about 90 degrees. In some embodiments, the second bend 740 can form an arc with an angle between about 45 degrees to about 135 degrees. The radius of curvature of the arc may be constant such that the second bend 740 forms a circular arc or may differ along the length of the second bend 740.

With continued reference to the frame 720 illustrated in FIG. 15, the lower anchoring feature 726 can extend generally downwardly from above a lower end of the lower region 734 of the inner frame body 722 and/or generally radially outward of the longitudinal axis of the prosthesis 700. As shown in the illustrated embodiment, the lower anchoring feature 726 can also extend upwardly towards an end 742 of the lower anchoring feature 726. As will be discussed in further detail below, components of the frame 120, such as the lower anchoring feature 726, can be used to attach or secure the prosthesis 700 to a native valve. For example, in some embodiments, the lower anchoring feature 726 can be used to attach or secure the prosthesis 700 to a native valve, such as a native mitral valve. In such an embodiment, the lower anchoring feature 726 can be positioned to contact or engage a native mitral valve annulus on a ventricular side, tissue beyond the native valve annulus on a ventricular side, native leaflets on a ventricular side, and/or other tissue at or around the implantation location during one or more phases of the cardiac cycle, such as systole and/or diastole. The lower anchoring feature 726 can beneficially eliminate, inhibit, or limit upward movement of the prosthesis 700 when subject to upwardly directed forces such as those which are applied on the prosthesis 700 during systole.

The intermediate anchoring feature 728 can be positioned at or proximate the intermediate region 732 of the frame body 722. The intermediate anchoring feature 728 can be positioned such that it is radially outward of the frame body 722. The intermediate anchoring feature 728 can be relatively flexible, resilient, and/or malleable. For example, the construction of the intermediate anchoring feature 728, such as the materials used and/or the geometry of the mesh, can be chosen to provide this flexibility, resilience, and/or flexibility. In some embodiments, the intermediate anchoring feature 728 can be formed from a metal such as, but not limited to, stainless steel, cobalt-chrome, and a shape memory metal such as Nitinol. The intermediate anchoring portion 728 can take the form of a wire mesh. In some embodiments, the intermediate anchoring portion 728 can be formed separately from the other portions of the frame 720. The intermediate anchoring portion 728 can be attached to other portions of the frame 720 using any of the fasteners and/or techniques described herein including, but not limited to, mechanical fasteners, such as sutures, staples, screws, rivets, interfacing members (e.g., tabs and slots which can be on the frame 720 and the intermediate anchoring feature 728), and any other type of mechanical fastener as desired, chemical fasteners such as adhesives and any other type of chemical fastener as desired, fastening techniques such as welding, soldering, sintering, and any other type of fastening technique as desired, and/or a combination of such fasteners and techniques. The frame 720 and the intermediate anchoring feature 728 can be indirectly attached via an intermediate component, such as the skirt 780. In some embodiments, the intermediate anchoring feature 728 can be maintained in position by wrapping the skirt 780 over the intermediate anchoring feature 728 and attaching ends of the skirt 780 to the frame 720. In some embodiments, the intermediate anchoring portion 728 can be integrally or monolithically formed with other portions of the frame 720.

The flexibility, resiliency, and/or malleability of the intermediate anchoring feature 728 can beneficially allow the intermediate anchoring feature 728 to conform to the anatomy of the body cavity in which it is positioned, such as tissue of a native heart wall, a native valve annulus, and/or leaflets. In some situations, such as when the intermediate anchoring feature 728 is positioned within a native mitral valve, the intermediate anchoring feature 728 can conform to the shape of the mitral valve annulus such that the anchoring feature 728 contacts or extends over one or more of: an atrial side of the native mitral valve annulus, an inner periphery of the native mitral valve annulus, and portions of the leaflets. Moreover, the flexibility, resiliency, and/or malleability can beneficially allow the intermediate anchoring feature 728 to be crimped to a smaller diameter during the delivery process, thereby allowing for the use of a smaller gauge delivery device.

As shown in the illustrated embodiment, at least a portion of the intermediate anchoring feature 728 can be positioned radially between the lower anchoring feature 726 and the frame body 722. In this manner, tissue of the body cavity can be positioned between the lower anchoring feature 726 and the intermediate anchoring feature 728. In some embodiments, portions of the lower anchoring feature 726 and the intermediate anchoring feature 728 are sufficiently proximate each other such that tissue of the body cavity positioned therebetween are pinched or engaged. For example, in situations where the prosthesis 700 is positioned within a native mitral valve, the native mitral valve annulus and/or leaflets can be pinched or engaged between the lower anchoring feature 726 and the intermediate anchoring feature 728. This can beneficially enhance securement of the prosthesis 700 to the body cavity. As shown in the illustrated embodiment, a diameter of the intermediate anchoring feature 728 can be greater at or proximate tips or ends of the lower anchoring feature 726 and can have a reduced diameter near a lower end of the intermediate anchoring feature 728. This can beneficially allow for a greater degree of pinching or clamping force at or proximate the tips of the lower anchoring feature 726 while providing substantial space for tissue of the body cavity, such as native leaflets, positioned between the frame body 722, the lower anchoring feature 728, and the intermediate anchoring feature 728.

As noted above, one or more of anchoring features 724, 726, 728 can contact or engage a native valve annulus, such as the native mitral valve annulus, tissue beyond the native valve annulus, native leaflets, and/or other tissue at or around the implantation location. In instances where the prosthesis 700 is positioned within a native mitral valve, the upper anchoring feature 724 can be positioned on an atrial side of the native mitral valve annulus, the lower anchoring feature 726 can be positioned on a ventricular side of the native mitral valve annulus, and the intermediate anchoring feature 728 can be positioned intra-annularly. While the anchoring features 724, 726, 728 have been illustrated as extending from the upper region 730, the lower region 734, and the intermediate region 732 of the frame body 722 respectively, it should be understood that the anchoring features 724, 726, 728 can be positioned along any other portion of the frame body 722 as desired. Moreover, while three anchoring features 724, 726, 728 have been included in the illustrated embodiment, it is contemplated that fewer or greater sets of anchoring features can be utilized.

The anchoring features 724, 726, 728 are preferably located along the prosthesis 700 with at least part of the foreshortening portion positioned between the anchoring features 724, 726, 728 so that a portion of the anchoring features 724, 726, 728 will move closer together with expansion of the prosthesis 700. As one example, this can allow the anchoring features 724, 726, 728 to close in on opposite sides of the native mitral annulus to thereby secure the prosthesis at the mitral valve. In some embodiments, the anchoring features 724, 726, 728 can be positioned such that the anchoring features 724, 726, 728 do not contact opposing portions of the native mitral annulus at the same time. For example, in some situations, the intermediate anchoring feature 726 and the upper anchoring feature 728 may contact the native mitral annulus while the upper anchoring feature 724 may not contact the native mitral annulus. This can be beneficial when upper anchoring feature 724 is used to provide stabilization and help align the prosthesis. In some embodiments, the anchoring features 724, 726, 728 can be positioned such that the anchoring features 724, 726 grasp opposite side of the native mitral annulus.

With reference next to the skirt 780 illustrated in FIG. 15, the skirt 780 can be attached to frame 720 and/or the valve body 760. The skirt 780 can be positioned around and secured to a portion of, or the entirety of, the exterior and/or interior of the frame 720. As shown, the skirt 780 can extend from the valve body 760 and extend along an interior of the upper anchoring feature 724. This can beneficially serve as a collector or funnel to direct blood into the inlet of the valve body 760. The skirt 780 can wrap around the ends of the upper anchoring feature 724 and extend downwardly. As shown, the skirt 780 can extend between the lower anchoring feature 726 and the intermediate anchoring feature 728. The skirt 780 can be attached to the frame 720 and/or the valve body 760 below the intermediate anchoring feature 728.

The skirt 780 can be annular and can extend entirely circumferentially around the frame 720. The skirt 780 can prevent or inhibit backflow of fluids, such as blood, around the prosthesis 700. For example, with the skirt 780 positioned annularly around an exterior of the frame 720, the skirt 780 can create an axial barrier to fluid flow exterior to the frame 720 when deployed within a body cavity such as a native valve annulus. The skirt 780 can encourage tissue in-growth between the skirt 780 and the natural tissue of the body cavity. This may further help to prevent leakage of blood flow around the prosthesis 700 and can provide further securement of the prosthesis 700 to the body cavity. In some embodiments, the skirt 780 can be tautly attached to the frame 720 such that the skirt 780 is generally not movable relative to the frame 720. In some embodiments, the skirt 780 can be loosely attached to the frame 720 such that the skirt 780 is movable relative to the frame 720. In some embodiments, blood may be allowed to flow into the skirt 780.

Although the prosthesis 700 has been described as including a frame 720, a valve body 760, and a skirt 780, it is to be understood that the prosthesis 700 need not include all components. For example, in some embodiments, the prosthesis 700 can include the frame 720 and the valve body 760 while omitting the skirt 780. Moreover, although the components of the prosthesis 700 have been described and illustrated as separate components, it is to be understood that one or more components of the prosthesis 700 can be integrally or monolithically formed.

With reference next to FIGS. 16-19, an embodiment of a prosthesis 800 in an expanded configuration, or components of the prosthesis 800, are illustrated. The prosthesis 800 can include a frame 820, a valve body 870, and a skirt 890. A longitudinal axis of the prosthesis 800 may be defined as the central axis that extends through the center of the prosthesis 800 between the upper and lower ends of the prosthesis 800. In some situations, the prosthesis 800 may be oriented such that an upper end of the prosthesis 800 is a proximal portion and a lower end of the prosthesis 800 is a distal portion.

Figure 18:
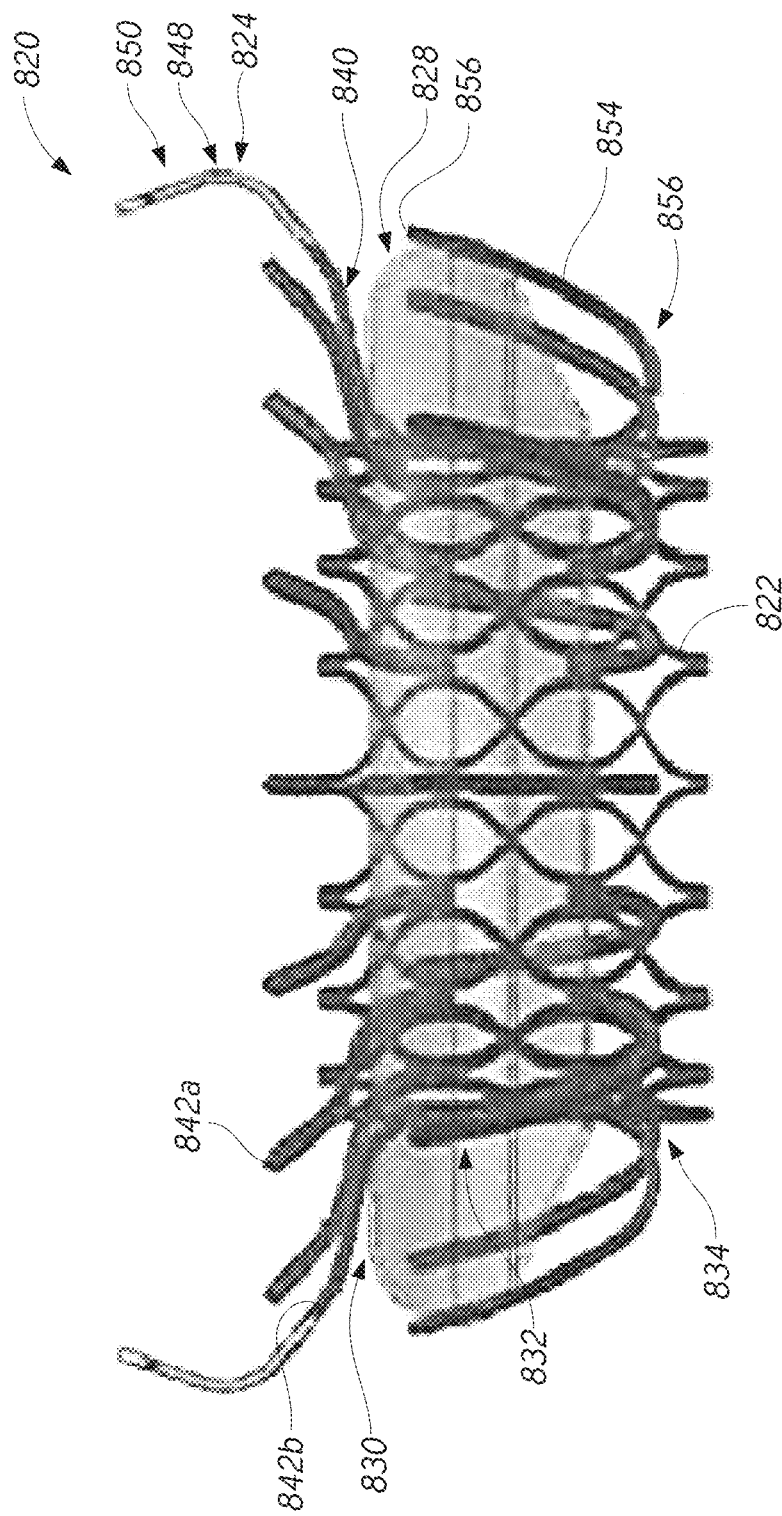
FIG. 18 is a side view of the frame and mesh anchoring feature of FIG. 16.
Figure 19:
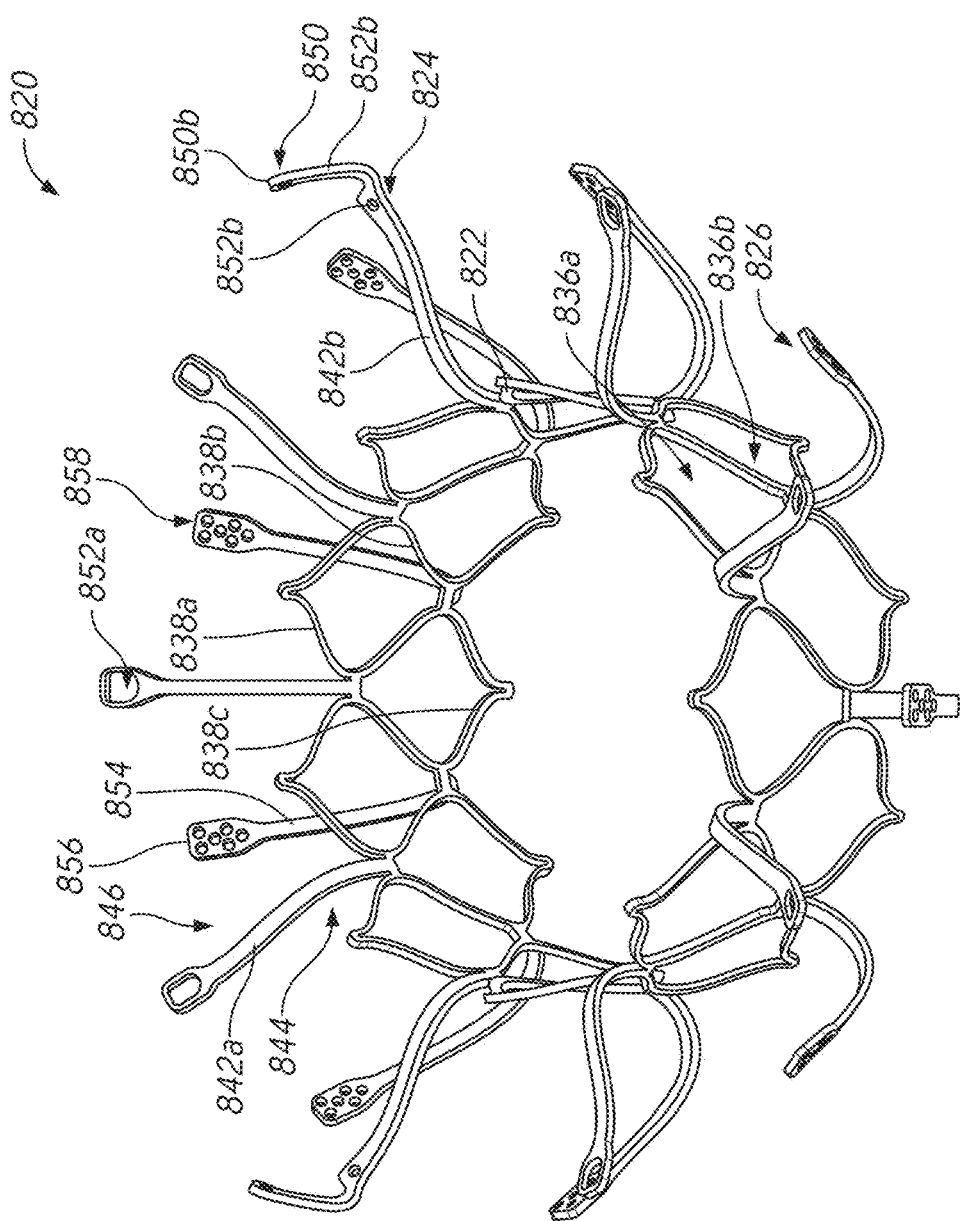
FIG. 19 is a top-oriented perspective view of the frame of FIG. 16.

With reference first to the frame 820 illustrated in FIGS. 18-19, the frame 820 can include a frame body 822, an upper anchoring feature 824, a lower anchoring feature 826, and an intermediate anchoring feature 828. The frame body 822 can include an upper region 830, an intermediate region 832, and a lower region 834. As shown, the frame body 822 can have a generally cylindrical shape such that the diameters of the upper region 830, the intermediate region 832, and the lower region 834 are generally constant. However, it is to be understood that the diameters of the upper region 830, the intermediate region 832, and/or the lower region 834 can be different.

In some embodiments, the diameter of the frame body 822 may be between about 40% to about 90% of the diameter of the native valve annulus, between about 60% to about 85%, of the diameter of the native valve annulus, between about 70% to about 80% of the diameter of the native valve annulus, any other sub-range between these ranges, or any other percentage as desired. In some embodiments, the diameter of the frame body 822 can be in the range of about 20 mm to about 40 mm when expanded, in the range of about 25 mm to about 35 mm when expanded, in the range of about 28 mm to about 32 mm when expanded, about 29 mm when expanded, any other sub-range within these ranges when expanded, or any other diameter when expanded as desired. Although the frame body 822 has been described and illustrated as being cylindrical or having circular cross-sections, it is to be understood that all or a portion of the frame body 822 can be have a non-circular cross-section such as, but not limited to, a D-shape, an oval or an otherwise ovoid cross-sectional shape.

In other embodiments, the diameter of portions of the frame body 822 such as the upper region 830, intermediate region 832, and/or lower region 834 may be chosen such that the frame body 822 is positioned at the periphery of the body cavity. For example, in embodiments where the prosthesis 800 is positioned within the native mitral valve, the inner frame body 822 may have a diameter which is about equal to the diameter of the native mitral valve annulus.

The frame 822 can include a plurality of struts with at least some of the struts forming cells 836*a-b*. Any number of configurations of struts can be used, such as rings of undulating struts shown forming ellipses, ovals, rounded polygons, and teardrops, but also chevrons, diamonds, curves, and various other shapes.

The upper and lower row of cells 836*a-b* can have a diamond or generally diamond shape. The rows of cells 836*a-b* can be formed via a combination of struts. As shown in the illustrated embodiment, the upper row of cells 836*a* can be formed from a first set of circumferentially-expansible struts 838*a* and a second set of circumferentially-expansible struts 838*b*. The lower row of cells 836*b* can be formed from the second set of circumferentially-expansible struts 838*b* and a third set of circumferentially-expansible struts 838*c*. The first, second, and third sets of struts 838*a-c* can have a zig-zag or undulating shape forming a repeating "V" shape. It is to be understood that some or all of the struts 838*a-c* may not form entirely straight segments. For example, the struts 838*a-c* can include some curvature such that the upper and/or lower apices are curved.

As shown in the illustrated embodiment, the upper and lower row of cells 836*a-b* extend in a direction generally parallel to the longitudinal axis of the prosthesis 800. There can be a row of nine cells 836*a* and a row of nine cells 836*b*. While each of the cells 836*a-b* are shown as having the same shape as other cells 836*a-b* of the same row, it is to be understood that the shapes of cells 836*a-b* within a row can differ. Moreover, it is to be understood that any number of rows of cells can be used and any number of cells may be contained in the rows. In some embodiments, the number of cells can correspond to the number of anchors or anchor tips forming the upper anchoring feature 824 and/or the lower anchoring feature 826. The number of cells in the upper and lower row of cells 836*a-b* can have a 1:1 correspondence with the number of anchors in the upper anchoring feature 824 and/or the lower anchoring feature 826 (i.e., nine cells in each row of cells 836*a-b* and nine anchors for the anchoring features 824, 826). It is to be understood that other ratios of numbers of cells per row to number of anchors per anchoring feature can be used such as, but not limited to, 3:1, 4:1, 5:1, 6:1, and other ratios as desired. In some embodiments, all three rows of cells 836*a-b* can have different numbers of cells. Moreover, it is to be understood that fewer or greater numbers of rows of cells can be used.

The geometry of cells 836*a-b* can allow the cells 836*a-b* to foreshorten as the frame 820 is expanded. As such, one or more of cells 836*a-b* can allow the frame 820 to foreshorten as the frame 820 is expanded. As described herein, foreshortening of the frame 820 can be used to secure the prosthesis to intralumenal tissue in a body cavity, for example tissue at or adjacent a native valve, such as a native valve annulus and/or leaflets. For example, expansion of the frame 820 can allow the upper frame anchoring feature 824, the lower anchoring feature 826, and/or the intermediate anchoring feature 828 to extend radially outward and draw closer to tissue of the body cavity, such as a native valve annulus and/or leaflets, to engage tissue of the body cavity.

The frame 820 can share characteristics, such as structure and/or functionality, which are the same as, or at least similar to, those of frames such as inner frames 120, 220, 400, 520*a-g*, 720.

As shown in the illustrated embodiment, the upper anchoring feature 824 can extend radially outwardly from the longitudinal axis of the prosthesis 800. In this manner, upper anchoring feature 824 can create a flared or shoulder portion 840 of the frame 820. As shown in the illustrated embodiment, the upper anchoring feature 824 can include one or more anchors 842*a-b*. The anchors 842*a-b* can extend from below an upper end of the frame body 822. For example, the anchors 842*a-b* can extend from a portion of the frame body 822 between the upper row of cells 836*a*. However, it is to be understood that the anchors 842*a-b* can extend from other portions of the frame body 822, such as upper apices of the upper row of cells 836*a*.

The anchors 842*a-b* can extend upwardly from the frame body 822. The anchors 842*a-b* can then extend radially outwardly via a bend 844. The bend 844 can be about a circumferential axis such that the anchors 842*a-b* extend in a direction more perpendicular to the longitudinal axis of the prosthesis 800 than the frame body 822. The bend 844 can be similar to the bend 738 discussed above in connection with prosthesis 700 illustrated in FIG. 15.

As shown, anchors 842*a*, 842*b* can include a second bend 846 above the bend 844. The bend 846 can be a clockwise bend about a circumferential axis such that the portion of the anchors 842a, 842b above the second bend 846 extends in a direction less perpendicular to the longitudinal axis of the prosthesis 800 than the portion of the anchors 842a, 842b below the second bend 846. The bend 846 can be similar to the bend 740 discussed above in connection with prosthesis 700 illustrated in FIG. 15.

Some anchors of the upper anchoring feature 824, such as anchors 842b, can have a greater length than other anchors of the upper anchoring feature 824, such as anchors 842a. As shown, anchors 842b can include a third bend 848 above the bend 846. The bend 848 can be about a circumferential axis such that the portion of the anchors 842b above the third bend 848 extends in a direction radially towards the longitudinal axis of the prosthesis 800. This can beneficially reduce the likelihood that the anchors 842b contact tissue of the body cavity. For example, in situations where the prosthesis 800 is positioned within a native mitral valve, the radially inward bend can reduce the likelihood of anchors 842b contacting the atrial wall.

In some embodiments, portions of anchors 842b can form part of a locking tab 850 having a strut 850a and an enlarged head 850b. The locking tab 850 can advantageously be used with multiple types of delivery systems. For example, the shape of the strut 850a and the enlarged head 850b can be used to secure the frame 850 to a "slot" based delivery system. The locking tabs 850 can include eyelets which can be used to secure the frame 820 to a "tether" based delivery system such as those which utilize sutures, wires, or fingers to control delivery of the frame 820. This can advantageously facilitate recapture and repositioning of the frame 820 in situ. In some embodiments, the frame 820 can be used with the delivery systems described herein, including but not limited to, those described in U.S. Pat. Nos. 8,414,644 and 8,652,203 and U.S. Publication Nos. 2015/0238315, the entireties of each of which are hereby incorporated by reference and made a part of this specification.

With continued reference to the frame 820 illustrated in FIGS. 18-19, the lower anchoring feature 826 can include one or more anchors 854. The anchors 854 can extend generally downwardly from above a lower end of the lower region 814 of the frame body 822. For example, the anchors 854 can extend from a portion of the frame body 822 between the lower row of cells 836b. However, it is to be understood that the anchors 854 can extend from other portions of the frame body 822, such as lower apices of the lower row of cells 836b. The anchors 854 can bend to extend generally radially outward of the longitudinal axis of the prosthesis 800. The anchors can extend upwardly towards an end or tip 856.

The anchors 854 can be used to attach or secure the prosthesis 800 to a native valve. For example, in some embodiments, the anchors 854 can be used to attach or secure the prosthesis 800 to a native valve, such as a native mitral valve. In such an embodiment, the anchors 854 can be positioned to contact or engage a native mitral valve annulus on a ventricular side, tissue beyond the native valve annulus on a ventricular side, native leaflets, and/or other tissue at or around the implantation location during one or more phases of the cardiac cycle, such as systole and/or diastole. The anchors 854 can beneficially eliminate, inhibit, or limit upward movement of the prosthesis 800 when subject to upwardly directed forces such as those which are applied on the prosthesis 800 during systole.

The tips or ends of the anchors 842a-b, 854 can advantageously provide atraumatic surfaces that may be used to contact or engage intralumenal tissue without causing unnecessary or undesired trauma to tissue. For example, the tips or ends can form flat, substantially flat, curved or other non-sharp surfaces to allow the tips to engage and/or grasp tissue, without necessarily piercing or puncturing through tissue. A looped end or looped anchor may assist the frame in not getting caught up on structures at or near the treatment location. For example, each loop can be configured so that when the prosthesis 800 is deployed in-situ and the anchors 842a-b, 854 expand away from the frame body 822, the movement of each loop from a delivered position to a deployed position avoids getting caught on the papillary muscles. As shown in the illustrated embodiment, the anchors 854 can include eyelets or holes 858 at or proximate the tips or ends. The eyelets or holes 858 can facilitate attachment of component, such as a cover and/or cushion, the tips or ends 856 of the anchors 842a-b, 854.

As shown in the illustrated embodiment, the upper and lower anchoring features 824, 826 can include twelve individual anchors; however, it is to be understood that a greater number or lesser number of individual anchors can be used. For example, the number of individual anchors can be chosen as a multiple of the number of commissures for the valve body 870. As such, for a prosthesis 800 with a valve body 870 having three commissures, the upper anchoring feature 824 and/or the lower anchoring feature 826 can have three individual anchors (1:1 ratio), six individual anchors (2:1 ratio), nine individual anchors (3:1 ratio), twelve individual anchors (4:1 ratio), fifteen individual anchors (5:1 ratio), or any other multiple of three. It is to be understood that the number of individual anchors need not correspond to the number of commissures of the valve body 870.

Moreover, while the prosthesis 800 includes anchoring features 824, 826 with twelve anchors each, it is to be understood that a greater number of anchors or a lesser number of anchors can be used. In some embodiments, instead of a 1:1 correspondence between the number of anchors in the upper frame anchoring feature 824 and the lower anchoring feature 826 (i.e., twelve anchors each), other ratios can be used. For example, a 1:2 or a 1:3 correspondence between the anchors, are possible such that the upper anchoring feature 824 or the lower anchoring feature 826 have fewer anchors than the other anchoring feature.

The intermediate anchoring feature 828 can be positioned at or proximate the intermediate region 832 of the frame body 822. The intermediate anchoring feature 828 can be positioned such that it is radially outward of the frame body 822. The intermediate anchoring feature 828 can be relatively flexible, resilient, and/or malleable. For example, the construction of the intermediate anchoring feature 828, such as the materials used and/or the geometry of the mesh, can be chosen to provide this flexibility, resilience, and/or flexibility. In some embodiments, the intermediate anchoring feature 828 can be formed from a metal such as, but not limited to, stainless steel, cobalt-chrome, and a shape memory metal such as Nitinol. The intermediate anchoring portion 828 can take the form of a wire mesh. In some embodiments, the intermediate anchoring portion 828 can be formed separately from the other portions of the frame 820. The intermediate anchoring portion 828 can be attached to other portions of the frame 820 using any of the fasteners and/or techniques described herein including, but not limited to, mechanical fasteners, such as sutures, staples, screws, rivets, interfacing members (e.g., tabs and slots which can be on the frame 820 and the intermediate anchoring feature 828), and any other type of mechanical fastener as desired, chemical fasteners such as adhesives and any other type of chemical fastener as desired, fastening techniques such as welding, soldering, sintering, and any other type of fastening technique as desired, and/or a combination of such fasteners and techniques. For example, in embodiments having a braided mesh with loops, sutures can be used to connect the edge loops to the frame body 822. The frame 820 and the intermediate anchoring feature 828 can be indirectly attached via an intermediate component, such as the skirt 890. In some embodiments, the intermediate anchoring feature 828 can be maintained in position by wrapping the skirt 890 over the intermediate anchoring feature 828 and attaching ends of the skirt 890 to the frame 820. In some embodiments, the intermediate anchoring portion 828 can be integrally or monolithically formed with other portions of the frame 820.

The flexibility, resiliency, and/or malleability of the intermediate anchoring feature 828 can beneficially allow the intermediate anchoring feature 828 to conform to the anatomy of the body cavity in which it is positioned, such as tissue of a native heart wall, a native valve annulus, and/or leaflets. In some situations, such as when the intermediate anchoring feature 828 is positioned within a native mitral valve, the intermediate anchoring feature 828 can conform to the shape of the mitral valve annulus such that an upper region of the intermediate anchoring feature 828 extends over an atrial side of the native mitral valve annulus, an intermediate region of the intermediate anchoring feature 828 conforms to the inner periphery of the native mitral valve annulus, and/or the lower region of the intermediate anchoring feature 828 contacts portions of the leaflets. Moreover, the flexibility, resiliency, and/or malleability can beneficially allow the intermediate anchoring feature 828 to be crimped to a smaller diameter during the delivery process, thereby allowing for the use of a smaller gauge delivery device.

As shown in the illustrated embodiment, at least a portion of the intermediate anchoring feature 828 can be positioned radially between the lower anchoring feature 826 and the frame body 822. In this manner, tissue of the body cavity can be positioned between the lower anchoring feature 826 and the intermediate anchoring feature 828. In some embodiments, portions of the lower anchoring feature 826 and the intermediate anchoring feature 828 are sufficiently proximate each other such that tissue of the body cavity positioned therebetween are pinched or engaged. For example, in situations where the prosthesis 800 is positioned within a native mitral valve, the native mitral valve annulus and/or leaflets can be pinched or engaged between the lower anchoring feature 826 and the intermediate anchoring feature 828. This can beneficially enhance securement of the prosthesis 800 to the body cavity.

As shown in the illustrated embodiment, the intermediate anchoring feature 828 can have a generally triangular, cross-sectional shape along a plane parallel to and extending through the longitudinal axis of the prosthesis 800. The intermediate anchoring feature 828 can have a greater diameter at or proximate tips or ends of the lower anchoring feature 826 and a reduced diameter near a lower end of the intermediate anchoring feature 828. This can beneficially allow for a greater degree of pinching or clamping force at or proximate the tips of the lower anchoring feature 826 while providing substantial space for tissue of the body cavity, such as native leaflets, positioned between the frame body 822, the lower anchoring feature 826, and the intermediate anchoring feature 828. However, it is to be understood that other cross-sectional shapes along a plane parallel to and extending through the longitudinal axis of the prosthesis 800. For example, the cross-section can be circular, semi-circular, elliptical, semi-elliptical, rectangular, and the like.

As noted above, one or more of anchoring features 824, 826, 828 can contact or engage a native valve annulus, such as the native mitral valve annulus, tissue beyond the native valve annulus, native leaflets, and/or other tissue at or around the implantation location. In instances where the prosthesis 800 is positioned within a native mitral valve, the upper anchoring feature 824 can be positioned on an atrial side of the native mitral valve annulus, the lower anchoring feature 826 can be positioned on a ventricular side of the native mitral valve annulus, and the intermediate anchoring feature 828 can be positioned intra-annularly. While the anchoring features 824, 826, 828 have been illustrated as extending from the upper region 830, the lower region 834, and the intermediate region 832 of the frame body 822 respectively, it should be understood that the anchoring features 824, 826, 828 can be positioned along any other portion of the frame body 822 as desired. Moreover, while three anchoring features 824, 826, 828 have been included in the illustrated embodiment, it is contemplated that fewer or greater sets of anchoring features can be utilized.

Figure 16:
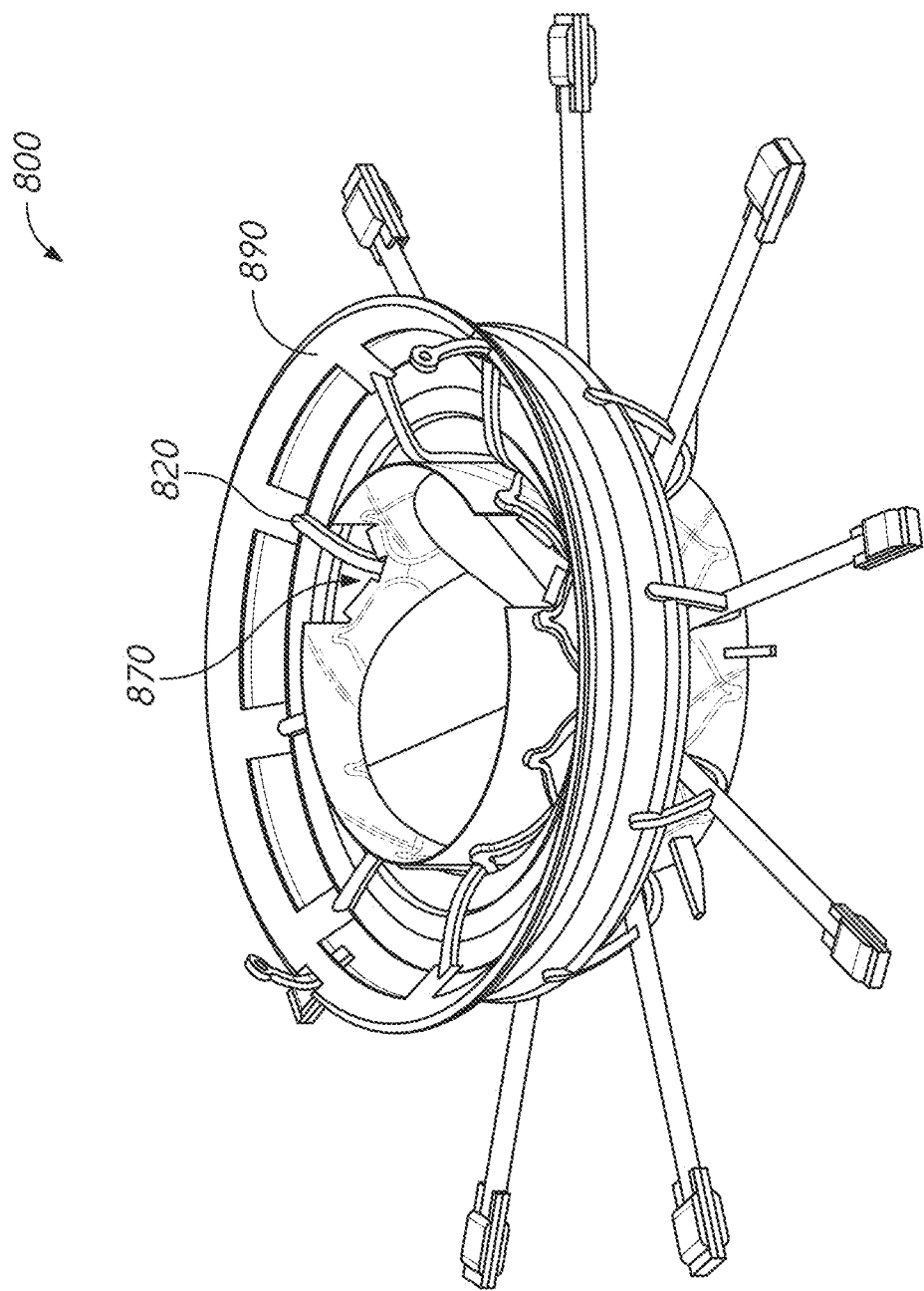
FIG. 16 is a top-oriented perspective view of an embodiment of a prosthesis having a frame, a mesh anchoring feature, a valve body, and a skirt in a partially assembled state.
Figure 17:
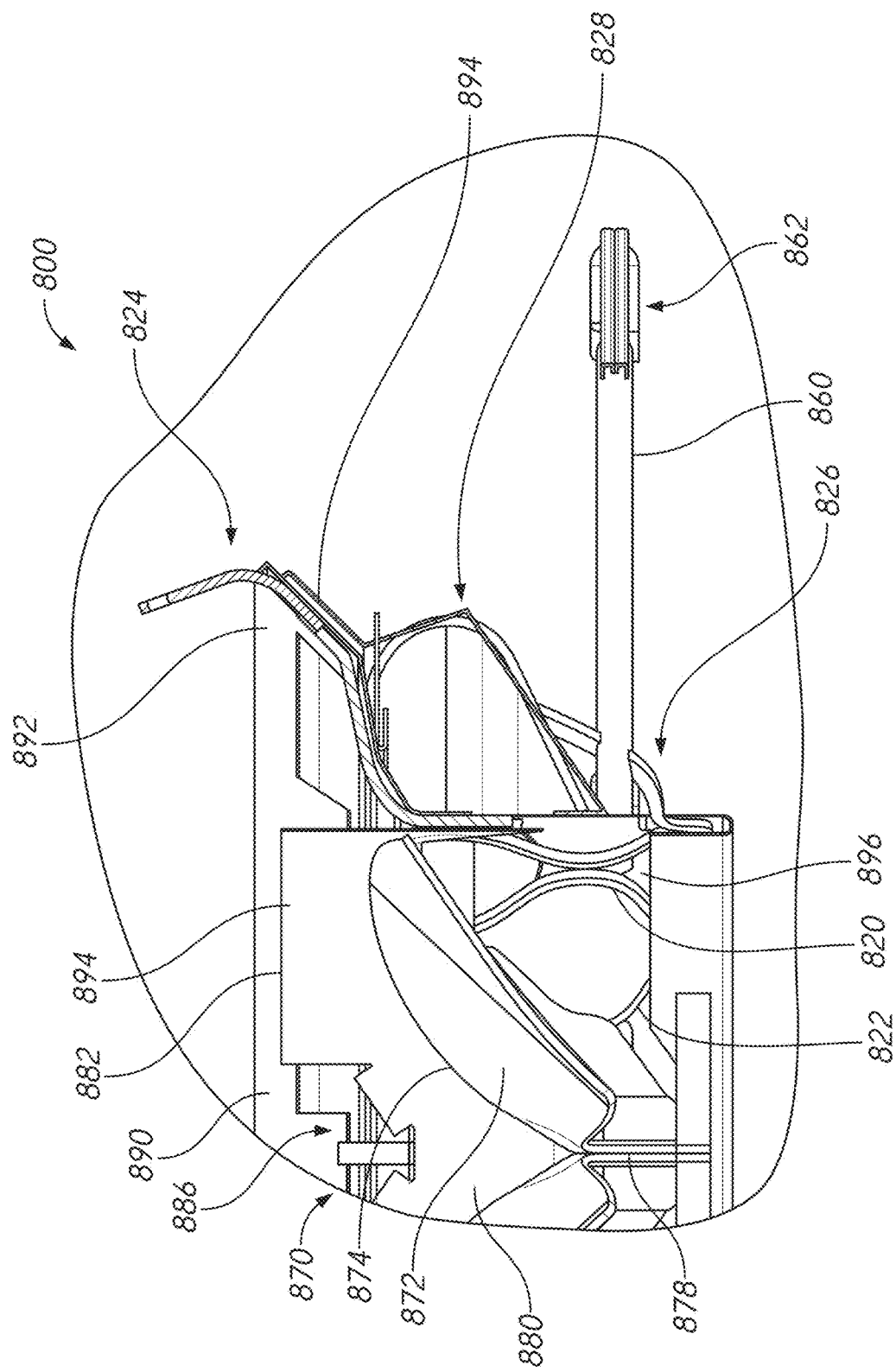
FIG. 17 is an enlarged, side-oriented cross-sectional view of the prosthesis of FIG. 16.

With reference back to the prosthesis 800 illustrated in FIGS. 16-17, covers 860 and/or cushions 862 can be used to surround or partially surround at least a portion of the anchoring features 824, 826, 828, such as anchors of the lower anchoring feature 826. As shown in the illustrated embodiment, a cover 860 can be positioned around portions of the anchors 854 preceding the tips or ends 856. A cushion 862 can be positioned to around the tips or ends 856. The covers 860 and/or cushions 862 can be similar to those described in U.S. Publication No. 2015/032800, which has been incorporated by reference in its entirety. It is to be understood that greater or fewer numbers of covers 860 and/or cushions 862 can be used with anchors 854. For example, a cover 860 and/or cushion 862 can be used on every other anchor such that there is a 1:2 ratio of covers 860 and/or cushions 862 to anchors The tips or ends 856 of the anchors 854 can be generally circumferentially offset with respect to the tips or ends of the anchors 842a, 842b. In other embodiments (not shown), the tips or ends 856 of the anchors 854 can be generally circumferentially aligned with respect to the tips or ends of the anchors 842a, 842b.

Preferably, each of the anchoring features 824, 826, 828 are positioned or extend generally radially outwardly from the prosthesis 800 so that the tips or ends of the anchoring features 824, 826, 828 are generally spaced away or radially outward from the rest of the frame body 822. As shown in the illustrated embodiment, at least some of the anchoring features, such as lower anchoring feature 826, can extend to a radial distance from an exterior surface of the frame body 822 that is about 120% or more of the expanded diameter of the frame body 822, that is about 130% or more of the expanded diameter of the frame body 822, that is about 140% or more of the expanded diameter of the frame body 822, that is about 150% or more of the expanded diameter of the frame body 822.

In some embodiments, all of the anchors of the lower anchoring feature 826 and/or all of the anchors of the upper frame anchoring feature 824 extend at least to this radial distance. In other embodiments, fewer than all of the anchors of the lower anchoring feature 826 and/or all of the anchors of the upper anchoring feature 824 extend to this radial distance. The outermost diameter of the anchoring features 824, 826, 828 may be greater than the diameter of frame body 822 as described above and may be in the range of about 35 mm to about 70 mm when expanded, in the range of about 35 mm to about 60 mm when expanded, in the range of about 40 mm to about 60 mm when expanded, in the range of about 45 mm to about 50 mm when expanded, any sub-range within these ranges when expanded, or any other diameter as desired. In some embodiments, the upper anchoring feature 824 can have a diameter of about 49 mm while the lower anchoring feature 826 and the intermediate anchoring feature 828 can have a diameter of about 46 mm.

Moreover, as will be discussed in further detail below, the anchoring features 824, 826, 828 are preferably located along the prosthesis 800 with at least part of the foreshortening portion positioned between the anchoring features 824, 826, 828 so that a portion of the anchoring features 824, 826, 828 will move closer together with expansion of the prosthesis 800. As one example, this can allow the anchoring features 824, 826, 828 to close in on opposite sides of the native mitral annulus to thereby secure the prosthesis at the mitral valve. In some embodiments, the anchoring features 824, 826, 828 can be positioned such that the anchoring features 824, 826, 828 do not contact opposing portions of the native mitral annulus at the same time. For example, in some situations, the intermediate anchoring feature 826 and the upper anchoring feature 828 may contact the native mitral annulus while the upper anchoring feature 824 may not contact the native mitral annulus. This can be beneficial when upper anchoring feature 824 is used to provide stabilization and help align the prosthesis. In some embodiments, the anchoring features 824, 826, 828 can be positioned such that the anchoring features 824, 826 grasp opposite side of the native mitral annulus.

With reference next to the valve body 870 illustrated in FIGS. 16-17, the valve body 870 can be positioned within the frame 820. The valve body 870 can be a replacement heart valve which includes a plurality of valve leaflets 872. The valve leaflets 872 can include a first edge 874, second edge (not shown), and tabs 878 for attaching the valve leaflets 872 together at commissures of the valve body 870. The tabs 878 can be used to secure the valve leaflets 872 to the frame 820. The first edge 874 can be an arcuate edge and can be generally fixed in position relative to the frame 820. The second edge can be a freely moving edge which can allow the valve body 870 to open and close.

The plurality of valve leaflets 872 can function in a manner similar to the native mitral valve, or to any other valves in the vascular system as desired. The plurality of valve leaflets 872 can open in a first position and then engage one another to close the valve in a second position. The plurality of valve leaflets 872 can be made to function as a one-way valve such that flow in one direction opens the valve and flow in a second direction opposite the first direction closes the valve. For example, as shown in the illustrated embodiment, the valve body 870 can open allow to blood to flow through the valve body 870 in a direction from an upper end to a lower end. The valve body 870 can close to inhibit blood flow through the valve body 870 in a direction from the lower end to the upper end. In situations where the prosthesis 800 is oriented such that an upper end is a proximal end and a lower end is a distal end, the valve body 870 can be positioned such that the valve body 870 can open to allow blood to flow through the valve body 870 in a proximal-to-distal direction and close to inhibit blood flow in a distal-to-proximal direction. The valve body 870 can be constructed so as to open naturally with the beating of the heart. For example, the valve body 870 can open during diastole and close during systole. The valve body 870 can replace a damaged or diseased native heart valve such as a diseased native mitral valve.

With continued reference to the valve body 870 illustrated in FIGS. 16-17, the valve body 870 can include a liner 880. The liner 880 can be used to assist with fluid flow through and/or around the prosthesis 880, such as through and around the inner frame 880 and the valve leaflets 872. The liner 880 can surround at least a portion of the valve leaflets 872 and be connected to one or more of the valve leaflets 872. For example, as shown in the illustrated embodiment, the one or more valve leaflets 872 can be attached to the liner 880 along the first edge 874 of the valve leaflets 872.

As shown in the illustrated embodiment, the liner 880 can be positioned within the interior of the inner frame 880 and can form an inner wall of the prosthesis 800. For example, the liner 880 can be positioned such that the liner 880 is radially inward, relative to the longitudinal axis of the prosthesis 800, from the struts of the frame 820. In this manner, the fluid pathway towards the valve leaflets 872 can be relatively smooth. It is also contemplated that the liner 880 can at least be partially positioned along an exterior of the frame 820 such that at least a portion of the liner 880 is radially outward, relative to the longitudinal axis of the prosthesis 800, from struts of the frame 820. As shown in the illustrated embodiment, the liner 880 can be positioned along an upper or inlet side of the frame 820. The liner 880 can extend from the first edge 874 of the valve leaflets 872 towards the upper end of the frame 820. The liner 880 can also extend below the first edge 874 of the valve leaflet 872 towards the lower end of the frame 820. The liner 880 can also be made to move with foreshortening portions of the frame 820.

In some embodiments, the liner 880 can extend the entire length of the frame 820 or the frame body 822. In other embodiments, it can extend along only part of the length of the frame body 822 as shown. In some embodiments, the ends of the valve leaflets 872 can coincide with ends of the liner 880. In addition, one or more of the ends of the frame body 822 can coincide with the ends of the liner 880. As shown in the illustrated embodiment, an end 882 of the liner 880 can be positioned between the upper end of the frame 820 and the valve leaflets 872. The end 882 of the liner 880 can extend above an upper end of the frame body 822. In some embodiments, the end 882 of the liner 880 can be positioned at or proximate an uppermost portion of the first or arcuate edge 874 of the valve leaflet 872.

Other shapes and configurations can also be used for the valve body 870. In some embodiments, the liner 880 may extend along the length of the leaflets, but is not connected to them. In the illustrated embodiment, the liner 880 is attached to the frame 820 and at least a portion of the leaflets 872, such as the first or arcuate edge 874, is attached to the liner 880. Portions of the valve leaflets 872, such as the portions of the first edge 874 and/or tabs 878, can also be attached to the frame 820. The liner 880 and/or the valve leaflets 872 can be attached to the frame 820 or to each other using any of the fasteners and/or techniques described herein including, but not limited to, mechanical fasteners, such as sutures, staples, screws, rivets, interfacing members (e.g., tabs and slots), and any other type of mechanical fastener as desired, chemical fasteners such as adhesives and any other type of chemical fastener as desired, fastening techniques such as welding, soldering, sintering, and any other type of fastening technique as desired, and/or a combination of such fasteners and techniques.

The liner 880 can be constructed in multiple different ways. The liner 880 can be made a layer of resilient material, such as such as knit polyester (e.g., polyethylene terephthalate (PET), polyvalerolactone (PVL)) or any other biocompatible material such as those which are wholly or substantially fluid impermeable, flexible, stretchable, deformable, and/or resilient. In some embodiments, the liner 880 can be made from a material that is more flexible than the valve leaflet material. The upper and/or lower end, such as end 882, of the liner 880 can be straight, curved, or have any other desired configuration. For example, as shown in the illustrated embodiment, the liner 880 can have one or more straight edges 884 and one or more slots 886 forming the end 882. It is to be understood that the liner 880, such as the straight edges 884, can be folded over a top end of the frame body 822. In other embodiments, the end 882 can be patterned to generally correspond to the undulations at one end of the frame 820. The liner 880 can be formed of one piece or multiple pieces.

In another embodiment of the liner 880, the end can extend past the frame 820 and can be wrapped around it. Thus, the liner 880 can extend from the inside of the frame 820 to the outside of the frame 820. The liner 880 can extend completely around the frame 820 for ¼, ⅓, ½, or more of the length of frame 820.

With reference next to the skirt 890 illustrated in FIGS. 16-17, the skirt 890 can be attached to frame 820 and/or the valve body 870. The skirt 890 can be positioned around a portion of, or the entirety of, the exterior of the frame 820 and/or the interior of the frame 820. As shown, the skirt 890 can extend from the valve body 870 and extend along an interior of the upper anchoring feature 824. The skirt 890 can wrap around the ends of the upper anchoring feature 870, or a portion thereof, and extend downwardly. For example, the skirt 890 can extend up to and wrap around the ends of the anchors 842a but not the ends of anchors 842b. This can advantageously allow the locking tabs 848 to remain uncovered to facilitate use with a delivery system. As shown, the skirt 890 can extend between the lower anchoring feature 826 and the intermediate anchoring feature 828. The skirt 890 can be attached to the frame 820 and/or the valve body 870 below the intermediate anchoring feature 828.

The skirt 890 can be annular and can extend entirely circumferentially around the frame 890. The skirt 890 can prevent or inhibit backflow of fluids, such as blood, around the prosthesis 800. For example, with the skirt 890 positioned annularly around an exterior of the frame 820, the skirt 890 can create an axial barrier to fluid flow exterior to the frame 820 when deployed within a body cavity such as a native valve annulus. The skirt 890 can encourage tissue in-growth between the skirt 890 and the natural tissue of the body cavity. This may further help to prevent leakage of blood flow around the prosthesis 800 and can provide further securement of the prosthesis 800 to the body cavity. In some embodiments, the skirt 890 can be tautly attached to the frame 820 and/or valve body 870. In some embodiments, the skirt 890 can be loosely attached around the frame 820 and/or valve body 870. In some embodiments, blood may be allowed to flow into the skirt 890.

As shown in the illustrated embodiment, the skirt 890 can have a first portion 892, a second portion 894, and a third portion 896. The first portion 892 can extend along an interior portion of the frame 820. For example, the first portion 892 can extend from the liner 880 of the valve body 870 and extend along an interior of the frame body 882 and/or the upper anchoring feature 824. The first portion 892 can extend up to the ends of the anchors 842a. The first portion 892 can also extend up to the ends of anchors 842b.

The second portion 894 can extend downwardly from an upper end of the first portion 892. The second portion 894 can extend along an exterior portion of the frame 820. For example, the second portion 894 can extend along an exterior of the upper anchoring feature 824 and/or the intermediate anchoring feature 828. The second portion 894 can be attached to the frame 820 at a position between the intermediate anchoring feature 828 and the lower anchoring feature 826.

The third portion 896 can extend along an exterior portion of the frame 820. For example, the third portion 896 can extend along an exterior of the frame body 822. The third portion 896 can extend upwardly from a lower end of the frame body 822. The third portion 896 can extend upwardly towards a lower end of the liner 880. In some embodiments, the third portion 896 can extend up to, or beyond, the lower end of the liner 880. As shown in the illustrated embodiment, the third portion 896 can be positioned between the frame body 822 and the intermediate anchoring feature 828.

The first portion 892, second portion 894, and third portions 896 can be formed from separate components. The components can be attached using any of the fasteners and/or techniques described herein including, but not limited to, mechanical fasteners, such as sutures, staples, screws, rivets, interfacing members (e.g., tabs and slots), and any other type of mechanical fastener as desired, chemical fasteners such as adhesives and any other type of chemical fastener as desired, fastening techniques such as welding, soldering, sintering, and any other type of fastening technique as desired, and/or a combination of such fasteners and techniques. In some embodiments, the skirt 890 can be formed from additional components. For example, the second portion 894 can be formed from an upper component and a lower component. In some embodiments, two or more portions of the skirt 890 can be integrally or monolithically formed.

Although the prosthesis 800 has been described as including a frame 820, a valve body 870, and a skirt 890, it is to be understood that the prosthesis 800 need not include all components. For example, in some embodiments, the prosthesis 800 can include the frame 820 and the valve body 870 while omitting the skirt 890. Moreover, although the components of the prosthesis 800 have been described and illustrated as separate components, it is to be understood that one or more components of the prosthesis 800 can be integrally or monolithically formed.

Figure 20:
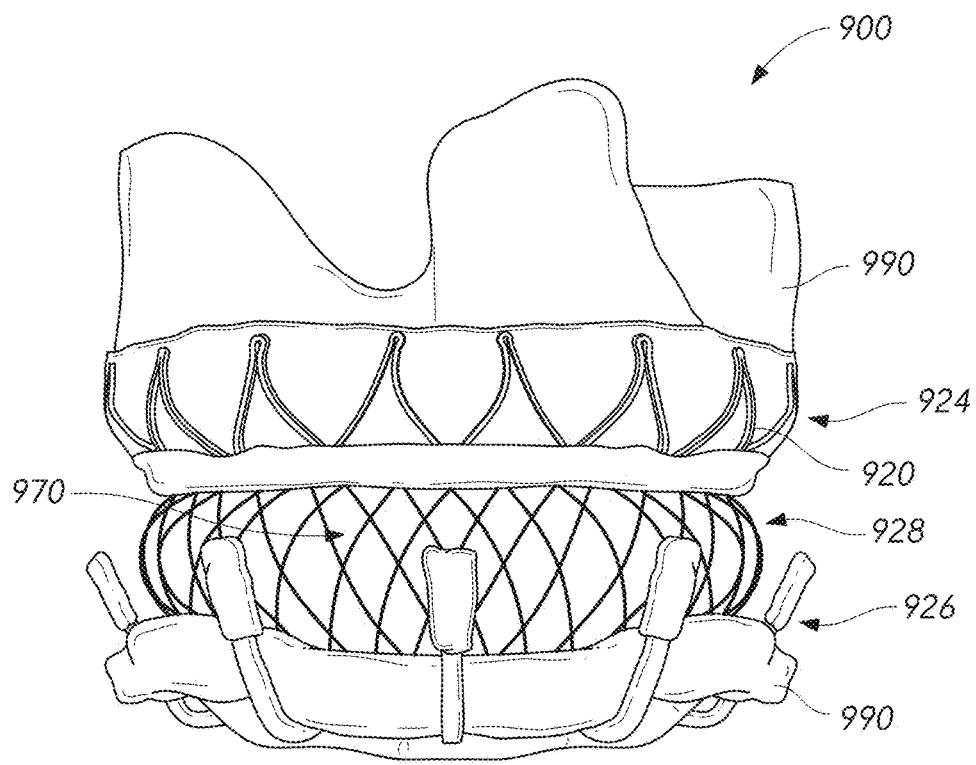
FIG. 20 is a side view of an embodiment of another embodiment of a prosthesis having a frame, a valve body, a braided seal, and a skirt in a partially assembled configuration.
Figure 21:
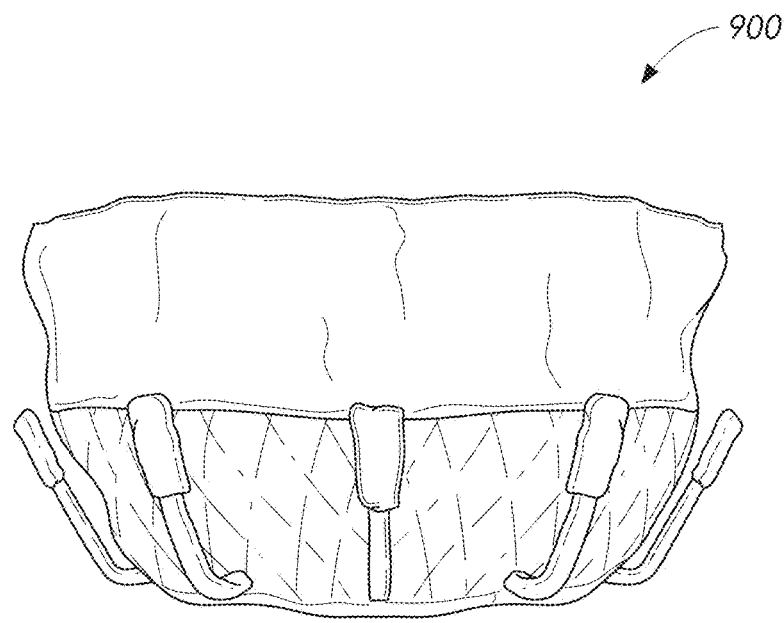
FIG. 21 is a side view of an embodiment of the prosthesis of FIG. 20 in an assembled configuration.
Figure 22:
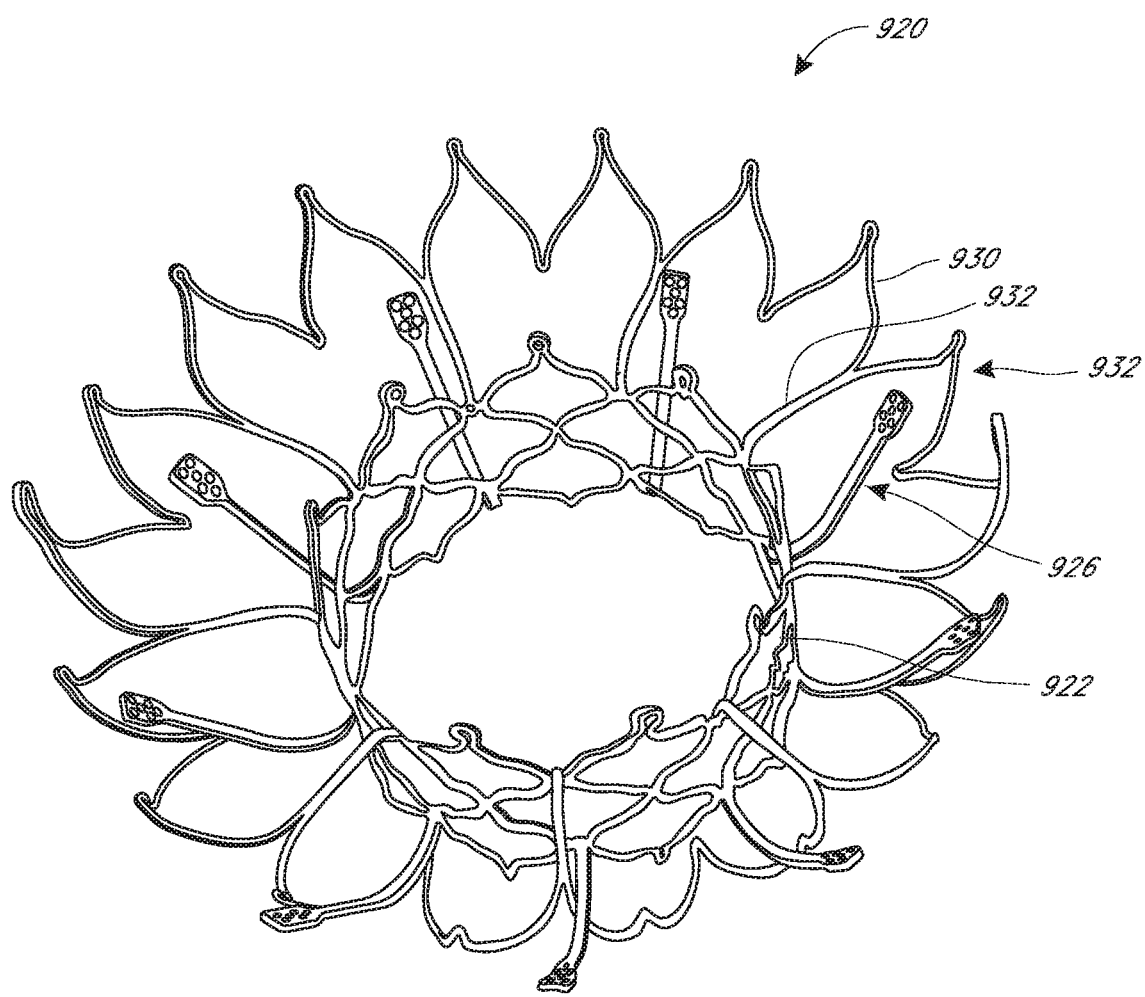
FIG. 22 is a top-oriented perspective view of another embodiment of the frame of FIG. 21.

With reference next to FIGS. 20-22, an embodiment of a prosthesis 900 in an expanded configuration, or components of the prosthesis 900, are illustrated. The prosthesis 900 can include a frame 920, a valve body 970, and a skirt 990. A longitudinal axis of the prosthesis 900 may be defined as the central axis that extends through the center of the prosthesis 900 between the upper and lower ends of the prosthesis 900. The prosthesis 900 can share characteristics, such as structure and/or functionality, which are the same as, or at least similar to, those of prosthesis 800 described in connection with FIGS. 16-19.

The frame 920 can share characteristics, such as structure and/or functionality, which are the same as, or at least similar to, those of frame 820 described in connection with FIGS. 16-19. The frame 920 can include a frame body 922, an upper anchoring feature 924, a lower anchoring feature 926, and an intermediate anchoring feature 928. As shown in the illustrated embodiment, the upper anchoring feature 924 can be formed from a row of circumferentially expansible struts 930. The circumferentially-expansible struts 930 can be attached to the frame body 922 via one or more struts 932. The intermediate anchoring feature 928 can be formed from a braided structure.

The skirt 990 can share characteristics, such as structure and/or functionality, which are the same as, or at least similar to, those of skirt 890 described in connection with FIGS. 16-19. Accordingly, reference should be made to the discussion of skirt 890 for further details pertaining to the skirt 990. As shown in FIG. 20, the skirt 990 can be formed from multiple components which can be attached together (as shown in FIG. 21).

Embodiments of Circumferentially Curved Anchoring Features

In some embodiments, the prostheses described herein can incorporate a circumferentially curved or inclined anchoring feature. In some situations, such as those in which the prostheses are implanted at a native mitral valve, the circumferential curve and/or incline can allow a greater number of chordae tendineae to be positioned between a frame body and the curved or inclined anchors. This can beneficially enhance securement of the frame to the native mitral valve. It is to be understood that the circumferentially curved or inclined anchoring feature can be used in combination with other anchoring features described herein or as a replacement for one or more of the anchoring features described herein.

Figure 23:
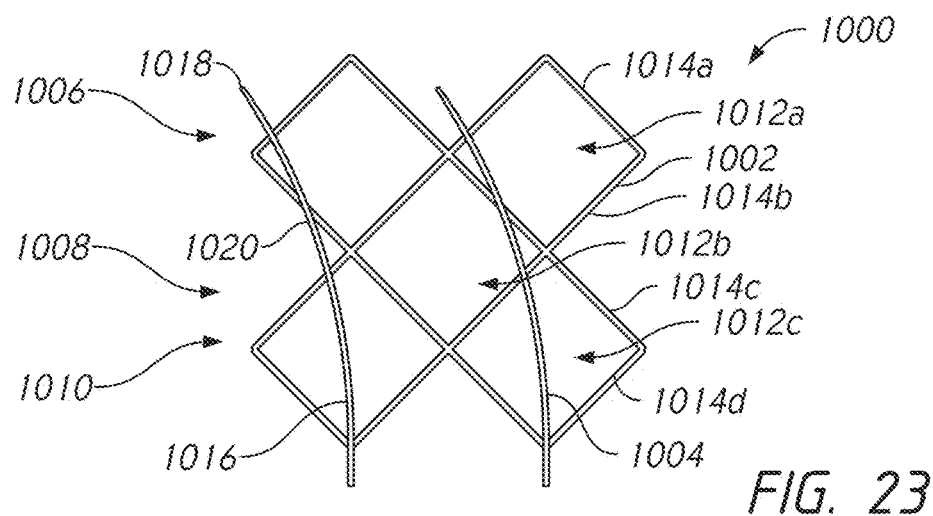
FIG. 23 is a side view of an embodiment of a portion of a frame having a circumferentially curved anchoring feature.
Figure 24:
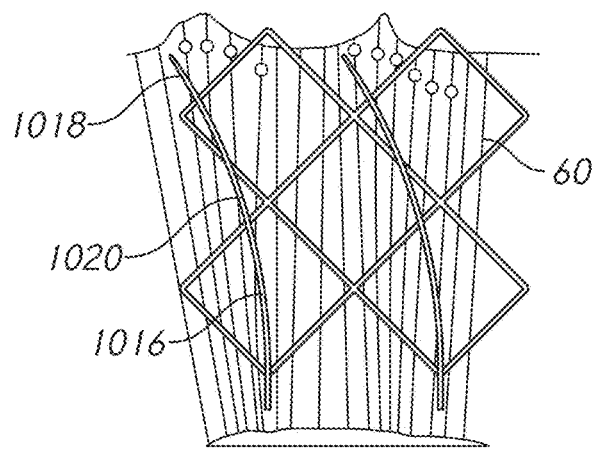
FIG. 24 is a side-oriented schematic view of the portion of the frame of FIG. 23 positioned between chordae tendineae of a heart.
Figure 25:
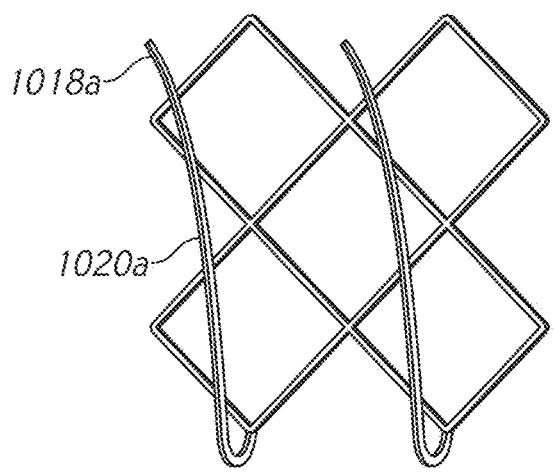
FIG. 25 is a side view of another embodiment of a portion of a frame having a circumferentially curved anchoring feature.

With reference next to FIGS. 23-25, a portion of an embodiment of a frame 1000 is illustrated. The frame 1000 can include a frame body 1002 and an anchoring feature 1004. A longitudinal axis of the frame 1000 may be defined as the central axis that extends through the center of the frame 1000 between the upper and lower ends of the frame 1000. Features of the frame 1000 can be incorporated in any of the prostheses described herein.

The frame body 1002 can include an upper region 1006, an intermediate region 1008, and a lower region 1010. As shown, the frame body 1002 can include a plurality of struts with at least some of the struts forming cells 1012*a-c*. The cells 1012*a-c* can have a diamond or generally diamond shape. However, it is to be understood that the cells 1012*a-c* can have different shapes such as those described in connection with other frames herein. Any number of configurations of struts can be used, such as rings of undulating struts shown forming ellipses, ovals, rounded polygons, and teardrops, but also chevrons, diamonds, curves, and various other shapes. For example, the frame body 1002 can be formed from circumferentially-expansible elements 1014*a-d*. While the struts 1014*a-d* are generally described and illustrated as being straight segments, it is to be understood that some or all of the struts 1014*a-d* may not form entirely straight segments. For example, the struts 1014*a-d* can include some curvature such that the upper and/or lower apices are curved.

The anchoring feature 1004 can include one or more anchors 1016. The anchors 1016 can extend from a lower region 1010 of the frame body 1002. For example, the anchors 1016 can extend downwardly and/or radially outwardly from a lower end of the lower region 1010. The anchors 1016 can also extend upwardly towards a tip or end 1018. As shown in the illustrated embodiment, at least a portion of the anchors 1016, such as the strut 1020 and/or the tip or end 1018, can be curved and/or inclined in a circumferential direction about the longitudinal axis of the frame 1000. For example, the portion of the strut 1020 which extends upwardly as well as the tip or end 1018 can be curved as shown in FIGS. 23 and 24. As another example, the entirety of the strut 1020*a*, including both portions which extend downwardly and upwardly, as well as the tip or end 1018*a* can be curved as shown in FIG. 25.

As discussed above, some of the anchoring features described herein can be positioned on a ventricular side of the native mitral valve annulus and/or tissue beyond the ventricular side of the annulus. The anchoring features may be positioned in this manner by extending around the native mitral valve leaflets, which include chordae tendineae 60 that connect a downstream end of the native mitral leaflets to the papillary muscle of the left ventricle. As shown in FIG. 24, the circumferential curve and/or incline can allow a greater number of chordae tendineae 60 to be positioned between the frame body 1002 and the anchors 1016. This can beneficially enhance securement of the frame 1000 to the native mitral valve.

With reference next to FIGS. 26 and 27, an embodiment of a frame 1100 is illustrated. The frame 1100 can include a frame body 1102, an upper anchoring feature 1104, and a lower anchoring feature 1106. A longitudinal axis of the frame 1100 may be defined as the central axis that extends through the center of the frame 1100 between the upper and lower ends of the frame 1100. Features of the frame 1100 can be incorporated in any of the prostheses described herein.

The frame body 1102 can include an upper region 1108, an intermediate region 1110, and a lower region 1112. As shown, the frame body 1102 can include a plurality of struts with at least some of the struts forming cells 1114*a-b*. The sides of cells 1114*a-b* can have a "bell-curve" shape. As shown in the illustrated embodiment, an upper portion of the first row of cells 1114*a* can be formed from circumferentially expansible struts 1116*a* and a lower portion of the first row of cells 1114*a* can be formed from circumferentially-expansible struts 1116*b*. The upper portion of the second row of cells 1114*b* can be formed from circumferentially expansible struts 1116*b* and a lower portion of the second row of cells 1114*b* can be formed from circumferentially-expansible struts 1116*c*. The frame body 1102 can include a plurality of interconnecting struts 1118*a-d*. The struts 1118*a-d* can be straight segments extending in a circumferential direction about the longitudinal axis of the frame 1100. These struts 1118*a-d* can form a flat upper end and lower end of the frame body 1102.

The upper anchoring feature 1104 can be similar to upper anchoring feature 924 described in connection with prosthesis 900 illustrated in FIGS. 20-22. The upper anchoring feature 1104 can be formed from a row of circumferentially expansible struts 1120. The circumferentially-expansible struts 1120 can be attached to the frame body 1102 via one or more struts 1122. The struts 1122 can be attached to the frame body 1102 at struts 1118*b*. However, it is to be understood that struts 1122 can extend from other portions of the frame body 1102, such as the upper and/or uppermost ends of cells 1102. The upper anchoring feature 1104 can include tips or ends 1124. The tips or ends can include eyelets 1126 which can allow other components of a prosthesis to be attached thereto, such as a skirt. Moreover, the eyelets 1126 can allow the prosthesis to be coupled to a delivery system.

The lower anchoring feature 1106 can include one or more anchors 1128. The anchors 1128 can include a strut 1130 and extend to a tip or end 1132. The anchors 1128 can extend from above a lower end of a lower region 1112 of the frame body 1002. For example, the anchors 1128 can extend downwardly and/or radially outwardly from struts 1118*c*. The anchors 1128 can also extend upwardly towards the tip or end 1132. As shown in the illustrated embodiment, at least a portion of the anchors 1016, such as a segment 1130*b* of strut 1130 and the tip or end 1132, can be curved and/or inclined in a circumferential direction about the longitudinal axis of the frame 1100. For example, the strut 1130 can incorporate a bend about an axis perpendicular to and/or passing through the longitudinal axis of the frame 1100. The bend can orient a second portion 1130*b* of the strut 1130 such that it is more inclined in a circumferential direction relative to the first portion 1130*a* of the strut 1130. As shown, the second portion 1130*b* can be inclined at an angle of about 30 degrees with respect to a plane parallel to and/or passing through the longitudinal axis of the frame 1100. In some embodiments, the second portion can be curved and/or inclined at an angle of between about 10 degrees to about 80 degrees relative to a plane parallel to and/or passing through the longitudinal axis of the frame 1100, about 15 degrees to about 60 degrees relative to a plane parallel to and/or passing through the longitudinal axis of the frame 1100, about 20 degrees to about 40 degrees relative to a plane parallel to and/or passing through the longitudinal axis of the frame 1100, about 30 degrees relative to a plane parallel to and/or passing through the longitudinal axis of the frame 1100, any sub-range within these ranges, and any other angle as desired.

Embodiments of Biased or Compressible Anchoring Features

In some embodiments, the prostheses described herein can incorporate a biased or compressible anchoring feature. The anchoring feature can be axially and/or radially biased or compressible. This can beneficially allow the anchoring feature to shift when subjected to forces, such as those which may be applied to an implanted anchoring feature during the cardiac cycle. This can significantly reduce the impact applied to tissue in contact with the anchor by spreading the applied force over a longer duration of time thereby reducing trauma to such tissue. In some embodiments, the biased or compressible anchoring features can be combined with cushions and/or covers described herein to further reduce trauma.

For example, tips or ends of an anchoring feature can be generally parallel to a longitudinal axis of the prosthesis and be in contact with a ventricular side of the native mitral valve annulus. Axial biasing or compression of such an anchoring feature can allow the anchoring feature to shift and apply the force over an extended duration of time to the ventricular side of the native mitral valve annulus. This can be particularly beneficial during systole in which the prosthesis is subject to a force tending to move the prosthesis towards the atrium. As another example, tips or ends of an anchoring feature can be generally perpendicular to a longitudinal axis of the prosthesis (e.g., a flange) and be in contact with an atrial side of the native mitral valve annulus. Radial biasing or compression of such an anchoring feature can allow the anchoring feature to shift and apply the force over an extended duration of time to the atrial side of the native mitral valve annulus.

Axial and/or radial biasing or compressibility can also the anchoring feature to better conform to tissue of the body cavity in which the anchoring feature is positioned. For example, similar to other prostheses described herein, the anchoring feature can include a plurality of individual anchors extending around a periphery of a frame. Each of the tips or ends of the anchors can independently shift to conform to the native anatomy, such as a native mitral annulus.

The axial and/or radially biasing or compressibility of the anchoring feature can also facilitate positioning within a delivery system. For example, the anchoring feature can shift to a position which better conforms to the shape of the delivery system, such as a sheath of the delivery system. As another example, the anchoring feature can radially compress to reduce the crimp profile of the anchoring feature.

It is to be understood that the biased or compressible anchoring features can be used in combination with other anchoring features described herein or as a replacement for one or more of the anchoring features described herein.

With reference to FIG. 48, an embodiment of a frame 2500 is illustrated. The frame 2500 can include a frame body 2502 and/or an anchoring feature 2504. The anchoring feature 2504 can include a strut 2504*a* connected to the frame body 2502. The strut 2504*a* can extend to a tip or end 2504*b*. As shown, the tip or end 2504*b* can be formed from a plurality of wires. These wires may be looped to form a generally three-dimensional teardrop shape. The wires may be compliant such that the tip or end 2504*b* can be axially and/or radially biased or compressed.

With reference next to FIG. 49, an embodiment of a frame 2550 is illustrated. The frame 2550 can include a frame body 2552 and/or an anchoring feature 2554. The anchoring feature 2554 can include a strut 2554*a* connected to the frame body 2552. The strut 2554*a* can extend to a tip or end 2554*b*. As shown, the tip or end 2554*b* can be formed from one or more wires. The one or more wires may be spiraled to form a generally three-dimensional conical shape. The wires may be compliant such that the tip or end 2554*b* can axially and/or radially biased or compressed.

With reference to FIG. 50, an embodiment of an anchoring feature 2600 is illustrated. The anchoring feature 2600 can include a strut 2602 which can be connected to a frame body (not shown). The strut 2602 can extend to a tip or end 2604. As shown, the tip or end 2604 can have a serpentine shape. The serpentine shape can allow the tip or end 2604 to axially compress as represented by arrow 2606. The serpentine shape can allow the tip or end 2604 to radially compress as represented by arrows 2608. In some embodiments, the tip or end 2604 can be biased radially outward (e.g., out-of-plane movement). This can be achieved by forming the material of the tip or end 2604 out of a thinner or more compliant material. In some embodiments, such as the anchoring feature 2650 illustrated in FIG. 51, the anchoring feature can include multiple prongs 2654*a*, 2654*b* having a serpentine shape.

With reference to FIG. 52, an embodiment of an anchoring feature 2700 is illustrated. The anchoring feature 2700 can include a strut 2702 which can be connected to a frame body (not shown). The strut 2702 can extend to a tip or end 2704. As shown, the tip or end 2704 can be formed from a plurality of cells. The cells can be foreshortening cells such as the illustrated diamond-shaped cells. The cells can allow the tip or end 2704 to axially compress as represented by arrow 2706. The cells can allow the tip or end 2704 to radially compress as represented by arrows 2708. In some embodiments, the tip or end 2704 can be biased radially outward (e.g., out-of-plane movement). This can be achieved by forming the material of the tip or end 2704 out of a thinner or more compliant material.

With reference to FIG. 53, an embodiment of an anchoring feature 2800 is illustrated. The anchoring feature 2800 can include a strut 2802 which can be connected to a frame body (not shown). The strut 2802 can extend to a tip or end 2804. As shown, the tip or end 2804 can be formed from one or more prongs 2806*a*, 2806*a*. The tip or end 2804 can include a component such as a plate 2808. The plate 2808 can advantageously increase the surface area of the tip or end 2804 thereby reducing pressures applied to tissue. The plate 2808 can be flexible to allow the plate 2808 to deform when subjected to forces. In some embodiments, the plate 2808 can be retained in a collapsed configuration prior to delivery. For example, the plate 2808 may be retained in a collapsed configuration via a suture. The suture may be biodegradable such that the plate 2808 expands after implantation.

In some embodiments, the tips or ends can be covered with a biodegradable material. This can allow the tips or ends to be retained in a compressed configuration when initially implanted into a body cavity. Over time, the material can biodegrade and allow the tips or ends to expand into the shapes illustrated above. In some embodiments, the entire anchoring feature can be formed from a biodegradable or resorbable material. In some implementations, the entire anchoring features can be resorbed after a duration of time sufficient to allow tissue ingrowth around the prosthesis. In some embodiments, the anchoring features can be removable. It is to be understood that other geometries and structures can be implemented with respect to the anchoring features described herein. Further details on such geometries and structures can be found in U.S. application Ser. No. 15/653,390, entitled REPLACEMENT HEART VALVE PROSTHESIS, filed on Jul. 18, 2017, the entirety of which has been incorporated herein by reference.

Other anchoring mechanisms are also contemplated. In some embodiments, the inner and/or outer frames can include one or more barbs to facilitate securement to tissue of a body cavity in which the prosthesis is positioned. In some embodiments, the inner and/or outer frames can include a tether which can be attached tissue of the body cavity. For example, the tether may be attached to a portion of the heart wall, such as an apex of the heart wall.

Exemplary Placement of Replacement Valves

Reference is now made to FIGS. 28A-30 which illustrate schematic representations of an embodiment of a prosthesis 1200 in an expanded configuration, having an inner frame portion 1202 and an outer frame portion 1204, positioned within a native mitral valve of a heart 10. As noted above, in some embodiments the prostheses described herein can be positioned within a native mitral valve. A portion of the native mitral valve is shown schematically and represents typical anatomy, including a left atrium 20 positioned above an annulus 40 and a left ventricle 30 positioned below the annulus 40. The left atrium 20 and left ventricle 30 communicate with one another through a mitral annulus 40. Also shown schematically in FIGS. 28A-30 is a native mitral leaflet 50 having chordae tendineae 60 that connect a downstream end of the mitral leaflet 50 to the papillary muscle of the left ventricle 30. The portion of the prosthesis 1200 disposed upstream of the annulus 40 (toward the left atrium) can be referred to as being positioned supra-annularly. The portion generally within the annulus 40 can be referred to as positioned intra-annularly. The portion downstream of the annulus 40 can be referred to as being positioned sub-annularly (toward the left ventricle). In the illustrated embodiment, only a part of the foreshortening portion is positioned intra-annularly or sub-annularly, and the rest of the prosthesis 1200 is supra-annular.

Figure 28A:
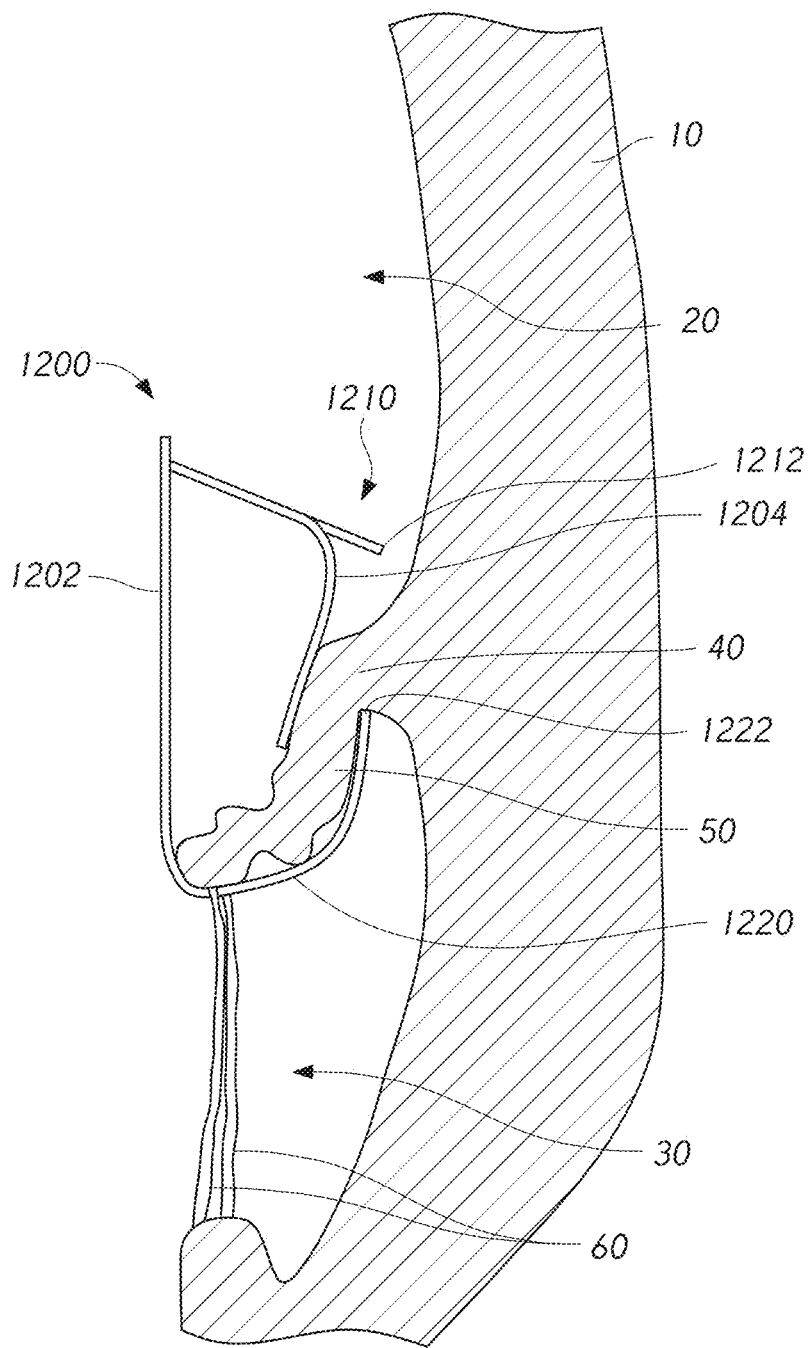
FIGS. 28-30 illustrate schematic representations of the prosthesis of FIG. 1 positioned within a heart, with FIGS. 28A-B illustrating the prosthesis in situ with distal anchors contacting the ventricular side of a mitral valve annulus, FIG. 29 illustrating the prosthesis in situ with distal anchors not contacting the ventricular side of the mitral valve annulus, and FIG. 30 illustrating the prosthesis in situ with distal anchors not extending between the chordae tendineae.
Figure 28B:
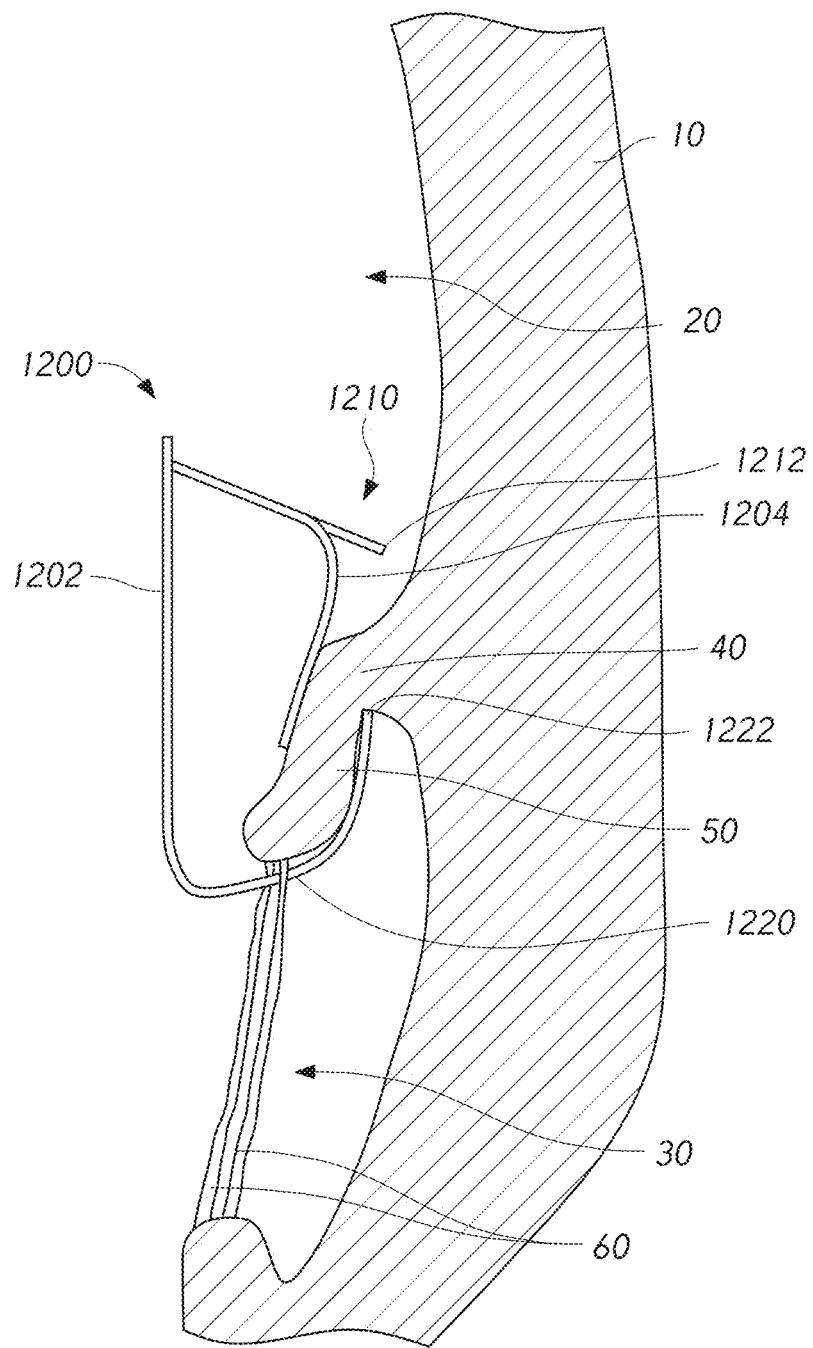
Figure 29:
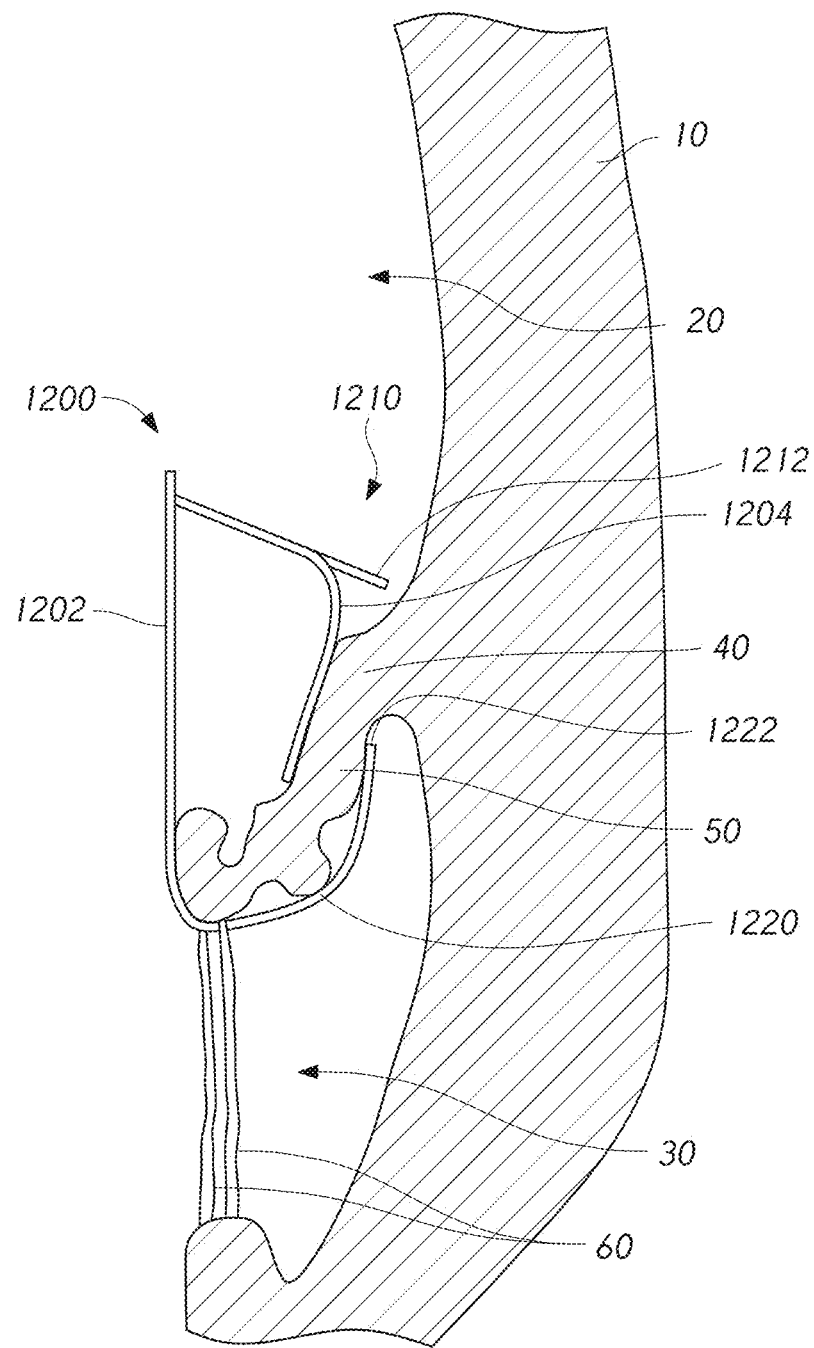

As shown in the situations illustrated in FIGS. 28A-30, the prosthesis 1200 can be disposed so that the mitral annulus 40 is between the upper or atrial anchoring feature 1210 and the lower or ventricular anchoring feature 1220 with a portion of the outer frame portion 1204 contacting the mitral annulus 40 along an inner edge or periphery. As shown in FIGS. 28A-29, portions of the mitral annulus 40 and/or the mitral leaflet 50 can be positioned between the outer frame portion 1204 and the lower anchoring feature 1220. The mitral annulus 40 and/or the mitral leaflet 50 can be pinched between the outer frame portion 1204 and the lower anchoring feature 1220. As shown, the outer frame portion 1204 is oriented radially inward to conform to the shape of mitral annulus 40 and/or the mitral leaflet 50. In an expanded configuration, the outer frame portion 1204 can be positioned radially outward in a natural, unbiased state. Accordingly, with the mitral annulus 40 and/or the mitral leaflet 50 positioned therebetween, the outer frame portion 1204 can be biased outward to apply a pinching force on the mitral annulus 40 and/or the mitral leaflet 50.

In some situations, the prosthesis 1200 can be positioned such that ends or tips 1222 of the lower anchoring feature 1220 can contact the ventricular side of the annulus 40 as shown, for example, in FIGS. 28A-B. In some situations, the prosthesis 1200 can be positioned such that ends or tips 1222 of the lower anchoring feature 1220 do not contact the annulus 40 as shown, for example, in FIG. 29, and may just contact a downstream side of the leaflet 50. In some situations, the prosthesis 1200 can be positioned such that the lower anchoring feature 1220 does not extend around the leaflet 50 as illustrated, but rather are positioned radially inward of the leaflet 50 as shown, for example, in FIG. 30. While FIGS. 28A-30 are described separately below, it should be understood that one or more of the situations illustrated in FIGS. 28A-30 may be present when the prosthesis 1200 is positioned at the implantation location, such as a native mitral valve. For example, in some situations the prosthesis 1200 may be positioned such that some portion of the anchoring feature 1220 may contact the annulus 40 while another portion of the lower anchoring feature 1220 may not. Moreover, it may be contemplated some in some situations, some portion of the anchoring feature 1220 may be positioned With reference first to the situations illustrated in FIGS. 28A-29, the prosthesis 1200 can be positioned so that the ends or tips 1222 of the lower anchoring feature 1220 are on a ventricular side of the mitral annulus 40 and the ends or tips 1212 of the upper anchoring feature 1210 are on an atrial side of the mitral annulus 40. The lower anchoring feature 1220 can be positioned such that the ends or tips 1222 of the lower anchoring feature 1220 are on a ventricular side of the native leaflets radially outwardly beyond a location where chordae tendineae 60 connect to free ends of the native leaflets 50. The lower anchoring feature 1220 may extend between at least some of the chordae tendineae 60 and, in some situations such as those shown in FIGS. 28A-B, can contact or engage a ventricular side of the annulus 40. It is also contemplated that in some situations, such as those shown in FIG. 29, the lower anchoring feature 1220 may not contact the annulus 40, though the lower anchoring feature 1220 may still contact the native leaflet 50. In some situations, the lower anchoring feature 1220 can contact tissue of the left ventricle 30 beyond the annulus 40 and/or a ventricular side of the leaflets 50.

During delivery, the lower anchoring feature 1220 (along with the inner frame portion 1202 and outer frame portion 1204) can be moved toward the ventricular side of the annulus 40 with the lower anchoring feature 1220 extending between at least some of the chordae tendineae 60 to provide tension on the chordae tendineae 60 after the prosthesis 1200 is finally delivered. The degree of tension provided on the chordae tendineae 60 can differ. For example, little to no tension may be present in the chordae tendineae 60 as shown in FIG. 28B where the leaflet 50 is shorter than or similar in size to the lower anchoring feature 1220. A greater degree of tension may be present in the chordae tendineae 60 as shown in FIG. 28A where the leaflet 50 is longer than the lower anchoring feature 1220 and, as such, takes on a compacted form and is pulled proximally. An even greater degree of tension may be present in the chordae tendineae 60 as shown in FIG. 29 where the leaflets 50 are even longer relative to the lower anchoring feature 1220. As shown in FIG. 29, the leaflet 50 is sufficiently long such that the lower anchoring feature 1220 does not contact the annulus 40.

The upper anchoring feature 1210 can be positioned such that the ends or tips 1212 of the upper anchoring feature 1210 are on or adjacent the atrial side of the annulus 40 and/or tissue of the left atrium 20 beyond the annulus 40. In some situations, some portion or all of the upper anchoring feature 1210 may only occasionally contact or engage atrial side of the annulus 40 and/or tissue of the left atrium 20 beyond the annulus 40. For example, as shown in FIGS. 28A-30, the upper anchoring feature 1210 may be spaced from the atrial side of the annulus 40 and/or tissue of the left atrium 20 beyond the annulus 40. The upper anchoring feature 1210 may be utilized to provide axial stability for the prosthesis 1200 and prevent off-axis orientation. Further, the upper anchoring feature 1210 can act as a safety feature without utilizing them for axial stability and off-axis orientation. For example, if the prosthesis 1200 is improperly deployed so that the prosthesis 1200 is deployed too low toward the left ventricle 30, the upper anchoring feature 1210 can prevent the prosthesis 1200 from falling into the left ventricle 30. It is to be understood that some or all of the upper anchoring feature 1210 may contact the atrial side of the annulus 40 and/or tissue of the left atrium 20 beyond the annulus 40.

Figure 30:
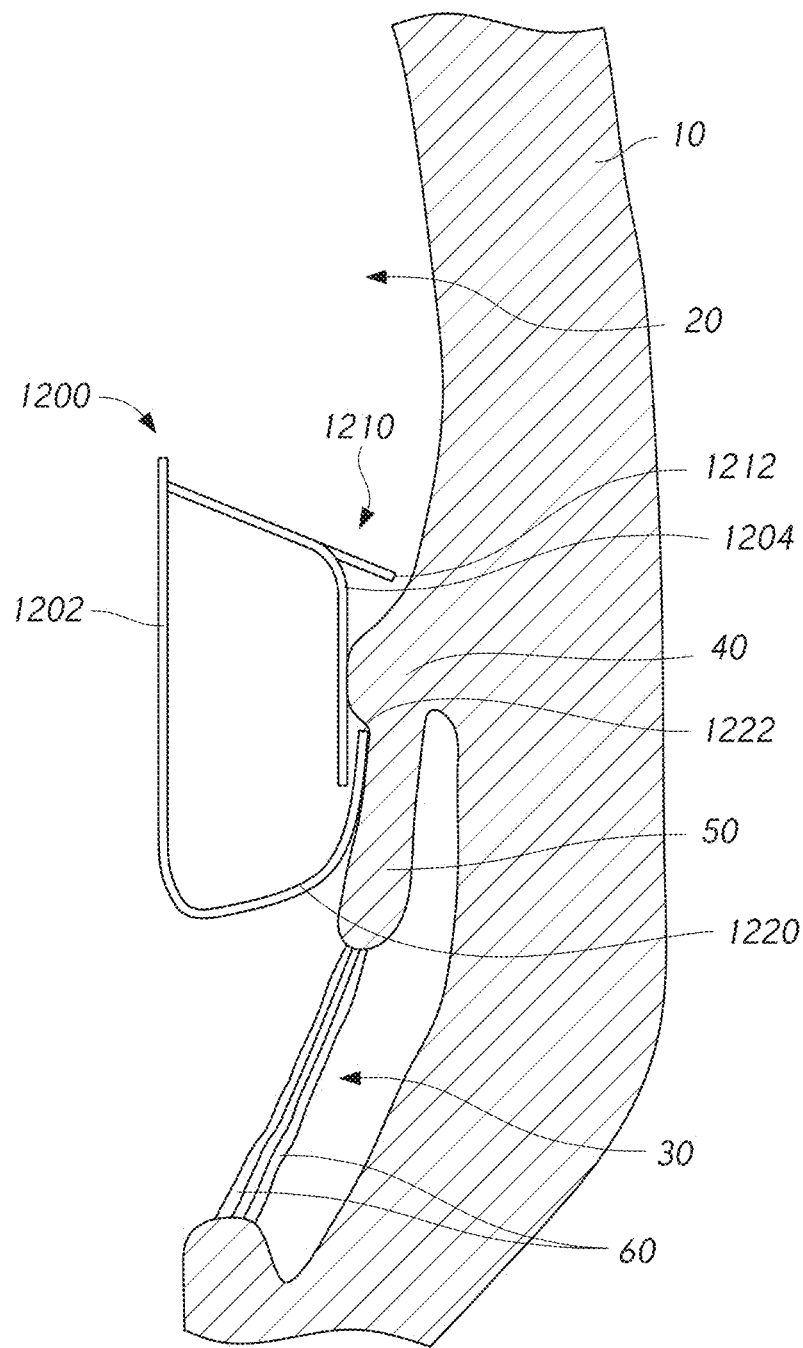

In some situations such as that shown in FIG. 30, the leaflet 50 may not be captured between the frame portions 1202, 1204 and a portion of the lower anchoring feature 1220. As shown, the portion of the lower anchoring feature 1220 may be positioned along an atrial surface of the leaflet 50. The portion of the lower anchoring feature 1220 may also be positioned along an inner surface of the annulus 40. It is also contemplated that the portion of the lower anchoring feature 1220 may exert a force against the leaflet 50 such that the leaflet 50 is pushed radially outward, relative to the longitudinal axis of the frame 1202, towards a wall of the heart 10. In such situations, the outer frame portion 1204 can still anchor intra-annularly and/or along an atrial side of the leaflet 50. In alternative situations (not shown), the outer frame portion 1204 can still anchor along a ventricular side of the annulus 40.

As noted above, although the in vivo situations of FIG. 28A-30 have been described separately, it should be understood that one or more of these situations may be present when a prosthesis is positioned at the implantation location, such as a native mitral valve. For example, a portion of the lower anchoring feature 1220 may not capture the leaflet 50 whereas the remaining portion may capture the leaflet 50.

Delivery of Prosthesis

The prostheses described herein can be delivered to a patient's native heart valve in various ways, such as by open surgery, minimally-invasive surgery, and percutaneous or transcatheter delivery through the patient's vasculature. In some embodiments, the prosthesis can be delivered to a patient's native mitral valve through procedure such as, but not limited to, a transapical procedure and a transseptal procedure. As noted above, the prostheses can be used with a variety of delivery systems such as "slot"-based and/or "tether"-based systems. For purposes of FIGS. 31 and 32, it is to be understood that the distal direction is towards the right of the drawing.

Figure 31:
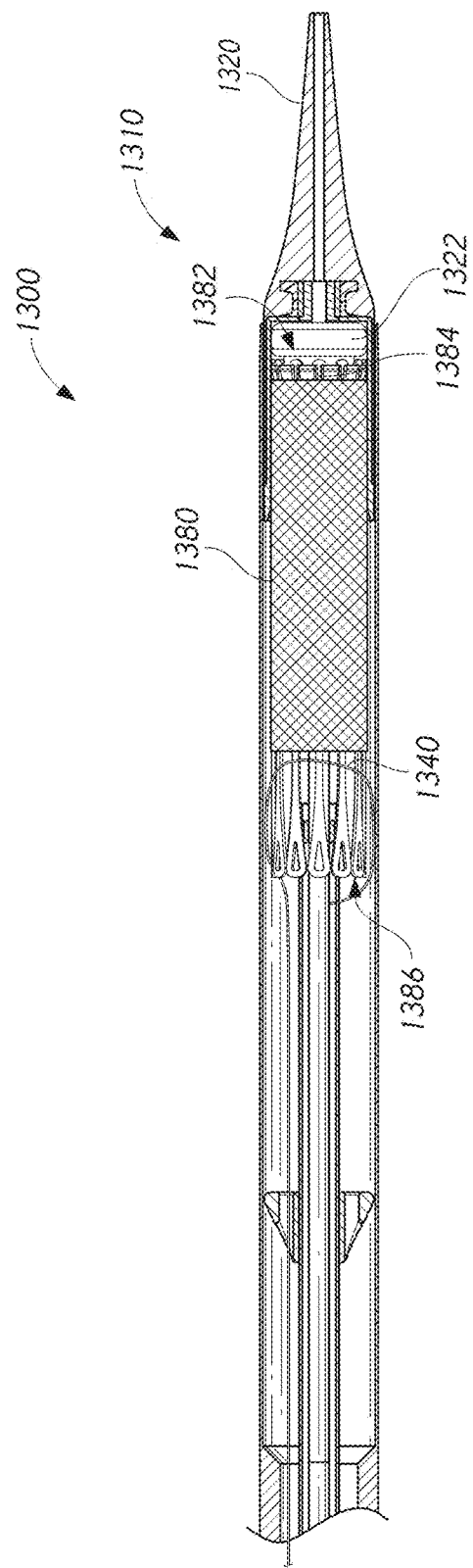
FIG. 31 is a cross-sectional view of a distal end of an embodiment of a delivery system loaded with an embodiment of a prosthesis.

With reference first to the system 1300 of FIG. 31, the system 1300 can include a delivery device 1310 with a prosthesis 1380 (illustrated schematically) contained within the delivery device 1310. A first end 1382 of the prosthesis 1380 can be placed in a compressed state such that the first end 1382 of the prosthesis 1380 is retained between a nose cone 1320 and an inner retention member 1322 when the inner retention member 1322 is received within and covered by the nose cone 1320. The inner retention member 1322 can include one or more slots which interface with locking tabs 1384. The interface between the locking tabs 1384 and slots of the inner retention member 1322 can inhibit axial movement of the prosthesis 1380 relative to the inner retention member 1322. When the first end 1382 of the prosthesis 1380 is uncovered, such as by moving the nose cone 1320 distally relative to the inner retention member 1322 or by moving the inner retention member 1322 proximally relative to the nose cone 1320, the first end 1382 of the prosthesis 1380 can be released. This release can be caused by the prosthesis 1380 transitioning from a collapsed configuration to an expanded configuration when the prosthesis 1380 is formed from a self-expanding material.

At least a second end 1386 of the prosthesis 1380 can be placed in a compressed state such that the second end 1386 of the prosthesis 1380 is retained within a hollow shaft member 1330. When the second end 1386 is uncovered, such as by moving the hollow shaft member 1330 proximally relative to the prosthesis 1380 or by moving the prosthesis 1380 distally relative to the hollow shaft member 1330, the second end 1386 of the prosthesis 1380 can be released. This release can be caused by the prosthesis 1380 transitioning from a collapsed configuration to an expanded configuration when the prosthesis 1380 is formed from a self-expanding material. In some embodiments, the delivery system 1310 can include a tether 1340 which can wrap around a portion of the prosthesis 1380, such as an anchoring feature on the second end 1386. The tether 1340 can be used to control expansion of a portion of the prosthesis 1380, such as the second end 1386, when the portion of the prosthesis 1380 is uncovered. For example, in some embodiments, the tether 1340 can be used to control the rate at which anchors positioned at the second end 1386 flip from the collapsed configuration to the expanded configuration such that the anchors extend towards the first end 1382.

In some embodiments, the system 1300 can be used in connection with a transapical procedure to access a native mitral valve. During such a procedure, the system 1300 can access a mitral valve through the apex of the heart. The anchoring feature on a ventricular side of the prosthesis 1380, such as the second end 1386, can be released on a ventricular side of the native mitral valve annulus. During delivery, the anchoring feature on a ventricular side of the annulus (along with the prosthesis 1380) can be moved toward the ventricular side of the annulus with the ventricular anchors extending between at least some of the chordae tendineae to provide tension on the chordae tendineae. The degree of tension provided on the chordae tendineae can differ. For example, little to no tension may be present in the chordae tendineae if the leaflet is shorter than or similar in size to the ventricular anchors. A greater degree of tension may be present in the chordae tendineae where the leaflet is longer than the ventricular anchors and, as such, takes on a compacted form and is pulled toward the native valve annulus. An even greater degree of tension may be present in the chordae tendineae where the leaflets are even longer relative to the ventricular anchors. The leaflet can be sufficiently long such that the ventricular anchors do not contact the annulus. After the anchoring feature on a ventricular side of the annulus is positioned, the remainder of the prosthesis 1380 can be deployed from the delivery system 1310.

Reference is now made to FIGS. 54A-54H which illustrate schematic representations of an embodiment of a prosthesis 2900 and a delivery system 2950 during various stages of deployment within a native mitral valve of a heart 10. The prosthesis 2900 can include an inner frame 2910 and an outer frame 2920. The inner frame 2910 can include an inner frame body 2912 and an inner frame anchoring feature 2914. The prosthesis 2900 can share characteristics, such as structure and/or functionality, which are the same as, or at least similar to, those of other prostheses described herein, such as prostheses 100, 200, 1500, 1600.

The delivery system 2950 can include a nose cone 2960 and an inner retention member 2962 at a first end of the delivery system 2950. The nose cone 2960 and inner retention member 2970 can retain an upper end of the prosthesis 2900. The delivery system 2950 can include a hollow shaft member 2980 and a tether 2990. The hollow shaft member 2980 can retain portions of the prosthesis 2900 therein. The tether 2990 can be tensioned to retain portions of the prosthesis 2900 in a collapsed state. The delivery system 2950 can share characteristics, such as structure and/or functionality, which are the same as, or at least similar to, those of other delivery systems described herein, such as delivery system 1310.

Figure 54A:
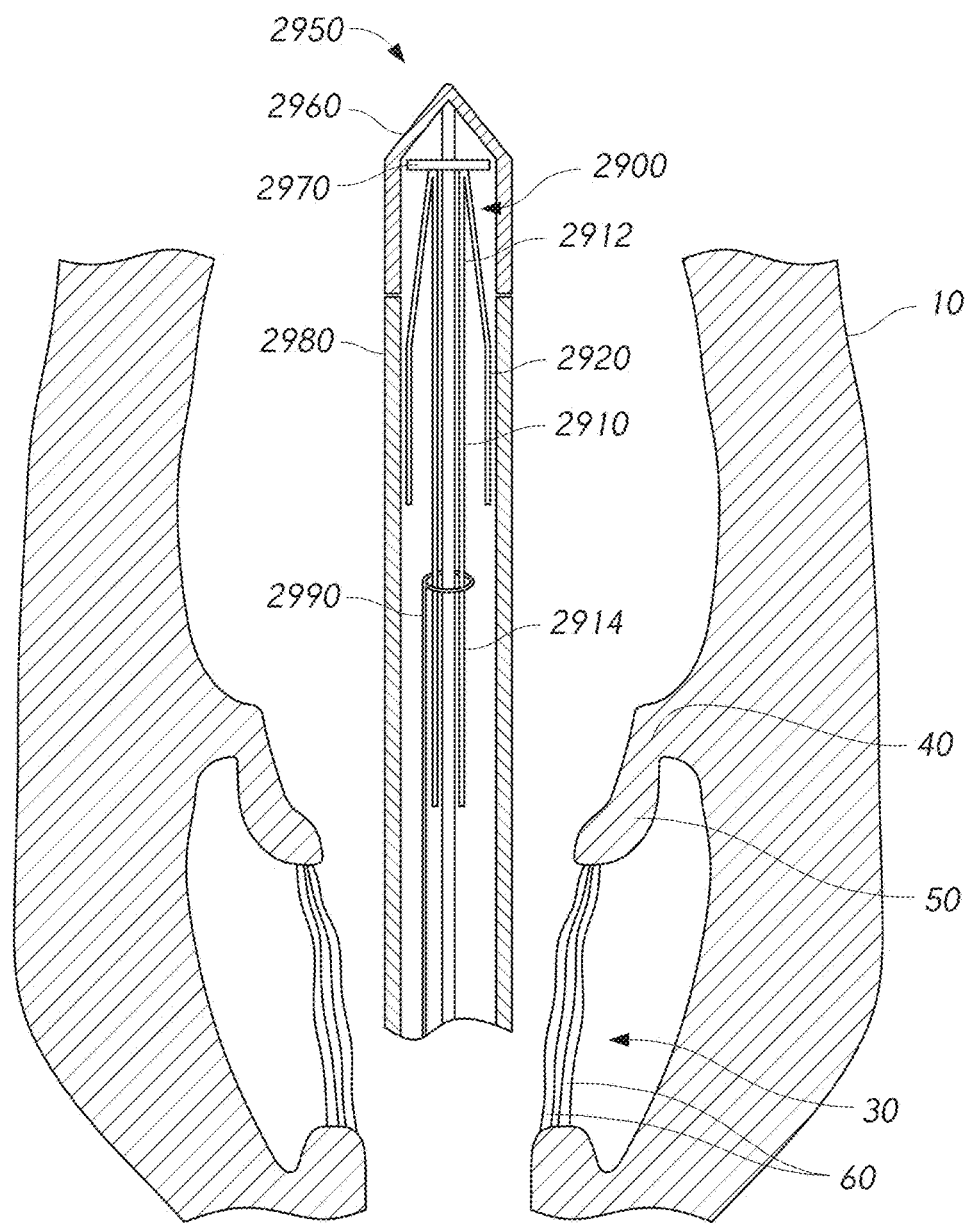
FIGS. 54A-57H illustrate schematic representations of delivery procedures utilizing embodiments of prostheses and delivery systems described herein.

With reference first to FIG. 54A, the prosthesis 2900 and delivery system 2950 can be introduced with the prosthesis 2900 in a fully collapsed configuration. As shown, the prosthesis 2900 and the delivery system 2950 can be introduced in a direction from the ventricle to the atrium (e.g., a transapical delivery procedure).

Figure 54B:
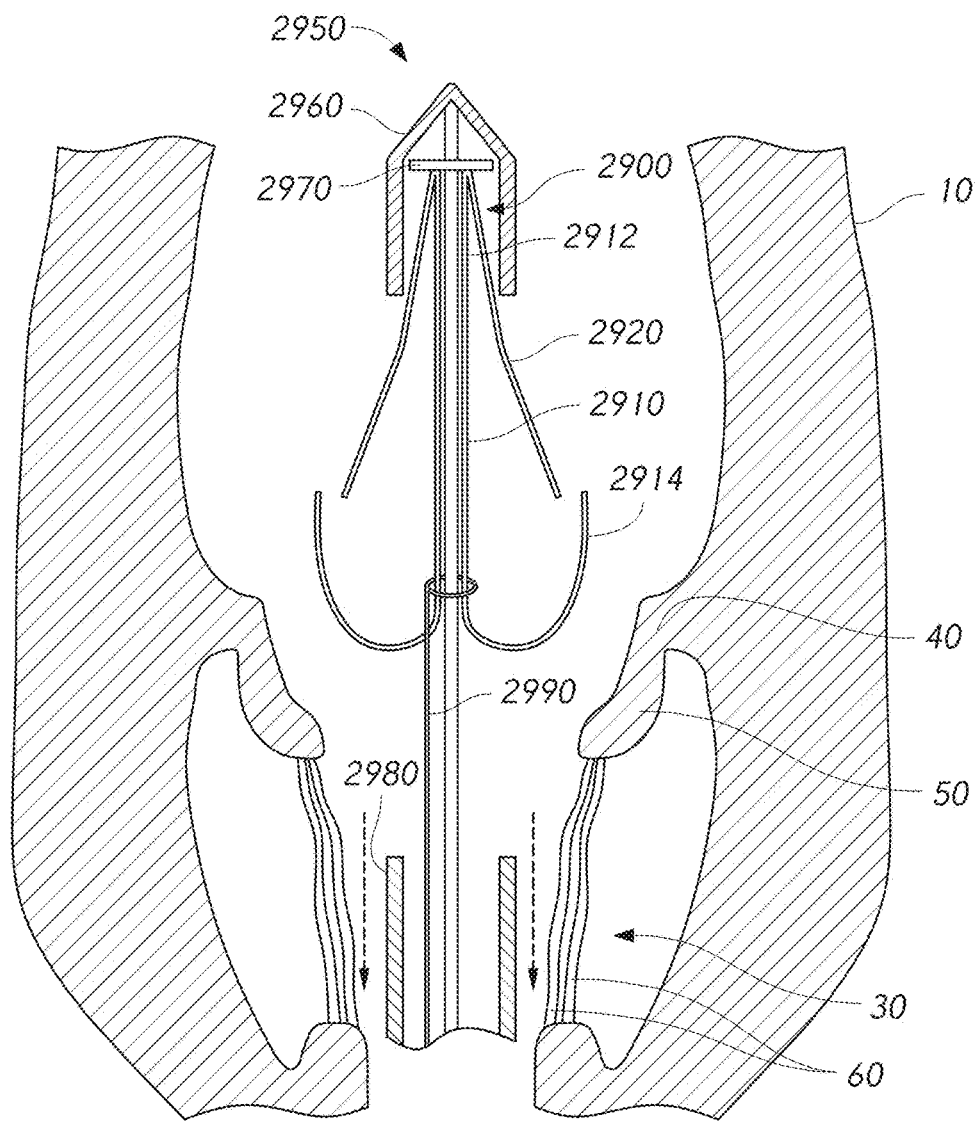

With reference next to FIG. 54B, the hollow shaft member 2980 can be retracted downwardly or proximally to expose the prosthesis 2900. This can allow the inner frame anchoring feature 2914 to transition to an expanded configuration. In some instances, a portion of the outer frame 2920 can also expand. As shown, the nose cone 2960 can be sized to retain at least a portion, or the entirety, of an upper region of the prosthesis 2900 in a collapsed or crimped configuration. This can beneficially reduce radial expansion of the prosthesis 2900 during this step of delivery. As shown in the illustrated embodiment, the inner frame anchoring feature 2914 can be positioned generally above the annulus 40 prior to allowing the inner frame anchoring feature 2914 to expand; however, it is to be understood that this step can occur while the inner frame anchoring feature 2914 is positioned within the annulus 40, below the annulus 40, or below the leaflets 50. Although the inner frame 2910 is shown in a fully collapsed configuration via tether 2990, it is to be understood that the inner frame 2910 can at least partially expand during this stage.

Figure 54C:
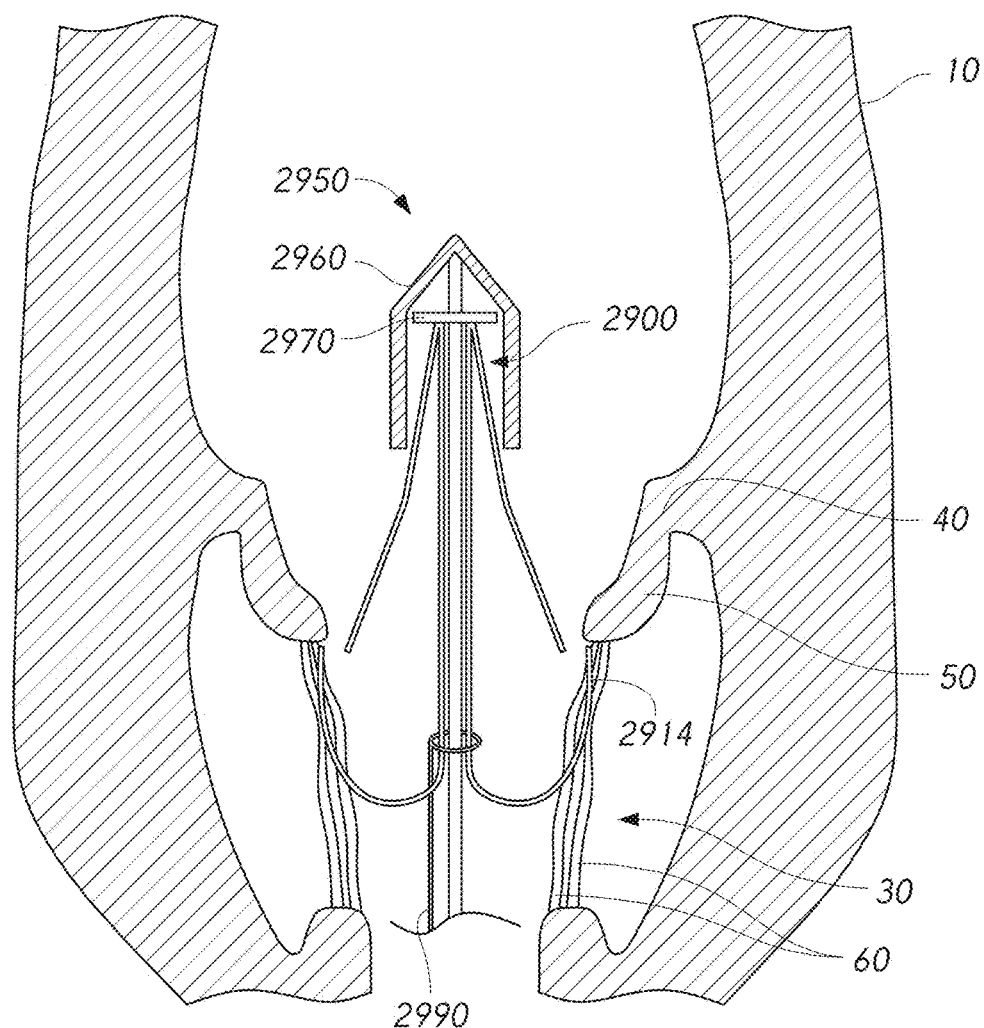
Figure 54D:
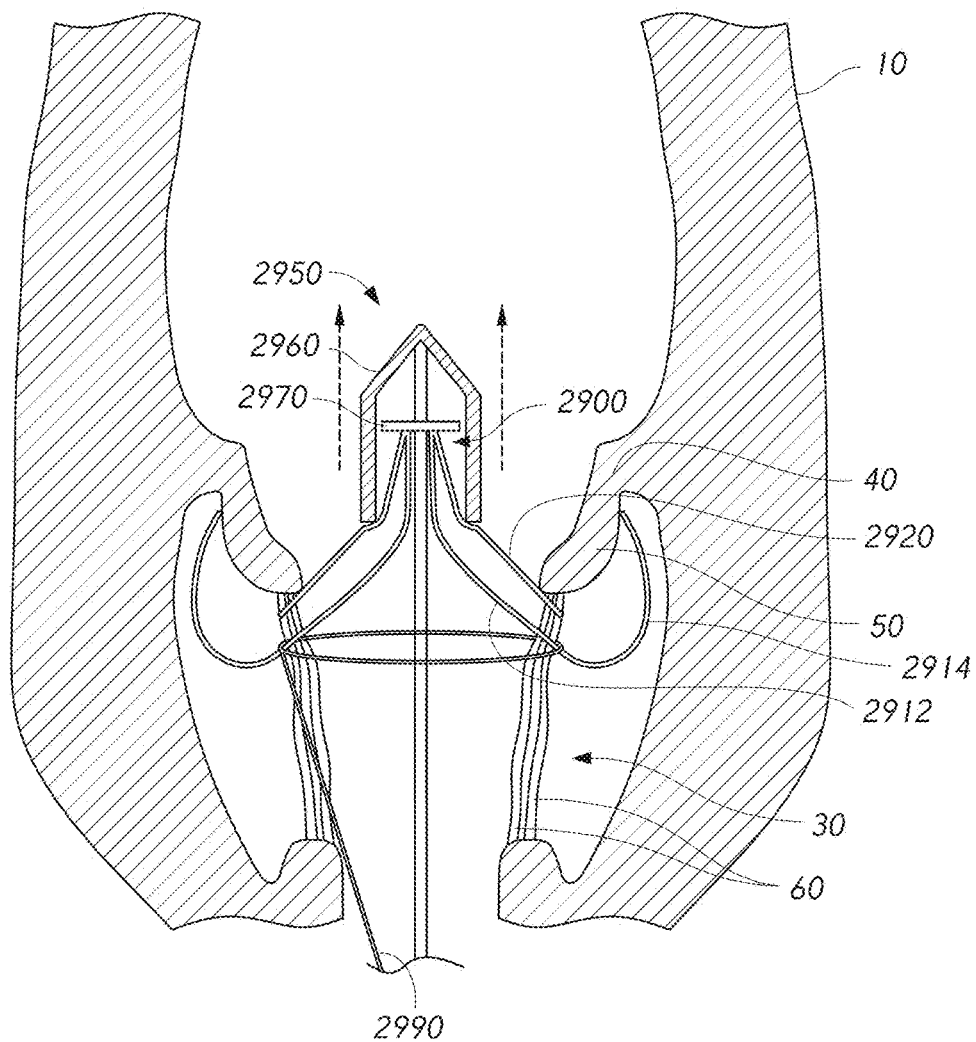

With reference next to in FIG. 54C, the prosthesis 2900 can be moved such that the inner frame anchoring feature 2914 is positioned below the annulus 40. As shown, the inner frame anchoring feature 2914 can be positioned below free edges of the leaflets 50. With reference next to FIG. 54D, the tether 2990 can be loosened to allow the inner frame 2910 to expand further radially outward. In some embodiments, the nose cone 2960 can be advanced upwardly or proximally relative to the inner retention member 2970 to allow the inner frame 2910 and/or outer frame 2920 to expand further. The prosthesis 2900 may be moved during this process to seat the inner frame anchoring feature 2914 against the annulus 40.

Figure 54E:
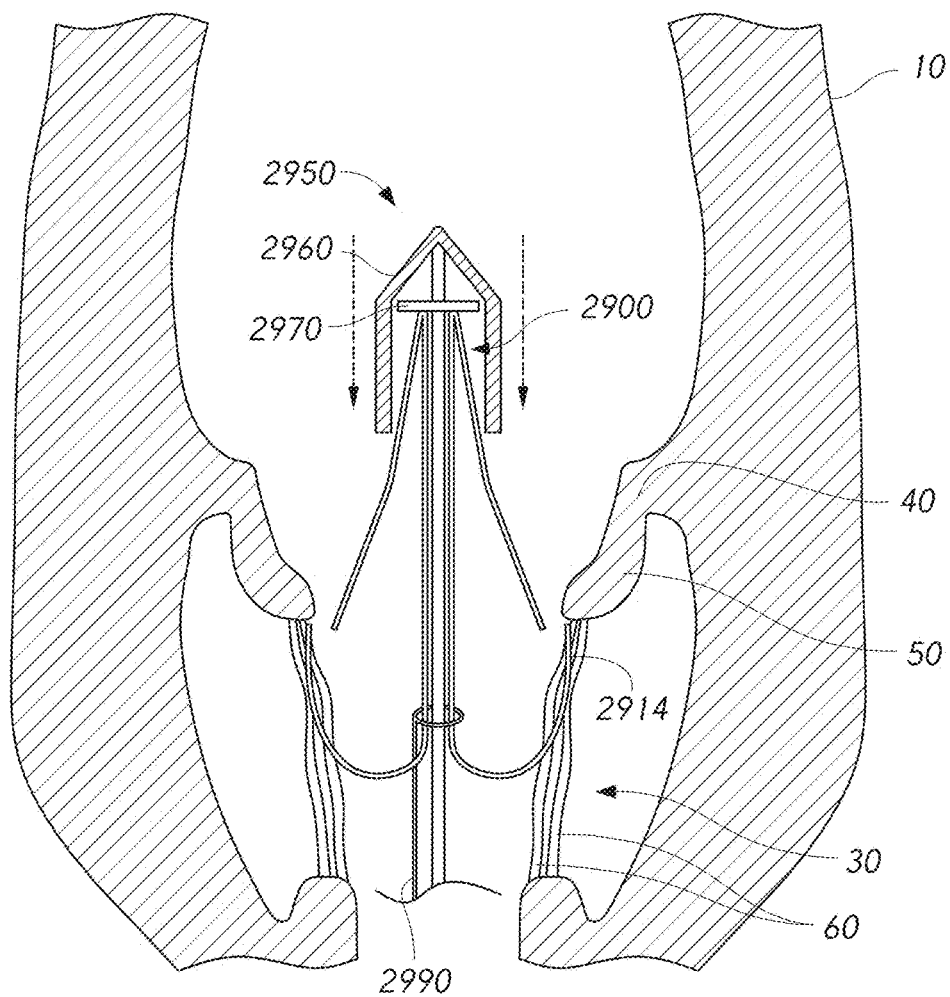
Figure 54F:
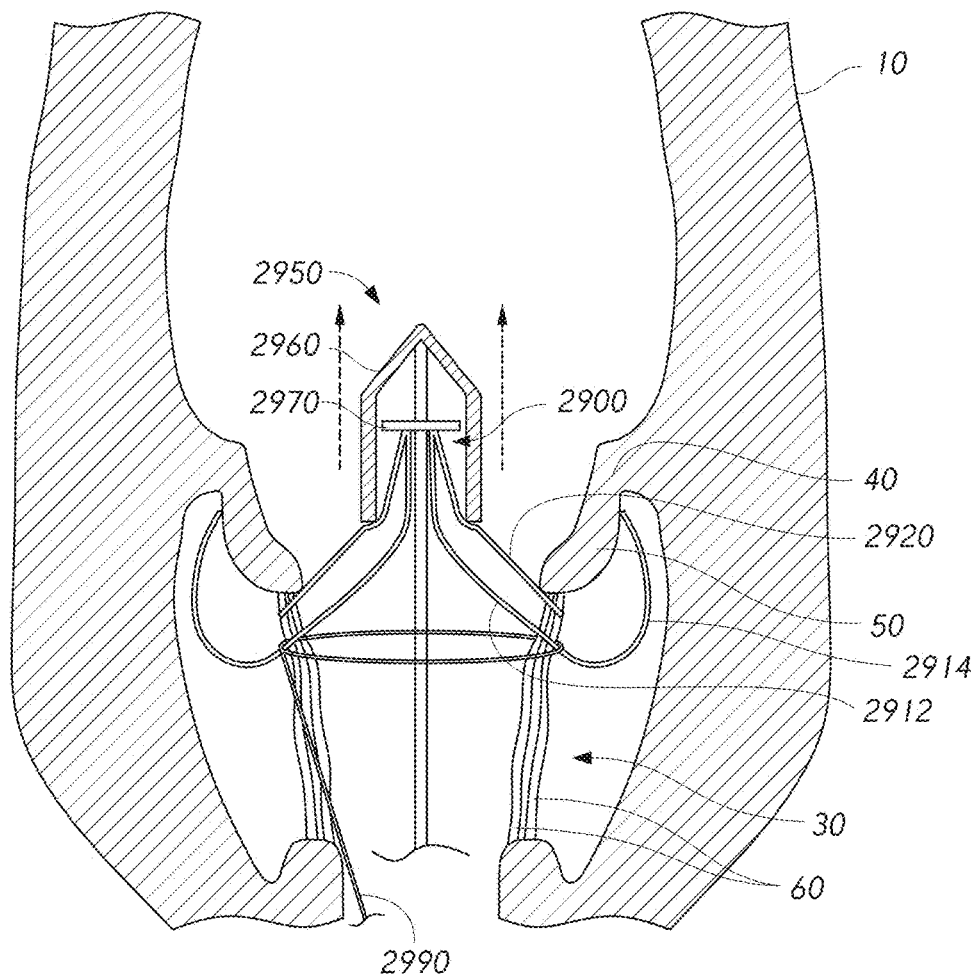

In some situations, a user may determine that the prosthesis 2900 should be repositioned. The prosthesis 2900 may be recaptured reversing the previous steps as shown in FIG. 54E. The inwardly tapered shape of the outer frame 2920 can facilitate the process of recapturing the device. For example, the inwardly tapered shape can function as a funnel which draws the outer frame 2920 and/or inner frame 2910 together when advancing the hollow shaft member 2980 over the outer frame 2920. The user may then re-expand the prosthesis 2900 as shown in FIG. 54F.

Figure 54G:
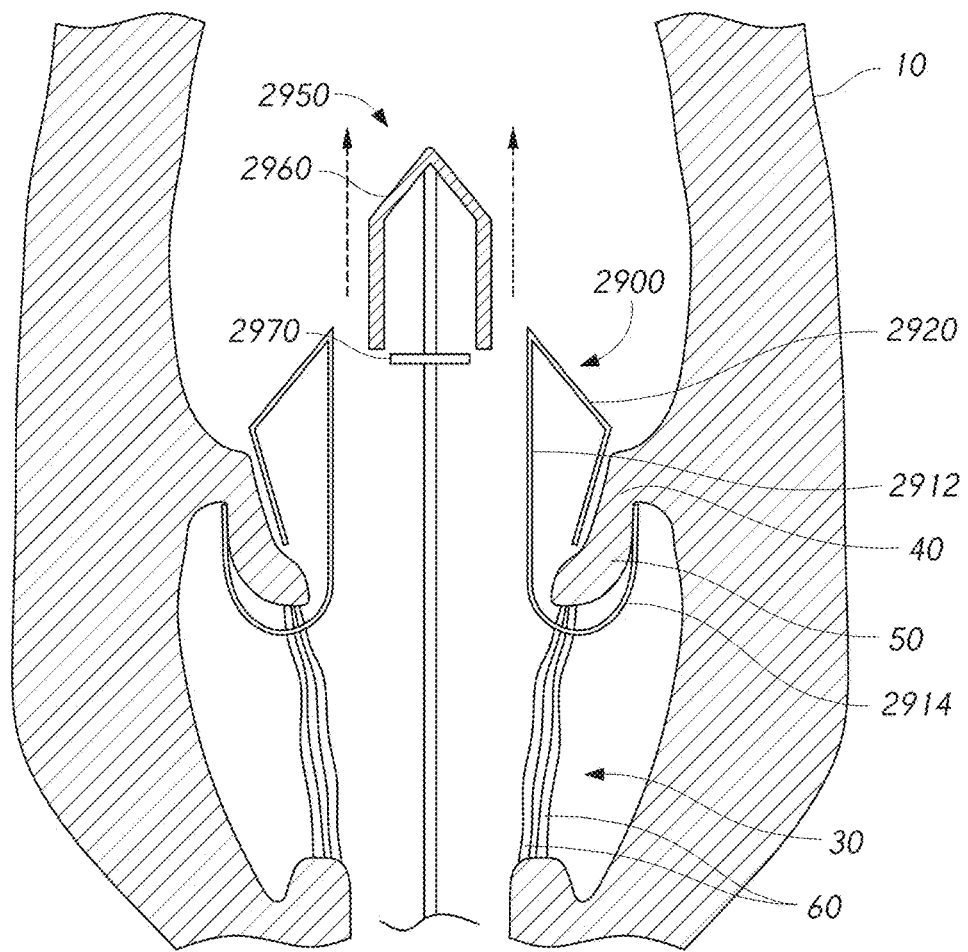
Figure 54H:
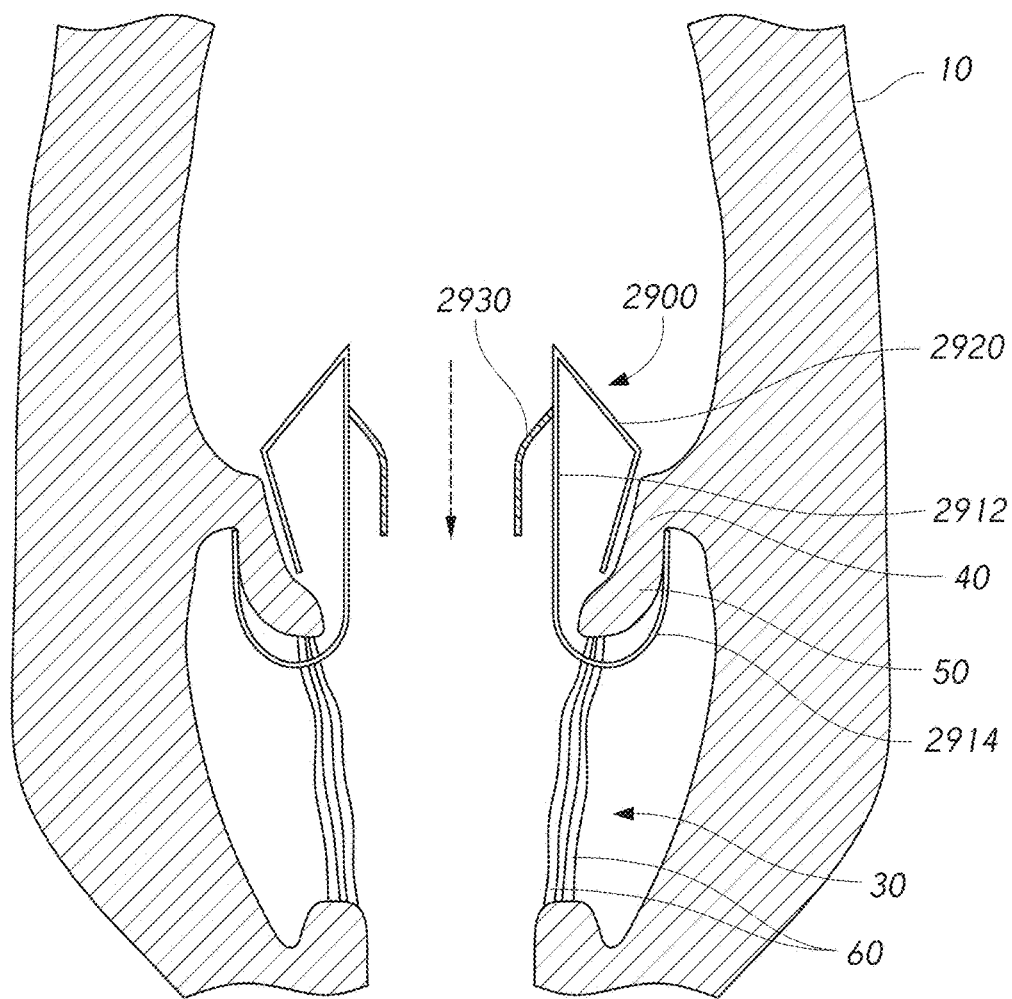
Figure 58:
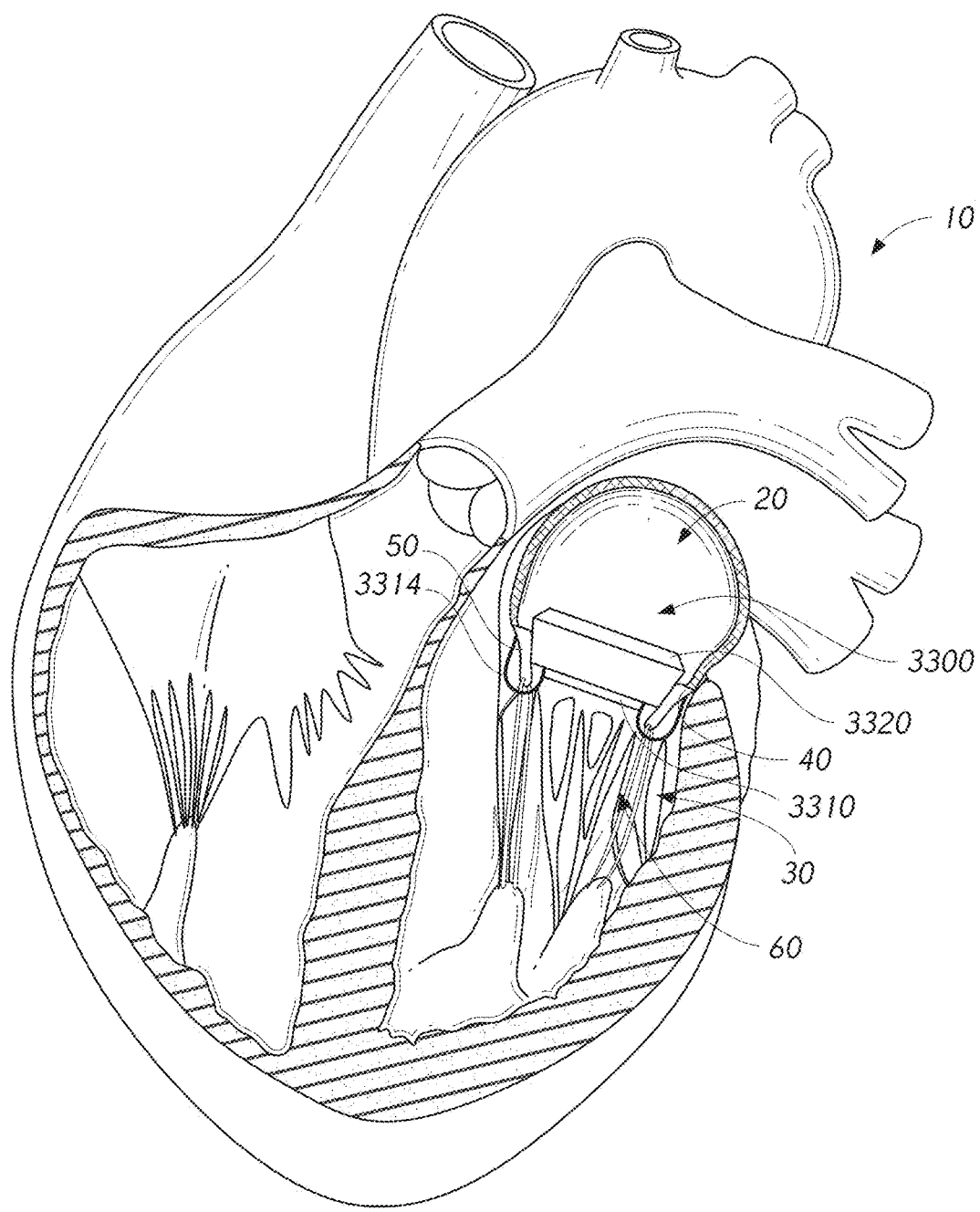
FIGS. 58 and 59 illustrate schematic representations of embodiments of prostheses positioned within a heart.

With reference next to FIG. 54G, the prosthesis 2900 can be fully deployed by advancing the nose cone 2960 further upwardly or proximally relative to the inner retention member 2970. As shown, the inner frame anchoring feature 2914 can be positioned between chordae tendineae 60 and contact a ventricular side of the annulus 40. Moreover, the annulus 40 and/or leaflets 50 can be engaged between the inner frame anchoring feature 2914 and the outer frame 2920. With reference next to FIG. 54H, the prosthesis 2900 is illustrated with the delivery system 2950 removed from the heart 10. As shown, prosthesis 2900 includes one or more flexible valve leaflets 2930 (e.g., three leaflets) which allow blood to flow in a direction from the left atrium 20 to the left ventricle 30. The inner frame 2910, inner frame anchoring feature 2914, and/or outer frame 2920 of prosthesis 2900 can be positioned similarly to the inner frame 3310, inner frame anchoring feature 3314, and/or outer frame 3320 of prosthesis 3300 shown in FIG. 58.

Reference is now made to FIGS. 55A-55H which illustrate schematic representations of an embodiment of a prosthesis 3000 and a delivery system 3050 during various stages of deployment within a native mitral valve of a heart 10. These steps can be similar to those described above in connection with FIGS. 54A-54F. The prosthesis 3000 can include an inner frame 3010 and an outer frame 3020. The inner frame 3010 can include an inner frame body 3012 and an inner frame anchoring feature 3014. The prosthesis 3000 can share characteristics, such as structure and/or functionality, which are the same as, or at least similar to, those of other prostheses described herein, such as prostheses 1900, 2000, 2200, 2400.

The delivery system 3050 can include a nose cone 3060 and an inner retention member 3062 at a first end of the delivery system 3050. The delivery system 3050 can include a hollow shaft member 3080 and a tether 3090. The delivery system 3050 can share characteristics, such as structure and/or functionality, which are the same as, or at least similar to, those of other delivery systems described herein, such as delivery system 1310.

Figure 55A:
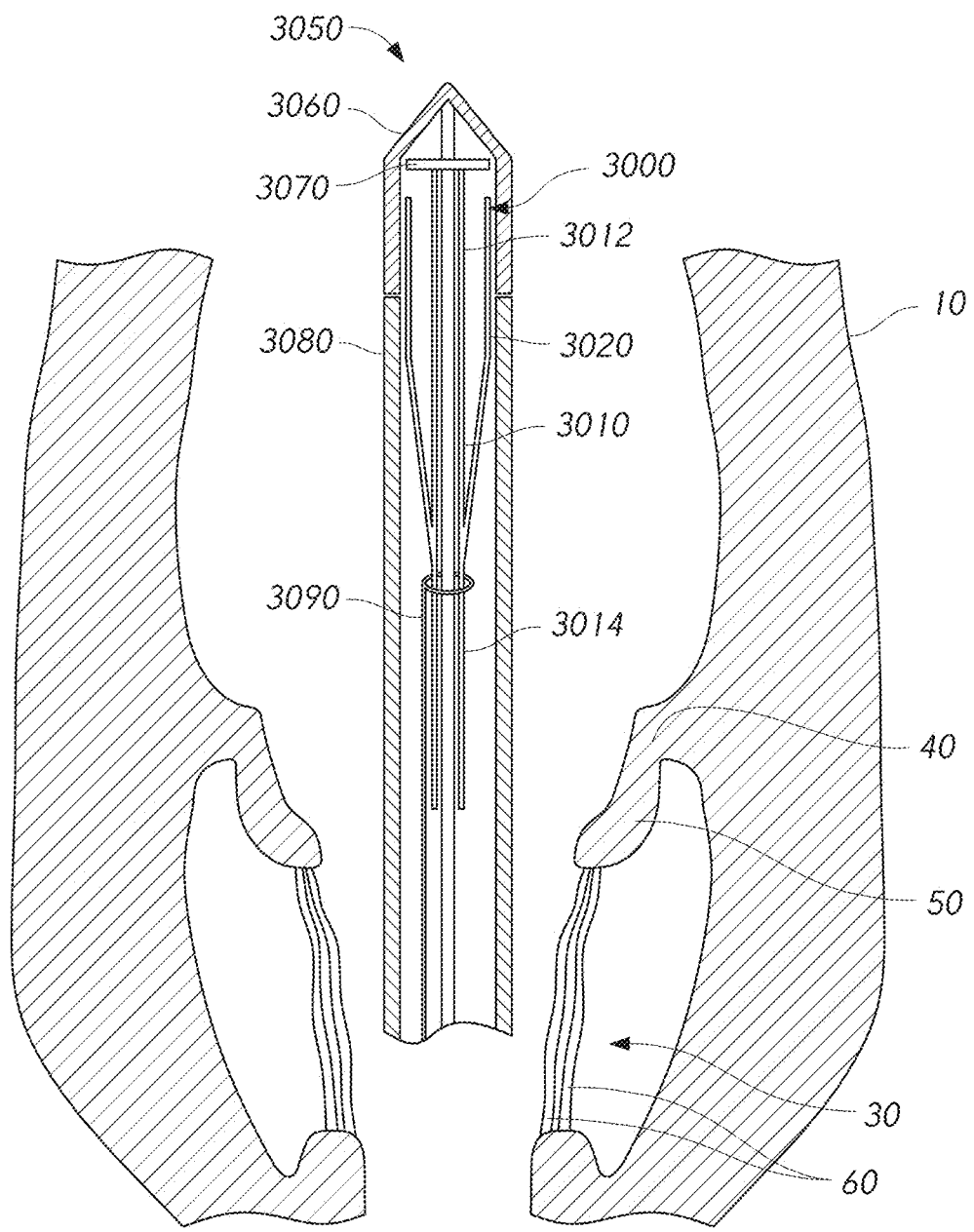
Figure 55B:
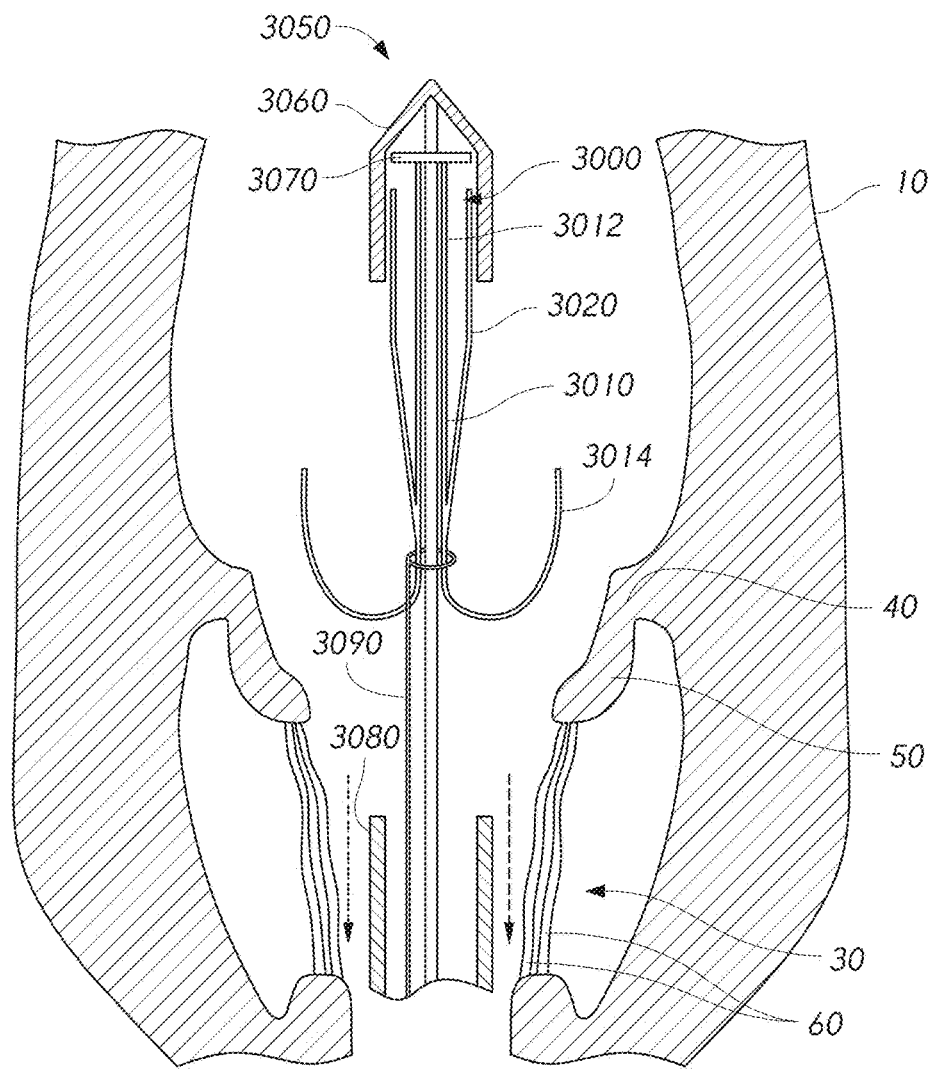

With reference first to FIG. 55A, the prosthesis 3000 and delivery system 3050 can be introduced with the prosthesis 3000 in a fully collapsed configuration. With reference next to FIG. 55B, the hollow shaft member 3080 can be retracted downwardly or proximally to expose the prosthesis 2900. As shown in the illustrated embodiment, the inner frame anchoring feature 2914 can be positioned generally above the annulus 40 prior to allowing the inner frame anchoring feature 2914 to expand; however, it is to be understood that this step can occur while the inner frame anchoring feature 2914 is positioned within the annulus 40, below the annulus 40, or below the leaflets 50. Although the inner frame 2910 is shown in a fully collapsed configuration via tether 2990, it is to be understood that the inner frame 2910 can at least partially expand during this stage.

Figure 55C:
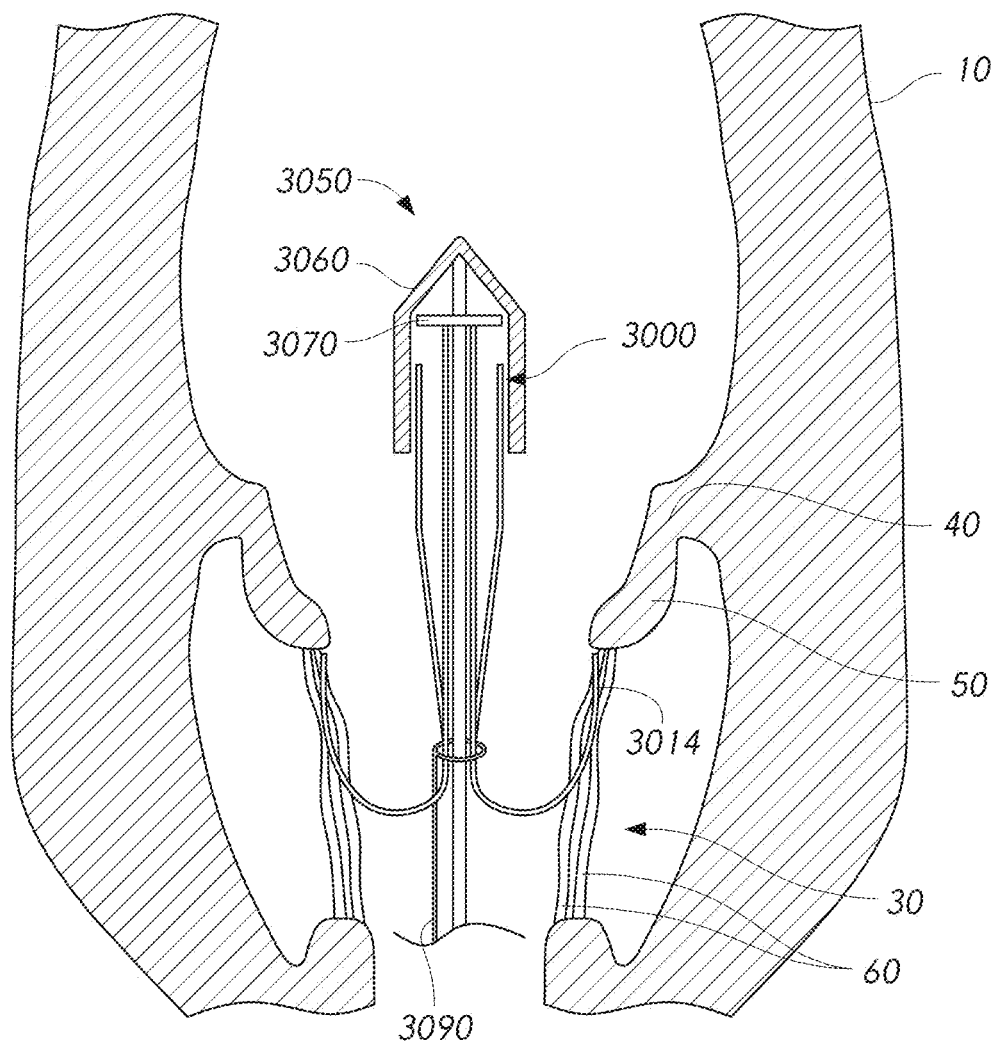

With reference next to in FIG. 55C, the prosthesis 3000 can be moved such that the inner frame anchoring feature 3014 is positioned below the annulus 40. As shown, the inner frame anchoring feature 3014 can be positioned below free edges of the leaflets 50. As shown in the illustrated embodiment, the geometry of the outer frame 3020 can advantageously increase a gap between the outer frame 3020 and the inner frame anchoring feature 3014. This can facilitate positioning the prosthesis 3000 such that the leaflets 50 are positioned between the outer frame 3020 and the inner frame anchoring feature 3014.

Figure 55D:
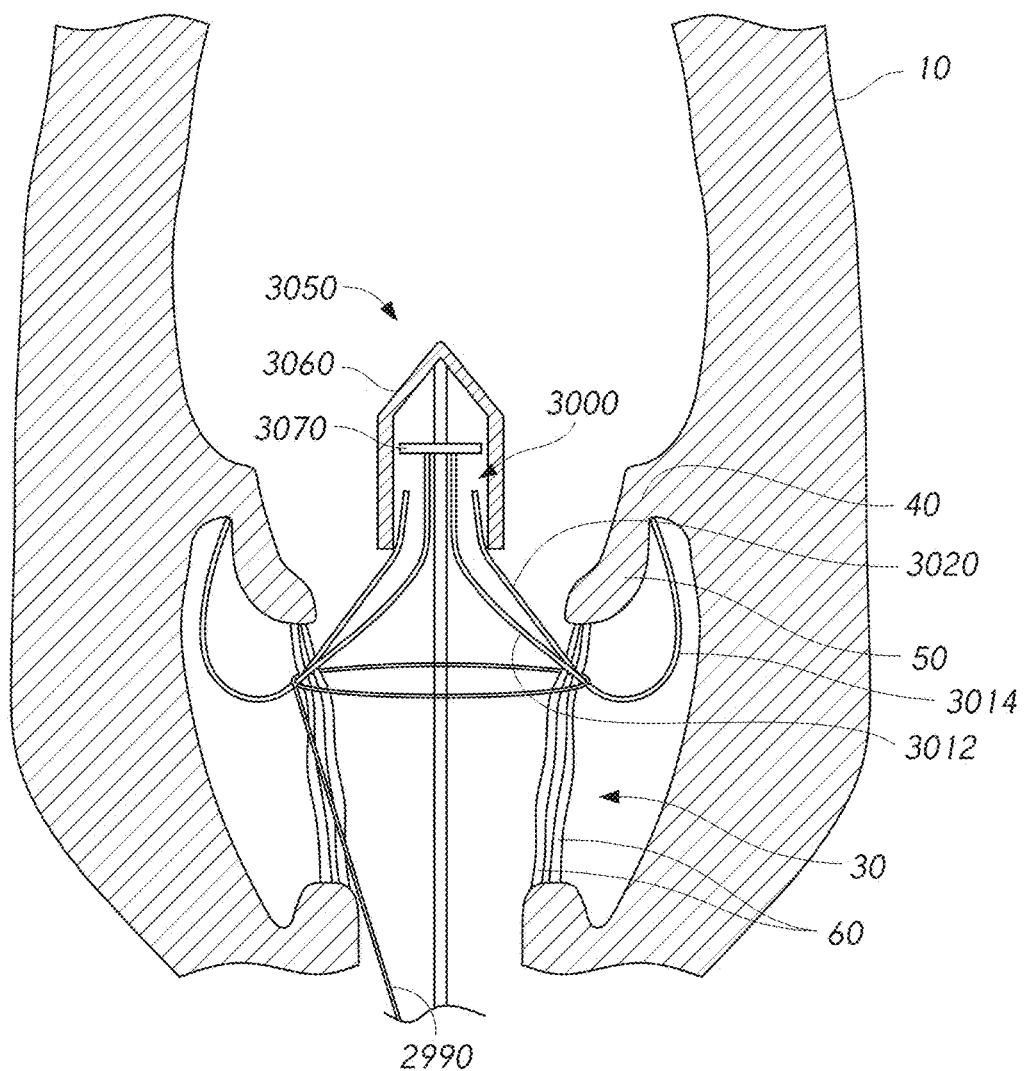

With reference next to FIG. 55D, the tether 3090 can be loosened to allow the inner frame 3010 to expand further radially outward. The prosthesis 3000 may be moved during this process to seat the inner frame anchoring feature 3014 against the annulus 40.

Figure 55E:
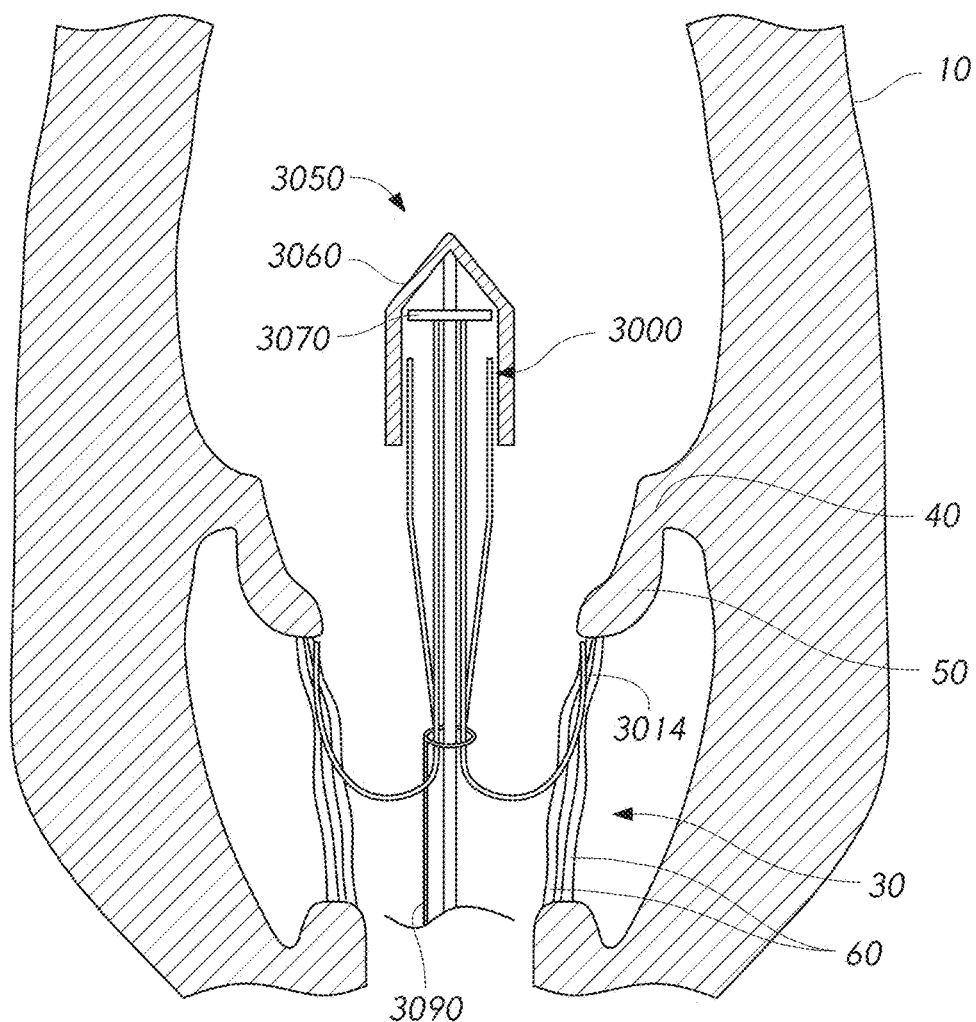
Figure 55F:
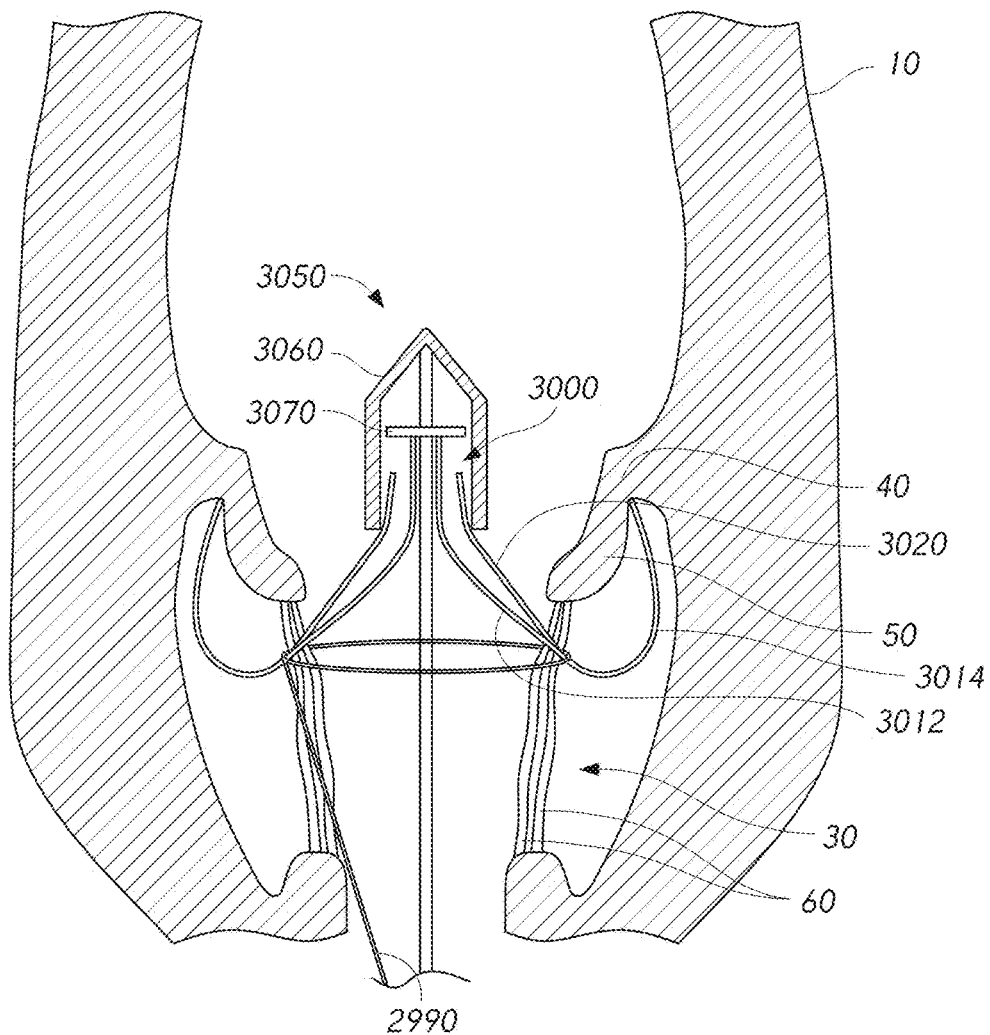
Figure 55G:
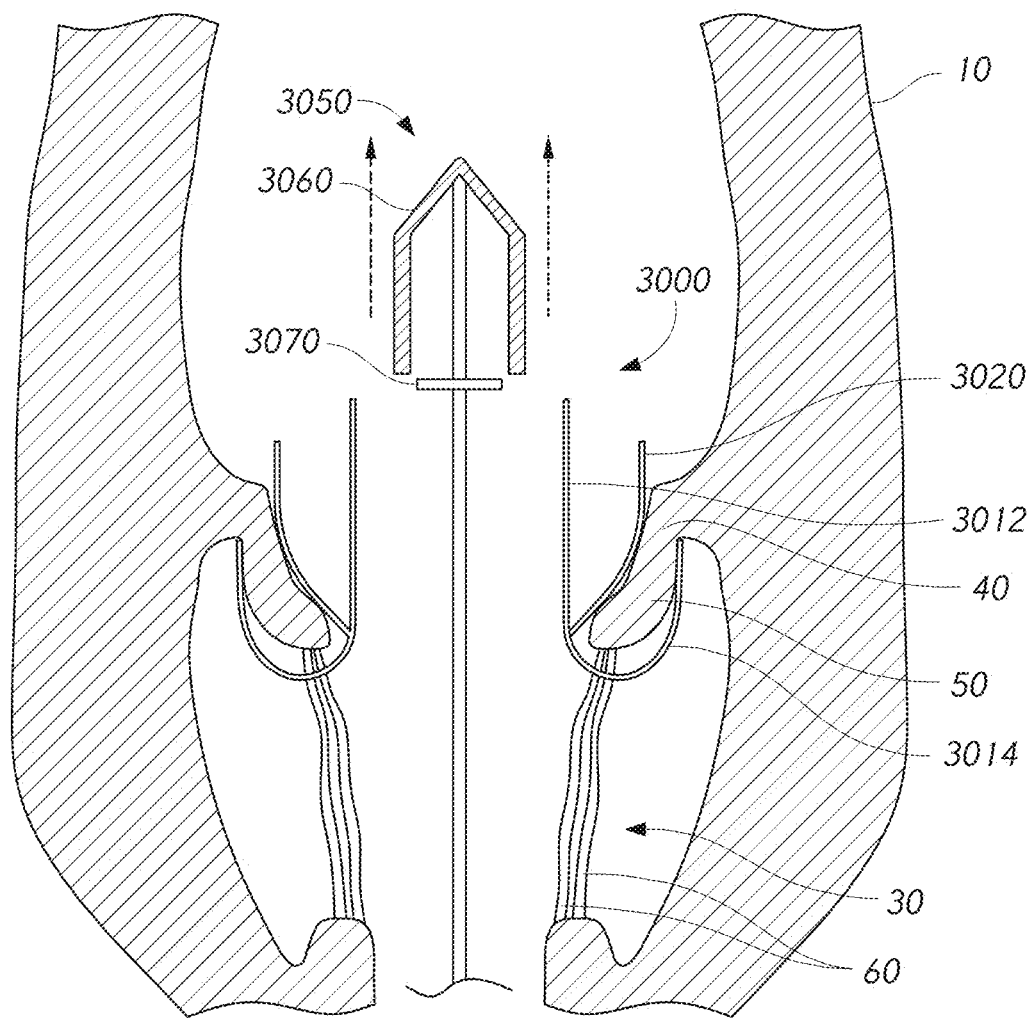
Figure 55H:
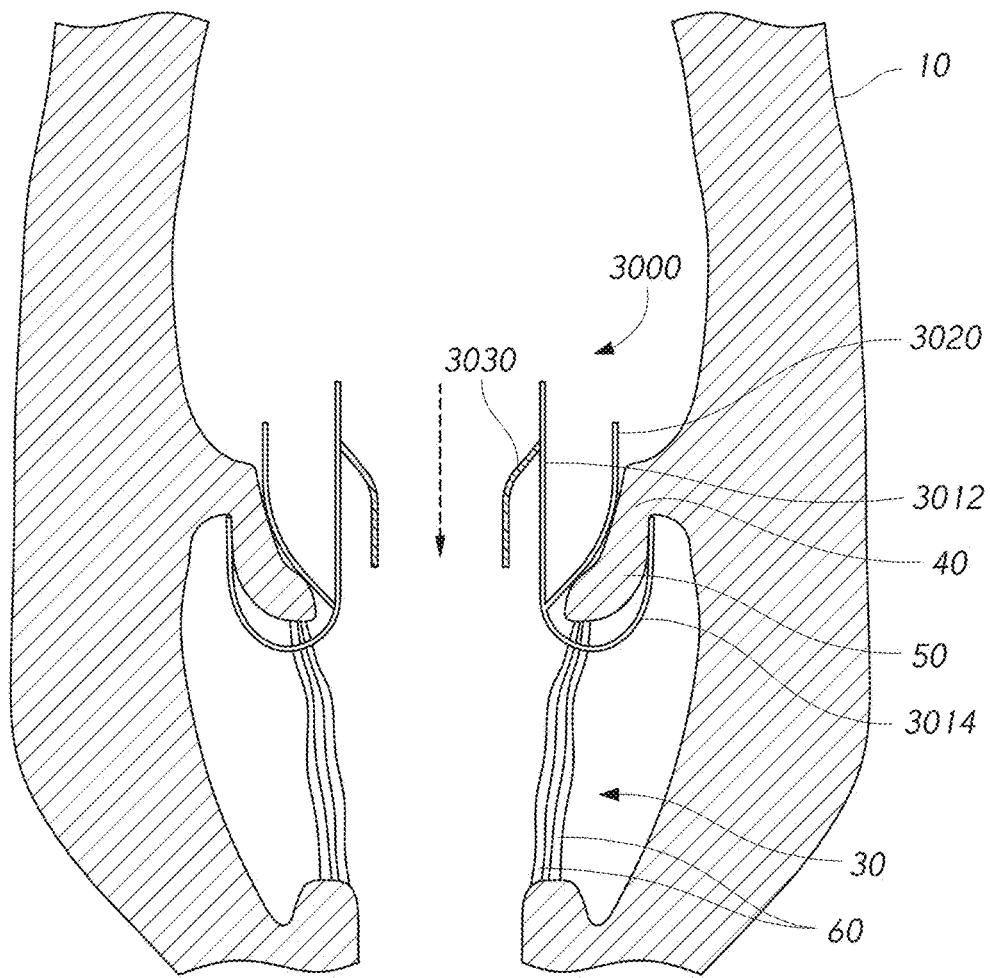
Figure 59:
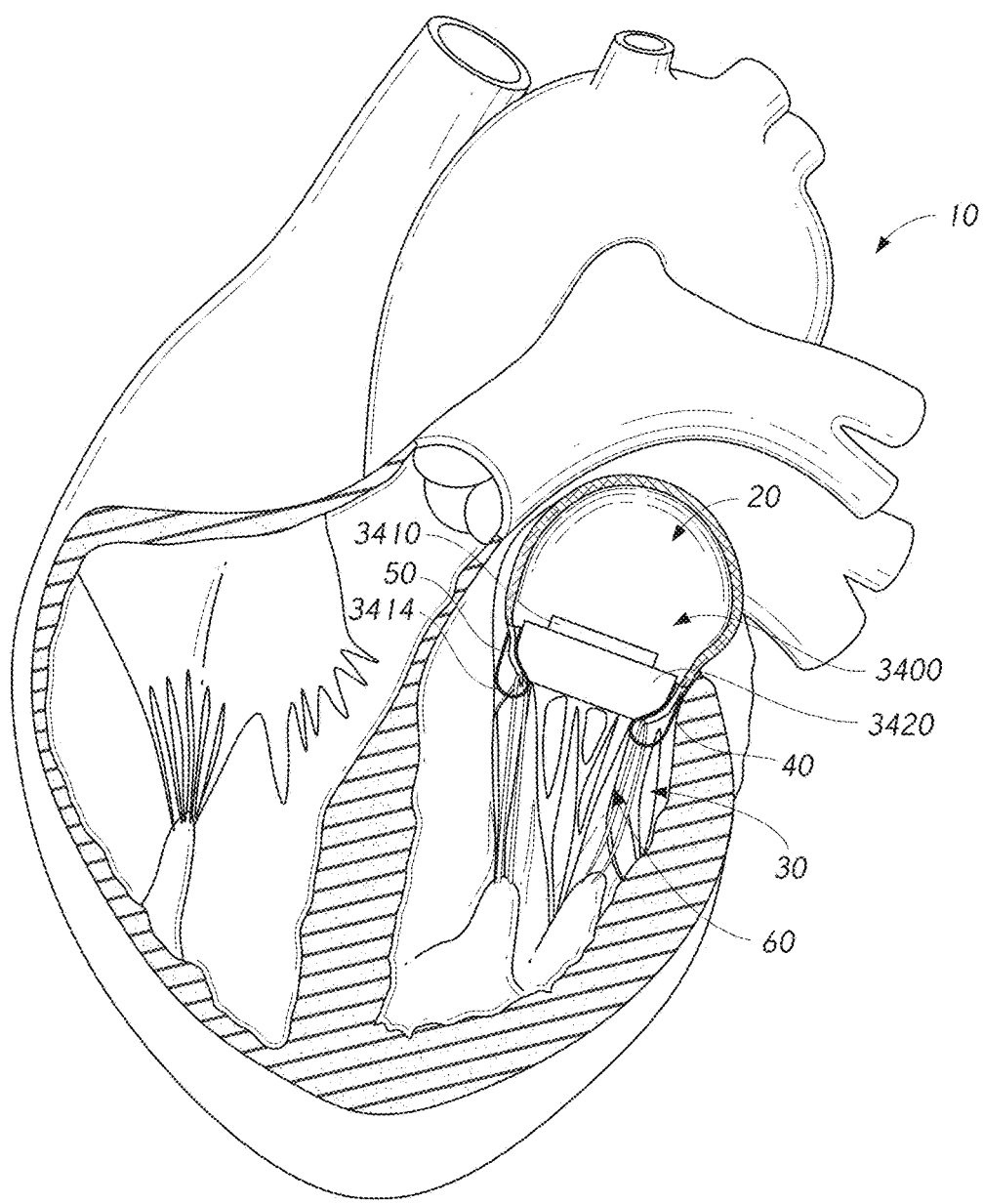

In some situations, a user may determine that the prosthesis 3000 should be repositioned. The prosthesis 3000 may be recaptured reversing the previous steps as shown in FIG. 55E. The user may then re-expand the prosthesis 3000 as shown in FIG. 55F. With reference next to FIG. 55G, the prosthesis 3000 can be fully deployed by advancing the nose cone 3060 further upwardly or proximally relative to the inner retention member 3070. With reference next to FIG. 55H, the prosthesis 3000 is illustrated with the delivery system 3050 removed from the heart 10. As shown, prosthesis 3000 includes one or more flexible valve leaflets 3030 (e.g., three leaflets) which allow blood to flow in a direction from the left atrium 20 to the left ventricle 30. The inner frame 3010, inner frame anchoring feature 3014, and/or outer frame 3020 of prosthesis 3000 can be positioned similarly to the inner frame 3410, inner frame anchoring feature 3414, and/or outer frame 3420 of prosthesis 3400 shown in FIG. 59.

Figure 32:
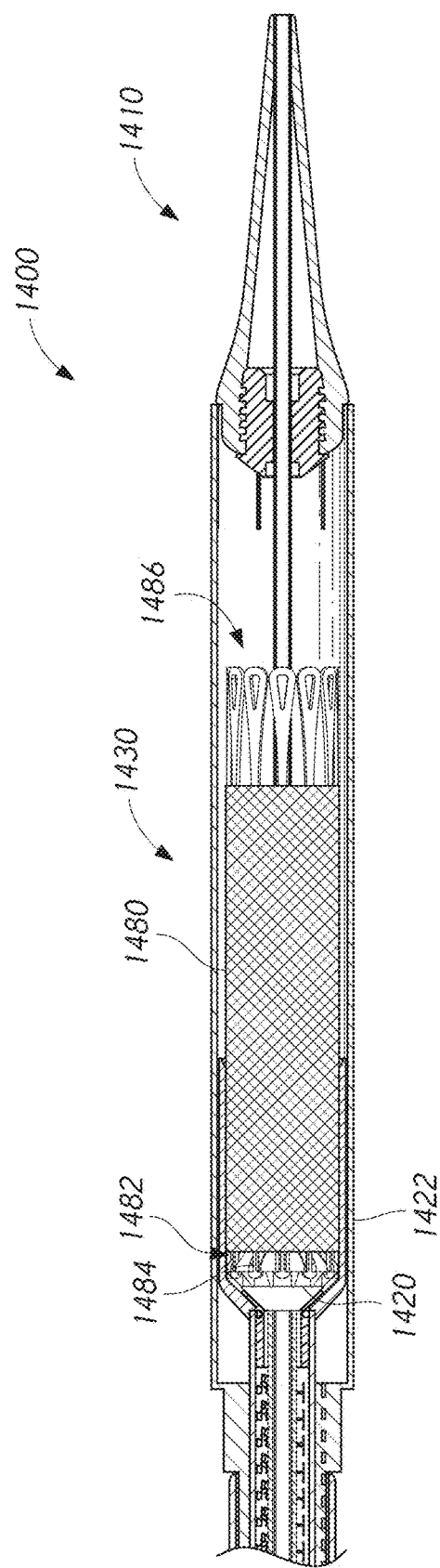
FIG. 32 is a cross-sectional view of a distal end of another embodiment of a delivery system loaded with another embodiment of a prosthesis.

With reference next to the system 1400 of FIG. 32, the system 1400 can include a delivery device 1410 with a prosthesis 1480 (illustrated schematically) contained within the delivery device 1410. A first end 1482 of the prosthesis 1480 can be placed in a compressed state such that the first end 1482 of the prosthesis 1480 is retained between an inner retention member 1420 and another portion of the delivery device, such as an outer retention member 1422, when the inner retention member 1420 is received within and covered by the outer retention member 1422. The interface between the locking tabs 1484 and slots of the inner retention member 1420 can inhibit axial movement of the prosthesis 1480 relative to the inner retention member 1420. When the first end 1482 of the prosthesis 1480 is uncovered, such as by moving the outer retention member 1422 proximally relative to the inner retention member 1420 or by moving the inner retention member 1420 distally relative to the outer retention member 1422, the first end 1482 of the prosthesis 1480 can be released from the inner retention member 1422. If the inner retention member 1420 is fully uncovered, the first end 1482 of the prosthesis 1480 can be released from the delivery device 1410. This release can be caused by the prosthesis 1480 transitioning from a collapsed configuration to an expanded configuration when the prosthesis 1480 is formed from a self-expanding material.

At least a second end 1486 of the prosthesis 1480 can be placed in a compressed state such that the second end 1486 of the prosthesis 1480 is retained within an outer sheath assembly 1430. When the second end 1486 is uncovered, such as by moving the outer sheath assembly 1430 proximally relative to the prosthesis 1480 or by moving the prosthesis 1480 distally relative to the outer sheath assembly 1430, the second end 1486 of the prosthesis 1480 can be released. This release can be caused by the prosthesis 1480 transitioning from a collapsed configuration to an expanded configuration when the prosthesis 1480 is formed from a self-expanding material. In some embodiments, anchors positioned at the second end 1486 can flip from the collapsed configuration to the expanded configuration such that they extend towards the first end 1482.

In some embodiments, the system 1400 can be used in connection with a transseptal procedure to access a native mitral valve. During such a procedure, the system 1400 can access a mitral valve through a septal puncture. The anchoring feature on a ventricular side of the prosthesis 1480, such as the second end 1486, can be released on a ventricular side of the native mitral valve annulus. During delivery, the anchoring feature on a ventricular side of the annulus (along with the prosthesis 1480) can be moved toward the ventricular side of the annulus with the ventricular anchors extending between at least some of the chordae tendineae to provide tension on the chordae tendineae. The degree of tension provided on the chordae tendineae can differ. For example, little to no tension may be present in the chordae tendineae if the leaflet is shorter than or similar in size to the ventricular anchors. A greater degree of tension may be present in the chordae tendineae where the leaflet is longer than the ventricular anchors and, as such, takes on a compacted form and is pulled toward the native valve annulus. An even greater degree of tension may be present in the chordae tendineae where the leaflets are even longer relative to the ventricular anchors. The leaflet can be sufficiently long such that the ventricular anchors do not contact the annulus. After the anchoring feature on a ventricular side of the annulus is positioned, the remainder of the prosthesis 1480 can be deployed from the delivery device 1410.

Reference is now made to FIGS. 56A-56H which illustrate schematic representations of an embodiment of a prosthesis 3100 and a delivery system 3150 during various stages of deployment within a native mitral valve of a heart 10. The prosthesis 3100 can include an inner frame 3110 and an outer frame 3120. The inner frame 3110 can include an inner frame body 3112 and an inner frame anchoring feature 3114. The prosthesis 3100 can share characteristics, such as structure and/or functionality, which are the same as, or at least similar to, those of other prostheses described herein, such as prostheses 100, 200, 1500, 1600.

The delivery system 3150 can include an inner retention member 3160 and a sheath 3170. The inner retention member 3160 and sheath 3170 can retain an upper end of the prosthesis 3100. The delivery system 3150 can share characteristics, such as structure and/or functionality, which are the same as, or at least similar to, those of other delivery systems described herein, such as delivery system 1410.

Figure 56A:
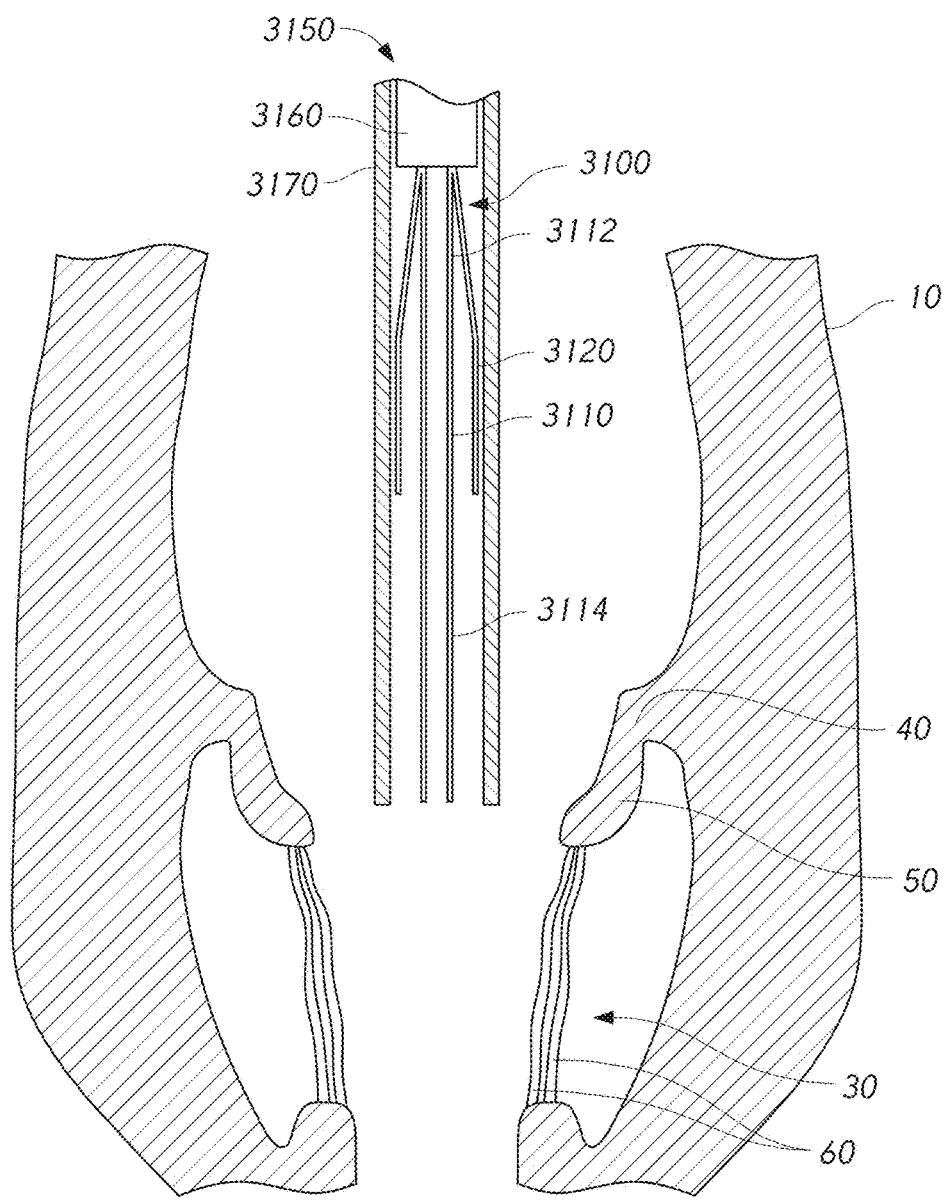

With reference first to FIG. 56A, the prosthesis 3100 and delivery system 3150 can be introduced with the prosthesis 3100 in a fully collapsed configuration. As shown, the prosthesis 3100 and the delivery system 3150 can be introduced in a direction from the atrium to the ventricle (e.g., a transseptal delivery procedure).

Figure 56B:
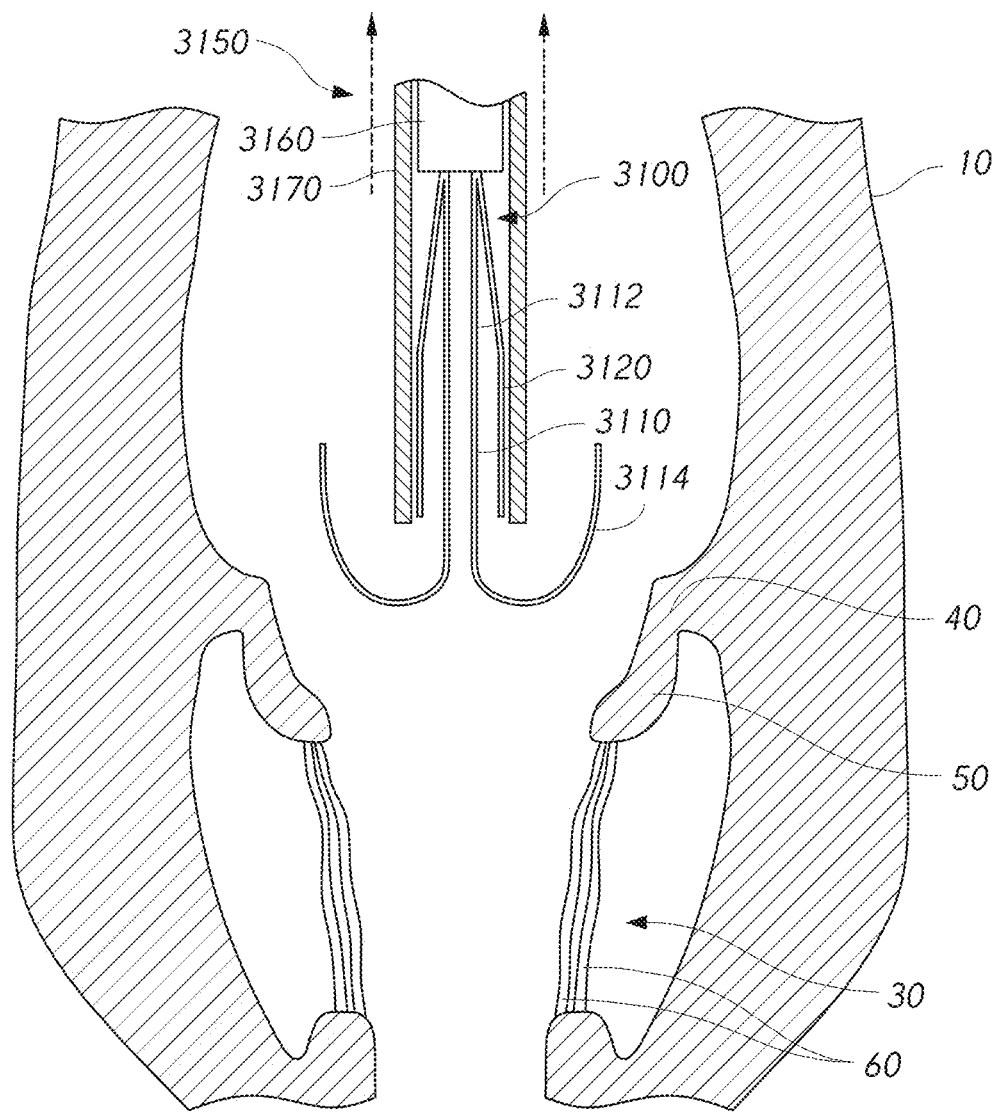

With reference next to FIG. 56B, the sheath 3170 can be retracted upwardly or proximally to expose the prosthesis 3100. This can allow the inner frame anchoring feature 3114 to transition to an expanded configuration. As shown in the illustrated embodiment, the inner frame anchoring feature 3114 can be positioned generally above the annulus 40 prior to allowing the inner frame anchoring feature 3114 to expand; however, it is to be understood that this step can occur while the inner frame anchoring feature 3114 is positioned within the annulus 40, below the annulus 40, or below the leaflets 50.

Figure 56C:
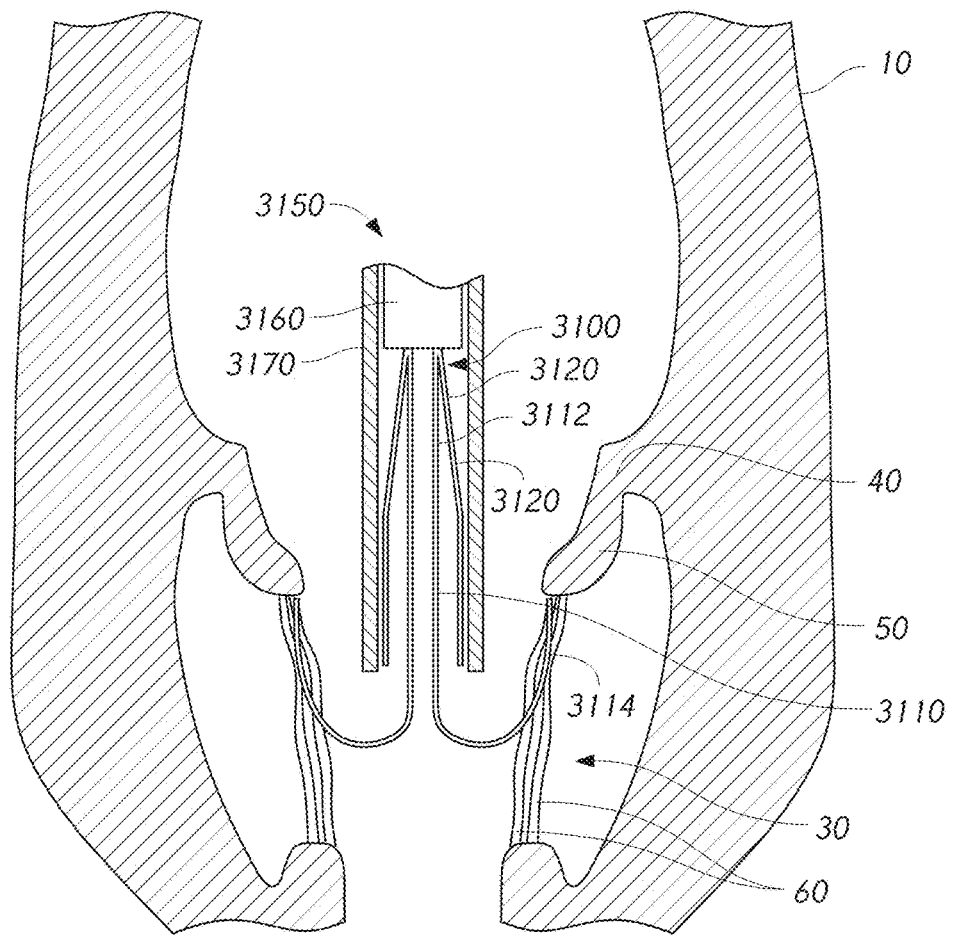
Figure 56D:
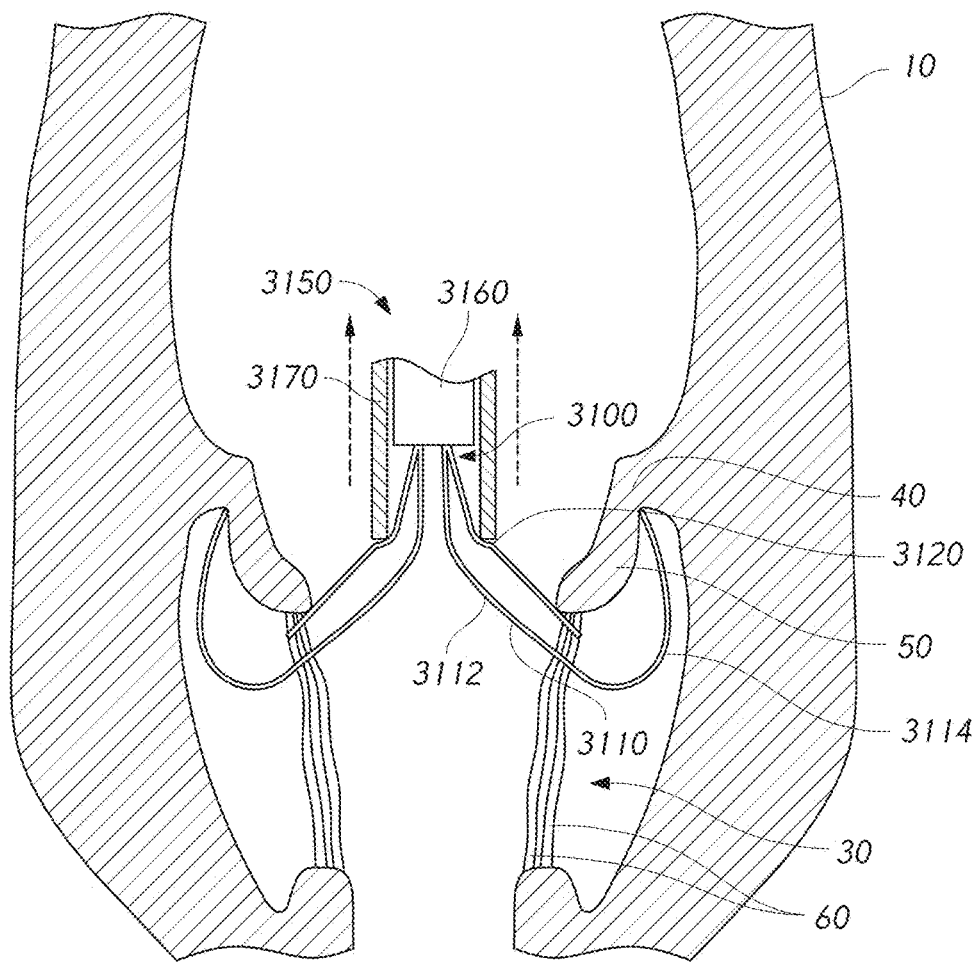

With reference next to in FIG. 56C, the prosthesis 3100 can be moved such that the inner frame anchoring feature 3114 is positioned below the annulus 40. As shown, the inner frame anchoring feature 3114 can be positioned below free edges of the leaflets 50. With reference next to FIG. 56D, the sheath 3170 can be further retracted to allow the inner frame 3110 and/or outer frame 3120 to expand further radially outward. The prosthesis 3100 may be moved during this process to seat the inner frame anchoring feature 3114 against the annulus 40.

Figure 56E:
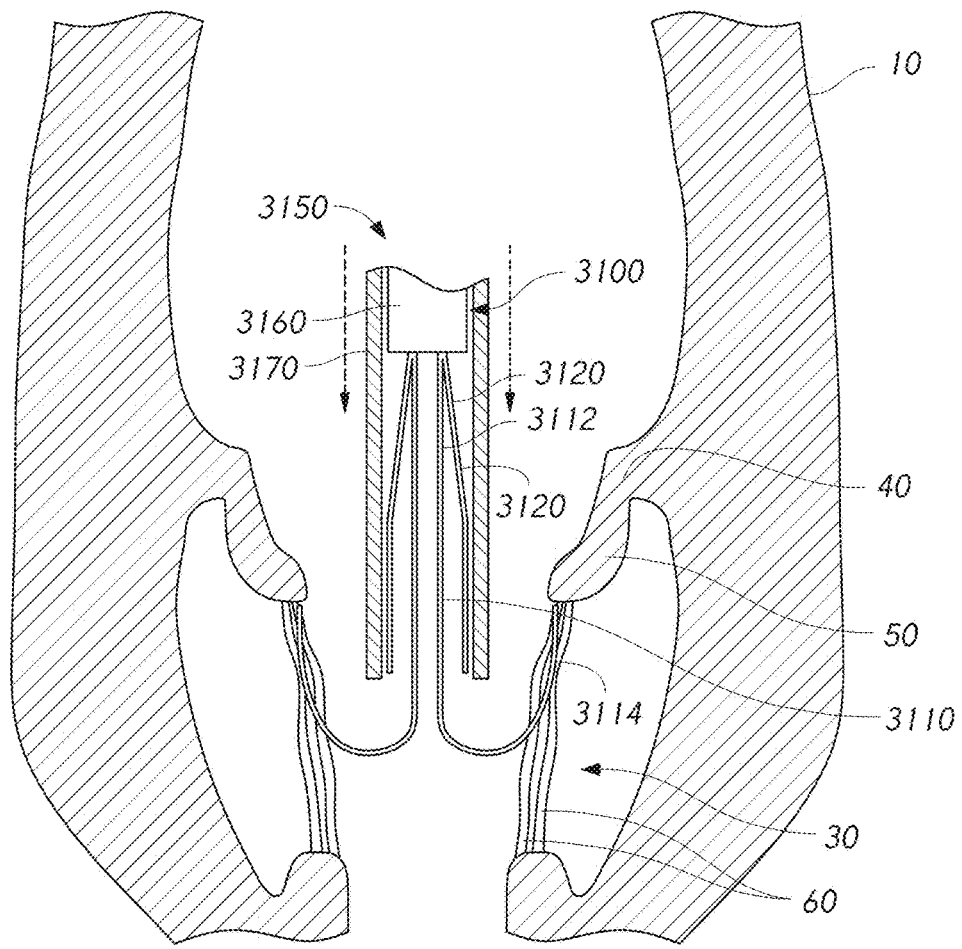
Figure 56F:
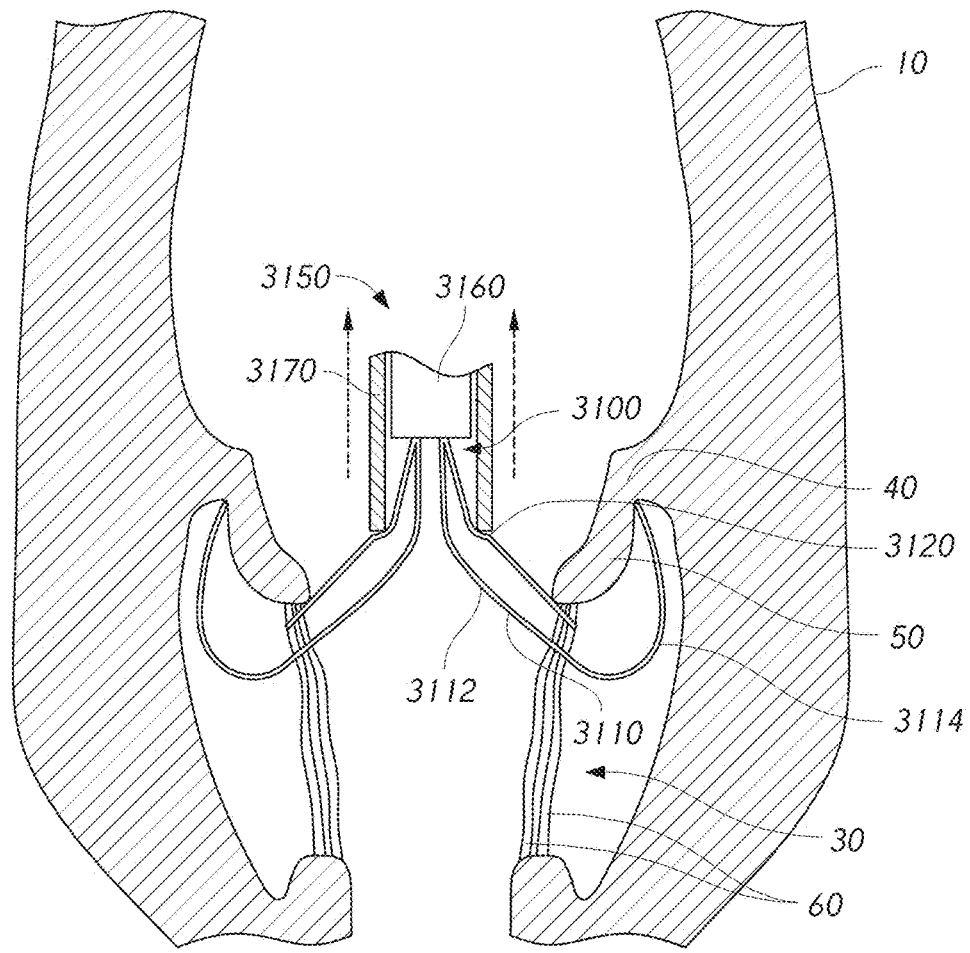

In some situations, a user may determine that the prosthesis 3100 should be repositioned. The prosthesis 3100 may be recaptured reversing the previous steps as shown in FIG. 56E. The inwardly tapered shape of the outer frame 3120 can facilitate the process of recapturing the device. For example, the inwardly tapered shape can function as a funnel which draws the outer frame 3120 and/or inner frame 3110 together when advancing the sheath 3170 over the outer frame 3120. The user may then re-expand the prosthesis 3100 as shown in FIG. 56F.

Figure 56G:
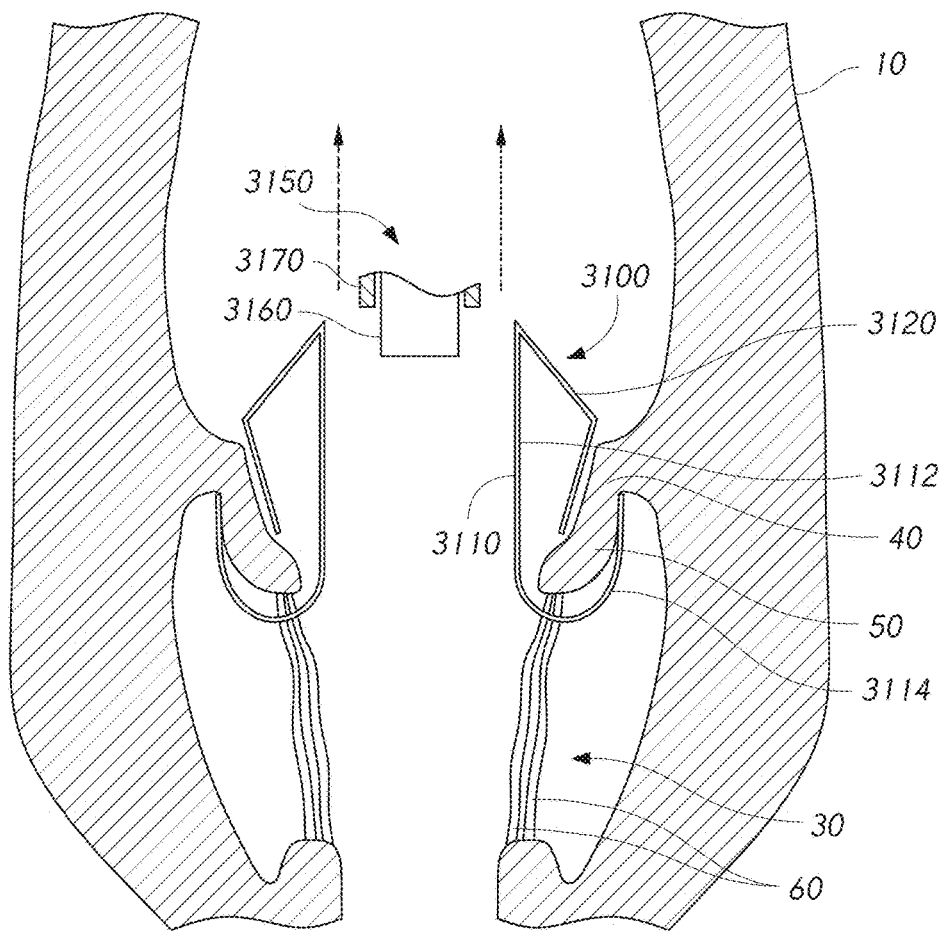
Figure 56H:
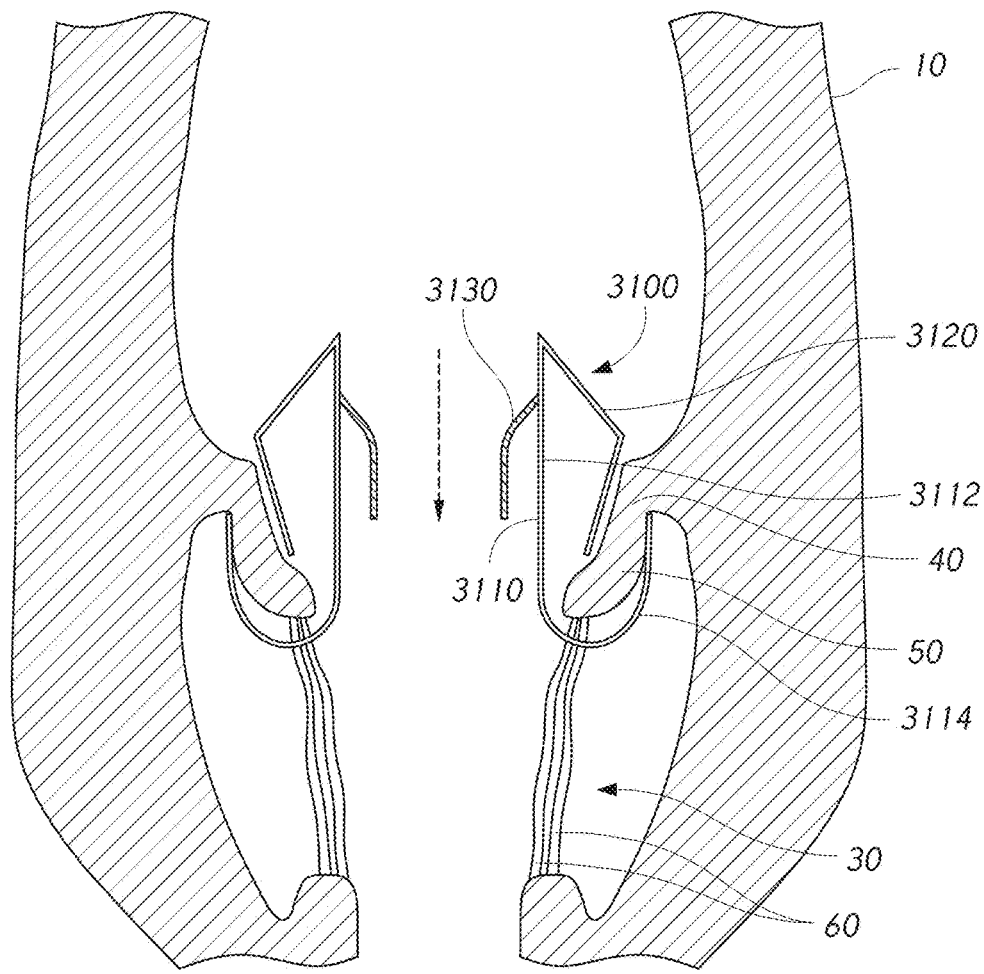

With reference next to FIG. 56G, the prosthesis 3100 can be fully deployed by further retracting the sheath 3170. As shown, the inner frame anchoring feature 3114 can be positioned between chordae tendineae 60 and contact a ventricular side of the annulus 40. Moreover, the annulus 40 and/or leaflets 50 can be engaged between the inner frame anchoring feature 3114 and the outer frame 3120. With reference next to FIG. 56H, the prosthesis 3100 is illustrated with the delivery system 3150 removed from the heart 10. As shown, prosthesis 3100 includes one or more flexible valve leaflets 3130 (e.g., three leaflets) which allow blood to flow in a direction from the left atrium 20 to the left ventricle 30. The inner frame 3110, inner frame anchoring feature 3114, and/or outer frame 3120 of prosthesis 3100 can be positioned similarly to the inner frame 3310, inner frame anchoring feature 3314, and/or outer frame 3320 of prosthesis 3300 shown in FIG. 58.

Reference is now made to FIGS. 57A-57F which illustrate schematic representations of an embodiment of a prosthesis 3200 and a delivery system 3250 during various stages of deployment within a native mitral valve of a heart 10. These steps can be similar to those described above in connection with FIGS. 56A-56F. The prosthesis 3200 can include an inner frame 3210 and an outer frame 3220. The inner frame 3210 can include an inner frame body 3212 and an inner frame anchoring feature 3214. The prosthesis 3200 can share characteristics, such as structure and/or functionality, which are the same as, or at least similar to, those of other prostheses described herein, such as prostheses 1900, 2000, 2200, 2400.

The delivery system 3250 can include an inner retention member 3260 and a sheath 3270. The delivery system 3250 can share characteristics, such as structure and/or functionality, which are the same as, or at least similar to, those of other delivery systems described herein, such as delivery system 1310.

Figure 57A:
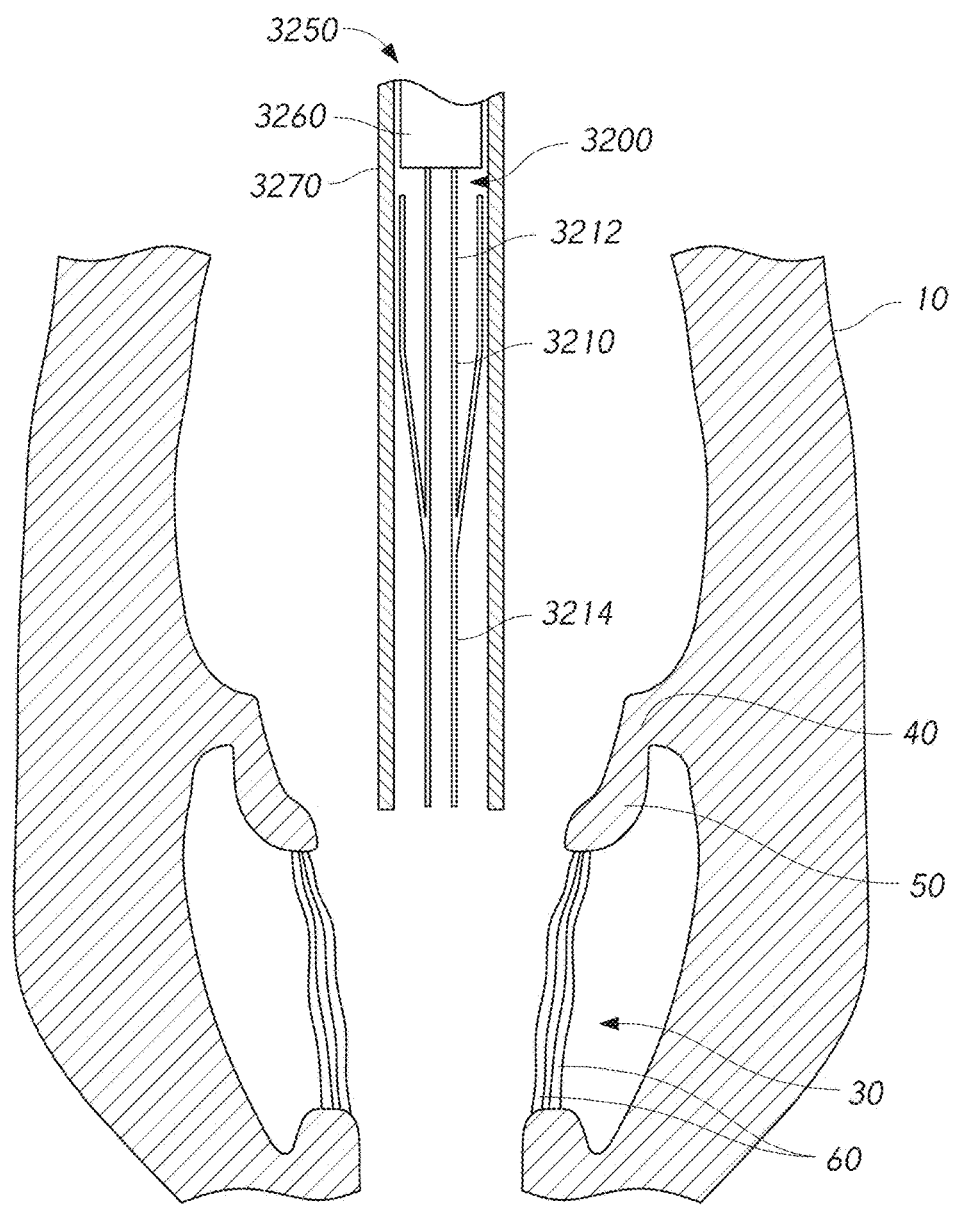
Figure 57B:
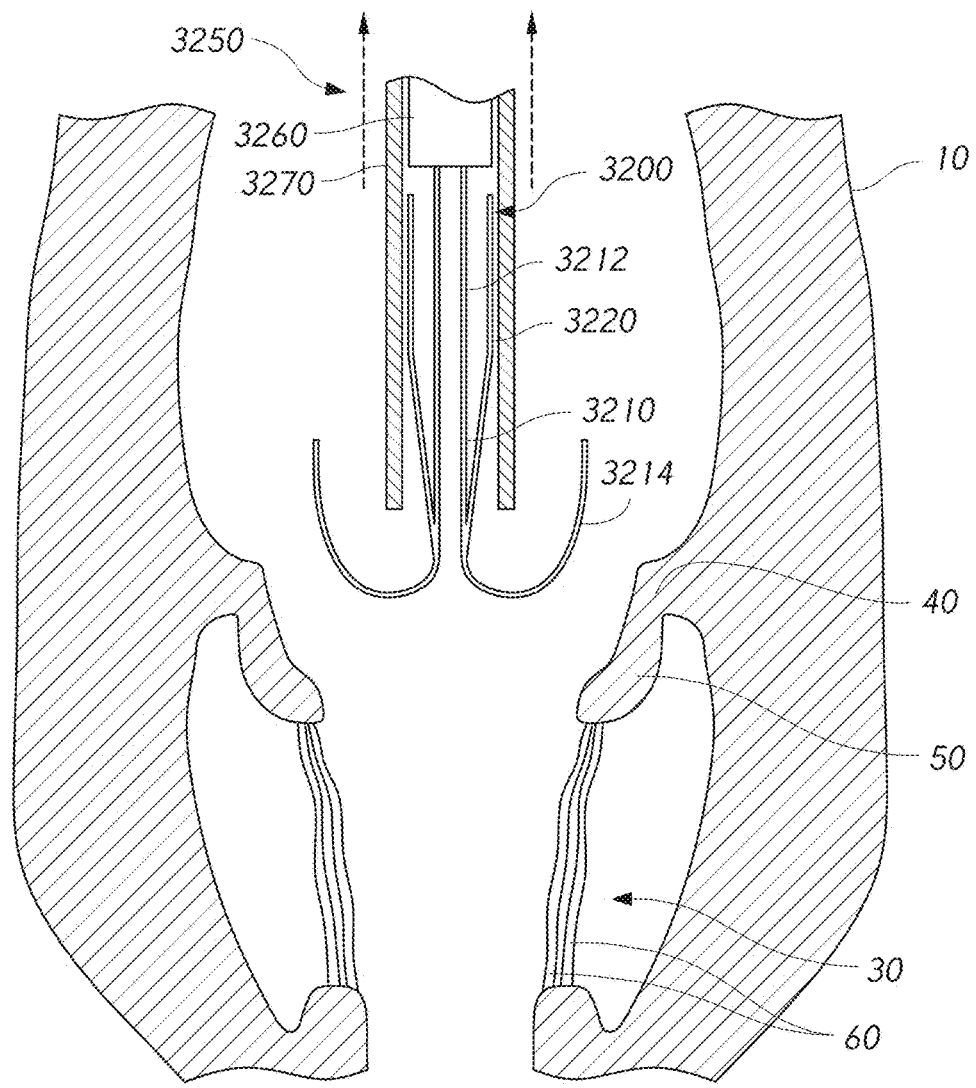

With reference first to FIG. 57A, the prosthesis 3200 and delivery system 3250 can be introduced with the prosthesis 3200 in a fully collapsed configuration. With reference next to FIG. 57B, the sheath 3270 can be retracted upwardly or proximally to expose the prosthesis 3200. As shown in the illustrated embodiment, the inner frame anchoring feature 3214 can be positioned generally above the annulus 40 prior to allowing the inner frame anchoring feature 3214 to expand; however, it is to be understood that this step can occur while the inner frame anchoring feature 3214 is positioned within the annulus 40, below the annulus 40, or below the leaflets 50.

Figure 57C:
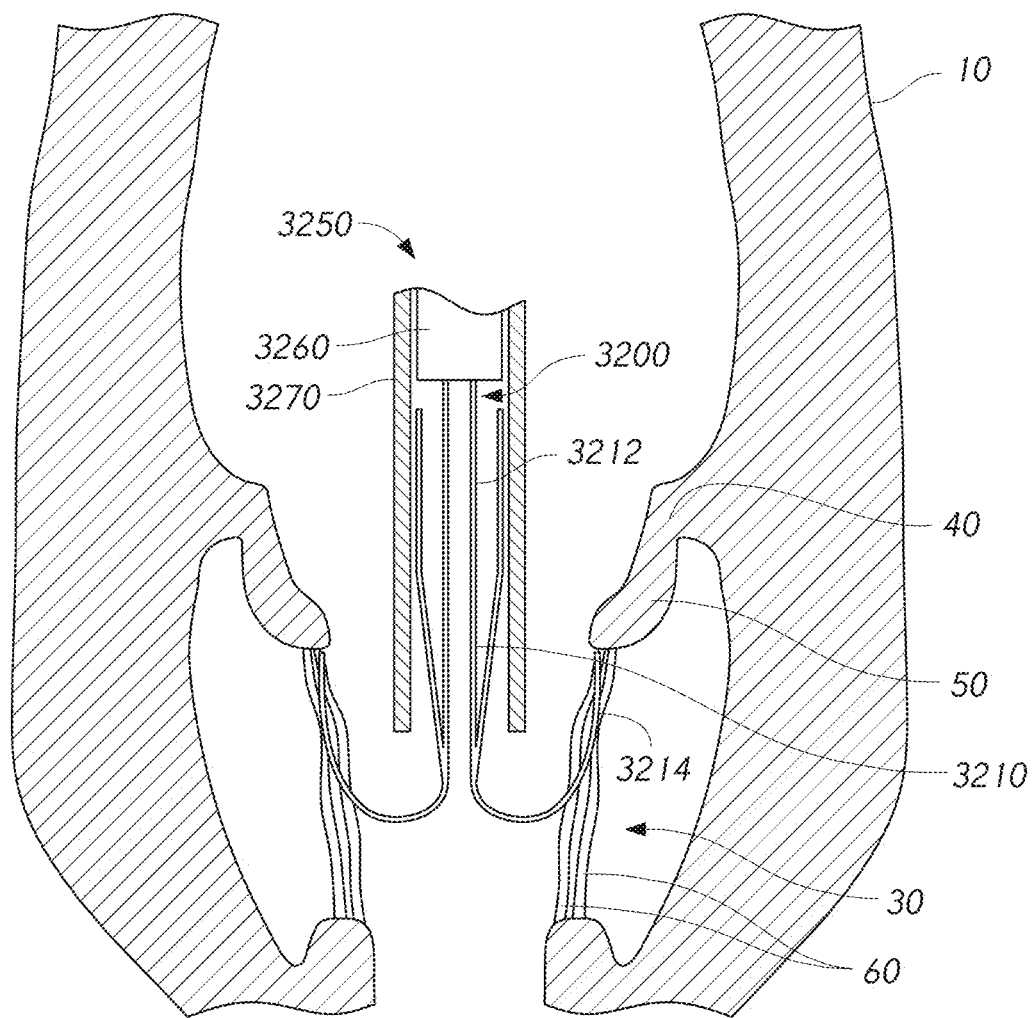
Figure 57D:
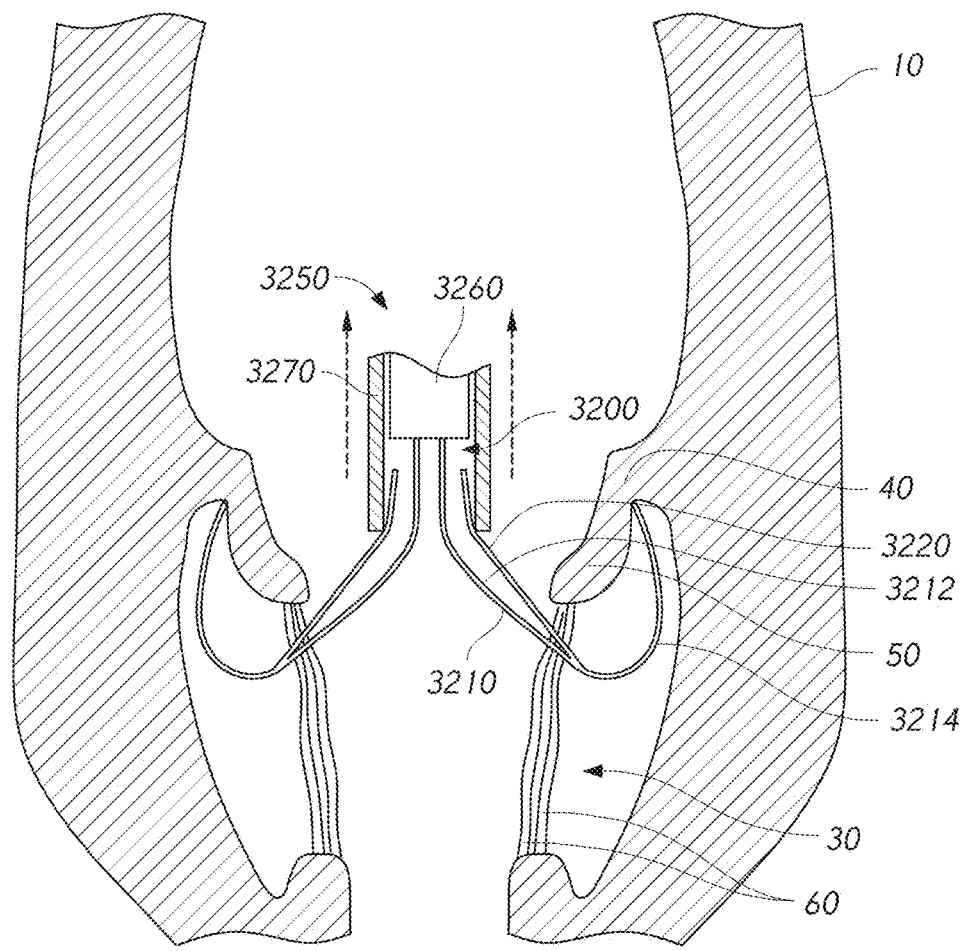

With reference next to in FIG. 57C, the prosthesis 3200 can be moved such that the inner frame anchoring feature 3214 is positioned below the annulus 40. With reference next to FIG. 55D, the sheath 3270 can be further retracted to allow the inner frame 3210 and/or outer frame 3220 to expand further radially outward. The prosthesis 3200 may be moved during this process to seat the inner frame anchoring feature 3214 against the annulus 40. As shown, the inner frame anchoring feature 3214 can be positioned below free edges of the leaflets 50. As shown in the illustrated embodiment, the geometry of the outer frame 3220 can advantageously increase a gap between the outer frame 3220 and the inner frame anchoring feature 3214. This can facilitate positioning the prosthesis 3200 such that the leaflets 50 are positioned between the outer frame 3220 and the inner frame anchoring feature 3214.

Figure 57E:
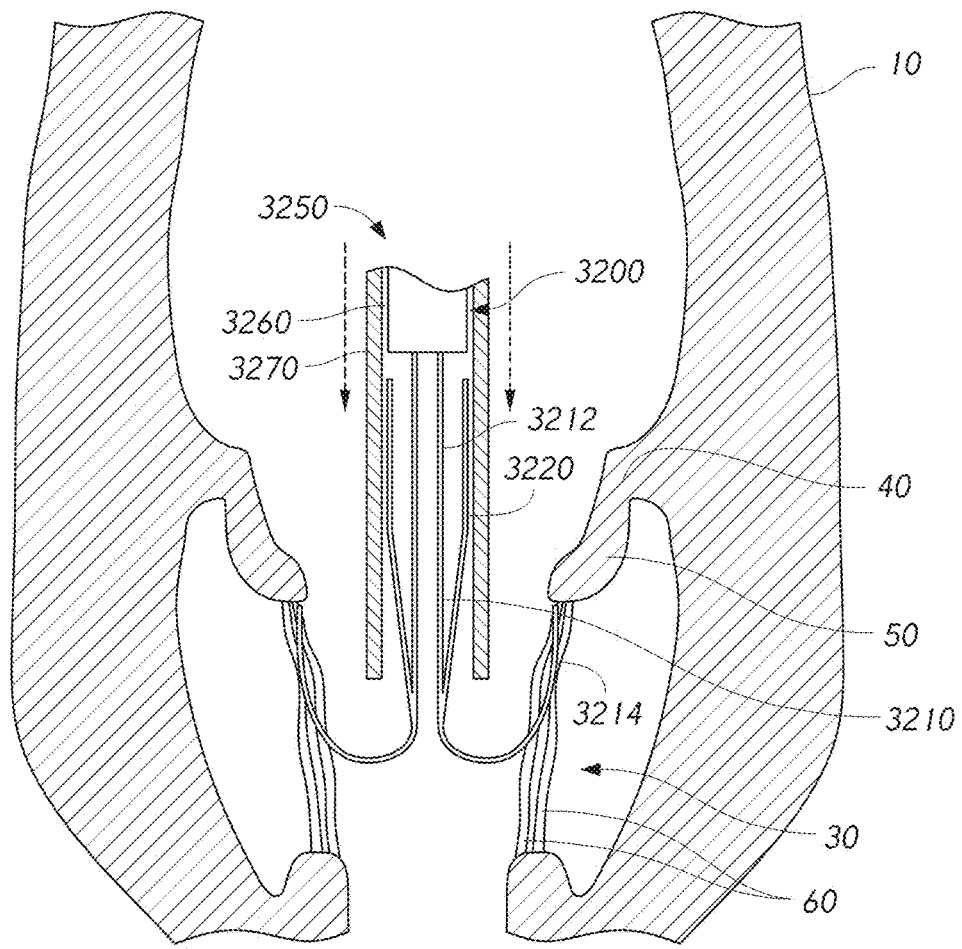
Figure 57F:
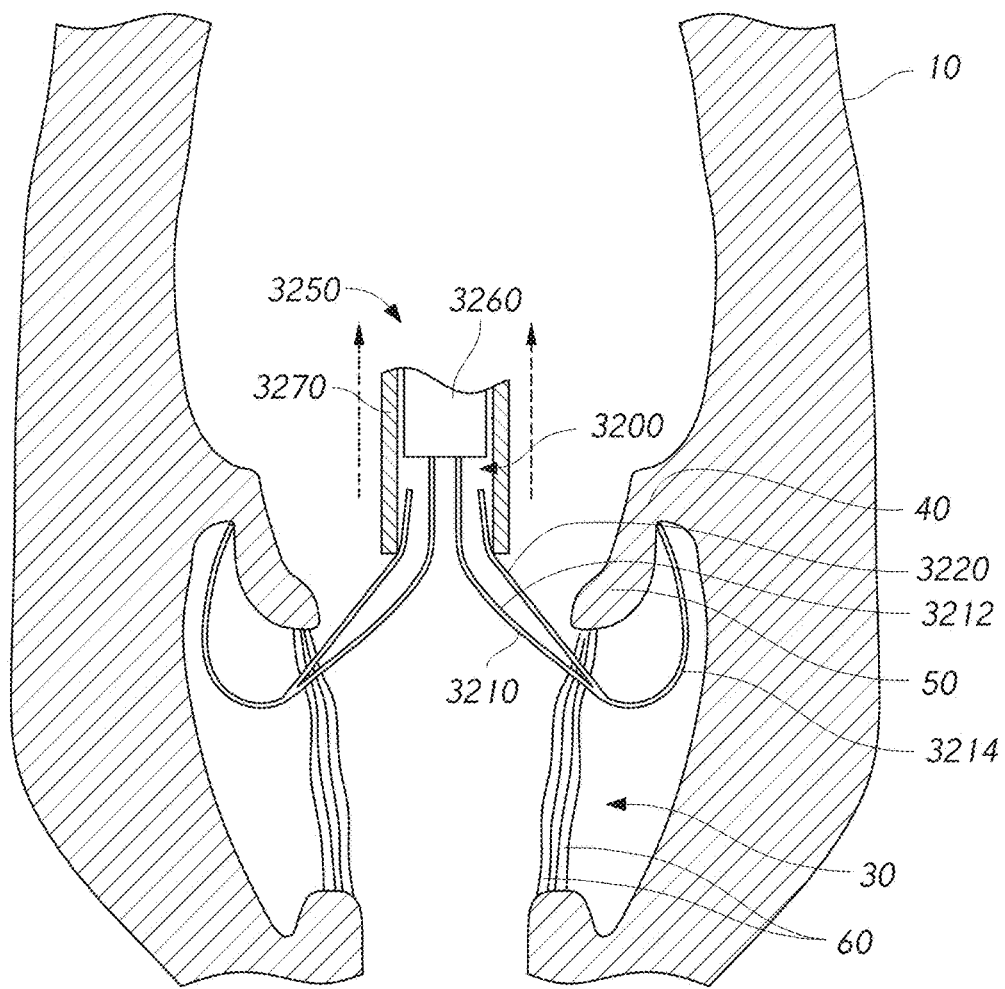
Figure 57G:
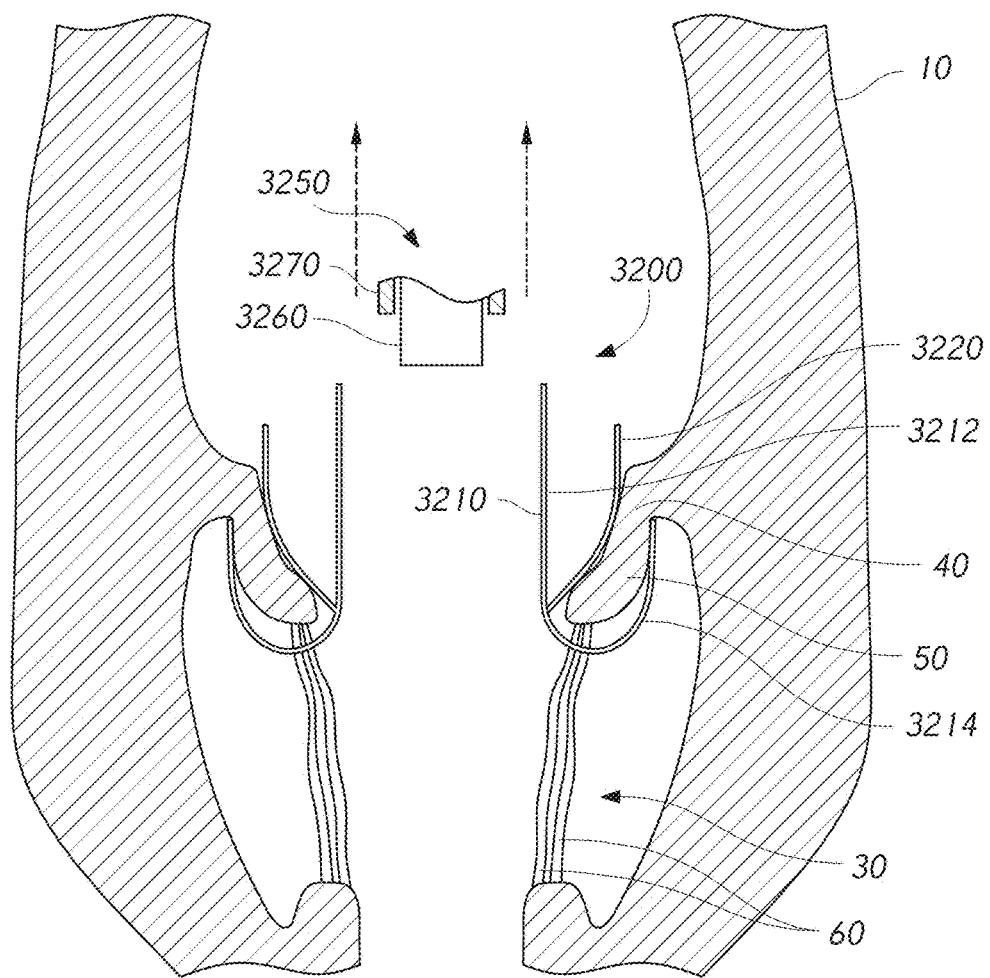
Figure 57H:
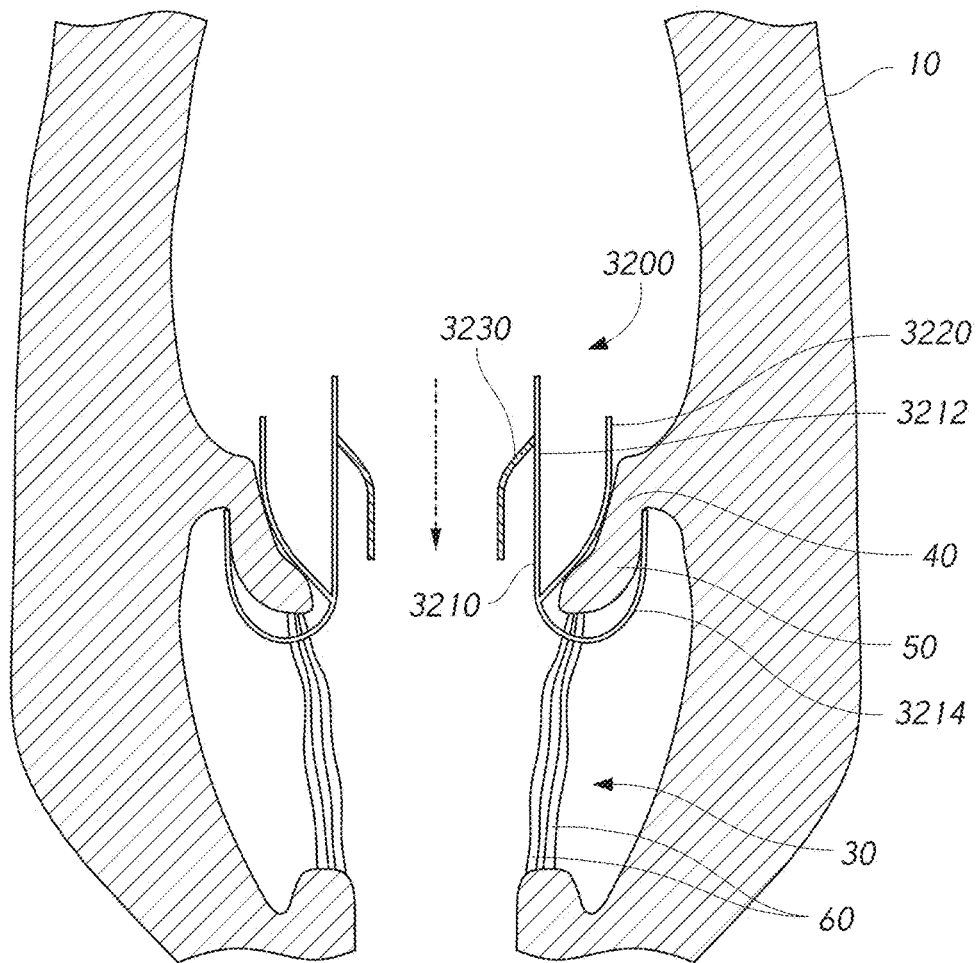

In some situations, a user may determine that the prosthesis 3200 should be repositioned. The prosthesis 3200 may be recaptured reversing the previous steps as shown in FIG. 57E. The user may then re-expand the prosthesis 3200 as shown in FIG. 57F. With reference next to FIG. 57G, the prosthesis 3200 can be fully deployed by further retracting the sheath 3170. With reference next to FIG. 57H, the prosthesis 3200 is illustrated with the delivery system 3250 removed from the heart 10. As shown, prosthesis 3200 includes one or more flexible valve leaflets 3230 which allow blood to flow in a direction from the left atrium 20 to the left ventricle 30. The inner frame 3210, inner frame anchoring feature 3214, and/or outer frame 3220 of prosthesis 3200 can be positioned similarly to the inner frame 3410, inner frame anchoring feature 3414, and/or outer frame 3420 of prosthesis 3400 shown in FIG. 59.

Other Embodiments

While certain embodiments have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope of the disclosure. Accordingly, the scope of the present disclosure is defined only by reference to the claims presented herein or as presented in the future.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A replacement heart valve prosthesis, the prosthesis comprising:
   an expandable frame configured to radially expand and contract for deployment within a native heart valve, the expandable frame having a longitudinal axis between upper and lower ends, the expandable frame comprising:
   a first frame portion comprising a first frame body having a plurality of body struts forming a plurality of rows of closed cells, a first anchoring feature comprising a plurality of anchoring struts each of which ends in a flared tip, and a plurality of cushions covering at least some of the flared tips, the first frame body comprising a generally cylindrical first upper region, a generally cylindrical first intermediate region, and a first lower region, wherein the first upper region includes a plurality of locking tabs each having an enlarged head attached to a strut, and wherein, when the prosthesis is in an expanded configuration:
   the first anchoring feature extends radially outwardly from the first lower region; and
   at least a portion of the first anchoring feature extends towards the first upper region;
   a second frame portion positioned radially outward of the first frame body, the second frame portion comprising a second frame body having a plurality of struts forming a zig-zag configuration and having a second upper region ending in a plurality of struts containing apertures, a second intermediate region, and a second lower region, wherein, when the prosthesis is in an expanded configuration:
   at least a portion of the second upper region extends radially outwardly from the first upper region;
   the second lower region is positioned radially between the first anchoring feature and the first frame body;
   the second intermediate portion is configured such that, when the prosthesis is deployed within the native heart valve, the second intermediate portion is positioned within a native valve annulus; and
   the second upper region is sutured to the first upper region;
   a valve body positioned within an interior of the first frame portion, the valve body comprising a plurality of leaflets configured to allow flow in a first direction and prevent flow in a second opposite direction; and
   a skirt, wherein at least a portion of the skirt extends along an exterior of the second frame portion and at least a portion of the skirt extends between the first frame portion and the second frame portion.

2. The replacement heart valve prosthesis of claim 1, wherein, when the prosthesis is in an expanded configuration, the second intermediate region is generally non-cylindrical.

3. The replacement heart valve prosthesis of claim 1, wherein the second frame portion and the first anchoring feature are sized such that, when the prosthesis is deployed and expanded within the native heart valve, at least one of native valve leaflets and the native valve annulus are pinched between the second frame portion and the first anchoring feature.

4. The replacement heart valve prosthesis of claim 1, wherein the first anchoring feature is sized such that, when the prosthesis is deployed and expanded within a native mitral valve, at least a portion of the first anchoring feature contacts a native mitral valve annulus on a ventricular side.

5. The replacement heart valve prosthesis of claim 1, wherein the second frame portion comprises a second anchoring feature.

6. The replacement heart valve prosthesis of claim 1, wherein the portion extending between the first frame portion and the second frame portion is attached to the valve body.

7. The replacement heart valve prosthesis of claim 1, wherein the valve body comprises one or more intermediate components, the one or more intermediate components positioned between the first frame body and the valve leaflets.

8. The replacement heart valve prosthesis of claim 1, wherein the first frame body forms a bulbous shape.

9. A replacement mitral valve prosthesis, comprising:
a valve body including three flexible leaflets made from pericardium; and
a self-expanding, metallic support structure surrounding and supporting the valve body, the support structure sized for deployment in a native mitral valve, the support structure comprising:
a cylindrical valve frame having an upper portion including tabs with enlarged heads, an intermediate portion, and a lower portion, the valve frame having at least two circumferential rows of closed cells;
a plurality of anchors coupled to the lower portion, each of the anchors extending radially outwardly and upwardly and ending in a flared tip, at least some of the flared tips having cushions; and
a sealing frame separate from, coupled to by sutures, and disposed radially outwardly of the valve frame, the sealing frame having an upper portion including a plurality of struts having apertures, an intermediate portion and a lower portion, wherein a clearance is provided between the sealing frame and the valve frame and wherein the plurality of anchors have ends disposed radially outwardly of the sealing frame.

10. The prosthesis of claim 9, wherein the upper portion of the sealing frame is coupled to the upper portion of the valve frame via the sutures.

11. The prosthesis of claim 9, wherein the sealing frame is more flexible than the valve frame for conforming to a mitral valve annulus.

12. The prosthesis of claim 9, wherein the support structure is adapted to capture native mitral valve leaflets between the sealing frame and the anchors.

13. The prosthesis of claim 9, wherein the intermediate portion of the sealing frame has a diameter in the range of about 35 mm to 55 mm.

14. The prosthesis of claim 9, wherein at least a portion of the sealing frame is covered by fabric.

15. The prosthesis of claim 9, wherein the lower portion of the sealing frame has a larger diameter than the upper portion of the sealing frame.

16. The prosthesis of claim 15, wherein the intermediate portion of the sealing frame has a larger diameter than the lower portion of the sealing frame.

17. The prosthesis of claim 9, wherein the valve frame is bulbous.

18. A replacement heart valve prosthesis, the prosthesis comprising:
an expandable frame configured to radially expand and contract for deployment within a native mitral heart valve, the expandable frame having a longitudinal axis between inlet and outlet ends, the expandable frame comprising:
a generally cylindrical inner frame comprising:
an inner frame inlet end including a plurality of locking tabs each having an enlarged head;
an intermediate section having a plurality of rows of closed cells;
an inner frame outlet end having a plurality of anchoring struts, the anchoring struts extending radially outwards and towards the inlet end; and
at least one cushion located on a flared tip of at least one of the plurality of anchoring struts;
an outer frame sutured to the inner frame, the outer frame comprising:
an outer frame inlet end extending generally parallel with the longitudinal axis and having a plurality of apertures configured for suturing to the inner frame; and
a bulbous section which first extends radially away from the longitudinal axis and then extends radially towards the longitudinal axis;
a skirt covering an exterior surface of the inner frame and an exterior surface of the outer frame, wherein the skirt creates separation between the inner frame and the outer frame; and
a valve body positioned within an interior of the inner frame, the valve body comprising a plurality of leaflets configured to allow flow in a first direction and prevent flow in a second opposite direction.

* * * * *